United States Patent [19]
Thorpe et al.

[11] Patent Number: 6,132,729
[45] Date of Patent: Oct. 17, 2000

[54] COMBINED TISSUE FACTOR AND CHEMOTHERAPEUTIC METHODS AND COMPOSITIONS FOR COAGULATION AND TUMOR TREATMENT

[75] Inventors: Philip E. Thorpe, Dallas, Tex.; Steven W. King, Foothill Ranch, Calif.; Boning Gao, Dallas, Tex.

[73] Assignee: Board of Regents, The University of Texas System, Austin, Tex.

[21] Appl. No.: 09/009,217

[22] Filed: Jan. 20, 1998

Related U.S. Application Data

[60] Provisional application No. 60/042,427, Mar. 27, 1997, provisional application No. 60/036,205, Jan. 27, 1997, and provisional application No. 60/035,920, Jan. 22, 1997.

[51] Int. Cl.$^7$ .................. A61K 39/00; A61K 39/395; A61K 38/00; C07K 14/00; C07K 35/14

[52] U.S. Cl. ............................ 424/198.1; 424/185.1; 424/178.1; 424/130.1; 514/2; 514/834; 530/827; 530/829; 530/381; 530/407

[58] Field of Search .............. 424/198.1, 178.1, 424/130.1, 185.1; 530/381, 827, 829, 407; 514/834, 12

[56] References Cited

U.S. PATENT DOCUMENTS

| | | | |
|---|---|---|---|
| 4,536,387 | 8/1985 | Sakamoto et al. | 424/426 |
| 5,017,556 | 5/1991 | O'Brien et al. | 514/2 |
| 5,110,730 | 5/1992 | Edgington et al. | 435/69.6 |
| 5,223,427 | 6/1993 | Edgington | 435/240.27 |
| 5,314,695 | 5/1994 | Brown | 424/450 |
| 5,346,991 | 9/1994 | Roy et al. | 530/350 |
| 5,374,617 | 12/1994 | Morrissey et al. | 514/8 |
| 5,437,864 | 8/1995 | Edgington et al. | 424/145.1 |
| 5,504,064 | 4/1996 | Morrissey et al. | 514/8 |
| 5,504,067 | 4/1996 | Morrissey et al. | 514/8 |
| 5,589,173 | 12/1996 | O'Brien et al. | 424/145.1 |
| 5,589,363 | 12/1996 | Roy et al. | 435/69.6 |
| 5,622,931 | 4/1997 | Edgington et al. | 514/12 |
| 5,726,147 | 3/1998 | Ruf et al. | 514/2 |
| 5,739,101 | 4/1998 | Roy et al. | 514/2 |

FOREIGN PATENT DOCUMENTS

| | | |
|---|---|---|
| WO 93/09804 | 5/1993 | WIPO. |
| WO 93/17715 | 9/1993 | WIPO. |
| WO 93/23074 | 11/1993 | WIPO. |
| WO 94/05328 | 3/1994 | WIPO. |
| WO 94/07515 | 4/1994 | WIPO. |
| WO 94/28017 | 12/1994 | WIPO. |
| WO 96/01653 | 1/1996 | WIPO. |

OTHER PUBLICATIONS

Co–Pending U.S. Application No. 09/009,822, filed Jan. 20, 1998; (Attorney Docket No. UTSD:517).

Co–Pending U.S. Application No. 09/009,656, filed Jan. 20, 1998; (Attorney Docket No. UTSD:537).

International Search Report Dated Jul. 31, 1998 (PCT/US98/01012)(UTFD:517P—).

Thorpe et al., "Tumor infarction: immunoconjugates that coagulate the vasculature of solid tumor," *Eighty–Sixth Annual Meeting of the American Association for Cancer Research*, Toronto, Ontario, Canada, Mar. 18–22, Abstract No. 2910, *Proc. Amer. Assoc. Cancer Res.* 36:448, 1995.

Burrows and Thorpe, "Eradication of large solid tumors in mice with an immunotoxin directed against tumor vasculature," *Proc. Natl. Acad. Sci. USA* 90:8996–9000, 1993.

Burrows et al., "A murine model for antibody–directed targeting of vascular endothelial cells in solid tumors," *Cancer Res.* 52:5954–5962, 1992.

Denekamp, "Vascular attack as a therapeutic strategy for cancer," *Cancer Metastasis Rev.* 9:267–282, 1990.

Dvorak et al., "Structure of solid tumors and their vasculature: implications for therapy with monoclonal antibodies," *Cancer Cells.* 3:77–85, 1991.

Edgington et al., "The structural biology of expression and function of tissue factor," *Thromb. Haemost.* 66(1):67–79, 1991.

Fisher et al., "Cloning and expression of human tissue factor cDNA," *Thromb. Res.* 48:89–99, 1987.

Hagemeier et al., "A monoclonal antibody reacting with endothelial cells of budding vessels in tumors and inflammatory tissues, and non–reactive with normal adult tissues," *Int. J. Cancer* 38:481–488, 1986.

Huang et al., "Tumor infarction in mice by antibody–directed targeting of tissue factor to tumor vasculature," *Science* 275:547–550, 1997.

Martin, "Tissue factor: molecular recognition and cofactor function," *FASEB J.* 9:852–859, 1995.

Morrissey et al., "Molecular cloning of the cDNA for tissue factor, the cellular receptor for initiation of the coagulation protease cascade," *Cell* 50:129–135, 1987.

Murray et al., "Tumor–derived factors which induce endothelial tissue factor and enhance the procoagulant response to TNF," *Int. J. Radiat. Biol.* 60:273–277, 1991.

Nawroth et al., "Tumor necrosis factor/cachectin–induced intravascular fibrin formation in meth A fibrosarcomas," *J. Exp. Med.* 168:637–648, 1988.

Nemerson, "Tissue factor and hemostasis," *Blood* 71(1):1–8, 1988.

(List continued on next page.)

*Primary Examiner*—Geetha P. Bansal
*Attorney, Agent, or Firm*—Williams, Morgan & Amerson

[57] ABSTRACT

The invention embodies the surprising discovery that Tissue Factor (TF) compositions and variants thereof specifically localize to the blood vessels within a vascularized tumor following systemic administration. The invention therefore provides methods and compositions comprising coagulation-deficient Tissue Factor for use in effecting specific coagulation and for use in tumor treatment. The TF compositions and methods of present invention may be used alone, as TF conjugates with improved half-life, or in combination with other agents, such as conventional chemotherapeutic drugs, targeted immunotoxins, targeted coaguligands, and/or in combination with Factor VIIa (FVIIa) or FVII activators.

46 Claims, 15 Drawing Sheets

OTHER PUBLICATIONS

Neuenschwander and Morrissey, "Roles of the membrane–interactive regions of factor VIIa and tissue factor. The factor VIIaGLa domain is dispensable for binding to tissue factor but important for activation of factor X," *J. Biol. Chem.* 269:8007–8013, 1994.

O'Brien et al., "Factor VIII–bypassing activity of bovine tissue factor using the canine hemophilic model," *J. Clin. Invest.* 82(1):206–211, 1988.

Paborsky et al., "Lipid association, but not the transmembrane domain, is required for tissue factor activity," *J. Biol. Chem.* 266(32):21911–21916, 1991.

Paborsky et al., "Purification of recombinant human tissue factor," *Biochemistry* 28(20): 8072–8077, 1989.

Rehemtulla et al., "High level expression of recombinant human tissue factor in chinese hamster ovary cells as a human thromboplastin," *Thromb. Haemost.* 65(5):521–527, 1991.

Ruf and Edgington, "Structural biology of tissue factor, the initiator of thrombogenesis in vivo," *FASEB J.* 8:385–390, 1994.

Ruf and Edgington, "Two sites in the tissue factor extracellular domain mediate the recognition of the ligand factor VIIa," *Proc. Natl. Acad. Sci. USA.* 88:8430–8434, 1991.

Ruf et al., "Phospholipid–independent and –dependent interactions required for tissue factor receptor and cofactor function," *J. Biol. Chem.* 266:2158–2166, 1991.

Ruf et al., "Tissue factor residues 157–167 are required for efficient proteolytic activation of factor X and factor VII," *J. Biol. Chem.* 267(31):22206–22210, 1992.

Ruf et al., "Cofactor residues lysine 165 and 166 are critical for protein substrate recognition by the tissue factor–factor VIIa protease complex," *J. Biol. Chem.* 267(9):6375–6381, 1992.

Sakai and Kisiel, "Formation of tissue factor activity following incubation of recombinant human tissue factor apoprotein with plasma lipoproteins," *Thromb. Res.* 60(3):213–222, 1990.

ten Cate et al., "The activation of factor X and prothrombin by recombinant factor VIIa in vivo is mediated by tissue factor," *J. Clin. Invest.* 92:1207–1212, 1993.

Warr et al., "Disseminated intravascular coagulation in rabbits induced by administration of endotoxin or tissue factor: effect of anti–tissue factor antibodies and measurement of plasma extrinsic pathway inhibitor activity," *Blood* 75(7):1481–1489, 1990.

Weiss et al., "Evidence for the presence of tissue factor activity on subendothelium," *Blood* 73(4):968–975, 1989.

Zacharski et al., "Tumor cell procoagulant and urokinase expression in carcinoma of the ovary," *J. Natl. Cancer Inst.* 85(15):1225–1230, 1993.

U.S. Application No. 08/273,567, filed Jul. 11, 1994; (Attorney Docket No. UTSD:419). (file history).

Co–Pending U.S. Application No. 08/482,369, filed Jun. 7, 1995; (Attorney Docket No. UTSD:433). (file history).

Co–Pending U.S. Application No. 08/485,482, filed Jun. 7, 1995; (Attorney Docket No. UTSD:456). (file history).

Co–Pending U.S. Application No. 08/487,427, filed Jun. 7, 1995; (Attorney Docket No. UTSD:457). (file history) U.S. Pat 60074555.

Co–Pending U.S. Application No. 08/479,733, filed Jun. 7, 1995; (Attorney Docket No. UTSD:459). (file history).

Co–Pending U.S. Application No. 08/472,631, filed Jun. 7, 1995; (Attorney Docket No. UTSD:460). (file history).

Co–Pending U.S. Application No. 08/479,727, filed Jun. 7, 1995; (Attorney Docket No. UTSD:461 and UTSD:462).

COMBINED TISSUE FACTOR AND CHEMOTHERAPEUTIC METHODS AND COMPOSITIONS FOR COAGULATION AND TUMOR TREATMENT

The present application is a non-provisional application and claims the benefit of provisional application Serial No. 60/042,427, filed Mar. 27, 1997; provisional application Serial No. 60/036,205, filed Jan. 27, 1997; and provisional application Serial No. 60/035,920, filed Jan. 22, 1997; the entire disclosures of each of which provisional applications are incorporated herein by reference without disclaimer.

The U.S. Government owns rights in the present invention pursuant to grant numbers ROI-CA59569, ROI-CA54168 and POI-HL16411 from the National Institutes of Health.

BACKGROUND OF THE INVENTION

1. Field of the Invention

The present invention relates generally to the fields of blood vessels and of coagulation. More particularly, it embodies the surprising finding that Tissue Factor compositions can localize to tumor vasculature and cause specific coagulation. Methods and compositions for effecting specific coagulation and for treating tumors with modified Tissue Factor (TF) compositions and combinations of TF and other molecules are particularly provided.

2. Description of Related Art

Tumor cell resistance to various chemotherapeutic agents represents a major problem in clinical oncology. Therefore, although many advances in the chemotherapy of neoplastic disease have been realized during the last 30 years, many of the most prevalent forms of human cancer still resist effective chemotherapeutic intervention.

A significant underlying problem that must be addressed in any treatment regimen is the concept of "total cell kill." This concept holds that in order to have an effective treatment regimen, whether it be a surgical or chemotherapeutic approach or both, there must be a total cell kill of all so-called "clonogenic" malignant cells, that is, cells that have the ability to grow uncontrolled and replace any tumor mass that might be removed. Due to the ultimate need to develop therapeutic agents and regimens that will achieve a total cell kill, certain types of tumors have been more amenable than others to therapy. For example, the soft tissue tumors (e.g., lymphomas), and tumors of the blood and blood-forming organs (e.g., leukemias) have generally been more responsive to chemotherapeutic therapy than have solid tumors such as carcinomas.

One reason for the susceptibility of soft and blood-based tumors to chemotherapy is the greater physical accessibility of lymphoma and leukemic cells to chemotherapeutic intervention. Simply put, it is much more difficult for most chemotherapeutic agents to reach all of the cells of a solid tumor mass than it is the soft tumors and blood-based tumors, and therefore much more difficult to achieve a total cell kill. Increasing the dose of chemotherapeutic agents most often results in toxic side effects, which generally limits the effectiveness of conventional anti-tumor agents.

It has long been quite clear that a significant need exists for the development of novel strategies for the treatment of solid tumors. One such strategy is the use of "immunotoxins", in which an anti-tumor cell antibody is used to deliver a toxin to the tumor cells. However, in common with the chemotherapeutic approach described above, this also suffers from certain drawbacks. For example, antigen-negative or antigen-deficient cells can survive and repopulate the tumor or lead to further metastases. Also, in the treatment of solid tumors, the tumor mass is generally impermeable to molecules of the size of the antibodies and immunotoxins. Therefore, the development of immunotoxins alone did not lead to particularly significant improvements in cancer treatment.

Certain investigators then developed the approach of targeting the vasculature of solid tumors. Targeting the blood vessels of the tumors has certain advantages in that it is not likely to lead to the development of resistant tumor cells or populations thereof. Furthermore, delivery of targeted agents to the vasculature does not have problems connected with accessibility, and destruction of the blood vessels should lead to an amplification of the anti-tumor effect as many tumor cells rely on a single vessel for their oxygen and nutrient supplies. Exemplary vascular targeting strategies are described in Burrows et al. (1992), in Burrows and Thorpe (1993) and in WO 93/17715. Such targeted delivery of anti-cellular agents to tumor vasculature provides quite promising strategies, however, the use of the toxin portions of these molecules still leaves room for improvement in vascular targeting.

Another approach for the targeted destruction of tumor vasculature has been reported in WO 96/01653, in which antibodies against tumor vasculature markers are used to deliver coagulants to the vasculature of solid tumors. The targeted delivery of coagulants in this manner has the advantage that significant toxic side effects are not likely to result from any background mis-targeting that may result due to any low level cross-reactivity of the targeting antibodies with the cells of normal tissues. The antibody-coagulant constructs for use in such directed anti-tumor therapy have been termed "coaguligands" (WO 96/01653).

Although the specific delivery of a coagulant to a tumor vessel marks a surprising advance, the use or manipulation of coagulation in connection with treatment of various human diseases and disorders has been practiced for some time. By way of example only, Morrissey and Comp have proposed the use of truncated Tissue Factor (tTF) in combination with Factor VIIa (FVIIa) in the treatment of patients, such as hemophiliacs, in which blood coagulation is impaired (U.S. Pat. Nos. 5,374,617; 5,504,064; and 5,504,067). Roy and Vehar have also developed Tissue Factor mutants that neutralize endogenous Tissue Factor and may be used as anti-coagulants, e.g., in the treatment of myocardial infarction (U.S. Pat. Nos. 5,346,991 and 5,589,363).

In further studies connected with Tissue Factor (TF), Edgington and colleagues have shown that, in contrast to normal melanocytes, malignant metastasizing human melanoma cells express high levels of TF, the major cellular initiator of the plasma coagulation protease cascades (WO 94/28017; WO 94/05328; U.S. Pat. No. 5,437,864). It was reported that inhibition of TF function and subsequent reduction in local protease generation resulted in significantly reduced numbers of tumor cells retained in the vasculature. This led to the suggestion that there was a direct correlation between TF expression and the metastatic phenotype of tumor cells. Edgington and colleagues proposed that a function of TF is required for successful implantation of tumor cells and that interference with TF function, or specific interference with cell surface expression of TF, is useful in inhibiting metastasis. These authors have therefore proposed treating cancer with antibodies directed against Tissue Factor.

SUMMARY OF THE INVENTION

In direct contrast to the above observations of Edgington and colleagues and the uses of anti-TF antibodies to treat cancer, the present inventors have demonstrated that truncated TF compositions and TF variants can, themselves, be employed in the treatment of solid tumors. The present invention was developed, in part, from the inventors' surprising discovery that truncated TF specifically localizes to the blood vessels within a vascularized tumor simply following systemic administration. This localization in the absence of any targeting moiety could not have been predicted from the previous detailed studies of the TF molecule. The self-localizing nature of TF, as described herein, also contrasts with the previously described uses of TF in the treatment of bleeding disorders, e.g., in hemophiliacs, in which TF delivery and action is either not localized or is limited to topical application to a specific area.

Therefore, in certain embodiments, the present invention provides methods for promoting coagulation in prothrombotic blood vessels of an animal or patient, which methods generally comprise administering to the animal a composition comprising a coagulation-deficient Tissue Factor (TF) compound in an amount effective to promote coagulation preferentially, or specifically, in the prothrombotic blood vessels.

As used throughout the entire application, the terms "a" and "an" are used in the sense that they mean "at least one", "at least a first", "one or more" or "a plurality" of the referenced components or steps, except in instances wherein an upper limit is thereafter specifically stated. Therefore "a coagulation-deficient Tissue Factor" means "at least a first coagulation-deficient Tissue Factor". The operable limits and parameters of combinations, as with the amounts of any single agent, will be known to those of ordinary skill in the art in light of the present disclosure.

The prothrombotic blood vessels may be associated with any one of a variety of angiogenic diseases, with a benign growth or with a vascularized tumor. In the context of the present invention, the term "a vascularized tumor" means a vascularized, malignant tumor. The present invention is particularly advantageous in treating vascularized tumors of at least about medium size and in treating large vascularized tumors.

The composition will generally be pharmaceutically acceptable and will preferably be administered to the animal systemically, such as via intravenous injection.

The methods of the invention are further described as methods for treating an animal or human patient having a disease associated with prothrombotic blood vessels, comprising administering to the animal an amount of at least a first coagulating composition comprising at least a first coagulation-deficient Tissue Factor compound effective to preferentially, or specifically, promote coagulation in the prothrombotic blood vessels associated with the benign or malignant disease site.

The essence of the invention may also be defined as a composition comprising at least a biologically effective amount of at least a first coagulation-deficient Tissue Factor compound for use in the preparation of a medicament for use in promoting coagulation preferentially, or specifically, in prothrombotic blood vessels of an animal, particularly those associated with a benign or malignant disease site.

In the methods, medicaments and uses of the present invention, one of the advantages lies in the fact that the simple provision of the coagulating composition into the systemic circulation of the animal results in the specific or preferential localization of the Tissue Factor compound to the disease site.

Preferred methods disclosed herein are those for use in promoting coagulation in the tumor vasculature of an animal or human subject having a vascularized tumor, which methods generally comprise administering to the animal one or more compositions comprising one or more coagulation-deficient Tissue Factor compounds in an amount sufficient to specifically or preferentially promote coagulation in the tumor vasculature. The treatment of mid-size or large vascularized tumors is particularly advantageous.

The treatment methods may be described as methods for treating an animal having a vascularized tumor, comprising administering to the animal a biologically effective amount of at least one coagulating composition that comprises an amount of at least a first coagulation-deficient Tissue Factor compound sufficient to specifically or preferentially promote coagulation in the vasculature of the tumor.

A further description is of a method for treating an animal or patient having a vascularized tumor which comprises systemically administering to the animal one or more compositions comprising one or a plurality of coagulation-deficient Tissue Factor compounds in an amount(s) and for a period of time(s) effective to promote coagulation specifically or preferentially in the vasculature of the vascularized tumor.

The anti-tumor effects of the present invention are particularly described in the methods characterized as comprising administering to an animal with a tumor a composition comprising at least one coagulation-deficient Tissue Factor compound in an amount effective to promote coagulation in the tumor vasculature and to specifically or preferentially cause tissue necrosis in the tumor.

These aspects of the invention also provide a composition comprising at least a biologically effective amount of at least a first coagulation-deficient Tissue Factor compound for use in the preparation of a medicament for use in promoting coagulation preferentially, or specifically, in the prothrombotic blood vessels associated with a malignant, vascularized tumor of an animal; wherein the medicament is thus intended for use in treating an animal with cancer by causing tumor blood vessel coagulation and tumor necrosis.

The terms "preferentially" and "specifically", as used herein in the context of promoting coagulation in prothrombotic blood vessels or tumor vasculature, and/or as used in the context of promoting coagulation sufficient to cause tissue necrosis in a disease site such as a tumor, mean that the Tissue Factor compound or TF-second agent combination functions to achieve coagulation and/or tissue necrosis that is substantially confined to the disease site, such as the tumor region, and does not substantially extend to causing coagulation or tissue necrosis in normal, healthy tissues.

The coagulation-deficient Tissue Factor compound or combinations thereof thus exert coagulative and/or tissue destructive effects in a disease or tumor site and yet have little or no coagulative or tissue destructive effects on normal, healthy cells or tissues. Coagulation and/or tissue destruction is therefore localized to the disease or tumor site and does not substantially or significantly extend to other major or important blood vessels or tissues. In the methods of the invention the function of healthy cells and tissues is therefore maintained substantially unimpaired.

The "coagulation-deficient Tissue Factors" of the invention will generally be Tissue Factor compounds that are at least about 100-fold less active than full length, native Tissue Factor, e.g., when assayed in an appropriate phospholipid environment. The Tissue Factor compounds will still have activity, and are preferably described as being between about 100-fold and about 1,000,000 less active than full length, native Tissue Factor, e.g., when assayed in an appropriate phospholipid environment.

The coagulation-impaired Tissue Factor compounds will preferably be at least about 1,000-fold less active than full length, native Tissue Factor; more preferably will be at least about 10,000-fold less active than full length, native Tissue Factor; even most preferably will be at least about 100,000-fold less active than full length, native Tissue Factor, e.g., when assayed in an appropriate phospholipid environment.

The "at least about 100,000-fold less active" is not the minimum, and the Tissue Factor compounds may be at least about 500,000-fold or about 1,000,000-fold less active than full length, native Tissue Factor, e.g., when assayed in an appropriate phospholipid environment.

The human Tissue Factor compounds will generally be preferred for human uses, but the use of other species of TF, including E. coli TF, is certainly not excluded. For ease of preparation, the coagulation-deficient Tissue Factor compounds will also preferably be prepared by recombinant expression, although this is not essential.

The Tissue Factor may be rendered coagulation deficient by being deficient in binding to a phospholipid surface and/or deficient in inserting into a phospholipid membrane or lipid bilayer. Preferred examples are "truncated Tissue Factors". As defined in U.S. Pat. No. 5,504,064, in which the compounds are used for different purposes, "truncated Tissue Factors" generally have an amino acid sequence differing from that of native Tissue Factor in that sufficient transmembrane amino acids that function to bind native Tissue Factor to phospholipid membranes are lacking from the truncated Tissue Factor protein so that the truncated Tissue Factor protein does not bind to phospholipid membranes.

Particular examples of truncated Tissue Factors are Tissue Factor compounds comprising about the first 219 contiguous amino acids from the native TF sequence, as further exemplified by a Tissue Factor compound that consists essentially of the amino acid sequence of SEQ ID NO:1. Although intended for use in different methods, U.S. Pat. No. 5,504,067 defines truncated Tissue Factors as Tissue Factor proteins having an amino acid sequence beginning at position 1 and terminating near position 219 of the defined Tissue Factor sequence.

Dimeric coagulation-deficient Tissue Factors may also be employed, including homodimeric and heterodimeric Tissue Factors. Exemplary TF dimers are disclosed herein as those that consist essentially of dimers of the amino acid sequence of SEQ ID NO:3 ($H_6$-tTF$_{219}$-cys-C' dimer), SEQ ID NO:6 ($H_6$-tTF$_{220}$-cys-C' dimer), SEQ ID NO:7 ($H_6$-tTF$_{221}$-cys-C' dimer) or SEQ ID NO:2 ($H_6$-N'-cys-tTF$_{219}$ dimer). Chemically conjugated dimers, as described in detail hereinbelow, are preferred for use in certain aspects of the present invention, although recombinantly produced dimers, in frame with in frame linkers, are also contemplated for use in particular embodiments.

The coagulation-impaired Tissue Factor compounds for use herewith may also be polymeric or multimeric Tissue Factors.

In certain embodiments, the Tissue Factor compound will be a mutant Tissue Factor deficient in the ability to activate Factor VII. Although useful alone, the most preferred uses of such mutants will be in conjunction with the co-administration of a biologically effective amount of at least one of Factor VIIa or an activator of Factor VII, such as when used with an amount of Factor VIIa sufficient to increase tumor vasculature coagulation and tumor necrosis in the animal.

Such mutants may be those that include a mutation in the amino acid region between about position 157 and about position 167 of SEQ ID NO:1. Exemplary, but by no means limiting mutants are those wherein, within SEQ ID NO:1, Trp at position 158 is changed to Arg; wherein Ser at position 162 is changed to Ala; wherein Gly at position 164 is changed to Ala; or wherein Trp at position 158 is changed to Arg and Ser at position 162 is changed to Ala. Defined examples of such mutants are those that consist essentially of the amino acid sequence of SEQ ID NO:8 or SEQ ID NO:9.

Any of the truncated, dimeric, multimeric and/or mutant coagulation-deficient Tissue Factor compounds may further be modified to increase the longevity, half life or "biological half life" of the TF molecule. Various modifications of the polypeptide structure may be made in order to effect such a change in properties.

Particular examples of TFs modified to increase their biological half life are those Tissue Factor compounds that have been operatively attached, and preferably covalently linked, to a carrier molecule, such as a protein carrier. The carriers are preferably inert carriers, such as, by way of example only, an albumin or a globulin. Non-protein carriers such as polysaccharides and synthetic polymers are also contemplated.

The operative attachment of a TF construct to an antibody or portion thereof is a currently preferred form of coagulation-deficient TF with increased biological half life. However, in the context of the first agent for use in the anti-cancer treatment strategies provide herein, the TF will be linked to an antibody that does not exhibit significant specific binding to a component of a tumor cell, tumor vasculature or tumor stroma. That is, wherein the Tissue Factor compound is not attached to an "anti-tumor" antibody, and wherein the resultant Tissue Factor compound is not a "tumor-targeted TF compound".

In such TF-antibody conjugates, the Tissue Factor compound may be operatively attached to an IgG molecule of so-called "irrelevant specificity", i.e., one that does not have immunobinding affinity for a component of a tumor cell, tumor vasculature or tumor stroma. The Tissue Factor compounds may equally be operatively attached to an Fc portion of an antibody, which has no specific targeting function in the context of antibody specificity. Further constructs contemplated are those wherein the Tissue Factor compound has been introduced into an IgG molecule in place of the $C_H3$ domain.

The surprisingly effective TF treatments of the present invention may be advantageously combined with one or more other treatments. For example, the treatment methods may further comprise administering to an animal or patient a biologically or therapeutically effective amount of at least a second therapeutic compound, such as at least one of a second therapeutic compound selected from the group consisting of Factor VIIa, an activator of Factor VII and at least a first anti-cancer agent.

The at least a first anti-cancer agent may be a "chemotherapeutic agent". As used herein, the term "chemotherapeutic agent" is used to refer to a classical chemotherapeutic agent or drug used in the treatment of malignancies. This term is used for simplicity notwithstanding the fact that other compounds, including immunotoxins, may be technically described as a chemotherapeutic agent in that they exert an anti-cancer effect. However, "chemotherapeutic" has come to have a distinct meaning in the art and is being used according to this standard meaning. "Chemotherapeutics" in the context of the present application therefore do not generally refer to immunotoxins, radiotherapeutic agents and such like, despite their operational overlap.

A number of exemplary chemotherapeutic agents are listed in Table II. Those of ordinary skill in the art will readily understand the uses and appropriate doses of chemotherapeutic agents, although the doses may well be reduced when used in combination with the present invention. A currently preferred chemotherapeutic agent is etoposide. A new class of drugs that may also be termed "chemotherapeutic agents" are agents that induce apoptosis. Any one or more of such drugs, including genes, vectors and antisense constructs, as appropriate, may also be used in conjunction with the present invention.

Appropriate anti-cancer agents further include specifically targeted toxic agents. For example, anti-cancer antibodies and, preferably, antibody constructs or conjugates comprising an antibody that specifically binds to a component of a tumor cell, tumor vasculature or tumor stroma, wherein the antibody is operatively attached or conjugated to at least a first cytotoxic or anti-cellular agent or to, e.g., at least a first coagulation factor.

By way of example only, the targeted construct or conjugate may be an antibody construct or conjugate that specifically binds to a tumor cell surface molecule; to a component of tumor vasculature, such as E-selectin, P-selectin, VCAM-1, ICAM-1, endoglin or an integrin; to a component adsorbed or localized in the vasculature or stroma, such as VEGF, FGF or TGFβ; to a component the expression of which is naturally or artificially induced in the tumor environment, such as E-selectin, P-selectin or an MHC Class II antigen. Non-antibody targeting agents include growth factors, such as VEGF and FGF; peptides containing the tripeptide R-G-D, that bind specifically to the tumor vasculature, and other targeting components such as annexins and related ligands.

The antibody constructs and conjugates may be operatively attached to at least a first cytotoxic or otherwise anti-cellular agent. They may also be operatively attached to at least a first coagulation factor. In attachment to coagulants, bispecific constructs may also be advantageously employed (e.g., using two antibody binding regions), although the covalent linkages are generally preferred for use with the toxins. Any one or more of the toxic or coagulating agents known in the art may be employed in such "immunotoxins" or "coaguligands", and Tissue Factor or Tissue Factor derivatives may also be employed as part of the coaguligands, where the coaguligand is the second, "anti-cancer agent".

The present invention therefore further provides methods for treating an animal or patient having a vascularized tumor, which methods generally comprise systemically administering to an animal one or more coagulation-deficient Tissue Factor compounds and one or more anti-cancer agents in a combined amount effective to coagulate the tumor vasculature and specifically induce tumor necrosis. The anti-cancer agent may be a chemotherapeutic agent, as exemplified by etoposide, an antibody, or an antibody construct or conjugate comprising an antibody that specifically binds to a component of a tumor cell, tumor vasculature or tumor stroma operatively attached to a cytotoxic agent or to a coagulation factor.

Whether the anti-cancer agent is a chemotherapeutic or antibody-based construct, the one or more anti-cancer agent (s) may be administered to the animal simultaneously, e.g., from a single composition or from two or more distinct compositions. The staggered or sequential administration of the one or more Tissue Factor compounds and the one or more anti-cancer agent(s) is also contemplated. The "sequential administration" requires that the TF and anti-cancer agent be administered to the animal at "biologically effective time intervals". For example, the Tissue Factor compound(s) may be administered to the animal at a biologically effective time prior to the anti-cancer agent(s), or the anti-cancer agent(s) may be administered to the animal at a biologically effective time prior to the Tissue Factor compound(s). Where a Tissue Factor compound is administered first, it will generally be given at a biologically effective time sufficient to allow the Tissue Factor compound to preferentially localize within the tumor vasculature prior to the administration of the anti-cancer agent(s).

The present invention further includes methods of using at least one of Factor VIIa or an activator of Factor VII to increase the effectiveness of any one or more of the coagulation-deficient Tissue Factor (TF) compounds that define the primary therapeutic. Such methods generally comprise further administering to an animal or patient a therapeutically effective amount of Factor VIIa or an activator of Factor VII.

In such embodiments, the use of Factor VIIa itself will be generally preferred. The Factor VIIa employed may consist essentially of the amino acid sequence from amino acid 61 to amino acid 212 of the Factor VII polypeptide sequence of SEQ ID NO:14.

Again, the Factor VIIa or Factor VII activator may be administered to the animal simultaneously with the coagulation-deficient Tissue Factor compound. As such, Factor VIIa may be administered to the animal or patient in a pre-formed Tissue Factor-Factor VIIa complex. In certain embodiments, the Tissue Factor-Factor VIIa complex will be an equimolar complex.

Further, the coagulation-deficient Tissue Factor compound and Factor VIIa compound may be administered to the animal using staggered or sequential administration. The prior administration of the Tissue Factor compound will generally be preferred and it will preferably be administered to the animal at a biologically effective time prior to the Factor VIIa compound. Such an effective prior administration of the Tissue Factor compound will generally be at a biologically effective time sufficient to allow the Tissue Factor compound to preferentially localize within the tumor vasculature prior to the administration of the Factor VIIa compound.

These methods of the invention may thus be further described as methods for promoting coagulation in the tumor vasculature of an animal or patient having a vascularized tumor, comprising systemically providing to the animal or patient a coagulation-deficient Tissue Factor compound and Factor VIIa or an activator of Factor VII in a combined amount sufficient to preferentially or specifically promote coagulation in the tumor vasculature.

The subject animal will preferably be provided with the coagulation-deficient Tissue Factor compound at a time prior to the provision of the Factor VIIa, wherein the time interval prior to Factor VIIa administration is effective for the Tissue Factor compound to preferentially or specifically localize within the tumor vasculature.

Further methods are described as methods for treating an animal having a vascularized tumor, comprising systemically administering to the animal a coagulation-deficient Tissue Factor compound and Factor VIIa in a combined amount effective to promote coagulation in the tumor vasculature and to specifically cause necrosis in the tumor. The pre-administration of Tissue Factor is generally preferred such that the Tissue Factor compound preferentially localize within the tumor vasculature and form a reservoir for subsequent Factor VIIa combination.

All such Factor VIIa combined treatments may be used with any coagulation-deficient Tissue Factor compound, such as truncated, dimeric, and/or mutant Tissue Factors and/or those with increased half lives. These methods are particularly useful for combination with Tissue Factor compounds that are deficient in the ability to activate Factor VII.

The combined treatment methods of the invention also encompass triple combinations using one or more coagulation-deficient Tissue Factor compounds, one or more anti-cancer agents and Factor VIIa or an activator of Factor VII.

The present invention further provides novel compositions in the form of compositions that comprise one or more coagulation-deficient Tissue Factor compounds that have been modified to increase their half life, other than wherein the modification consists of attaching the Tissue Factor compound to an antibody that binds to a component of a tumor cell, tumor vasculature or tumor stroma.

The "increased half life Tissue Factor compounds" encompass all the coagulation-deficient Tissue Factor compounds described above, such as truncated, dimeric, polymeric, and/or mutant Tissue Factors.

The increased half life Tissue Factor compounds preferably comprise a coagulation-deficient Tissue Factor compound that is operatively attached, e.g., covalently attached, to a carrier molecule. Protein carriers are currently preferred, as exemplified by albumins or globulins, although non-protein carriers are also contemplated.

One class of increased half life coagulation-deficient Tissue Factor compounds are those that are operatively attached to an antibody or portion thereof, such as an IgG molecule or to an Fc portion of an antibody. Tissue Factors introduced into a contiguous portion of an IgG molecule, e.g., in place of the $C_H3$ domain, are also contemplated.

The invention still further provides a series of novel therapeutic kits for use in conjunction with the methods of the invention. Certain kits will comprise, preferably in suitable container means, at least a first coagulation-deficient Tissue Factor compound in combination with at least a first anti-cancer agent.

The coagulation-deficient Tissue Factor compounds may be one or more of the coagulation-deficient Tissue Factors described herein, such as truncated, dimeric, polymeric, and/or mutant Tissue Factors, including mutant Tissue Factors deficient in the ability to activate Factor VII. Where such Factor VII activation mutants are employed in the kit, the kit may optionally further comprise a biologically effective amount of Factor VIIa.

The term "anti-cancer agent" is used as described above and covers chemotherapeutic agents, such as etoposide; and antibody-based anti-cancer agents, such as antibody conjugates comprising an antibody that specifically binds to a component of a tumor cell, tumor vasculature or tumor stroma operatively attached to a cytotoxic agent or to a coagulation factor, including a Tissue Factor or a Tissue Factor derivative.

Further therapeutic kits of the invention generally comprise, preferably in suitable container means, a mutant Tissue Factor compound that is deficient in the ability to activate Factor VII in combination with Factor VIIa. Previously, the mutants of this category have been thought to be so lacking in activity that they could not be used therapeutically to induce coagulation, but only to act as an antagonist of wild type TF and to inhibit coagulation. Only the combination of substantially active truncated Tissue Factor with Factor VIIa has been previously proposed, this being in connection with the treatment of bleeding disorders.

The present invention thus provides the novel combination of a mutant Tissue Factor compound that is more significantly impaired in its coagulating ability than truncated Tissue Factor, preferably by virtue of being deficient in the ability to activate Factor VII, in conjunction with Factor VIIa. The Factor VIIa will become "exogenous Factor VIIa" following administration to an animal. These kits therefore preferably comprise, in suitable container means, a biologically effective amount of a mutant Tissue Factor compound deficient in the ability to activate Factor VII in combination with a biologically effective amount of at least one of Factor VIIa or an activator of Factor VII. Activators of Factor VII may substitute for the Factor VIIa in such kits, or may be employed in addition to the Factor VIIa. Supplementary agents may also be added.

The TF mutants for use in such kits are exemplified by those that include a mutation in the amino acid region between about position 157 and about position 167 of SEQ ID NO:1. These are exemplified by those mutants that wherein, within SEQ ID NO:1, Trp at position 158 is changed to Arg; wherein Ser at position 162 is changed to Ala; wherein Gly at position 164 is changed to Ala; or wherein Trp at position 158 is changed to Arg and Ser at position 162 is changed to Ala. Further :examples are those mutant TFs that consist essentially of the amino acid sequence of SEQ ID NO:8 or SEQ ID NO:9.

Combined treatment kits comprising, preferably in suitable container means, at least a first coagulation-deficient Tissue Factor compound, at least a first anti-cancer agent and Factor VIIa or an activator of Factor VII are also provided by the invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4A: Induction of coagulation by cell-bound tTF. A20 cells ($10^5$ cells, 100 μl) were incubated with antibodies (0.33 μg) and tTF (0.17 μg) for 1 hour at 4° C. Calcium chloride (12.5 mM) and citrated mouse plasma were added to the cells and the time for the first fibrin strands to form was recorded (clotting time, seconds; horizontal axis). Sample number is shown on the vertical axis. Sample 1 includes no added antibodies or tTF (control), sample 2 includes B21-2/10H10 antibody, sample 3 includes tTF, sample 4 includes B21-2/OX7 antibody plus tTF, sample 5 includes CAMPATH-2/10H10 antibody plus tTF, sample 6 includes 10H10 F(ab')$_2$ antibody plus tTF, sample 7 includes 10H10 Fab' antibody plus tTF, sample includes B21-2 F(ab')$_2$ antibody plus tTF, sample 9 includes B21-2 Fab' antibody plus tTF, sample 10 includes B21-2/10H10 antibody plus tTF. FIG. 4B: Relationship between the number of bound tTF molecules and plasma coagulation time. The A20 cells ($10^5$ cells, 100 μl) were incubated with varying concentrations of B21-2/10H10 plus an excess of tTF for 1 hour at 4° C. in the presence of sodium azide and were then washed, warmed to 37° C. Calcium chloride (12.5 mM) and citrated mouse plasma (a different batch from that in A) were added to the cells and the time for the first fibrin strands to form was recorded (clotting time, seconds; vertical axis). The number of tTF molecules bound to the cells (○) was determined in a parallel study with $^{125}$I-tTF (log scale; horizontal axis). Values represent the means of three measurements, with SD.

FIG. 12A: Mice with 0.8 to 1.0 cm diameter C1300(Muγ) tumors were given two intravenous injections of B21-2/10H10-tTF coaguligand (●) spaced 6 days apart (arrows). Mice in control groups received equivalent doses of tTF alone (□), CAMPATH-2/10H10 plus tTF (Δ), or phosphate buffered saline (○). Mice that received B21-2/OX7 and tTF had similar tumor responses to those in animals receiving tTF alone. Administration of B21-2/10H10 alone did not affect tumor growth. Each group contained 12 to 27 mice. Points represent the mean tumor volume per group (±SEM). Mean tumor volume (cm$^3$) is shown on the vertical axis, days after first treatment is shown on the horizontal axis. FIG. 12B: Nu/nu mice bearing small (350 mm$^3$) subcutaneous C1300 Muγ tumors were injected intravenously with 16–20 μg tTF$_{219}$ (■) or phosphate buffered saline (○). The treatment was repeated one week later. Tumors were measured daily and tumor volumes (+one standard deviation) were calculated. The number of mice per treatment group was 8–10. Mean tumor volume (cm$^3$) is shown on the vertical axis, days after first treatment is shown on the horizontal axis.

SEQUENCE SUMMARY

Figure 1:
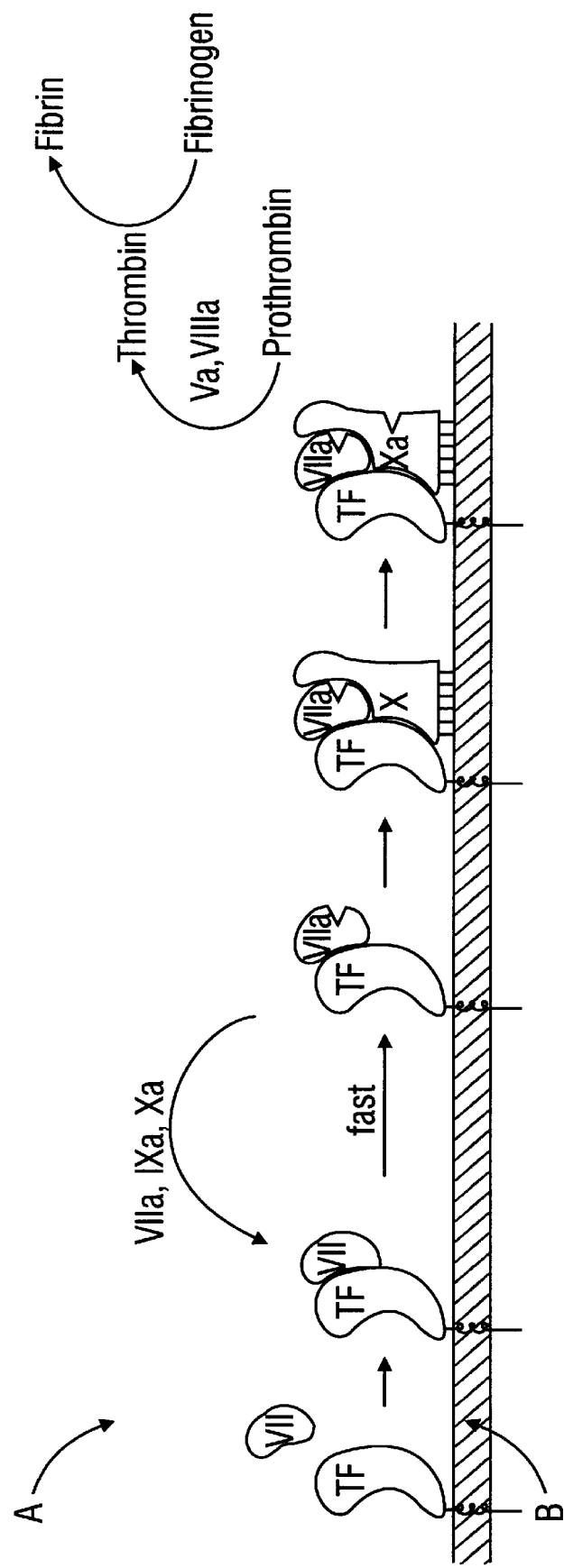
FIG. 1: Induction of coagulation of plasma by full length TF. Blood (A) is shown in contact with the cell membrane (B).

| SEQ ID NO: 1 | Amino Acid Sequence of tTF$_{219}$ |
| SEQ ID NO: 2 | Amino Acid Sequence of H$_6$-N'-cys-tTF$_{219}$ |
| SEQ ID NO: 3 | Amino Acid Sequence of H$_6$-tTF$_{219}$-cys-C' |
| SEQ ID NO: 4 | Amino Acid Sequence of N'-cys-tTF$_{219}$ |
| SEQ ID NO: 5 | Amino Acid Sequence of tTF$_{219}$-cys-C' |
| SEQ ID NO: 6 | Amino Acid Sequence of H$_6$-tTF$_{220}$-cys-C' |
| SEQ ID NO: 7 | Amino Acid Sequence of H$_6$-tTF$_{221}$-cys-C' |
| SEQ ID NO: 8 | Amino Acid Sequence of tTF$_{219}$ (W 158 R) |
| SEQ ID NO: 9 | Amino Acid Sequence of tTF$_{219}$ (G 164 A) |
| SEQ ID NO: 10 | cDNA sequence for tTF. |
| SEQ ID NO: 11 | Full genomic sequence of Tissue Factor |
| SEQ ID NO: 12 | Amino acid sequence of Tissue Factor |
| SEQ ID NO: 13 | Factor VII DNA |
| SEQ ID NO: 14 | Factor VII amino acid |

| | |
|---|---|
| SEQ ID NO: 15 | 5' primer for tTF amplification |
| SEQ ID NO: 16 | 3' Primer for tTF amplification |
| SEQ ID NO: 17 | 5' primer GlytTF complimentary DNA amplification primer |
| SEQ ID NO: 18 | 5' primer for Preparation of tTF and the 5' half of the linker DNA |
| SEQ ID NO: 19 | 3' primer for Preparation of tTF and the 5' half of the linker DNA |
| SEQ ID NO: 20 | 5' primer for Preparation of the 3' half of the linker DNA and tTF DNA |
| SEQ ID NO: 21 | 3' primer for Preparation of the 3' half of the linker DNA and tTF DNA |
| SEQ ID NO: 22 | 5' primer for Cys [tTF] Linker [tTF] construction |
| SEQ ID NO: 23 | 3' primer for Cys [tTF] Linker [tTF] construction |
| SEQ ID NO: 24 | 5' primer for [tTF] Linker [tTF]cys |
| SEQ ID NO: 25 | 3' primer for [tTF] Linker [tTF]cys |
| SEQ ID NO: 26 | primer for [tTF] G164A formation |
| SEQ ID NO: 27 | primer for [tTF] W158R S162A |

DESCRIPTION OF ILLUSTRATIVE EMBODIMENTS

Solid tumors and carcinoma account for more than 90% of all cancers in man (Shockley et al., 1991). The therapeutic uses of monoclonal antibodies and immunotoxins have been investigated in the therapy of lymphomas and leukemias (Lowder et al., 1987; Vitetta et al., 1991), but have been disappointingly ineffective in clinical trials against carcinomas and other solid tumors (Byers and Baldwin, 1988; Abrams and Oldham, 1985).

A principal reason for the ineffectiveness of antibody-based treatments is that macromolecules are not readily transported into solid tumors (Sands, 1988; Epenetos et al., 1986). Even when these molecules get into the tumor mass, they fail to distribute evenly due to the presence of tight junctions between tumor cells (Dvorak et al., 1991), fibrous stroma (Baxter et al., 1991), interstitial pressure gradients (Jain, 1990) and binding site barriers (Juweid et al., 1992).

In developing new strategies for treating solid tumors, the methods that involve targeting the vasculature of the tumor, rather than the tumor cells themselves, offer distinct advantages. Inducing a blockade of the blood flow through the tumor, e.g., through tumor vasculature specific fibrin formation, would interfere with the influx and efflux processes in a tumor site, thus resulting in anti-tumor effect. Arresting the blood supply to a tumor may be accomplished through shifting the procoagulant-fibrinolytic balance in the tumor-associated vessels in favor of the coagulating processes by specific exposure to coagulating agents. Accordingly, antibody-coagulant constructs and bispecific antibodies have been generated and used in the specific delivery of a coagulant to the tumor environment (WO 96/01653).

However, the requirement for specificity, although not so stringent as with immunotoxins, is still important. To achieve specificity, it has generally been believed that an effector molecule, whether a toxin or a coagulant, needs to be conjugated or functionally associated with a targeting molecule, such as an antibody or other ligand with specificity for the tumor environment. Such targeting entities may be directed to the tumor cells themselves, although it is now believed to be preferable to use targeting molecules directed against components of the tumor vasculature or tumor stroma. A number of appropriate target molecules have been identified that are specifically or preferentially expressed, localized, adsorbed to or inducible on the cells or in the environment of the tumor vasculature and/or stroma.

Although the tumor vasculature and stroma targeting methods can be quite effective, it will be recognized that to practice such targeting methodology still requires a certain knowledge and requires the preparation of suitable conjugates or coordinated molecular complexes. For example, in targeting a coagulant to the tumor vasculature, one must identify an appropriate vascular antigen, prepare an antibody or ligand that binds to the target antigen, choose an appropriate coagulant, link the coagulant to the antibody or ligand or otherwise form a functional association of the two components, and conduct the localization protocols using doses that do not result in significant mis-direction of the agent. Although such methods can be readily and successfully practiced, one can see that advantages would result from the development of methodology that included less preparative steps and could therefore be performed in a more cost-effective manner.

The present invention provides such new methods for effecting specific blood coagulation, as exemplified by tumor-specific coagulation, without the need for targeting molecules, such as antibodies. This is achieved by administering compositions comprising coagulant-deficient Tissue Factor, which was discovered to specifically promote coagulation in the tumor vasculature, despite the fact that it lacks any recognized tumor targeting component. The present invention provides that such coagulation-impaired TF compositions may be administered alone, as TF conjugates with improved half-life, in combination with conventional chemotherapeutics, in combination with targeted immunotoxins or coaguligands, in combination with Factor VIIa (FVIIa) or FVIIa activators or in any of the foregoing combinations.

A. Tissue Factor

Figure 21:
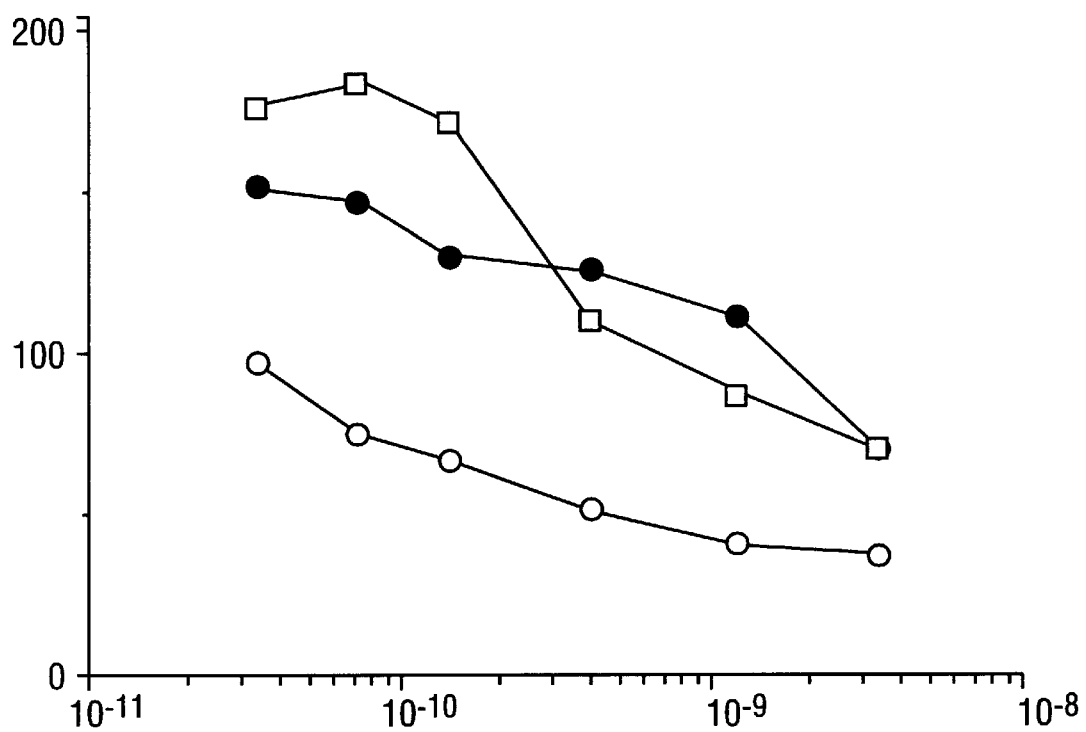
FIG. 21: Weak coagulation of mouse plasma by cell associated tTF$_{219}$ (W158R) and tTF$_{219}$ (G164A) mutants. A20 lymphoma cells (I-A$^d$ positive) were treated at room temperature with the "capture" bispecific antibody, B21-2/10H10, recognizing both I-A$^d$ and tTF. Cells were washed and tTF$_{219}$ (○), tTF$_{219}$ (W158R) (●) or tTF$_{219}$ (G164A) (□) were added at a range of concentrations (concentration, M; horizontal axis). Cells were washed and warmed to 37° C. Calcium and citrated mouse plasma were added and the time for the first strands of fibrin to form was recorded (clotting time, seconds; vertical axis).
Figure 22:
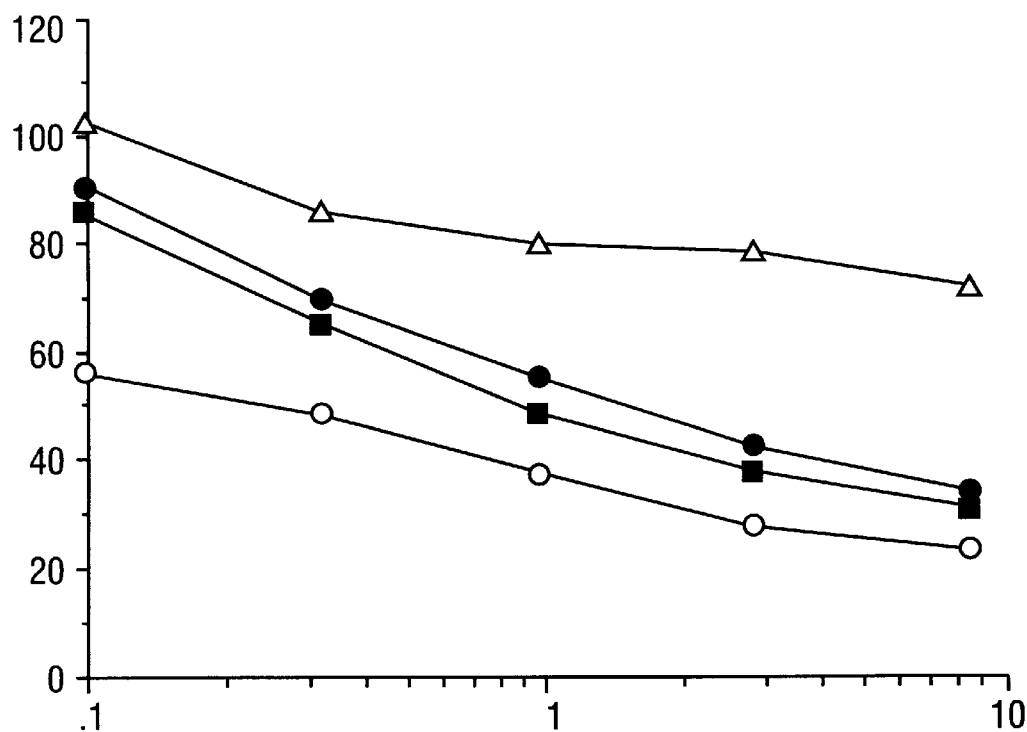
FIG. 22: Restoration of the coagulation-inducing activity of mutant tTF$_{219}$ (G164A) and (W158R) by Factor VIIa. A20 lymphoma cells (I-A$^d$ positive) were treated at room temperature with the "capture" bispecific antibody, B21-2/10H10, recognizing both I-A$^d$ and tTF. Cells were washed and not treated (△), or were treated with: tTF$_{219}$ (○); tTF$_{219}$ (G164A) (■) or tTF$_{219}$ (W158R) (●); each with Factor VIIa addition at a range of concentrations (concentration, nM; horizontal axis). Cells were washed and warmed to 37° C. Calcium and citrated mouse plasma were added and the time for the first strands of fibrin to form was recorded (clotting time, seconds; vertical axis).

Tissue Factor (TF) is the major initiating receptor for the thrombogenic (blood coagulation) cascades (Davie, et al. 1991). TF is a single chain, 263 amino acid membrane glycoprotein (SEQ ID NO:12), and its primary sequence has structural similarity with the chemokine receptor family (Edgington et al., 1991). TF is a transmembrane cell surface receptor and functions as the receptor and cofactor for Factor VIIa. TF binds Factor VIIa to form a proteolytically active complex on the cell surface (Ruf and Edgington, 1991b, 1994; Ruf et al., 1991, 1992a, 1992b). This complex rapidly activates the serine protease zymogens Factors IX and X by limited proteolysis, leading to the formation of thrombin and, ultimately, a blood clot (FIG. 21).

Thus, TF is an activator of the extrinsic pathway of blood coagulation and is not in direct contact with the blood under physiologically normal conditions (Osterud et al., 1986; Nemerson, 1988; Broze, 1992; Ruf and Edgington, 1994). In vascular damage or activation by certain cytokines or endotoxin, however, TF will be exposed to the blood, either by the (sub)endothelial cells (Weiss et al., 1989) or by certain blood cells (Warr et al., 1990). TF will then complex with Factor VIIa, which under normal conditions circulates at low concentrations in the blood (Wildgoose et al., 1992), and the TF/Factor VIIa complex will start the coagulation cascade through the activation of factor X into Factor Xa. The cascade will ultimately result in the formation of fibrin (FIG. 1). For this sequence of events to occur, the TF:VIIa complex has to be associated with a phospholipid surface upon which the coagulation-initiation complexes with Factors IX or X can assemble (Ruf and Edgington, 1991a; Ruf et al., 1992c; Paborsky et al., 1991; Bach et al., 1986; Krishnaswamy et al., 1992; ten Cate et al., 1993).

A limited number of cells constitutively express TEF. Lung and central nervous system tissues contain high levels of TF activity, with TF being found in bronchial mucosa and alveolar epithelial cells in the lung and in glial cells and astrocytes in the nervous system. Expression of TF has also been reported in cardiac myocytes, renal glomeruli, and in certain epithelial or mucosal tissues of the intestine, bladder and respiratory tract. It can thus be seen that TF is generally constitutively expressed at tissue barriers between body tissues and the external environment (Drake et al., 1989; Ruf and Edgington, 1994).

TF is also present at tissue boundaries between organs, such as in the organ capsules of the liver, spleen and kidney, and is also present in the adventitia of arteries and venules. The expression of TF in this manner allows TF to function in the arrest of internal bleeding. It is therefore relevant to note that TF is absent in the joints and skeletal muscle of hemophiliacs, which are the primary sites of bleeding in these patients.

TF is typically not expressed to any significant degree on cells of the blood or the surface of endothelial cells that form the vasculature under normal conditions, but its expression by (sub)endothelial cells and monocytes within the vasculature can be induced by infectious agents. Monocytes, for example, are induced to express TF by cytokines and T cells. Expression of TF in the vasculature typically will result in disseminated intravascular coagulation or localized initiation of blood clots or thrombogenesis. In this context, it is important to note that TF must be available at all sites of the body where coagulation would be necessary following tissue damage, infection or other insults. Therefore, TF should be equally available to all such tissue sites and should not be generally reserved within any particular localized area of the body.

Certain studies have led to the delineation of a connection between TF and the development of the neoplastic phenotype in certain types of tumors (Ruff and Edgington, 1994). In fact, increasing levels of TF have been reported to be a prognostic indicator of the metastatic potential of malignant melanoma (Mueller, et al., 1992). It has been reasoned that a generalized activation of the coagulation cascade could damage the vasculature leading to access of tumor cells or tumor cell-derived vesicles to the general circulation, allowing such tumor cells to seed and cause metastatic tumor outgrowth.

Irrespective of the underlying mechanism, the studies described above have led Edgington and colleagues to propose the use of antibodies directed against TF in cancer treatment (WO 94/05328). These authors have therefore proposed that antibodies with binding affinity for TF have therapeutic utility in cancer treatment, particularly in connection with those patients believed to be at risk for the development of metastatic tumors. This intent has led to the development of hybridomas producing monoclonal antibodies that react with human TF (U.S. Pat. No. 5,223,427).

In addition to the use in cancer treatment, anti-TF antibodies have also been proposed for use in inhibiting excessive coagulation, which may also be used in connection with the treatment of septic shock and in moderating inflammatory responses (Morrissey et al., 1988; U.S. Pat. No. 5,223, 427), or in the treatment of myocardial infarction, where the antibodies are used as TF antagonists (U.S. Pat. No. 5,589, 173). The combined use of anti-TF antibodies and other thrombolytic agents to dissolve occluding thrombi is particularly disclosed in U.S. Pat. No. 5,589,173. A specific method for using such antibodies is in the inhibition of coagulation in an extracorporeal circulation procedure in which blood is removed from a patient during a surgical procedure, such as a cardiopulmonary bypass procedure (U.S. Pat. No. 5,437,864).

As is developed more fully below (Section B), human TF has been cloned and available for some time (Morrissey et al., 1987; Edgington et al., 1991; U.S. Pat. No. 5,110,730). In certain early studies, the same protein currently identified as human TF may be referred to as human TF heavy chain protein or the heavy chain of TF. The gene encodes a polypeptide precursor of 295 amino acids in length, which includes a peptide leader with alternative cleavage sites, which is now known to lead to the formation of a protein of 263 amino acids in length. The recombinant expression of human TF in CHO cells has been reported to lead to the production of TF at a level that is described as being one of the highest expression levels reported for a recombinant transmembrane receptor following production in mammalian cells (Rehemtulla et al., 1991).

A recombinant form of TF has been constructed that contains only the cell surface or extracellular domain (Stone, et al., 1995) and lacks the transmembrane and cytoplasmic regions of TF. This 'truncated' TF (tTF) is 219 amino acids in length and is a soluble protein with approximately $10^5$ times less factor X-activating activity relative to native transmembrane TF in an appropriate phospholipid membrane environment (Ruf, et al., 1991b). This difference in activity is because the TF:VIIa complex binds and activates Factors IX and X far more efficiently when associated with a negatively charged phospholipid surface (Ruf, et al, 1991b; Paborsky, et al., 1991).

Despite the significant impairment of coagulative capacity of the tTF, tTF can promote blood coagulation when tethered or functionally associated by some other means with a phospholipid or membrane environment. For example, it is demonstrated herein that using a bispecific antibody that binds tTF to a plasma membrane antigen allows restoration of useful coagulating activity. This led one of the present inventors to develop methods for the specific coagulation of tumor vascular in vivo by using targeting constructs to deliver tTF or variants thereof specifically to the tumor vascular or stroma (WO 96/01653). Intravenous administration of such a "coaguligand" leads to localization of the coagulants within the tumor, thrombosis of the tumor vessels, and resultant tumor necrosis.

The development of the intelligent, targeted delivery of coagulants to the tumor vasculature, as exemplified using a bispecific targeting antibody-tTF composition, may be seen as representing an improvement over classic immunotoxin therapy. In fact, such coaguligand treatment induces thrombosis of tumor vessels in less than 30 minutes, in comparison to about 6 hours necessary to achieve the same effect following administration of an immunotoxin. Furthermore, there was no notable side effects as a result of the coaguligand treatment. Although the targeted delivery of a coagulant such as tTF was surprisingly effective, this stills requires the preparation of the "targeting construct".

Other studies of TF with vastly different objectives have also been reported to identify uses for tTF that do not rely on their association with a targeting agent. In this regard, tTF has lately been considered as a candidate for use in treating disorders such as hemophilia. This work may have developed from the attempts to use apo-TF in such treatments. Apo-TF is a delipidated preparation of TF that was proposed for infusion into hemophiliacs, based upon the hypothesis that this molecule would spontaneously and preferentially incorporate itself or associate with exposed membrane surfaces available at sites of injury. Thus, it was reasoned that apo-TF could be useful in such treatments without leading to significant side effects (O'Brien et al., 1988; U.S. Pat. No. 5,017,556).

The apo-TF therapy has been proposed for use in chronic bleeding disorders characterized by a tendency towards hemorrhage, both inherited and acquired. U.S. Pat. No. 5,017,556 describes such disorders as those connected with the deficiency of Factors VIII, IX or XI; or those connected with the acquisition of inhibitors to Factors V, VIII, IX, XI, XII and XIII. The use of apo-TF, characterized as being substantially devoid of the naturally occurring lipid of Tissue Factor and possessing substantially no procoagulant activity prior to administration, was acknowledged to be in contrast to the expected results, which would have been reasoned to lead to toxicity. It now appears that the results described in U.S. Pat. No. 5,017,556 generally represent an anomaly in the art, and these studies have been contradicted by other researchers working in this field.

In fact, during attempts to put studies based upon those described above into practice, experimental animals were observed to develop side effects such as disseminated intervascular coagulation (DIC). This led to the conclusion that the intravenous administration of apo-TF is too dangerous to use (Sakai and Kisiel, 1990; U.S. Pat. Nos. 5,374,617; 5,504,064; and 5,504,067).

The development of the soluble, truncated form of TF has not been recognized as solving the problems associated with TF or apo-TF. For example, tTF has been dismissed as an alternative to TF, due to the fact that it has been characterized as having almost no procoagulant activity when tested with normal plasma (Paborsky et al., 1991; U.S. Pat. No. 5,374,617).

The potential uses for tTF possible prior to the present invention are thus confined to the targeted delivery of tTF, e.g., using antibodies, and the possible use of tTF to treat a limited number of disorders when used in combination with other accessory molecules necessary for restoration of sufficient activity (U.S. Pat. No. 5,374,617). This second possibility has been exploited in certain limited circumstances by combining the use of tTF with the administration of the clotting factor, Factor VIIa. The combined use of Factor VIIa with tTF results in restoration of sufficient coagulant activity for this combination to be of use in treating bleeding disorders, such as hemophilia. However, in contrast to the targeted delivery of coagulants such as tTF discussed in WO 96/01653, the tTF and Factor VIIa combination therapy includes no concept of specific targeting. This therapy has therefore been proposed for use only in connection with patients in which coagulation is impaired (U.S. Pat. Nos. 5,374,617; 5,504,064; and 5,504,067).

The group of patients most readily identified with such impaired coagulation mechanisms are hemophiliacs, including those suffering from hemophilia A and hemophilia B, and those that have high titers of antibodies directed to clotting factors. In addition, this combined tTF and Factor VIIa treatment has been proposed for use in connection with patients suffering from severe trauma, post-operative bleeding or even cirrhosis (U.S. Pat. Nos. 5,374,617; 5,504,064; and 5,504,067). Both systemic administration by infusion and topical application have been proposed as useful in such therapies. These therapies can thus be seen as supplementing the body with two clotting type "factors" in order to overcome any natural limitations in these or other related molecules in the coagulation cascade in order to arrest bleeding at a specific site.

Roy et al. have also proposed the use of certain Tissue Factor mutants in the treatment of myocardial infarction, particularly in the prevention of the reocclusion of coronary arteries (U.S. Pat. No. 5,346,991). As such, the Tissue Factor mutants are being used as "thrombolytic agents", and are described as medicaments capable of lysing a fibrin-platelet thrombus in order to permit blood to again flow through an affected blood vessel. The TF mutants described are designed with the intention of being capable of neutralizing the effects of endogenous TF. Their use in connection with myocardial infarction therapy is said to permit early reperfusion, prevent reocclusion and to therefore limit tissue necrosis.

The artificial means of recreating the natural environment in the context described above is linked to the natural processes, wherein Tissue Factor was described as being constitutively present at boundaries between organs in order to allow it to function as an initiating molecule to arrest the bleeding. However, such limitation of bleeding episodes in hemophiliacs naturally needs to be achieved without tipping the balance of the coagulation pathways into widespread coagulation, which would be detrimental to such patients and would inhibit the oxygen supply to the particular tissue or organ in question. Therefore, widespread circulation and activity of tTF would be undesirable and would not, in fact, be expected to occur from the studies described above.

Although tTF has not previously been shown to have any capacity to preferentially localize within a given site, and despite its known greatly diminished coagulative ability relative to native, full length Tissue Factor, the present invention demonstrates that when systematically administered to animals with solid tumors, tTF induces specific coagulation of the tumor's blood supply, resulting in tumor regression. The various aspects of the present invention are therefore based on the discovery of the selective thrombosis of the tumor vessels by tTF.

A1. Coagulation-Deficient TF

The surprising finding of the inventors that tTF specifically localized within tumors sufficiently so as to cause anti-tumor effect was discovered during studies using tTF as a control in antibody-coagulant ("coaguligand") tumor targeting studies. From this initial discovery, the inventors developed the various aspects of the invention disclosed herein. The Tissue Factor compounds or constructs for use in the present invention have thus been developed from the original tTF first employed. Accordingly, various TF constructs may now be employed, including many different forms of tTF, longer but still impaired TFs, mutants TFs, any truncated, variant or mutant TFs modified or otherwise conjugated to improve their half-life, and all such functional equivalents thereof. However, it will be understood that each of the TF constructs for use in the invention are unified by the need to be "coagulation-deficient". As detailed herein below, there are various structural considerations that may be employed in the design of candidate coagulation-deficient TFs, and various assays are available for confirming that the candidate TFs are indeed suitable for use in the treatment aspects of the present invention. Given that the technological skills for creating a variety of compounds, e.g., using molecular biology, are routine to those of ordinary skill in the art, and given the extensive structural and functional guidance provided herein, the ordinary artisan will be readily able to make and use a number of different coagulation-deficient TFs in the context of the present invention.

Also as described in significant detail herein, any one or more of the variety of TFs may also be combined with other agents for use in the advantageous treatment of solid tumors and other diseases associated with prothrombotic fluid vessels. In addition to combination with standard treatments, such as surgery and radiotherapy, the coagulation approach of the present invention may also be combined with the administration of classical chemotherapeutic drugs, other immunotoxins or coaguligands, or with additional clotting factors, as exemplified by Factor VIIa.

Given that the combined treatments of the invention are expected to give an additive, enhanced or even synergistic anti- tumor effect, those of skill in the art will also readily appreciate that TF constructs that have less than optimal properties in the types of in vitro and in vivo assays described herein may still be used in the context of the present invention. For example, should a candidate coagulation-deficient TF construct have a coagulating activity towards the lower end of the scale recommended herein, such a molecule may still prove to be useful in combination with chemotherapeutics, clotting factors or other anti-cancer agents. Equally, candidate coagulation-deficient TF constructs that may be considered to have a coagulating activity sufficiently high to cause concerns regarding side effects, may still prove to be useful after careful in vivo studies using experimental animals and in clinical studies beginning with low doses. Therefore, the following guidelines concerning the coagulation-deficient TF molecules are provided only as exemplary teaching, and those of ordinary skill in the art will readily appreciate that TF molecules that do not exactly fit within the structural and quantitative guidelines presented herein may still have significant therapeutic utility in the context of the present invention. Although determining this fact may often generally require in vivo tests in animals, such tests are routine to those of ordinary skill in the art and simply require administration and monitoring.

A2. Structural Considerations for Coagulation-Deficient TF

Those of skill in the art will readily appreciate that the TF molecules for use in the present invention cannot be substantially native TF. This is evident as natural TF and close variants thereof are particularly active in promoting coagulation. Therefore, upon administration to an animal or patient, this would lead to widespread coagulation and would be lethal. Therefore, formulations of intact, natural TF should be avoided. Likewise, attempts to modulate the TF activity by manipulating its physical environment are not believed to be particularly productive in the context of the present invention. For example, the apo-TF approach of O'Brien and colleagues (1988) should be avoided due to the DIC that is expected to result.

Figure 2:
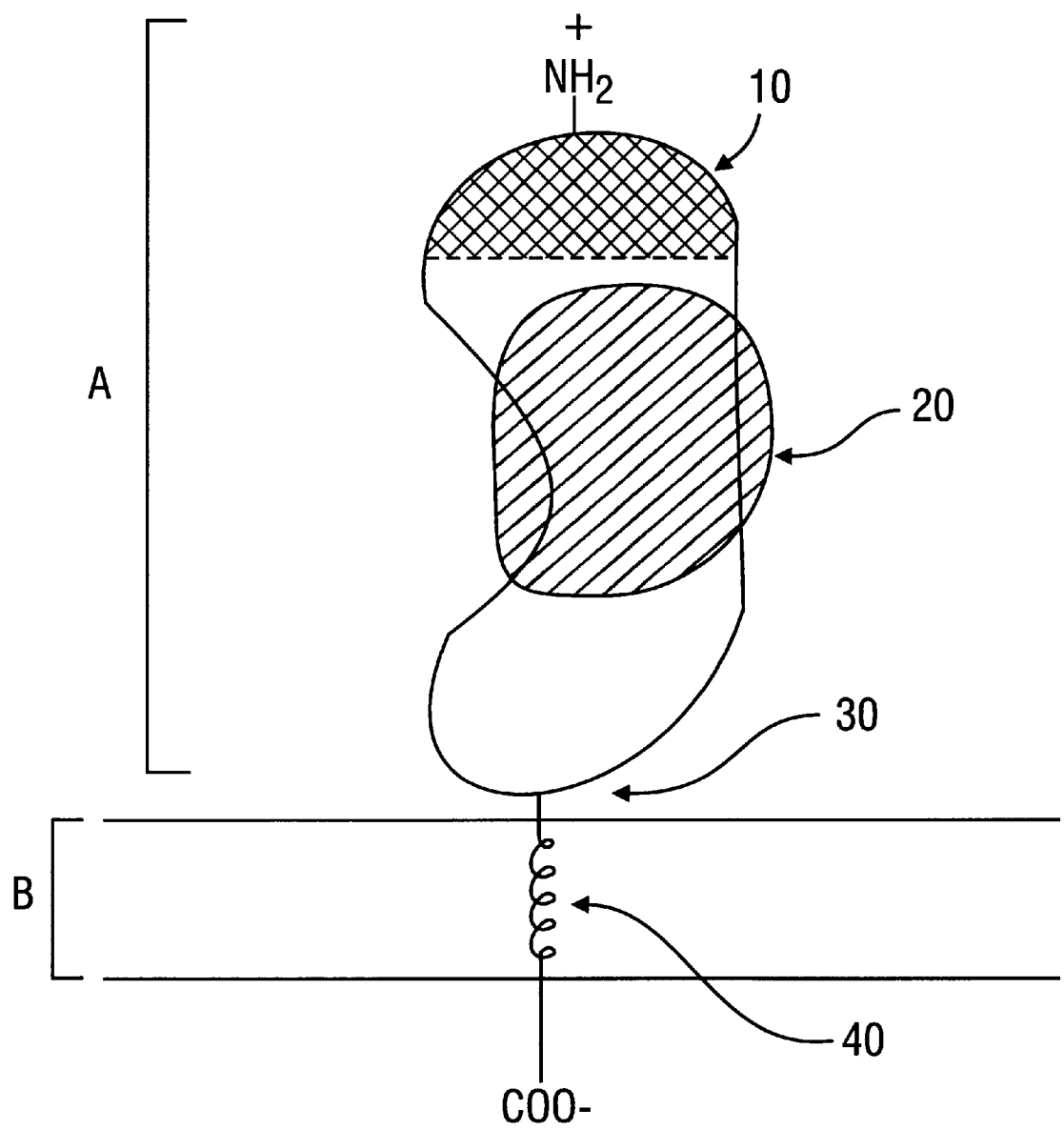
FIG. 2: Domain structure of TF. Depicted are the extracellular domain (A; amino acids 1–219), and the cell membrane (B). The $NH_2$ domain (10) is depicted as cross-hatched, the Factor VII/VIIa binding region (20) is depicted as hatched. The transmembrane domain (40) begins at amino acid 220 (30) and spans the cell membrane. The transmembrane domain of TF is deleted or otherwise rendered non-functional to generate a functional tTF of the present invention. In certain tTF compositions the $NH_2$ domain may also be deleted or rendered non-functional.

FIG. 2 is provided herein as an instructive model concerning the domains of the native TF molecule. It is an objective of the invention to provide TF molecules that do not substantially associate with the plasma membrane. Naturally, truncation of the molecule is the most direct manner in which to achieve a modified TF that does not bind to the membrane. These types of truncated constructs are described more fully below. However, actual truncation or shortening of the molecule is not the only mechanism by which operative TF variants may be created. By way of example only, mutations may be introduced into the C-terminal region of the molecule that normally traverses the membrane in order to prevent proper membrane insertion. It is contemplated that the insertion of various additional amino acids, or the mutation of those residues already present, may be used to effect such membrane expulsion. Therefore, modifications that may be considered in this regard are those that reduce the hydrophobicity of the C-terminal portion of the molecule so that the thermodynamic properties of this region are no longer favorable to membrane insertion.

In considering making structural modifications to the native TF molecule, those of skill in the art will be aware of the need to maintain significant portions of the molecule sufficient for the resultant TF variant to be able to function to promote at least some coagulation. An important consideration is that the TF molecule should substantially retain its ability to bind to Factor VII or Factor VIIa. By reference to FIG. 2, it will be seen that the VII/VIIa binding region is generally central to the molecule and such region should therefore be substantially maintained in all TF variants proposed for use in the present invention. The particular location of this binding region and optional use of mutants, either alone or in combination with other agents, is discussed in more detail below.

Nonetheless, certain sequence portions from the N-terminal region of the native TF are also contemplated to be dispensable. Therefore, one may introduce mutations into this region or may employ deletion mutants (N-terminal truncations) into the candidate TF molecules for use herewith. Given these guidelines, those of skill in the art will appreciate that the following exemplary truncated, dimeric, multimeric and mutant TF constructs are by no means limiting and that many other functionally equivalent molecules may be readily prepared and used.

A3. Exemplary Coagulation-Deficient TF Constructs

The following exemplary Tissue Factor compositions, including the truncated, dimeric, multimeric and mutated versions, may exist as distinct polypeptides or may be conjugated to inert carriers, such as immunoglobulins, as described herein below.

i. Truncated Tissue Factor

As used herein, the term "truncated" when used in connection with TF means that the particular TF construct is lacking certain amino acid sequences. The term truncated thus means Tissue Factor constructs of shorter length, and differentiates these compounds from other Tissue Factor constructs that have reduced membrane association or binding. Although modified but substantially full-length TFs may thus be considered as functional equivalents of truncated TFs ("functionally truncated"), the term "truncated" is used herein in its classical sense to mean that the TF molecule is rendered membrane-binding deficient by removal of sufficient amino acid sequences to effect this change in property.

Accordingly, a truncated TF protein or polypeptide is one that differs from native TF in that a sufficient amount of the transmembrane amino acid sequence has been removed from the molecule, as compared to the native Tissue Factor. A "sufficient amount" in this context is an amount of transmembrane amino acid sequence originally sufficient to enter the TF molecule in the membrane, or otherwise mediate functional membrane binding of the TF protein. The removal of such a "sufficient amount of transmembrane spanning sequence" therefore creates a truncated Tissue Factor protein or polypeptide deficient in phospholipid membrane binding capacity, such that the protein is substantially a soluble protein that does not significantly bind to phospholipid membranes, and that substantially fails to convert Factor VII to Factor VIIa in a standard TF assay, and yet retains so-called catalytic activity including activating Factor X in the presence of Factor VIIa. U.S. Pat. No. 5,504,067 is specifically incorporated herein by reference for the purposes of further describing such truncated Tissue Factor proteins.

The preparation of particular truncated Tissue Factor constructs is described herein below. Preferably, the Tissue Factors for use in the present invention will generally lack the transmembrane and cytosolic regions (amino acids 220–263 of SEQ ID NO:12) of the protein. However, there is no need for the truncated TF molecules to be limited to molecules of the length of 219 amino acids. Therefore, constructs of between about 210 and about 230 amino acids in length may be used. In particular, the constructs may be about 210, 211, 212, 213, 214, 215, 216, 217, 218, 219, 220, 221, 222, 223, 224, 225, 226, 227, 228, 229, or about 230 amino acids in length. Naturally, it will be understood that the intention is to substantially delete the transmembrane region of about 23 amino acids from the truncated molecule. Therefore, in truncated TF constructs that are longer than about 218–222 amino acids in length, the significant sequence portions thereafter will generally be comprised of about the 21 amino acids that form the cytosolic domain of the native TF molecule. In this regard, the truncated TF constructs may be between about 231, 232, 233, 234, 235, 236, 237, 238, 239, 240, or about 241 amino acids in length.

In certain preferred embodiments, tTF may be designated as the extracellular domain of mature Tissue Factor protein. Therefore, in exemplary preferred embodiments, tTF may have the amino acid sequence of SEQ ID NO:1, comprising residues 1–219 of the mature protein (SEQ ID NO:12). SEQ ID NO:1 may be encoded by, for example, SEQ ID NO:10. Of course, SEQ ID NO:1 is only an exemplary tTF and any Tissue Factor protein derived from the nucleic acid sequence SEQ ID NO:11, or related sequences, which possesses the desirable properties of high affinity binding to Factor VII or to Factor VIIa and possesses a generally reduced procoagulation cofactor activity will be useful as disclosed herein.

ii. Dimeric Tissue Factor Constructs

Previously it has been shown that it is possible for native Tissue Factor on the surface of J82 bladder carcinoma cells to exist as a dimer (Fair et al., 1987). The binding of one Factor VII or Factor VIIa molecule to one Tissue Factor molecule may also facilitate the binding of another Factor VII or Factor VIIa to another Tissue Factor (Fair et al, 1987; Bach et al., 1986). Furthermore, Tissue Factor shows structural homology to members of the cytokine receptor family (Edgington et al., 1991) some of which dimerize to form active receptors (Davies and Wlodawer, 1995). As such it is contemplated that the truncated Tissue Factor compositions of the present invention may be useful as dimers.

Accordingly, any of the truncated, mutated or otherwise coagulation-deficient Tissue Factor constructs disclosed herein, or an equivalent thereof, may be prepared in a dimeric form for use in the present invention. As will be known to those of ordinary skill in the art, such TF dimers may be prepared by employing the standard techniques of molecular biology and recombinant expression, in which two coding regions are prepared in-frame and expressed from an expression vector. Equally, various chemical conjugation technologies may be employed in connection with the preparation of TF dimers. The individual TF monomers may be derivatized prior to conjugation. All such techniques would be readily known to those of skill in the art.

If desired, the Tissue Factor dimers or multimers may be joined via a biologically-releasable bond, such as a selectively-cleavable linker or amino acid sequence. For example, peptide linkers that include a cleavage site for an enzyme preferentially located or active within a tumor environment are contemplated. Exemplary forms of such peptide linkers are those that are cleaved by urokinase, plasmin, thrombin, Factor IXa, Factor Xa, or a metalloproteinase, such as collagenase, gelatinase or stromelysin.

In certain embodiments, the Tissue Factor dimers may further comprise a hindered hydrophobic membrane insertion moiety, to later encourage the functional association of the Tissue Factor with the phospholipid membrane, but only under certain defined conditions. As described in the context of the truncated Tissue Factors, hydrophobic membrane-association sequences are generally stretches of amino acids that promote association with the phospholipid environment due to their hydrophobic nature. Equally, fatty acids may be used to provide the potential membrane insertion moiety. Such membrane insertion sequences may be located either at the N-terminus or the C-terminus of the TF molecule, or generally appended at any other point of the molecule so long as their attachment thereto does not hinder the functional properties of the TF construct. The intent of the hindered insertion moiety is that it remains non-functional until the TF construct localizes within the tumor environment, and allows the hydrophobic appendage to become accessible and even further promote physical association with the membrane. Again, it is contemplated that biologically-releasable bonds and selectively-cleavable sequences will be particularly useful in this regard, with the bond or sequence only being cleaved or otherwise modified upon localization within the tumor environment and exposure to particular enzymes or other bioactive molecules.

By way of example only, the inventors have constructed dimeric tTF corresponding to a dimer of C'-cys-tTF$_{219}$ (dimer of SEQ ID NO:3); a dimer of C'-cys-tTF$_{220}$ (dimer of SEQ ID NO:6); a dimer of C'-cys-tTF$_{221}$ (dimer of SEQ ID NO:7); and a dimer of H$_6$-N'-cys-tTF$_{219}$ (dimer of SEQ ID NO:2). However, it will now be understood that each of the foregoing sequences are exemplary and by no means limiting of the dimeric structures that may be created and used in accordance with the present invention.

iii. Tri and Multimeric Tissue Factor Constructs

In other embodiments the tTF constructs of the present invention may be multimeric or polymeric. In this context a "polymeric construct" contains 3 or more Tissue Factor constructs of the present invention. A "multimeric or polymeric TF construct" is a construct that comprises a first TF molecule or derivative operatively attached to at least a second and a third TF molecule or derivative, and preferably, wherein the resultant multimeric or polymeric construct is still deficient in coagulating activity as compared to wild-type TF. In preferred embodiments, the multimeric and polymeric TF constructs for use in this invention are multimers or polymers of truncated TF molecules, which may be optionally combined with other coagulation-deficient TF constructs or variants. The multimers may comprise between about 3 and about 20 such TF molecules, with between about 3 and about 15 or about 10 being preferred and between about 3 and about 10 being most preferred. Naturally, TF multimers of at least about 3, 4, 5, 6, 7, 8, 9 or 10 or so are included within the present invention. The individual TF units within the multimers or polymers may also be linked by selectively-cleavable peptide linkers or other biological-releasable bonds as desired. Again, as with the TF dimers discussed above, the constructs may be readily made using either recombinant manipulation and expression or using standard synthetic chemistry.

iv. Factor VII Activation Mutants

Even further TF constructs useful in context of the present invention are those mutants deficient in the ability to activate Factor VII. The basis for the utility of such mutants lies in the fact that they are also "coagulation-deficient". Such "Factor VII activation mutants" are generally defined herein as TF mutants that bind functional Factor VII/VIIa, proteolytically activate Factor X, but are substantially free from the ability to proteolytically activate Factor VII. Accordingly, such constructs are TF mutants that lack Factor VII activation activity.

The ability of such Factor VII activation mutants to function in promoting tumor-specific coagulation is based upon both the localization of the TF construct to tumor vasculature, and the presence of Factor VIIa at low levels in plasma. Upon administration of such a Factor VII activation mutant, the mutant would generally localize within the vasculature of a vascularized tumor, as would any TF construct of the invention. Prior to localization, the TF mutant would be generally unable to promote coagulation in any other body sites, on the basis of its inability to convert Factor VII to Factor VIIa. However, upon localization and accumulation within the tumor region, the mutant will then encounter sufficient Factor VIIa from the plasma in order to initiate the extrinsic coagulation pathway, leading to tumor-specific thrombosis.

As is developed more fully below, the most preferred use of the Factor VII activation mutants is in combination with the co-administration of Factor VIIa. Although useful in and of themselves, as described above, such mutants will generally have less than optimal activity given that Factor VIIa is known to be present in plasma only at low levels (about 1 ng/ml, in contrast to about 500 ng/ml of Factor VII in plasma; U.S. Pat. Nos. 5,374,617; 5,504,064; and 5,504, 067). Therefore, the co-administration of exogenous Factor VIIa along with the Factor VII activation mutant is considerably preferred over the administration of the mutants alone. In that these mutants are expected to have almost no side effects, their combined use with simultaneous, preceding or subsequent administration of Factor VIIa is a particularly advantageous aspect of the present invention.

Any one or more of a variety of Factor VII activation mutants may be prepared and used in connection with either aspect of the present invention. There is a significant amount of scientific knowledge concerning the recognition sites on the TF molecule for Factor VII/VIIa. By way of example only, one may refer to the articles by Ruf and Edgington (1991a), Ruf et at. (1992c), and to WO 94/07515 and WO 94/28017, each specifically incorporated herein by reference for further guidance on these matters. It will thus be understood that the Factor VII activation region generally lies between about amino acid 157 and about amino acid 167 of the TF molecule. However, it is contemplated that residues outside this region may also prove to be relevant to the Factor VII activating activity, and one may therefore consider introducing mutations into any one or more of the residues generally located between about amino acid 106 and about amino acid 209 of the TF sequence (WO 94/07515). In terms of the preferred region, one may generally consider mutating any one or more of amino acids 147, 152, 154, 156, 157, 158, 159, 160, 161, 162, 163, 164, 165, 166 and/or 167. With reference to the generally preferred candidate mutations outside this region, one may refer to the following amino acid substitutions: S16, T17, S39, T30, S32, D34, V67, L104, B105, T106, R131, R136, V145, V146, F147, V198, N199, R200 and K201, with amino acids A34, E34 and R34 also being considered (WO 94/28017).

As mentioned, preferably the Tissue Factors are rendered deficient in the ability to activate Factor VII by altering one or more amino acids from the region generally between about position 157 and about position 167 in the amino acid sequence, when referring to SEQ ID NO:12. Exemplary mutants are those wherein Trp at position 158 is changed to Arg (SEQ ID NO:8); wherein Ser at position 162 is changed to Ala; wherein Gly at position 164 is changed to Ala (SEQ ID NO:9); and the double mutant wherein Trp at position 158 is changed to Arg and Ser at position 162 is changed to Ala. Of course these are exemplary mutations and it is envisioned that any Tissue Factor mutant having an altered amino acid composition that has the desirable characteristic of binding to Factor VII/VIIa but not activating the coagulation cascade will be useful in the context of the present invention.

A4. Quantitative In Vitro Assessment of Coagulant Deficiency

The Tissue Factor constructs of the present invention, whether they are truncated, mutated, truncated and mutated, dimeric, multimeric, conjugated to inert carriers to increase their half-life, or any combination of the foregoing, are each coagulation-deficient as compared to native, wild-type Tissue Factor. By the term "coagulation-deficient", as used herein, is meant that the TF constructs have an impaired ability to promote coagulation such that their administration into the systemic circulation of an animal or human patient does not lead to significant side effects or limiting toxicity. A TF construct can be readily analyzed in order to determine whether it meets this definition, simply by conducting a test in an experimental animal. However, the following detailed guidance is provided to assist those of skill in the art in the prior characterization and selection of appropriate candidates coagulation-deficient TF constructs, in order that any experimental animal studies may be conducted efficiently and cost-efficiently.

In quantitative terms, the coagulation-deficient TFs will be 100-fold or more less active than full length, native TF, that is, they will be 100-fold or more less able to induce coagulation of plasma than is full length, native TF when tested in an appropriate phospholipid environment.

More preferably, the impaired TFs should be 1,000-fold or more less able to induce coagulation of plasma than is full length, wild type TF in an appropriate phospholipid environment; even more preferably, the TFs should be 10,000-fold or more less able to induce coagulation of plasma than full length, wild type TF in such an environment; and most preferably, the impaired TFs should be 100,000-fold or more less able to induce coagulation of plasma than is full length, native TF in an appropriate phospholipid environment. It will be appreciated that this "100,000-fold" generally corresponds to one of the currently preferred constructs, the truncated Tissue Factor of 219 amino acids in length (SEQ ID NO:1).

Inherent within the definition of "X-fold or more less able to induce coagulation of plasma" is the concept that the subject TF undergoing investigation is still able to induce coagulation of plasma. Evidently, a TF that has been modified to render its completely unable to induce coagulation will generally not be useful in the context of the present invention. TFs that are less active than wild-type TF in the controlled, phospholipid assays by about 500,000-fold are still contemplated to have utility in connection herewith. Similarly, all TF variants and mutants that are between about 500,000-fold and about 1,000,000-fold less able to induce coagulation of plasma than is full length, native TF in an appropriate phospholipid environment are still envisioned to have utility in certain embodiments. However, it is generally considered that 1,000,000-fold ($10^6$) impairment of activity will generally be about the least active that one would consider for use in the present invention. Furthermore, those TF constructs that are towards the less active end of the stated range may find most utility in connection with certain, defined treatments regimens, or in combined therapies. The choice of particular TF variant and therapeutic strategy will be readily determined by one of ordinary skill in the art.

Notwithstanding that there will be certain preferred and/or optimal uses and combinations of the various TF elements, the coagulation-deficient TFs for use in the present invention will generally be between about 100-fold and about 1,000,000-fold less active than wild-type TF; more preferably, will be between about 1,000-fold and about 100,000-fold less active; and may be categorized as less active by any number within the stated ranges, including by about 10,000-fold. The ranges themselves may also be varied between about 1,000-fold and 1,000,000-fold, or between about 10,000-fold and 500,000-fold, or such like.

Any one or more of a number of in vitro plasma coagulation activity assays may be employed in connection with the quantitative testing of candidate coagulation-deficient Tissue Factors. For example, one method of conducting an innate plasma coagulation activity assay is as follows:

1) add about 50 µl plasma (human or mouse) to plastic tubes at about 37° C.;
2) add about 50 µl of relipidated full length TF (preferably from a commercial source, such as American Diagnostics Inc., Greenwich, Conn.) at a range of concentrations in a suitable buffer such as calcium-free phosphate or HEPES buffered saline, pH 7.4 at 37° C. To other tubes add the Tissue Factor candidate truncated or mutant version at a range of concentrations in the same buffer.
3) add about 50 µl 30 mM $CaCl_2$ at about 37° C.;
4) record the time for the first fibrin strands to form; and
5) Construct a standard curve of full length TF concentration (mol per liter) against coagulation time. Construct a curve of the candidate mutant TF concentration (mol per liter) against coagulation time. Calculate the difference in activity between the full length TF and the "test" TF by comparing the concentration of each needed to give a coagulation time equivalent to about half the maximal decrease in coagulation time. The "test" mutant TF should be more than 100-fold less able than the full length TF on a molar basis to induce coagulation of plasma.

Variations of this type of assay can be conducted, as would be evident to one of ordinary skill in the art. For example, one may conduct the assays based upon the attachment of Tissue Factor and the candidate Tissue Factor construct to a cell membrane or phospholipid surface, for example, using an antibody or other ligand to effect such an attachment. In such assays, the candidate or test truncated TF or TF mutant should be greater than 100-fold less effective at inducing coagulation of plasma than wild-type TF, when it is attached by means of an antibody or other ligand to a cell membrane or phospholipid surface. With Tissue Factor mutants that do not allow Factor VII to be efficiently converted to Factor VIIa, it may be necessary to add Factor VIIa to the plasma to obtain this level of activity. In an exemplary assay, such activity can be measured using the following method:

1) Cells such as A20 mouse lymphoma cells ($I-A^d$ positive) (e.g., $4 \times 10^6$ cells/ml, 50 µl) in a buffer such as phosphate-buffered saline are incubated for about 1 hour at about room temperature with an attachment-promoting agent, such as a bispecific antibody (50 µg/ml, 25 µl), e.g., in terms of A20 cells, consisting of a Fab' arm of an antibody such as the B21-2 antibody directed against $I-A^d$, linked to Fab' arm of an antibody such as the 10H10 antibody directed against a non-inhibitory epitope on TF;
2) Prepare an identical set of tubes which contain cells, but no bispecific antibody or other tethering agent;
3) Wash the cells effectively, e.g., twice at room temperature, and resuspend the cells in about 50 µl of phosphate buffered saline.
4) Add varying concentrations of the candidate TF mutants in phosphate buffered saline (about 50 µl) at about room temperature. The bispecific antibody or other tethering agent captures the TF mutant and brings it into close approximation to the cell surface. Factor VIIa (1–10 nM) is added in addition to the TF mutant when it is desired to determine the activity in the presence of Factor VIIa. The total volume per tube is adjusted to about 150 µl with phosphate buffered saline. Tubes are incubated for about 1 h at about room temperature;
5) Warm the cells to about 37° C.
6) Add calcium chloride (about 50 mM, 50 µl) and citrated mouse or human plasma (about 50 µl) at about 37° C.
7) Record the time for the first fibrin strands to form; and
8) Plot coagulation time (in seconds) against concentration of TF mutant (mol per liter) for cells coated or not coated with tethering agent, e.g., bispecific antibody. The TF mutant concentration that gives a coagulation time equivalent to approximately half the maximal decrease in coagulation time (usually 50–100 sec) is calculated. The enhancement in coagulation activity given by the bispecific antibody is calculated and should be in excess of 100-fold.

It is envisioned that candidate TF compositions prepared by the present invention may be tested using assays similar to those described above to confirm that their functionality has been maintained, but that their ability to promote coagulation has been impaired by at least the required amount of about 100-fold and preferably by about 1,000-fold, more preferably by about 10,000-fold, and most preferably by about 100,000-fold.

In embodiments where it is contemplated that an additional agent should ultimately be used in combination with the candidate coagulation-deficient TF, it is important that the additional factor or agent be included in the in vitro assay. A particularly relevant example is the analysis of a Factor VII activation mutant, which should preferably be analyzed in conjunction with the addition of Factor VIIa. However, Factor VIIa is not the only additional component that may be tested in this manner. In general, the additional agents may be termed "additional candidates". To identify an additional candidate, or to optimize preferred amounts of the candidates for use in the present invention, one would conduct assays such as those described above in parallel. That is, one would measure or determine the coagulation in the absence of the additional candidate, and then one would add the candidate substance to the composition and re-determine the time and/or extent of the blood coagulation. An additional candidate substance that functions in combination with a TF mutant or variant to result in an overall level of coagulation that is between about 100-fold and about 1,000,000-fold less than that observed with native TF will again be an appropriate combination for use in the context of the present invention.

Those of ordinary skill in the art will understand that each of the foregoing in vitro assays and variations thereof are relatively simple to establish and perform. In this manner, a panel of candidates TF variants and combinations of TFs with other agents can be tested and the most promising candidates selected for further studies, particularly for experimental testing in an animal or human trial.

Notwithstanding that the foregoing assays are believed to be particularly useful in connection with the present invention, the in vitro testing contemplated for use herewith is not limited to such assays. Accordingly, one may conduct any type of coagulation or procoagulation assay that one desires. For example, for further details regarding tTF and procoagulation assays, the skilled practitioner is referred to U.S. Pat. Nos. 5,437,864; 5,223,427; and 5,110,730 and PCT publication numbers WO 94/28017; WO 94/05328; and WO 94/07515, each of which are specifically incorporated by reference herein for the purposes of even further supplementing the present disclosure in regard to assays.

A5. Confirmatory in Vivo Studies

It will be understood by those of skill in the art that the candidate coagulation-deficient Tissue Factor mutants, variants or combinations of such with additional agents, should generally be tested in an in vivo setting prior to use in a human subject. Such pre-clinical testing in animals is routine in the art. To conduct such confirmatory tests, all that is required is an art-accepted animal model of the disease in question, such as an animal bearing a solid tumor. Any animal may be used in such a context, such as, e.g., a mouse, rat, guinea pig, hamster, rabbit, dog, chimpanzee, or such like. In the context of cancer treatment, studies using small animals such as mice are widely accepted as being predictive of clinical efficacy in humans, and such animal models are therefore preferred in the context of the present invention as they are readily available and relatively inexpensive, at least in comparison to other experimental animals.

The manner of conducting an experimental animal test will be straightforward to those of ordinary skill in the art. All that is required to conduct such a test is to establish equivalent treatment groups, and to administer the test compounds to one group while various control studies are conducted in parallel on the equivalent animals in the remaining group or groups. One monitors the animals during the course of the study and, ultimately, one sacrifices the animals to analyze the effects of the treatment.

One of the most useful features of the present invention is its application to the treatment of vascularized tumors. Accordingly, anti-tumor studies can be conducted to determine the specific thrombosis within the tumor vasculature and the anti-tumor effects overall. As part of such studies, the specificity of the effects should also be monitored, including evidence of coagulation in other vessels and tissues and the general well being of the animals should be carefully monitored.

In the context of the treatment of solid tumors, it is contemplated that effective TF constructs and effective amounts of the constructs will be those constructs and amounts that generally result in at least about 10% of the vessels within a vascularized tumor exhibiting thrombosis, in the absence of significant thrombosis in non-tumor vessels; preferably, thrombosis will be observed in at least about 20%, about 30%, about 40%, or about 50% also of the blood vessels within the solid tumor mass, without significant non-localized thrombosis. In the treatment of large tumors, such positive effects have been routinely observed by the present inventors. Indeed, tumors have been analyzed in which at least about 60%, about 70%, about 80%, about 85%, about 90%, about 95% or even up to and including about 99% of the tumor vessels have become thrombotic. Naturally, the more vessels that exhibit thrombosis, the more preferred is the treatment, so long as the effect remains specific, relatively specific or preferential to the tumor-associated vasculature and so long as coagulation is not apparent in other tissues to a degree sufficient to cause significant harm to the animal.

Following the induction of thrombosis within the tumor blood vessels, the surrounding tumor tissues become necrotic. The successful use of the constructs of the invention, or the doses thereof, can thus also be assessed in terms of the expanse of the necrosis induced specifically in the tumor. Again, the expanse of cell death in the tumor will be assessed relative to the maintenance of healthy tissues in all other areas of the body. TF agents, combinations or optimal doses will have therapeutic utility in accordance with the present invention when their administration results in at least about 10% of the tumor tissue becoming necrotic (10% necrosis). Again, it is preferable to elicit at least about 20%, about 30%, about 40% or about 50% necrosis in the tumor region, without significant, adverse side-effects. Such beneficial effects have again been observed by the present inventors. Naturally, it will be preferable to use constructs and doses capable of inducing at least about 60%, about 70%, about 80%, about 85%, about 90%, about 95% up to and including 99% tumor necrosis, so long as the constructs and doses used do not result in significant side effects or other untoward reactions in the animal.

All of the above determinations can be readily made and properly assessed by those of ordinary skill in the art. For example, attendant scientists and physicians can utilize such data from experimental animals in the optimization of appropriate doses for human treatment. In subjects with advanced disease, a certain degree of side effects can be tolerated. However, patients in the early stages of disease can be treated with more moderate doses in order to obtain a significant therapeutic effect in the absence of side effects. The effects observed in such experimental animal studies should preferably be statistically significant over the control levels and should be reproducible from study to study.

Those of ordinary skill in the art will further understand that TF constructs, combinations and doses that result in tumor-specific thrombosis and necrosis towards the lower end of the effective ranges quoted above may nonetheless still be useful in connection with the present invention. For example, in embodiments where a continued application of the active agents is contemplated, an initial dose of a construct that results in only about 10% thrombosis and/or necrosis will nonetheless be useful, particularly as it is often observed that this initial reduction "primes" the tumor to further destructive assault upon subsequent re-application of the therapy. In any event, even if upwards of about 40% or so tumor inhibition is not ultimately achieved (which is the general goal), it will be understood that any induction of thrombosis and necrosis is nonetheless useful in that it represents an advance over the state of the patients prior to treatment.

As discussed above in connection with the in vitro test system, it will naturally be understood that combinations of agents intended for use together should be tested and optimized together. By way of example only, the Factor VIIa activation mutant of the present invention fall into this category and should generally be tested in conjunction with the simultaneous, prior or subsequent administration of exogenous Factor VIIa. Similarly, the individual TF constructs of the present invention can be straightforwardly analyzed in combination with one or more chemotherapeutic drugs, immunotoxins, coaguligands or such like. Analysis of the combined effects of such agents would be determined and assessed according to the guidelines set forth above.

A6. Biologically Functional Equivalents

As discussed, tTF compositions useful in the present invention are those that will generally promote coagulation at least 100-fold less effectively than wild type TF. In other embodiments the tTF promotes coagulation at least $10^3$ fold less effectively, in yet other embodiments the tTF promotes coagulation at least $10^4$ or even $10^5$ times less effectively than wild type TF, with TFs that are about $10^6$ times or so less active than wild type TF being about the intended minimum activity required.

Exemplary TFs are those that lack the transmembrane and cytosolic region (amino acids 220–263). An exemplary tTF of the present invention is given in SEQ ID NO:1 and contains amino acids 1–219 of wild type Tissue Factor (SEQ ID NO:12). Of course this is only an exemplary tTF and other tTF construct are contemplated, for example, a construct comprising amino acids 1–220; 2–219, 3–219 or any other truncation of SEQ ID NO:12 that renders the molecule lacking in the transmembrane domain and/or cytosolic domains of wild type Tissue Factor otherwise results in a functionally comparative molecule. Mutants are also contemplated, as described in detail above.

Using the detailed guidance provided above, even further equivalents of the TFs can be made. Modifications and changes may be made in the structure of TF and still obtain a molecule having like or otherwise desirable characteristics. For example certain amino acids may be substituted for other amino acids in a protein structure without appreciable loss of interactive binding capacity, such as, for example, binding to Factor VIIa. Since it is the interactive capacity and nature of a protein that defines that protein's biological functional activity, certain amino acid sequence substitutions can be made in a protein sequence (or of course, the underlying DNA sequence) and nevertheless, obtain a protein with like (agonistic) properties. It is thus contemplated that various changes may be made in the sequence of TF (SEQ ID NO:12) proteins and peptides (or underlying DNA sequence, SEQ ID NO:11) without appreciable loss of their biological utility or activity.

It also is well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distinct proteins/peptides with different substitutions may easily be made and used in accordance with the invention.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte and Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is thus understood that an amino acid can be substituted for another having a similar hydrophilicity value and still obtain a biologically equivalent protein. As detailed in U.S. Pat. No. 4,554,101 (incorporated herein by reference), the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon hydrophilicity values, the substitution of amino acids whose hydrophilicity values are within ±2 is preferred, those which are within ±1 are particularly preferred, and those within ±0.5 are even more particularly preferred.

B. Tissue Factor Polynucleotides

B1. DNA Segments

The polynucleotides encoding the TFs of the present invention may encode an entire TF protein, so long as it is coagulation-deficient, a functional TF protein domain, or any TF polypeptide, mutant or variant in accordance with the detailed guidance set forth herein. Whether one desires to prepare a truncated TF, a mutant TF or a truncated and mutated TF, the underlying useful DNA segment and gene will be generally the same. In that the human DNA for the entire TF molecule is available, it will generally be preferred to use this human construct given that clinical treatment in humans is intended. However, the use of other TF genes is by no means excluded, so long as the protein produced does not elicit significant immunological or other untoward reactions upon administration to a human patient. The methods and compositions described in U.S. Pat. No. 5,110,730 are specifically incorporated herein by reference for the purposes of even further supplementing Applicants' disclosure concerning the genes and DNA segments for use herewith.

The polynucleotides may be derived from genomic DNA, i.e., cloned directly from the genome of a particular organism. In other embodiments, however, the polynucleotides may be complementary DNA (cDNA). cDNA is DNA prepared using messenger RNA (mRNA) as template. Thus, a cDNA does not contain any interrupted coding sequences and usually contains almost exclusively the coding region(s) for the corresponding protein. In other embodiments, the polynucleotide may be produced synthetically. As is known to those of skill in the art, it is generally preferred to use a cDNA construct in the recombinant expression given that such constructs are easier to manipulate and use. The use of longer, genomic clones up to and including full length sequences are, however, by no means excluded.

Although a surprising feature of the present invention is that the TF constructs preferentially are specifically localized in the vasculature of a solid tumor and induce specific anti-tumor effects therein, it is also contemplated that the TF proteins and polypeptides may be delivered to the tumor environment using a recombinant vector that expresses the TF products. Such "gene therapy" approaches to cancer treatment can be readily practiced by reference to certain scientific references concerning appropriate constructs and protocols. By way of example only, one may use a viral vector, such as a retroviral vector, herpes simplex virus, HSV (U.S. Pat. No. 5,288,641), cytomegalovirus; adeno-associated virus, AAV (U.S. Pat. No. 5,139,941); and/or an adenoviral vector.

The genomic human DNA sequence for TF is provided in SEQ ID NO:11, with the corresponding amino acid sequence being provided in SEQ ID NO:12. Should one desire to express Factor VII, the DNA and amino acid sequences are provided in SEQ ID NO:13 and SEQ ID NO:14, respectively.

It is contemplated that natural variants of TF exist that have different sequences than those disclosed herein. Thus, the present invention is not limited to use of the provided polynucleotide sequence for TF but, rather, includes use of any naturally-occurring variants. The present invention also encompasses chemically synthesized mutants of these sequences, intelligently designed following an application of the structural and quantitated functional considerations detailed above.

Another kind of sequence variant results from codon variation. Because there are several codons for most of the 20 normal amino acids, many different DNA's can encode the TF. Reference to Table I will allow such variants to be identified.

TABLE I

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

B2. Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants. Suitable techniques are also described in U.S. Pat. No. 4,888,286, incorporated herein by reference.

Although the foregoing methods are suitable for use in mutagenesis, the use of the polymerase chain reaction (PCR™) is generally now preferred. This technology offers a quick and efficient method for introducing desired mutations into a given DNA sequence. The following text particularly describes the use of PCR™ to introduce point mutations into a sequence, as may be used to change the amino acid encoded by the given sequence. Adaptations of this method are also suitable for introducing restriction enzyme sites into a DNA molecule.

In this method, synthetic oligonucleotides are designed to incorporate a point mutation at one end of an amplified segment. Following PCR™, the amplified fragments are blunt-ended by treating with Klenow fragments, and the blunt-ended fragments are then ligated and subcloned into a vector to facilitate sequence analysis.

To prepare the template DNA that one desires to mutagenize, the DNA is subcloned into a high copy number vector, such as pUC19, using restriction sites flanking the area to be mutated. Template DNA is then prepared using a plasmid miniprep. Appropriate oligonucleotide primers that are based upon the parent sequence, but which contain the desired point mutation and which are flanked at the 5' end by a restriction enzyme site, are synthesized using an automated synthesizer. It is generally required that the primer be homologous to the template DNA for about 15 bases or so. Primers may be purified by denaturing polyacrylamide gel electrophoresis, although this is not absolutely necessary for use in PCR™. The 5' end of the oligonucleotides should then be phosphorylated.

The template DNA should be amplified by PCR™, using the oligonucleotide primers that contain the desired point mutations. The concentration of $MgCl_2$ in the amplification buffer will generally be about 15 mM. Generally about 20–25 cycles of PCR™ should be carried out as follows: denaturation, 35 sec. at 95° C.; hybridization, 2 min. at 50° C.; and extension, 2 min. at 72° C. The PCR™ will generally include a last cycle extension of about 10 min. at 72° C. After the final extension step, about 5 units of Klenow fragments should be added to the reaction mixture and incubated for a further 15 min. at about 30° C. The exonuclease activity of the Klenow fragments is required to make the ends flush and suitable for blunt-end cloning.

The resultant reaction mixture should generally be analyzed by nondenaturing agarose or acrylamide gel electrophoresis to verify that the amplification has yielded the predicted product. One would then process the reaction mixture by removing most of the mineral oils, extracting with chloroform to remove the remaining oil, extracting with buffered phenol and then concentrating by precipitation with 100% ethanol. Next, one should digest about half of the amplified fragments with a restriction enzyme that cuts at the flanking sequences used in the oligonucleotides. The digested fragments are purified on a low gelling/melting agarose gel.

To subcdone the fragments and to check the point mutation, one would subclone the two amplified fragments into an appropriately digested vector by blunt-end ligation. This would be used to transform *E. coli,* from which plasmid DNA could subsequently be prepared using a miniprep. The amplified portion of the plasmid DNA would then be analyzed by DNA sequencing to confirm that the correct point mutation was generated. This is important as Taq DNA polymerase can introduce additional mutations into DNA fragments.

The introduction of a point mutation can also be effected using sequential PCR™ steps. In this procedure, the two fragments encompassing the mutation are annealed with each other and extended by mutually primed synthesis. This fragment is then amplified by a second PCR™ step, thereby avoiding the blunt-end ligation required in the above protocol. In this method, the preparation of the template DNA, the generation of the oligonucleotide primers and the first PCR™ amplification are performed as described above. In this process, however, the chosen oligonucleotides should be homologous to the template DNA for a stretch of between about 15 and about 20 bases and must also overlap with each other by about 10 bases or more.

In the second PCR™ amplification, one would use each amplified fragment and each flanking sequence primer and carry PCR™ for between about 20 and about 25 cycles, using the conditions as described above. One would again subclone the fragments and check that the point mutation was correct by using the steps outlined above.

In using either of the foregoing methods, it is generally preferred to introduce the mutation by amplifying as small a fragment as possible. Of course, parameters such as the melting temperature of the oligonucleotide, as will generally be influenced by the GC content and the length of the oligo, should also be carefully considered. The execution of these methods, and their optimization if necessary, will be known to those of skill in the art, and are further described in various publications, such as *Current Protocols in Molecular Biology,* 1995, incorporated herein by reference.

B3. Expression Constructs and Protein Production

Throughout this application, the term "expression construct" is meant to include any type of genetic construct containing a nucleic acid coding for a gene product in which part or all of the nucleic acid encoding sequence is capable of being transcribed. The transcript will generally be translated into a protein. Thus, expression preferably includes both transcription of a TF gene and translation of a TF mRNA into a TF protein product.

A technique often employed by those skilled in the art of protein production today is to obtain a so-called "recombinant" version of the protein, to express it in a recombinant cell and to obtain the protein from such cells. These techniques are based upon the "cloning" of a DNA molecule encoding the protein from a DNA library, i.e., on obtaining a specific DNA molecule distinct from other portions of DNA. This can be achieved by, for example, cloning a cDNA molecule, or cloning a genomic-like DNA molecule. Techniques such as these would be appropriate for the production of particular TF compositions in accordance with the present invention. Recombinant fusion proteins are discussed in further detail herein below, and in U.S. Pat. No. 5,298,599, incorporated herein by reference for the purposes of further exemplification of fusion protein production and use.

For the expression of TF, once a suitable (full-length if desired) clone or clones have been obtained, whether they be cDNA based or genomic, one may proceed to prepare an expression system for the recombinant preparation of TFs. The engineering of DNA segment(s) for expression in a prokaryotic or eukaryotic system may be performed by techniques generally known to those of skill in recombinant expression. It is believed that virtually any expression system may be employed in the expression of these proteins.

Such proteins may be successfully expressed in eukaryotic expression systems, e.g., CHO cells, as described by Rehemtulla et al. (1991), however, it is envisioned that bacterial expression systems, such as *E. coli* pQE-60 will be particularly useful for the large-scale preparation and subsequent purification of the proteins or peptides. cDNAs for TF may be expressed in bacterial systems, with the encoded proteins being expressed as fusions with β-galactosidase, ubiquitin, *Schistosoma japonicum* glutathione S-transferase, and the like. It is believed that bacterial expression will have advantages over eukaryotic expression in terms of ease of use and quantity of materials obtained thereby. The techniques of U.S. Pat. Nos. 5,298,599 and 5,346,991 are also incorporated herein by reference to even further supplement the soluble Tissue Factor production methods disclosed herein, with U.S. Pat. No. 5,346,991 being particularly incorporated for the purposes of even further supplementing the disclosure regarding the creation and production of Tissue Factor mutants and variants.

In order for the construct to effect expression of a TF transcript, the polynucleotide encoding the TF polynucleotide will be under the transcriptional control of a promoter. A "promoter" refers to a DNA sequence recognized by the synthetic machinery of the host cell, or introduced synthetic machinery, that is required to initiate the specific transcription of a gene. The phrase "under transcriptional control" means that the promoter is in the correct location in relation to the polynucleotide to control RNA polymerase initiation and expression of the polynucleotide. The term promoter will be used here to refer to a group of transcriptional control modules that are clustered around the initiation site for RNA polymerase II.

In terms of microbial expression, U.S. Pat. Nos. 5,583,013; 5,221,619; 4,785,420; 4,704,362; and 4,366,246 are incorporated herein by reference for the purposes of even further supplementing the present disclosure in connection with the expression of genes in recombinant host cells.

B4. Purification of Tissue Factor and Related Compositions

Once the peptides have been expressed they may be isolated and purified using protein purification techniques well known to those of skill in the art. Such compositions will be employed alone or in combination with antibodies, chemotherapeutics and effector ligands as therapeutic agents in the treatment of tumors as detailed herein below. Exemplary peptides of the present invention are shown in SEQ ID NO: 1–SEQ ID NO:9, of course it is understood that these are only exemplary and any mutations, alterations or naturally occurring variants of these sequences are also contemplated to be useful in conjunction with the present invention.

Protein purification techniques are well known to those of skill in the art. These techniques tend to involve the fractionation of the cellular milieu to separate the protein of interest from other components of the mixture. Analytical methods particularly suited to the preparation of a pure peptide are ion-exchange chromatography, exclusion chromatography, polyacrylamide gel electrophoresis, isoelectric focusing and the like. A particularly efficient method of purifying peptides is fast protein liquid chromatography or even HPLC.

Various other techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

As disclosed herein in detail, the generally preferred techniques for purifying expressed TF constructs for use in the present invention involve the generation of a TF molecule that includes an affinity purification tag and the use of an affinity separation matrix for obtaining the TF construct free from most or all contaminating species. Many such fusion protein tags are known to those of ordinary skill in the art and such expression and separating protocols can be easily executed. Technology is also available for cleaving the original affinity tag prior to use of the released protein or polypeptide, which may be effected by inserting a protease-sensitive linker between the affinity tag and the protein of interest. Such methodology is indeed employed in connection with aspects of the present invention. U.S. Pat. No. 5,298,599 is also instructive in this regard. However, it is also known that many such tags do not impair the ability of the expressed protein to carry out their biological functions, and removal of a tag is not necessarily required prior to use of the TF construct in the present invention.

C. Pharmaceutical Compositions and Kits

Pharmaceutical compositions of the present invention will generally comprise an effective amount of the tTF dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

C1. Parenteral Formulations

The tTF of the present invention will often be formulated for parenteral administration, e.g., formulated for injection via the intravenous, intramuscular, sub-cutaneous or other such routes, including direct instillation into a tumor or disease site. The preparation of an aqueous composition that contains a tumor-targeted coagulant agent as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The tTF compositions can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. Formulations are easily administered in a variety of dosage forms, such as the type of injectable solutions described above, but drug release capsules and the like can also be employed.

Suitable pharmaceutical compositions in accordance with the invention will generally include an amount of the coagulation-deficient TF admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biological Standards.

The therapeutically effective doses are readily determinable using an animal model, as shown in the studies detailed herein. Experimental animals bearing solid tumors are frequently used to optimize appropriate therapeutic doses prior to translating to a clinical environment. Such models are known to be very reliable in predicting effective anti-cancer strategies. For example, mice bearing solid tumors, such as used in the Examples, are widely used in pre-clinical testing. The inventors have used such art-accepted mouse models to determine working ranges of tTF that give beneficial anti-tumor effects with minimal toxicity.

In addition to the compounds formulated for parenteral administration, such as intravenous or intramuscular injection, other pharmaceutically acceptable forms are also contemplated, e.g., tablets or other solids for oral administration, time release capsules, liposomal forms and the like. Other pharmaceutical formulations may also be used, dependent on the condition to be treated. For example, topical formulations that are appropriate for treating pathological conditions such as dermatitis and psoriasis; and ophthalmic formulations for diabetic retinopathy.

As described in detail herein, it is contemplated that certain benefits will result from the manipulation of the coagulation-deficient TF constructs to provide them with a longer in vivo half-life. Such techniques include, but are not limited to, manipulation or modification of the TF molecule itself, and also conjugation of TF constructs to inert carriers, such as various protein or non-protein components, including immunoglobulins and Fc portions. Such compositions are herein termed TF constructs with longer half-life. It will be understood that longer half-life is not coextensive with the pharmaceutical compositions for use in "slow release". Slow release formulations are generally designed to give a constant drug level over an extended period. Increasing the half-life of a drug, such as a TF construct in accordance with the present invention, is intended to result in high plasma levels upon administration, which levels are maintained for a longer time, but which levels generally decay depending on the pharmacokinetics of the construct. Although currently not preferred, slow release formulations of the TF construct and combinations thereof are by no means excluded from use in the present invention.

C2. Therapeutic Kits

The present invention also provides therapeutic kits comprising the tTF constructs described herein. Such kits will generally contain, in suitable container means, a pharmaceutically acceptable formulation of at least one coagulation-deficient TF construct in accordance with the invention. The kits may also contain other pharmaceutically acceptable formulations, such as those containing components to target the tTF constructs; extra coagulation factors, particularly Factor VIIa; bispecific antibodies, T cells, or other functional components for use in, e.g., antigen induction; components for use in antigen suppression, such as a cyclosporin, if necessary; distinct anti-tumor site antibodies or immunotoxins; and any one or more of a range of chemotherapeutic drugs.

The kits may have a single container means that contains the tTF, with or without any additional components, or they may have distinct container means for each desired agent. Kits comprising the separate components necessary to make a bispecific coagulating ligand or immunotoxin are also contemplated. Certain preferred kits of the present invention include a coagulation-deficient TF construct that is impaired in the ability to activate Factor VII, packaged in a kit for use in combination with the co-administration of exogenous Factor VIIa. In such kits, the TF mutant and the Factor VIIa may be pre-complexed, either in a molar equivalent combination, or with one component in excess of the other; or each of the TF and Factor VIIa components of the kit may be maintained separately within distinct containers prior to administration to a patient. Other preferred kits include any coagulation-deficient TF in combination with a "classic" chemotherapeutic agent. This is exemplary of the considerations that are applicable to the preparation of all such TF kits and kit combinations in general.

When the components of the kit are provided in one or more liquid solutions, the liquid solution is an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container means.

The container means of the kit will generally include at least one vial, test tube, flask, bottle, syringe or other container means, into which the tTF, and any other desired agent, may be placed and, preferably, suitably aliquoted. Where additional components are included, the kit will also generally contain a second vial or other container into which these are placed, enabling the administration of separated designed doses. The kits may also comprise a second/third container means for containing a sterile, pharmaceutically acceptable buffer or other diluent.

The kits may also contain a means by which to administer the tTF to an animal or patient, e.g., one or more needles or syringes, or even an eye dropper, pipette, or other such like apparatus, from which the formulation may be injected into the animal or applied to a diseased area of the body. The kits of the present invention will also typically include a means for containing the vials, or such like, and other component, in close confinement for commercial sale, such as, e.g., injection or blow-molded plastic containers into which the desired vials and other apparatus are placed and retained.

D. Treatment

D1. Prothrombotic Vessels

The compositions and methods provided by this invention are broadly applicable to the treatment of any disease, such as a benign or malignant tumor, having as a component of the disease "prothrombotic vessels". Such vasculature-associated diseases most particularly include solid, malignant tumors, and also benign tumors, such as BPH. However, the treatment of diabetic retinopathy, vascular restenosis, arteriovenous malformations (AVM), meningioma, hemangioma, neovascular glaucoma and psoriasis; and also angiofibroma, arthritis, atherosclerotic plaques, corneal graft neovascularization, hemophilic joints, hypertrophic scars, osler-weber syndrome, pyogenic granuloma retrolental fibroplasia, scleroderma, trachoma, vascular adhesions, synovitis, dermatitis and even endometriosis are certainly not excluded.

The present invention is based upon the use of TF constructs or TF in combination with other agents, wherein the TF construct or combination has sufficient thrombogenic activity to disturb the procoagulant environment within the specific disease-associated vessels, such as those of a vascularized tumor, in the direction of thrombosis. The environment in vessels in normal tissues is fibrinolytic, whereas that in tumor vessels is procoagulant, i.e., predisposed towards thrombosis. The procoagulant changes in tumor vessels result in part from local release of the endothelial cell-activating cytokines, IL-1 and TNFα. IL-1 is secreted by most tumor cells and by activated macrophages. TNFα is secreted by host cells which have infiltrated into the tumor, including activated lymphocytes, macrophages, NK cells and LAK cells.

IL-1 and TNFα induce a variety of changes on vascular endothelium, including the upregulation of Tissue Factor, the down-regulation of plasminogen activators and the upregulation of the inhibitor of plasminogen activators, PAI-1 (Nawroth and Stern, 1986; Nawroth et al., 1988). These effects are further magnified by tumor derived factors (Murray et al., 1991; Ogawa et al., 1990), possibly VEGF. The collective result of these and other changes is that the endothelium becomes better able to support the formation of thrombi and less able to dissolve fibrin, producing a predisposition toward thrombosis.

Figure 3:
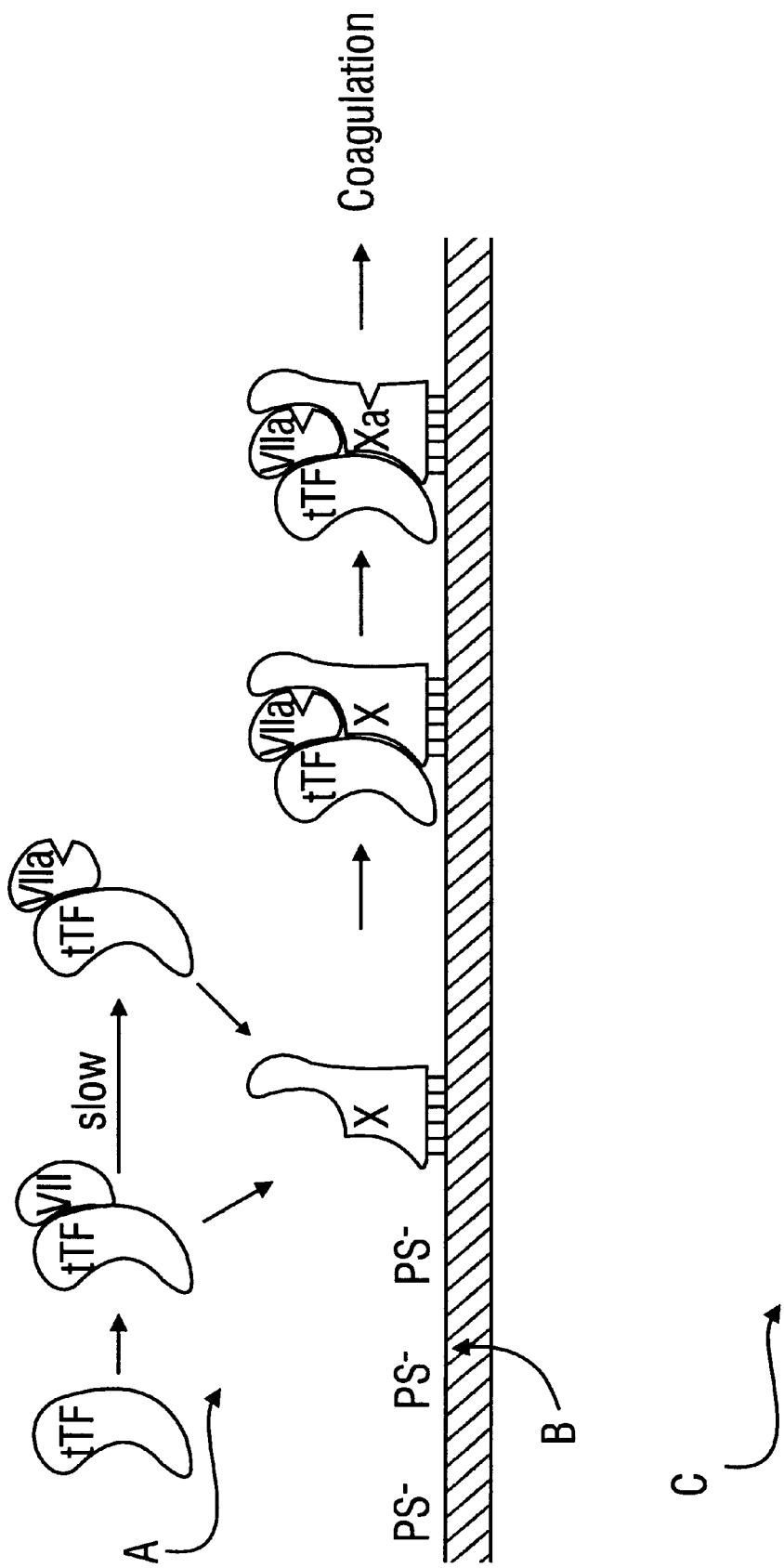
FIG. 3: Model for tTF induced coagulation of tumor vasculature. Blood (A) is depicted in contact with the cell membrane (B) of the tumor vascular endothelium (C). The prothrombotic tumor endothelium has Factor IX, X (shown) or TFPI/Xa plus phosphatidyl serine ($PS^-$) on its surface, which binds tTF-VII or tTF-VIIa, leading to coagulation.

Therefore, in light of the scientific phenomena described above, the inventors contemplate that when coagulation-deficient TFs are administered, they have enough residual thrombogenic activity to tip the coagulation cascade balance towards thrombosis in vessels that are generally prothrombotic in nature (FIG. 3). Although a mechanistic understanding of the scientific reasoning is not necessary in order to practice the present invention, it will be understood that the foregoing explanation is one mechanism by which the invention may operate. This mechanism is based less upon the specific localization of the TFs within the vessels of a vascularized tumor, as opposed to other vessels, but it is nonetheless surprising that an equal biodistribution of the TF, if this indeed occurs, can lead to an unequal effect on coagulation within disease sites such as within solid tumors. Given that it is, naturally, an inherent property of the tumor to maintain a network of blood vessels and to continue in the angiogenic process, it is evident that the tumor-associated blood vessels cannot be so predisposed towards thrombosis that they spontaneously or readily support coagulation, as such coagulation would necessarily result in the arrest of oxygen and nutrients to the tumor cells and would cause the tumor to self-destruct. Evidently, this does not occur.

It will be readily appreciated that the present invention has significant utility in the treatment of disease, such as vascularized tumors, irrespective of an understanding of the mechanisms by which specific coagulation may be induced in disease-associated vessels. However, the inventors further reason that another mechanism underlying the possible surprising action of the TF constructs is that the TFs selectively bind to certain vascular endothelial cells in preference to those in other tissues or sites of the body (FIG. 3). Accordingly, should tTF selectively bind to tumor vascular endothelium after injection, this would bring it into contact with a lipid surface and promote the assembly of coagulation initiation complexes in the tumor vessels. Perhaps, because of the prothrombotic nature of tumor vessels, there is an increase in the local concentration of Factors VIIa, IXa, Xa, Tissue Factor pathway inhibitor (TFPI) or other molecules that interact with TF, thus encouraging the localization.

The methods of the present invention may be employed to test the localization of tTF by labeling tTF, injecting it into tumor-bearing mice, and determining whether it did indeed localize within tumor vessels. Although of scientific interest, conducting such studies are not necessary to practice the present invention, given that the administration of coagulation-deficient TF constructs advantageously results in specific anti-tumor effects irrespective of the precise mechanism of action that underlies this phenomenon.

The present uses of coagulation-deficient TF molecules for promoting coagulation in prothrombotic blood vessels are distinct to the previous uses proposed for TF constructs, such as tTF in combination with Factor VIIa. tTF and Factor VIIa have been proposed for combined use in the treatment of bleeding disorders, such as hemophilia (U.S. Pat. Nos. 5,374,617; 5,504,064; and 5,504,067). U.S. Pat. Nos. 5,346, 991 and 5,589,363 also describe the use of K165A and K166A TF mutants in inhibiting coagulation in the treatment of myocardial infarction, and provide recombinant DNA sequences and vectors for their production.

It will be instantly appreciated that the targets of the previous methodology are in direct contrast to the prothrombotic blood vessels targeted by the present invention. The "prothrombotic" blood vessels are in a dynamic state that pre-disposes them to coagulation, but in which coagulation does not occur in the natural environment. This is exemplified by the blood vessels within a vascularized tumor being categorized as prothrombotic, but with the tumor maintaining a sufficient blood supply throughout necessary to support the maintenance and outgrowth of the tumor. In contrast, the target sites within an individual with a bleeding disorder, are by their very nature significantly deficient in their ability to support coagulation. The combined tTF and Factor VIIa methodology intended primarily for use in hemophiliacs has also been proposed for use in conjunction with the control of postoperative bleeding or severe trauma in which an external insult has prevented the necessary coagulation process from being effective. This again is unlike the intent of the present invention.

The most important use of the present invention is believed to be in connection with the treatment of vascularized, malignant tumors. However, in addition to the various diseases and disorders listed above, the invention is also contemplated for use in the therapy of other benign growths. A particular example of such is benign prostatic hyperplasia (BPH), which may be treated in accordance with the particular doses and treatment regimens set forth below. The treatment of BPH may also be combined with other treatments currently practiced in the art. For example, targeting of immunotoxins to markers localized within BPH, such as PSA, is certainly contemplated.

D2. Cancer and Treatment

The tTF localization and specific coagulation of the invention is most preferably exploited for therapeutic uses of tTF in the treatment of cancers and tumors. These uses may employ tTF alone or in combination with chemotherapeutic agents and/or immunotoxins or coaguligands. The compositions and methods provided by this invention are broadly applicable to the treatment of any malignant tumor having a vascular component. Typical vascularized tumors are the solid tumors, particularly carcinomas, which require a vascular component for the provision of oxygen and nutrients. Exemplary solid tumors that may be treated using the invention include, but are not limited to, carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, neuroblastomas, and the like.

The present invention is contemplated for use in the treatment of any patient that presents with a solid tumor. However, in that the present invention is particularly successful in the treatment of solid tumors of moderate or large sizes, patients in these categories are likely to receive more significant benefits from treatments in accordance with the methods and compositions provided herein. In general, the invention can be used to treat tumors of about 0.3–0.5 cm and upwards, although it is a better use of the invention to treat tumors of greater than 0.5 cm in size. From the studies already conducted in acceptable animal models, it is believed that tumors of about 1.0 or about 1.2 cm represent the size of solid tumors that are most effectively attacked by the TF constructs of the present invention. Therefore, patients presenting with tumors of between about 1.0 and about 2.0 cm in size will be in the preferred treatment group of patients in connection with the present TF therapies, although tumors up to and including the largest tumors found in humans may also be treated.

Although the present invention is not generally intended as a preventative or prophylactic treatment, use of the invention is certainly not confined to the treatment of patients having tumors of moderate or large sizes. There are many reasons underlying this aspect of the breadth of the invention. For example, a patient presenting with a primary tumor of moderate size or above may also have various other metastatic tumors that are considered to be small-sized or even in the earlier stages of metastatic tumor seeding. Given that the TF constructs and combinations of the invention are generally administered into the systemic circulation of a patient, they will naturally have effects on the secondary, smaller and metastatic tumors, although this may not be the primary intent of the treatment. Furthermore, even in situations where the tumor mass as a whole is a single small tumor, certain beneficial anti-tumor effects will result from the use of the present treatments.

The guidance provided above regarding the most suitable patients for use in connection with the present invention is intended as teaching that certain patient's profiles may assist with the selection of patients that may be treated by the present invention, or that may, perhaps, be better treated using other anti-cancer treatment strategies. Nonetheless, the fact that a preferred or otherwise more effective treatment is perceived to exist in connection with a certain category of patients, does not in any way negate the basic utility of the present invention in connection with the treatments of all patients having a vascularized tumor. A further consideration is the fact that the initial assault on a tumor, as provided by the TF therapy of the present invention, may be small in any measurable and immediate effects, but may predispose the tumor to further therapeutic treatments such that the subsequent treatment results in an overall synergistic effect or even leads to total remission or cure.

It is not believed that any particular type of tumor should be excluded from treatments using the present invention. As the intent of the therapy is to coagulate the tumor vasculature, and as the vasculature is substantially or entirely the same in all solid tumors, it will be understood that the present methodology is widely or entirely applicable to the treatment of all solid tumors, irrespective of the particular phenotype or genotype of the tumor cells themselves. However, the type of tumor cells may be relevant to the use of the invention in combination with secondary therapeutic agents, particularly anti-tumor cell immunotoxins and/or coaguligands.

Those of ordinary skill in the art will understand that certain types of tumors may be more amenable to the induction of thrombosis and necrosis using the present invention. The phenomena is observed in experimental animals, and may occur in human treatments. For example, it is known that the HT29 model tumor system is relatively difficult to coagulate; whereas the C1300 tumor model is generally more amenable to the induction of thrombosis and subsequent necrosis. Such considerations will be taken into account in conducting both the pre-clinical studies in experimental animals and in optimizing the doses for use in treating any particular patient or group of patients.

As detailed above in the discussions concerning the in vivo quantitative studies, there are realistic objectives that may be used as a guideline in connection with pre-clinical testing before proceeding to clinical treatment. However, this is more a matter of cost-effectiveness than overall usefulness, and is a mechanism for selecting the most advantageous compounds and doses. In regard to their basic utility, any construct or combination thereof that results in any consistent detectable thrombosis and anti-tumor effects will still define a useful invention. Thrombotic and necrotic effects should be observed in between about 10% and about 40–50% of the tumor blood vessels and tumor tissues, upwards to between about 50% and about 99% of such effects being observed. It will also be understood that even in such circumstances where the anti-tumor effects of the TF construct and combinations are towards the low end of this range, it may be that this therapy is still equally or even more effective than all other known therapies in the context of the particular tumor targets. It is unfortunately evident to a clinician that certain tumors cannot be effectively treated in the intermediate or long term, but that does not negate the usefulness of the present therapy, particularly where it is about as effective as the other strategies generally proposed.

In designing appropriate doses of the coagulation-deficient TF constructs and combinations, one may readily extrapolate from the animal studies described herein in order to arrive at appropriate doses for clinical administration. To achieve this conversion, one would account for the mass of the agents administered per unit mass of the experimental animal, and yet account for the differences in the body surface area between the experimental animal and the human patient. All such calculations are well known and routine to those of ordinary skill in the art. For example, in taking the successful dose of 16 $\mu$g per mouse (total body weight of about 20 g), and applying the calculation outlined above, the equivalent dose for use in a human patient would be about 2 mg. Accordingly, using this information, the inventors contemplate that useful doses of coagulation-deficient TF for use in human administration would be between about 0.2 milligrams and about 200 milligrams of the TF construct per patient. Notwithstanding this stated range, it will be understood that, given the parameters and detailed guidance presented above, further variations in the active or optimal ranges would still be encompassed within the present invention.

The doses contemplated will therefore generally be between about 0.2 mg and about 180 milligrams; between 0.5 and about 160 milligrams; between 1 and about 150 milligrams; between about 5 and about 125 milligrams; between about 10 and about 100 milligrams; between about 15 and about 80 milligrams; between about 20 and about 65 milligrams; between about 30 and about 50 milligrams; about 40 milligrams; or in any particular range using any of the foregoing recited exemplary doses or any value intermediate between the particular stated ranges. Although doses in and around about 1 milligram, 2 milligrams, 3 milligrams, 4 milligrams and about 5 milligrams are currently preferred, it will be understood that lower doses may be more appropriate in combination with other agents, and that high doses can still be tolerated, particularly given the fact that the TF agents for use in the invention are not themselves cytotoxic and even if certain adverse side effects do occur, this should not necessarily result in coagulation that cannot be counteracted by normal homeostatic mechanisms, which is believed to lessen the chances of significant toxicity to healthy tissues.

The intention of the therapeutic regimens of the present invention is generally to produce the maximum anti-tumor effects whilst still keeping the dose below the levels associated with unacceptable toxicity. In addition to varying the dose itself, the administration regimen can also be adapted to optimize the treatment strategy. A currently preferred treatment strategy is to administer between about 0.2 milligrams and about 200 milligrams of the TF construct or combination thereof about 3 times within about a 7 day period. For example, doses would be given on about day 1, day 3 or 4 and day 6 or 7. In administering the particular doses themselves, one would preferably provide a pharmaceutically acceptable composition to the patient systemically. Intravenous injection is generally preferred, and the most preferred method is to employ a continuous infusion over a time period of about 1 or 2 hours or so. Although it is not required to determine such parameters prior to treatment using the present invention, it should be noted that the studies detailed herein result in at least some thrombosis being observed specifically in the blood vessels of a solid tumor within about 30 minutes of injection, and that the tumor cells themselves begin to die within about 3 to 4 hours. Widespread tumor necrosis is generally observed in the next about 24 hours, up to and including greater than 90% necrosis being observed.

E. Combination Therapies

The methods of the present invention may be combined with any other methods generally employed in the treatment of the particular disease or disorder that the patient exhibits. For example, in connection with the treatment of solid tumors, the methods of the present invention may be used in combination with classical approaches, such as surgery, radiotherapy and the like. So long as a particular therapeutic approach is not known to be detrimental in itself, or counteracts the effectiveness of the TF therapy, its combination with the present invention is contemplated. When one or more agents are used in combination with the TF therapy, there is no requirement for the combined results to be additive of the effects observed when each treatment is conducted separately, although this is evidently desirable, and there is no particular requirement for the combined treatment to exhibit synergistic effects, although this is certainly possible and advantageous.

In terms of surgery, any surgical intervention may be practiced in combination with the present invention. In connection with radiotherapy, any mechanism for inducing DNA damage locally within tumor cells is contemplated, such as γ-irradiation, X-rays, UV-irradiation, microwaves and even electronic emissions and the like. The directed delivery of radioisotopes to tumor cells is also contemplated, and this may be used in connection with a targeting antibody or other targeting means. Cytokine therapy also has proven to be an effective partner for combined therapeutic regimens. Various cytokines may be employed in such combined approaches. Examples of cytokines include IL-1α IL-1β, IL-2, IL-3, IL-4, IL-5, IL-6, IL-7, IL-8, IL-9, IL-10, IL-11, IL-12, IL-13, TGF-β, GM-CSF, M-CSF, G-CSF, TNFα, TNFβ, LAF, TCGF, BCGF, TRF, BAF, BDG, MP, LIF, OSM, TMF, PDGF, IFN-α, IFN-β, IFN-γ. Cytokines are administered according to standard regimens, consistent with clinical indications such as the condition of the patient and relative toxicity of the cytokine.

E1. Chemotherapeutic Combinations and Treatment

In certain embodiments, the present invention shows that the anti-tumor activity of tTF is enhanced when administered in combination with a chemotherapeutic agent. The mechanisms by which the drugs enhance the anti-tumor activity of tTF have not been precisely defined, but the inventors believe that the drug kills proliferating tumor cells creating necrotic areas that cause phagocytic cells to infiltrate the tumor. IL-1, TNFα and other cytokines released by the infiltrating cells then activate the tumor vascular endothelium making it better able to support coagulation by tTF, a generally weak thrombogen. The drug thus enhances the thrombotic action of tTF.

Another possibility for the enhanced actions of TF and anti-cancer drugs is that tTF induces the formation of thrombi in tumor vessels, thereby trapping drug within the tumor. While drug is cleared from the rest of the body, it remains within the tumor. The tumor cells are thus exposed to a higher concentration of drug for a longer period of time. This entrapment of drug within the tumor may also make it possible to reduce the dose of drug, making the treatment safer as well as more effective.

Irrespective of the mechanisms by which the enhanced tumor destruction is achieved, the combined treatment aspects of the present invention have evident utility in the effective treatment of disease. To use the present invention in combination with the administration of a chemotherapeutic agent, one would simply administer to an animal a coagulation-deficient TF construct in combination with the chemotherapeutic agent in a manner effective to result in their combined anti-tumor actions within the animal. These agents would therefore be provided in an amount effective and for a period of time effective to result in their combined presence within the tumor vasculature and their combined actions in the tumor environment. To achieve this goal, the TF and chemotherapeutic agents may be administered to the animal simultaneously, either in a single composition or as two distinct compositions using different administration routes.

Alternatively, the TF treatment may precede or follow the chemotherapeutic agent treatment by intervals ranging from minutes to weeks. In embodiments where the chemotherapeutic factor and TF are applied separately to the animal, one would generally ensure that a significant period of time did not expire between the time of each delivery, such that the chemotherapeutic agent and TF composition would still be able to exert an advantageously combined effect on the tumor. In such instances, it is contemplated that one would contact the tumor with both agents within about 5 minutes to about one week of each other and, more preferably, within about 12–72 hours of each other, with a delay time of only about 12–48 hours being most preferred. In some situations, it may be desirable to extend the time period for treatment significantly, where several days (2, 3, 4, 5, 6 or 7) or even several weeks (1, 2, 3, 4, 5, 6, 7 or 8) lapse between the respective administrations. It also is conceivable that more than one administrations of either the TF or the chemotherapeutic agent will be desired. To achieve tumor regression, both agents are delivered in a combined amount effective to inhibit its growth, irrespective of the times for administration.

A variety of chemotherapeutic agents are intended to be of use in the combined treatment methods disclosed herein. Chemotherapeutic agents contemplated as exemplary include, e.g., etoposide (VP-16), adriamycin, 5-fluorouracil (5FU), camptothecin, actinomycin-D, mitomycin C, cisplatin (CDDP) and even hydrogen peroxide. In certain embodiments, the use of etoposide has already been shown to be effective in regression of tumor in size when administered in combination with the tTF compositions of the present invention.

As will be understood by those of ordinary skill in the art, the appropriate doses of chemotherapeutic agents will be generally around those already employed in clinical therapies wherein the chemotherapeutics are administered alone or in combination with other chemotherapeutics. By way of example only, agents such as cisplatin, and other DNA alkylating may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Further useful agents include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 mg/m$^2$ at 21 day intervals for adriamycin, to 35–50 mg/m$^2$ for etoposide intravenously or double the intravenous dose orally.

Agents that disrupt the synthesis and fidelity of polynucleotide precursors may also be used. Particularly useful are agents that have undergone extensive testing and are readily available. As such, agents such as 5-fluorouracil (5-FU) are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Exemplary chemotherapeutic agents that are useful in connection with combined therapy are listed in Table II. Each of the agents listed therein are exemplary and by no means limiting. The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

TABLE II

CHEMOTHERAPEUTIC AGENTS USEFUL IN NEOPLASTIC DISEASE

| CLASS | TYPE OF AGENT | NONPROPRIETARY NAMES (OTHER NAMES) | DISEASE |
|---|---|---|---|
| Alkylating Agents | Nitrogen Mustards | Mechlorethamine (HN$_2$) | Hodgkin's disease, non-Hodgkin's lymphomas |
| | | Cyclophosphamide Ifosfamide | Acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas |
| | | Melphalan (t-sarcolysin) | Multiple myeloma, breast, ovary |
| | | Chlorambucil | Chronic lymphocytic leukemia, primary macroglobulinemia, Hodgkin's disease, non-Hodgkin's lymphomas |
| | Ethyleneimenes and Methylmelamines | Hexamethylmelamine | Ovary |
| | | Thiotepa | Bladder, breast, ovary |
| | Alkyl Sulfonates | Busulfan | Chronic granulocytic leukemia |
| | Nitrosoureas | Carmustine (BCNU) | Hodgkin's disease, non-Hodgkin's lymphomas, primary brain tumors, multiple myeloma, malignant melanoma |
| | | Lomustine (CCNU) | Hodgkin's disease, non-Hodgkin's lymphomas, primary brain tumors, small-cell lung |
| | | Semustine (methyl-CCNU) | Primary brain tumors, stomach, colon |
| | | Streptozocin (streptozotocin) | Malignant pancreatic insulinoma, malignant carcinoid |
| | Triazines | Dacarbazine (DTIC; | Malignant melanoma, Hodgkin's |

TABLE II-continued

CHEMOTHERAPEUTIC AGENTS USEFUL IN NEOPLASTIC DISEASE

| CLASS | TYPE OF AGENT | NONPROPRIETARY NAMES (OTHER NAMES) | DISEASE |
|---|---|---|---|
| | | dimethyltriazenoimidaz olecarboxamide) | disease, soft-tissue sarcomas |
| Antimetabolites | Folic Acid Analogs | Methotrexate (amethopterin) | Acute lymphocytic leukemia, choriocarcinoma, mycosis fungoides, breast, head and neck, lung, osteogenic sarcoma |
| | Pyrimidine Analogs | Fluouracil (5-fluorouracil; 5-FU) | Breast, colon, stomach, pancreas, ovary, head and neck, urinary bladder, |
| | | Floxuridine (fluorode-oxyuridine; FUdR) | premalignant skin lesions (topical) |
| | | Cytarabine (cytosine arabinoside) | Acute granulocytic and acute lymphocytic leukemias |
| | Purine Analogs and Related Inhibitors | Mercaptopurine (6-mercaptopurine; 6-MP) | Acute lymphocytic, acute granulocytic and chronic granulocytic leukemias |
| | | Thioguanine (6-thioguanine; TG) | Acute granulocytic, acute lymphocytic and chronic granulocytic leukemias |
| | | Pentostatin (2-deoxycoformycin) | Hairy cell leukemia, mycosis fungoides, chronic lymphocytic leukemia |
| Natural Products | Vinca Alkaloids | Vinblastine (VLB) | Hodgkin's disease, non-Hodgkin's lymphomas, breast, testis |
| | | Vincristine | Acute lymphocytic leukemia, neuroblastoma, Wilms' tumor, rhabdomyosarcoma, Hodgkin's disease, non-Hodgkin's lymphomas, small-cell lung |
| | Epipodophyllotoxins | Etoposide | Testis, small-cell lung and other lung, breast, Hodgkin's disease, non-Hodgkin's lymphomas, acute granulocytic leukemia, Kaposi's sarcoma |
| | | Tertiposide | |
| | Antibiotics | Dactinomycin (actinomycin D) | Choriocarcinoma, Wilms' tumor, rhabdomyosarcoma, testis, Kaposi's sarcoma |
| | | Daunorubicin (daunomycin; rubidomycin) | Acute granulocytic and acute lymphocytic leukemias |
| | | Doxorubicin | Soft-tissue, osteogenic and other sarcomas; Hodgkin's disease, non-Hodgkin's lymphomas, acute leukemias, breast, genitourinary, thyroid, lung, stomach, neuroblastoma |
| | | Bleomycin | Testis, head and neck, skin, esophagus, lung and genitourinary tract; Hodgkin's disease, non-Hodgkin's lymphomas |
| | | Plicamycin (mithramycin) | Testis, malignant hypercalcemia |
| | | Mitomycin (mitomycin C) | Stomach, cervix, colon, breast, pancreas, bladder, head and neck |
| | Enzymes | L-Asparaginase | Acute lymphocytic leukemia |
| | Biological Response Modifiers | Interferon alfa | Hairy cell leukemia., Kaposi's sarcoma, melanoma, carcinoid, renal cell, ovary, bladder, non-Hodgkin's lymphomas, mycosis fungoides, multiple myeloma, chronic granulocytic leukemia |
| Miscellaneous Agents | Platinum Coordination Complexes | Cisplatin (cis-DDP) Carboplatin | Testis, ovary, bladder, head and neck, lung, thyroid, cervix, endometrium, neuroblastoma, osteogenic sarcoma |
| | Anthracenedione | Mitoxantrone | Acute granulocytic leukemia, breast |
| | Substituted Urea | Hydroxyurea | Chronic granulocytic leukemia, polycythemia vera, essental thrombocytosis, malignant melanoma |
| | Methyl Hydrazine Derivative | Procarbazine (N-methylhydrazine, MIH) | Hodgkin's disease |
| | Adrenocortical Suppressant | Mitotane (o,p'-DDD) | Adrenal cortex |
| | | Aminoglutethimide | Breast |
| Hormones and Antagonists | Adrenocorticosteroids | Prednisone (several other equivalent preparations available) | Acute and chronic lymphocytic leukemias, non-Hodgkin's lymphomas, Hodgkin's disease, breast |

TABLE II-continued

CHEMOTHERAPEUTIC AGENTS USEFUL IN NEOPLASTIC DISEASE

| CLASS | TYPE OF AGENT | NONPROPRIETARY NAMES (OTHER NAMES) | DISEASE |
| --- | --- | --- | --- |
| | Progestins | Hydroxyprogesterone caproate<br>Medroxyprogesterone acetate<br>Megestrol acetate | Endometrium, breast |
| | Estrogens | Diethylstilbestrol<br>Ethinyl estradiol (other preparations available) | Breast, prostate |
| | Antiestrogen | Tamoxifen | Breast |
| | Androgens | Testosterone propionate<br>Fluoxymesterone (other preparations available) | Breast |
| | Antiandrogen | Flutamide | Prostate |
| | Gonadotropin-releasing hormone analog | Leuprolide | Prostate |

E2. Immunotoxin and Coaguligand Combinations and Therapy

Any one or more of the coagulation-deficient TF constructs of the invention may be used in combination with immunotoxins (ITs) and/or coaguligands in which the targeting portion thereof (e.g., antibody or ligand) is directed to a relatively specific marker of the tumor cells, tumor vasculature or tumor stroma. In common with the chemotherapeutic agents discussed above, it is possible that the use of a coagulation-deficient TF construct in combination with a targeted toxic agent (IT) or coagulant (coaguligand) will result in the distinct agents being directed against different targets within the tumor environment. This should result in additive, markedly greater than additive or even synergistic results.

In connection with the preparation and use of exemplary immunotoxins and coaguligands, the following patent application disclosures are specifically incorporated herein by reference for the purposes of even further supplementing the present teachings: U.S. Ser. Nos. 07/846,349; 08/295,868; 08/205,330; 08/350,212; 08/273,567; and 08/482,369.

At least one binding region of the second agents employed in combination with the tTF constructs of the present invention will be a component that is capable of delivering a toxin or coagulating agent to the tumor region, i.e., capable of localizing within a tumor site. As somewhat wider distribution of a coagulating agent will not be associated with severe side effects, there is a less stringent requirement imposed on the targeting element of coaguligands than with immunotoxins. Either targeting agent may be directed to components of tumor cells; components of tumor vasculature; components that bind to, or are generally associated with, tumor cells; components that bind to, or are generally associated with, tumor vasculature; components of the tumor extracellular matrix or stroma or those bound therein; and even cell types found within the tumor vasculature.

With coaguligands, the burden of very stringent targeting, e.g., as imposed when using immunotoxins, is lessened. Therefore, to achieve specific targeting means that coagulation is promoted in the tumor vasculature relative to the vasculature in non-tumor sites. Thus, specific targeting of a coaguligand is a functional term rather than a purely physical term relating to the biodistribution properties of the targeting agent, and it is not unlikely that useful targets may be not be entirely tumor-restricted, and that targeting ligands which are effective to promote tumor-specific coagulation may nevertheless be found at other sites of the body following administration.

i. Tumor Cell Targets

The malignant cells that make up the tumor may be targeted using a ligand or bispecific ligand that has a region capable of binding to a relatively specific marker of the tumor cell. Toxins kill the tumor cells and, in that binding to tumor cells will localize an associated coagulating agent to the tumor, specific coagulation will be achieved.

Many so-called "tumor antigens" have been described, any one which could be employed as a target in connection with the combined aspects of the present invention. A large number of exemplary solid tumor-associated antigens are listed herein below. The preparation and use of antibodies against such antigens is well within the skill of the art, and exemplary antibodies include from gynecological tumor sites: OC 125; OC 133; OMI; Mo v1; Mo v2; 3C2; 4C7; $ID_3$; DU-PAN-2; F 36/22; $4F_7/7A_{10}$; OV-TL3; B72.3; $DF_3$; $2C_8/2F_7$; MF 116; Mov18; CEA 11H5; CA 19-9 (1116NS 19-9); H17-E2; 791T/36; $NDOG_2$; H317; 4D5, 3H4, 7C2, 6E9, 2C4, 7F3, 2H11, 3E8, 5B8, 7D3, SB8; HMFG2; 3.14.A3; from breast tumor sites: DF3; NCRC-11; 3C6F9; MBE6; CLNH5; MAC 40/43; EMA; HMFG1 HFMG2; 3.15.C3; M3, M8, M24; M18; 67-D-11; D547Sp, D75P3, H222; Anti-EGF; LR-3; TA1; H59; 10-3D-2; HmAB1,2; MBR 1,2,3; 24.17.1; 24.17.2 (3E1.2); F36/22.M7/105; C11, G3, H7; B6.2; B1.1; Cam 17.1; SM3; SM4; C-Mul (566); 4D5 3H4, 7C2, 6E9, 2C4, 7F3, 2H11, 3E8, 5B8, 7D3, 5B8; OC 125; MO v2; DU-PAN-2; $4F_7/7A_{10}$; $DF_3$; B72.3; cccccCEA 11; H17-E2; 3.14.A3; FO23C5; from colorectal tumor sites: B72.3; (17-1A) 1083-17-1A; CO17-1A; ZCE-025; AB2; HT-29-15; 250-30.6; 44X14; A7; GA73.3; 791T/36; 28A32; 28.19.8; X MMCO-791; DU-PAN-2; $ID_3$; CEA 11-H5; $2C_8/2F_7$; CA-19-9 (1116NS 19-9); PR5C5; PR4D2; PR4D1; from melanoma sites 4.1; 8.22 $M_{17}$; 96.5; 118.1, 133.2, (113.2); $L_1$, $L_{10}$, $R_{10}(R_{19})$; $I_{12}$;$K_5$; 6.1;R24; 5.1; 225.28S; 465.12S; 9.2.27;F11;376.96S; 465.12S; 15.75; 15.95;Mel-14;Mel-12;Me3-TB7; 225.28SD; 763.24TS; 705F6; 436910; M148;from gastrointestinal tumors: ID3;DU-PAN-2;OV-TL3;B72.3;CEA 11-H5; 3.14.A3;C COLI; CA-19-9 (1116NS 19-9) and CA50;OC125;from lung tumors: 4D5 3H4, 7C2, 6E9, 2C4, 7F3, 2H11, 3E8, 5B8, 7D3, SB8;MO v2;B72.3;DU-PAN-2;CEA 11-H5;MUC 8-22;MUC 2-63; MUC 2-39;MUC 7-39;and from miscellaneous tumors: PAb 240;PAb 246;PAb 1801; ERIC-1;M148;FMH25; 6.1;CA1; 3F8; 4F$_7$/7A$_{10}$; 2C$_8$/2F$_7$;CEA 11-H5.

Another means of defining a targetable tumor is in terms of the characteristics of a tumor cell itself, rather than describing the biochemical properties of an antigen expressed by the cell. Accordingly, the skilled artisan is referred to the ATCC catalogue for the purpose of exemplifying human tumor cell lines that are publicly available (from ATCC Catalogue). Exemplary cell lines include J82;RT4;ScaBER; T24;TCCSUP;5637;SK-N-MC; SK-N-SH; SW 1088;SW 1783;U-87 MG; U-118 MG; U-138 MG; U-373 MG; Y79;BT-20;BT-474; MCF7;MDA-MB-134-VI; MDA-MD-157;MDA-MB-175-VII; MDA-MB-361;SK-BR-3;C-33 A; HT-3;ME-180;MS751;SiHa; JEG-3;Caco-2;HT-29;SK-CO-1;HuTu 80;A-253;FaDu; A-498; A-704;Caki-1;Caki-2;SK-NEP-1;SW 839;SK-HEP-1;A-427;Calu-1;Calu-3;Calu-6; SK-LU-1;SK-MES-1;SW 900;EB1;EB2;P3HR-1;HT-144;Malme-3M; RPMI-7951; SK-MEL-1;SK-MEL-2;SK-MEL-3;SK-MEL-5;SK-MEL-24;SK-MEL-28;SK-MEL-31;Caov-3; Caov-4;SK-OV-3;SW 626;Capan-1;Capan-2;DU 145;A-204;Saos-2;SK-ES-1; SK-LMS-1; SW 684;SW 872;SW 982;SW 1353;U-2 OS; Malme-3;KATO III; Cate-1B; Tera-1;Tera-2; SW579;AN3 CA; HEC-1-A; HEC-1-B; SK-UT-1;SK-UT-1B; SW 954;SW 962;NCI-H69; NCI-H128;BT-483;BT-549;DU4475;HBL-100;Hs 578Bst; Hs 578T; MDA-MB-330;MDA-MB-415; MDA-MB-435S; MDA-MB-436;MDA-MB-453;MDA-MB-468;T-47D; Hs 766T; Hs 746T; Hs 695T; Hs 683;Hs 294T; Hs 602;JAR; Hs 445;Hs 700T; H4;Hs 696;Hs 913T; Hs 729;FHs 738Lu; FHs 173We; FHs 738B1;NIH:0VCAR-3;Hs 67;RD-ES; ChaGo K-1; WERI-Rb-1; NCI-H446;NCI-H209;NCI-H146;NCI-H441;NCI-H82; 1H9;NCI-H460;NCI-H596; NCI-H676B; NCI-H345;NCI-H820;NCI-H520;NCI-H661;NCI-H510A; D283 Med; Daoy; D341 Med; AML-193 and MV4-11.

One may consult the ATCC Catalogue of any subsequent year to identify other appropriate cell lines. Also, if a particular cell type is desired, the means for obtaining such cells, and/or their instantly available source, will be known to those of skill in the particular art. An analysis of the scientific literature will thus readily reveal an appropriate choice of cell for any tumor cell type desired to be targeted.

(a) Anti-Tumor Cell Antibodies

A straightforward means of recognizing a tumor antigen target is through the use of an antibody that has binding affinity for the particular antigen. An extensive number of antibodies are known that are directed against solid tumor antigens. Certain useful anti-tumor antibodies are listed above. However, as will be instantly known to those of skill in the art, certain of the antibodies listed will not have the appropriate biochemical properties, or may not be of sufficient tumor specificity, to be of use therapeutically. An example is MUC8-22 that recognizes a cytoplasmic antigen. Antibodies such as these will generally be of use only in investigational embodiments, such as in model systems or screening assays.

Generally speaking, antibodies for use in these aspects of the present invention will preferably recognize antigens that are accessible on the cell-surface and that are preferentially, or specifically, expressed by tumor cells. Such antibodies will also preferably exhibit properties of high affinity, such as exhibiting a $K_d$ of <200 nM, and preferably, of <100 nM, and will not show significant reactivity with life-sustaining normal tissues, such as one or more tissues selected from heart, kidney, brain, liver, bone marrow, colon, breast, prostate, thyroid, gall bladder, lung, adrenals, muscle, nerve fibers, pancreas, skin, or other life-sustaining organ or tissue in the human body. The "life-sustaining" tissues that are the most important for the purposes of the present invention, from the standpoint of low reactivity, include heart, kidney, central and peripheral nervous system tissues and liver. The term "significant reactivity", as used herein, refers to an antibody or antibody fragment, that, when applied to the particular tissue under conditions suitable for immunohistochemistry, will elicit either no staining or negligible staining with only a few positive cells scattered among a field of mostly negative cells.

Particularly promising antibodies contemplated for use in the present invention are those having high selectivity for the solid tumor. For example, antibodies binding to TAG 72 and the HER-2 proto-oncogene protein, which are selectively found on the surfaces of many breast, lung and colorectal cancers (Thor et al., 1986;Colcher et al., 1987;Shepard et al., 1991); MOv18 and OV-TL3 and antibodies that bind to the milk mucin core protein and human milk fat globule (Miotti et al., 1985;Burchell et al., 1983); and the antibody 9.2.27 that binds to the high $M_r$ melanoma antigens (Reisfeld et al., 1982). Further useful antibodies are those against the folate-binding protein, which is known to be homogeneously expressed in almost all ovarian carcinomas; those against the erb family of oncogenes that are over-expressed in squamous cell carcinomas and the majority of gliomas; and other antibodies known to be the subject of ongoing pre-clinical and clinical evaluation.

The antibodies B3, KSI/4, CC49, 260F9, XMMCO-791, D612 and SM3 are believed to be particularly suitable for use in clinical embodiments, following the standard pre-clinical testing routinely practiced in the art. B3 (U.S. Pat. No. 5,242,813;Brinkmann et al., 1991) has ATCC Accession No. HB 10573;KSI/4 can be made as described in U.S. Pat. No. 4,975,369;and D612 (U.S. Pat. No. 5,183,756) has ATCC Accession No. HB 9796.

Another means of defining a tumor-associated target is in terms of the characteristics of the tumor cell, rather than describing the biochemical properties of an antigen expressed by the cell. Accordingly, the inventors contemplate that any antibody that preferentially binds to a tumor cell may be used as the targeting component of an immunotoxin or coaguligand. The preferential tumor cell binding is again based upon the antibody exhibiting high affinity for the tumor cell and not having significant reactivity with life-sustaining normal cells or tissues, as defined above.

The invention also provides several means for generating an antibody for use in the targeted coagulation methods described herein. To generate a tumor cell-specific antibody, one would immunize an animal with a composition comprising a tumor cell antigen and, as described more fully in below, select a resultant antibody with appropriate specificity. The immunizing composition may contain a purified, or partially purified, preparation of any of the antigens in listed above; a composition, such as a membrane preparation, enriched for any of the antigens in listed above; any of the cells listed in listed above; or a mixture or population of cells that include any of the cell types listed above.

Of course, regardless of the source of the antibody, in the practice of the invention in human treatment, one will prefer to ensure in advance that the clinically-targeted tumor expresses the antigen ultimately selected. This is achieved by means of a fairly straightforward assay, involving antigenically testing a tumor tissue sample, for example, a surgical biopsy, or perhaps testing for circulating shed antigen. This can readily be carried out in an immunological screening assay such as an ELISA (enzyme-linked immunosorbent assay), wherein the binding affinity of antibodies from a "bank" of hybridomas are tested for reactivity against the tumor. Antibodies demonstrating appropriate tumor selectivity and affinity are then selected for the preparation of bispecific antibodies of the present invention.

Due to the well-known phenomenon of cross-reactivity, it is contemplated that useful antibodies may result from immunization protocols in which the antigens originally employed were derived from an animal, such as a mouse or a primate, in addition to those in which the original antigens were obtained from a human cell. Where antigens of human origin are used, they may be obtained from a human tumor cell line, or may be prepared by obtaining a biological sample from a particular patient in question. Indeed, methods for the development of antibodies that are "custom-tailored" to the patient's tumor are known (Stevenson et al., 1990) and are contemplated for use in connection with this invention.

(b) Further Tumor Cell Targets and Binding Ligands

In addition to the use of antibodies, other ligands could be employed to direct a coagulating agent to a tumor site by binding to a tumor cell antigen. For tumor antigens that are over-expressed receptors (estrogen receptor, EGF receptor), or mutant receptors, the corresponding ligands could be used as targeting agents.

In an analogous manner to endothelial cell receptor ligands, there may be components that are specifically, or preferentially, bound to tumor cells. For example, if a tumor antigen is an over-expressed receptor, the tumor cell may be coated with a specific ligand in vivo. It seems that the ligand could then be targeted either with an antibody against the ligand, or with a form of the receptor itself Specific examples of these type of targeting agents are antibodies against TIE-1 or TIE-2 ligands, antibodies against platelet factor 4, and leukocyte adhesion binding protein.

ii. Other Disease Targets

In further embodiments, TFs in combination with ITs or coaguligands that bind to a target molecule that is specifically or preferentially expressed in a disease site other than a tumor site may be employed.

Exemplary target molecules associated with other diseased cells include, for example, leukocyte adhesion molecules, that are associated with psoriasis; FGF, that is associated with proliferative diabetic retinopathy; platelet factor 4, that is associated with the activated endothelium of various diseases; and VEGF, that is associated with vascular proliferative disease. It is believed that an animal or patient having any one of the above diseases would benefit from the specific induction of coagulation in the disease site and optionally from targeted toxin delivery.

Diseases that are known to have a common angio-dependent pathology, as described in Klagsburn and Folkman (1990), may also be treated as described herein. In particular, a vascular endothelial cell-targeted ligand or a stroma-targeted ligand will be used to achieve coagulation in the disease site. The treatment of BPH, diabetic retinopathy, vascular restenosis, vascular adhesions, AVM, meningioma, hemangioma, neovascular glaucoma, rheumatoid arthritis and psoriasis are particularly contemplated at the present time.

iii. Disease-Associated Vasculature Cell Targets

The cells of the vasculature are intended as targets for use in the present invention. In these cases, at least one binding region of the immunotoxin or coaguligand will be capable of binding to an accessible marker preferentially expressed by disease-associated vasculature endothelial cells. The exploitation of the vascular markers is made possible due to the proximity of the vascular endothelial cells to the disease area and to the products of the local aberrant physiological processes. For example, tumor vascular endothelial cells are exposed to tumor cells and tumor-derived products that change the phenotypic profile of the endothelial cells.

Tumor cells are known to elaborate tumor-derived products, such as lymphokines, monokines, colony-stimulating factors, growth factors and angiogenic factors, that act on the nearby vascular endothelial cells (Kandel et al., 1991;Folkman, 1985a, 1985b) and cytokines (Burrows et al., 1991;Ruco et al., 1990;Borden et al., 1990). The tumor products bind to the endothelial cells and serve to selectively induce expression of certain molecules. It is these induced molecules that may be targeted using the tumor endothelium-specific toxin and/or coagulant delivery provided by certain aspects of the present invention. Vascular endothelial cells in tumors proliferate at a rate 30-fold greater than those in miscellaneous normal tissues (Denekamp et al., 1982), suggesting that proliferation-linked determinants could also serve as markers for tumor vascular endothelial cells.

In certain embodiments of the invention, the targeting component of the immunotoxins or coaguligands will be a component that has a relatively high degree of specificity for tumor vasculature. These targeting components may be defined as components that bind to molecules expressed on tumor endothelium, but that have little or no expression at the surface of normal endothelial cells. Such specificity may be assessed by the standard procedures of immunostaining of tissue sections, which are routine to those of skill in the art. In terms of coaguligands, it is generally proposed that the molecules to be targeted using the bispecific ligands or antibodies of this invention will be those that are expressed on tumor vasculature at a higher level than on normal endothelial cells.

(a) Vascular Endothelial Cell Markers in Disease

Molecules that are known to be preferentially expressed at the surface of vascular endothelial cells in a disease site or environment are herein termed "natural disease-associated vascular endothelial cell markers". This term is used for simplicity to refer to the endothelial cell components that are expressed in diseases connected with increased or inappropriate angiogenesis or endothelial cell proliferation. One particular example are the tumor endothelial cell components that are expressed in situ in response to tumor-derived factors. These components are also termed "naturally-induced tumor endothelial cell markers".

Both VEGF/VPF (vascular endothelial growth factor/vascular permeability factor) and components of the FGF (fibroblast growth factor) family are concentrated in or on tumor vasculature. The corresponding receptors therefore provide a potential target for attack on tumor vasculature. For example, VEGF receptors are known to be upregulated on tumor endothelial cells, as opposed to endothelial cells in normal tissues, both in rodents and man (Thieme et al., 1995). Possibly, this is a consequence of hypoxia—a characteristic of the tumor microenvironment (Leith et al., 1992). FGF receptors are also upregulated three-fold on endothelial cells exposed to hypoxia, and so are believed to be upregulated in tumors (Bicknell and Harris et al., 1992).

The TGF $\beta$ (transforming growth factor $\beta$) receptor (endoglin) on endothelial cells is upregulated on dividing cells, providing another target. One of the present inventors found that endoglin is upregulated on activated and dividing HUVEC in culture, and is strongly expressed in human tissues on endothelial cells at sites of neovascularization, including a broad range of solid tumors and fetal placenta. In contrast, endothelial cells in the majority of miscellaneous non-malignant adult tissues, including preneoplastic lesions, contain little or no endoglin. Importantly, endoglin expression is believed to correlate with neoplastic progression in the breast, as shown by benign fibroadenomas and early carcinomas binding low levels of TEC-4 and TEC-11 antibodies, and late stage intraductal carcinomas and invasive carcinomas binding high levels of these antibodies.

Other natural disease-associated vascular endothelial cell markers include a TIE, VCAM-1, P-selectin, E-selectin (ELAM-l), $\alpha_v\beta_3$ integrin, pleiotropin and endosialin, each of which may be targeted using the invention.

(b) Cytokine-Inducible Vascular Endothelial Markers

Due to the nature of disease processes, which often result in localized dysfunction within the body, methods are available to manipulate the disease site whilst leaving other tissues relatively unaffected. This is particularly true in malignant and benign tumors, which exist as distinct entities within the body of an animal. For example, the tumor environment may be manipulated to create additional markers that are specific for tumor vascular endothelial cells. These methods generally mimic those that occur naturally in solid tumors, and also involve the local production of signaling agents, such as growth factors or cytokines, that induce the specific expression of certain molecules at the surface of the nearby vascular endothelial cells.

The group of molecules that may be artificially induced to be expressed at the surface of vascular endothelial cells in a disease or tumor environment are herein termed "inducible endothelial cell markers", or specifically, "inducible tumor endothelial cell markers". This term is used to refer to those markers that are artificially induced, i.e., induced as a result of manipulation by the hand of man, rather than those that are induced as part of the disease or tumor development process in an animal. The term "inducible marker", as defined above, is chosen for simple reference in the context of the present application, notwithstanding the fact that "natural markers" are also induced, e.g., by tumor-derived agents.

Thus, although not required to practice the invention, techniques for the selective elicitation of vascular endothelial antigen targets on the surface of disease-associated vasculature are available that may, if desired, be used in conjunction with the invention. These techniques involve manipulating the antigenic expression, or cell surface presentation, such that a target antigen is expressed or rendered available on the surface of disease-associated vasculature and not expressed or otherwise rendered accessible or available for binding, or at least to a lesser extent, on the surface of normal endothelium.

Tumor endothelial markers can be induced by tumor-derived cytokines (Burrows et al., 1991;Ruco et al., 1990) and by angiogenic factors (Mignatti et al., 1991). Examples of cell surface markers that may be specifically induced in the tumor endothelium and then targeted using a bispecific coagulating ligand, as provided by the invention, include those listed in Table III (Bevilacqua et al., 1987;Dustin et al., 1986;Osborn et al., 1989;Collins et al., 1984).

The mechanisms for the induction of the proposed markers; the inducing, or "intermediate cytokine", such as IL-1 and IFN-γ; and the leukocyte cell type and associated cytokine-activating molecule, whose targeting will result in the release of the cytokine, are also set forth in Table III. In the induction of a specific marker, a bispecific "cytokine-inducing" or "antigen-inducing" antibody is generally required. This antibody will selectively induce the release of the appropriate cytokine in the locale of the tumor, thus selectively inducing the expression of the desired target antigen by the vascular endothelial cells. The bispecific antibody cross-links cells of the tumor mass and cytokine-producing leukocytes, thereby activating the leukocytes to release the cytokine.

The preparation and use of bispecific antibodies such as these is predicated in part on the fact that cross-linking antibodies recognizing CD3, CD14, CD16 and CD28 have previously been shown to elicit cytokine production selectively upon cross-linking with the second antigen (Qian et al., 1991). In the context of the present invention, since only successfully tumor cell-crosslinked leukocytes will be activated to release the cytokine, cytokine release will be restricted to the locale of the tumor. Thus, expression of the desired marker, such as E-selectin, will be similarly limited to the endothelium of the tumor vasculature.

TABLE III

POSSIBLE INDUCIBLE VASCULAR TARGETS

| INDUCIBLE ENDOTHELIAL CELL MOLECULES | ACRONYM | SUBTYPES/ALIASES (MOLECULAR FAMILY) | INDUCING CYTOKINES | LEUKOCYTES WHICH PRODUCE THOSE CYTOKINES | LEUKOCYTE MOLECULES WHICH, WHEN CROSSLINKED BY MONOCLONAL ANTIBODIES ACTIVATE THE CELLS TO PRODUCE CYTOKINES |
|---|---|---|---|---|---|
| Endothelial-Leukocyte Adhesion Molecule-1 | ELAM-1 E-selectin | — (Selectin) | IL-1, TNF-α, (TNF-β) (Bacterial Endotoxin) | monocytes | CD14 |
| | | | | macrophages mast cells | CD14 FcR for IgE |
| Vascular Cell Adhesion Molecule-1 | VCAM-1 | Inducible Cell Adhesion Molecule-110 (INCAM-110) (Immunoglobulin Family) | (Bacterial Endotoxin) IL-1, TNF-α | monocytes | CD14 |
| | | | | macrophages mast cells | CD14 FcR for IgE |

TABLE III-continued

POSSIBLE INDUCIBLE VASCULAR TARGETS

| INDUCIBLE ENDOTHELIAL CELL MOLECULES | ACRONYM | SUBTYPES/ALIASES (MOLECULAR FAMILY) | INDUCING CYTOKINES | LEUKOCYTES WHICH PRODUCE THOSE CYTOKINES | LEUKOCYTE MOLECULES WHICH, WHEN CROSSLINKED BY MONOCLONAL ANTIBODIES ACTIVATE THE CELLS TO PRODUCE CYTOKINES |
|---|---|---|---|---|---|
| | | | TNF-β, IL-4 | helper T cells | CD2, CD3, CD28 |
| | | | TNF | NK cells | FcR for IgG (CD16) |
| Intercellular Adhesion Molecule-1 | ICAM-1 | — (Immunoglobulin Family) | IL-1, TNFα (Bacterial Endotoxin) | monocytes | CD14 |
| | | | | macrophages | CD15 |
| | | | | mast cells | FcR for IgE |
| | | | TNF-β, IFNγ | T helper cells | CD2, CD3, CD28 |
| | | | | NK cells | FcR for IgG (CD16) |
| The Agent for Leukocyte Adhesion Molecule-1 | LAM-1 Agent | MEL-14 Agent (Mouse) | It-1, TNFα (Bacterial Endotoxin) | monocytes | CD14 |
| | | | | macrophages | CD14 |
| | | | | mast cells | FcR for IgE |
| Major Histocompatability Complex Class II Antigen | MHC Class, II | HLA-DR  - Human<br>HLA-DP<br>HLA-DQ<br>I-A       - Mouse<br>I-E | IFN-γ | helper T cells | CD2, CD3, CD28 |
| | | | | NK cells | FcR for IgG (CD16) |

It is important to note that, from the possible inducible markers listed in Table III, E-selectin and MHC Class II antigens, such as HLA-DR, HLA-DP and HLA-DQ (Collins et al., 1984), are by far the most preferred targets for use in connection with clinical embodiments. The other adhesion molecules of Table III appear to be expressed to varying degrees in normal tissues, generally in lymphoid organs and on endothelium, making their targeting perhaps appropriate only in animal models or in cases where their expression on normal tissues can be inhibited without significant side-effects. The targeting of E-selectin or an MHC Class II antigen is preferred as the expression of these antigens will likely be the most direct to promote selectively in tumor-associated endothelium.

E-selectin

The targeting of an antigen that is not expressed on the surfaces of normal endothelium is the most straightforward form of the induction methods. E-selectin is an adhesion molecule that is not expressed in normal endothelial vasculature or other human cell types (Cotran et al., 1986), but can be induced on the surface of endothelial cells through the action of cytokines such as IL-1, TNF, lymphotoxin and bacterial endotoxin (Bevilacqua et al., 1987). It is not induced by IFN-γ (Wu et al., 1990). The expression of E-selectin may thus be selectively induced in tumor endothelium through the selective delivery of such a cytokine, or via the use of a composition that causes the selective release of such cytokines in the tumor environment.

Bispecific antibodies are one example of a composition capable of causing the selective release of one or more of the foregoing or other appropriate cytokines in the tumor site, but not elsewhere in the body. Such bispecific antibodies are herein termed "antigen-inducing antibodies" and are, of course, distinct from any bispecific antibodies of the invention that have targeting and coagulating components. Antigen-inducing antibodies are designed to cross-link cytokine effector cells, such as cells of monocyte/macrophage lineage, T cells and/or NK cells or mast cells, with tumor cells of the targeted solid tumor mass. This cross-linking would then effect a release of cytokine that is localized to the site of cross-linking, i.e., the tumor.

Effective antigen-inducing antibodies recognize a selected tumor cell surface antigen on the one hand and, on the other hand, recognize a selected "cytokine activating" antigen on the surface of a selected leukocyte cell type. The term "cytokine activating" antigen is used to refer to any one of the various known molecules on the surfaces of leukocytes that, when bound by an effector molecule, such as an antibody or a fragment thereof or a naturally-occurring agent or synthetic analog thereof, be it a soluble factor or membrane-bound counter-receptor on another cell, promotes the release of a cytokine by the leukocyte cell. Examples of cytokine activating molecules include CD14 (the LPS receptor) and FcR for IgE, which will activate the release of IL-1 and TNFα; and CD16, CD2 or CD3 or CD28, which will activate the release of IFNγ and TNFβ, respectively.

Once introduced into the bloodstream of an animal bearing a tumor, such an antigen-inducing bispecific antibody will bind to tumor cells within the tumor, cross-link those tumor cells with effector cells, e.g., monocytes/macrophages, that have infiltrated the tumor, and thereafter effect the selective release of cytokine within the tumor. Importantly, however, without cross-linking of the tumor and leukocyte, the antigen-inducing antibody will not effect the release of cytokine. Thus, no cytokine release will occur in parts of the body removed from the tumor and, hence, expression of cytokine-induced molecules, e.g., E-selectin, will occur only within the tumor endothelium.

A number of useful "cytokine activating" antigens are known, which, when cross-linked with an appropriate bispecific antibody, will result in the release of cytokines by the cross-linked leukocyte. The generally preferred target for this purpose is CD14, which is found on the surface of monocytes and macrophages. When CD14 is cross linked it stimulates monocytes/macrophages to release IL-1 (Schutt et al., 1988;Chen et al., 1990), and possibly other cytokines, which, in turn stimulate the appearance of E-selectin on nearby vasculature. Other possible targets for cross-linking in connection with E-selectin induction and targeting include FcR for IgE, found on Mast cells; FcR for IgG (CD 16), found on NK cells; as well as CD2, CD3 or CD28, found on the surfaces of T cells. Of these, CD14 targeting is generally preferred due to the relative prevalence of monocyte/macrophage infiltration of solid tumors as opposed to the other leukocyte cell types.

In an exemplary induction embodiment, an animal bearing a solid tumor is injected with bispecific (Fab'—Fab') anti-CD14/anti-tumor antibody (such as anti-CEA, 9.2.27 antibody against high Mr melanoma antigens OV-TL3 or MOv 18 antibodies against ovarian associated antigens). The antibody localizes in the tumor, by virtue of its tumor binding activity, and then activates monocytes and macrophages in the tumor by crosslinking their CD14 antigens (Schutt et. al., 1988;Chen et. al., 1990). The activated monocytes/macrophages have tumoricidal activity (Palleroni et. al., 1991) and release IL-1 and TNF which rapidly induce E-selectin antigens on the tumor vascular endothelial cells (Bevilacqua et. al., 1987;Pober et. al., 1991).

MHC Class II Antigens

The second preferred group of inducible markers contemplated for use with the present invention are the MHC Class II antigens (Collins et al., 1984), including HLA-DR, HLA-DP and HLA-DQ. Class II antigens are expressed on vascular endothelial cells in most normal tissues in several species, including man. Studies in vitro (Collins et al., 1984;Daar et al., 1984; O'Connell et al., 1990) and in vivo (Groenewegen et al., 1985) have shown that the expression of Class II antigens by vascular endothelial cells requires the continuous presence of IFN-γ which is elaborated by $T_{H1}$ cells and, to a lesser extent, by NK cells and CD8$^+$ T cells.

MHC Class II antigens are not unique to vascular endothelial cells, and are also expressed constitutively on B cells, activated T cells, cells of monocyte/macrophage lineage and on certain epithelial cells, both in mice (Hammerling, 1976) and in man (Daar et al., 1984). Due to the expression of MHC Class II antigens on "normal" endothelium, their targeting is not quite so straightforward as E-selectin. However, the induction and targeting of MHC Class II antigens is made possible by using in conjunction with an immunosuppressant, such as Cyclosporin A (CsA), that has the ability to effectively inhibit the expression of Class II molecules in normal tissues (Groenewegen et al., 1985). The CsA acts by preventing the activation of T cells and NK cells (Groenewegen et al., 1985;DeFranco, 1991), thereby reducing the basal levels of IFN-γ below those needed to maintain Class II expression on endothelium.

There are various other cyclosporins related to CsA, including cyclosporins A, B, C, D, G, and the like, that also have immunosuppressive action and are likely to demonstrate an ability to suppress Class II expression. Other agents that might be similarly useful include FK506 and rapamycin.

Thus, the practice of the MHC Class II induction and targeting embodiment requires a pretreatment of the tumor-bearing animal with a dose of CsA or other Class II immunosuppressive agent that is effective to suppress Class II expression. In the case of CsA, this will typically be on the order of about 10 to about 30 mg/kg body weight. Once suppressed in normal tissues, Class II antigens can then be selectively induced in the tumor endothelium, again through the use of a bispecific antibody.

In this case, the antigen-inducing bispecific antibody will have specificity for a tumor cell marker and for an activating antigen found on the surface of an effector cell that is capable of inducing IFN-γ production. Such effector cells will generally be helper T cells ($T_H$) or Natural Killer (NK) cells. In these embodiments, it is necessary that T cells, or NK cells if CD16 is used, be present in the tumor to produce the cytokine intermediate in that Class II antigen expression is achieved using IFN-γ, but is not achieved with the other cytokines. Thus, for the practice of this aspect of the invention, one will desire to select CD2, CD3, CD28, or most preferably CD28, as the cytokine activating antigen for targeting by the antigen-inducing bispecific antibody.

The T cells that should be activated in the tumor are those adjacent to the vasculature since this is the region most accessible to cells and is also where the bispecific antibody will be most concentrated. The activated T cells should then secrete IFN-γ which induces Class II antigens on the adjacent tumor vasculature.

The use of a bispecific (Fab'—Fab') antibody having one arm directed against a tumor antigen and the other arm directed against CD28 is currently preferred. This antibody will cross-link CD28 antigens on T cells in the tumor which, when combined with a second signal (provided, for example, by IL-1 which is commonly secreted by tumor cells (Burrows et al., 1991;Ruco et al, 1990), has been shown to activate T cells through a $CA^{2+}$-independent non-CsA-inhibitable pathway (Hess et al., 1991;June et al., 1987;Bjorndahl et al., 1989).

The preparation of antibodies against various cytokine activating molecules is also well known in the art. For example, the preparation and use of anti-CD14 and anti-CD28 monoclonal antibodies having the ability to induce cytokine production by leukocytes has now been described by several laboratories (reviewed in Schutt et al., 1988;Chen et al., 1990, and June et al., 1990, respectively). Moreover, the preparation of monoclonal antibodies that will stimulate leukocyte release of cytokines through other mechanisms and other activating antigens is also known (Clark et al., 1986;Geppert et al., 1990).

In still further embodiments, the inventors contemplate an alternative approach for suppressing the expression of Class II molecules, and selectively eliciting Class II molecule expression in the locale of the tumor. This approach, which avoids the use of both CsA and a bispecific activating antibody, takes advantage of the fact that the expression of Class II molecules can be effectively inhibited by suppressing IFN-γ production by T cells, e.g., through use of an anti-CD4 antibody (Street et al., 1989). Using this embodiment, IFN-γ production is inhibited by administering anti-CD4, resulting in the general suppression of Class II expression. Class II is then induced only in the tumor site, e.g., using tumor-specific T cells which are only activatable within the tumor.

In this mode of treatment, one will generally pretreat an animal or human patient with a dose of anti-CD4 that is effective to suppress IFN-γ production and thereby suppress the expression of Class II molecules. Effective doses are contemplated to be, for example, on the order of about 4 to about 10 mg/kg body weight. After Class II expression is suppressed, one will then prepare and introduce into the bloodstream an IFN-γ-producing T cell clone (e.g., $T_h1$ or cytotoxic T lymphocyte, CTL) specific for an antigen expressed on the surface of the tumor cells. These T cells localizes to the tumor mass, due to their antigen recognition capability and, upon such recognition, then release IFN-γ. In this manner, cytokine release is again restricted to the tumor, thus limiting the expression of Class II molecules to the tumor vasculature.

The IFN-γ-producing T cell clone may be obtained from the peripheral blood (Mazzocchi et al., 1990), however, a preferred source is from within the tumor mass (Fox et al., 1990). The currently preferred means of preparing such a T cell clone is to remove a portion of the tumor mass from a patient; isolate cells, using collagenase digestion, where necessary; enrich for tumor infiltrating leukocytes using density gradient centrifugation, followed by depletion of other leukocyte subsets by, e.g., treatment with specific antibodies and complement; and then expand the tumor infiltrating leukocytes in vitro to provide the IFN-γ producing clone. This clone will necessarily be immunologically compatible with the patient, and therefore should be well tolerated by the patient.

It is proposed that particular benefits will be achieved by further selecting a high IFN-γ producing T cell clone from the expanded leukocytes by determining the cytokine secretion pattern of each individual clone every 14 days. To this end, rested clones will be mitogenically or antigenically-stimulated for about 24 hours and their culture supernatants assayed, e.g., using a specific sandwich ELISA technique (Cherwinski et al., 1989), for the presence of IL-2, IFN-γ, IL-4, IL-5 and IL-10. Those clones secreting high levels of IL-2 and IFN-γ, the characteristic cytokine secretion pattern of $T_{H1}$ clones, will be selected. Tumor specificity will be confirmed using proliferation assays.

Furthermore, one will prefer to employ as the anti-CD4 antibody an anti-CD4 Fab, because it will be eliminated from the body within 24 hours after injection and so will not cause suppression of the tumor-recognizing T-cell clones that are subsequently administered. The preparation of T cell clones having tumor specificity is generally known in the art, as exemplified by the production and characterization of T cell clones from lymphocytes infiltrating solid melanoma tumors (Maeda et al., 1991).

In using either of the MHC Class II suppression-induction methods, additional benefits will likely result from the fact that anti-Class II antibodies injected intravenously do not appear to reach the epithelial cells or the monocytes/macrophages in normal organs other than the liver and spleen. Presumably this is because the vascular endothelium in most normal organs is tight, not fenestrated as it is in the liver and spleen, and so the antibodies must diffuse across basement membranes to reach the Class II-positive cells. Also, any B cell elimination that may result, e.g., following cross-linking, is unlikely to pose a significant problem as these cells are replenished from Class II negative progenitors (Lowe et al., 1986). Even B cell killing, as occurs in B lymphoma patients, causes no obvious harm (Vitetta et al., 1991).

In summary, although the tumor coagulating compositions and antibodies of the present invention are elegantly simple, and do not require the induction of antigens for their operability, the combined use of an antigen-inducing bispecific antibody with this invention is also contemplated. Such antibodies would generally be administered prior to the bispecific coagulating ligands of this invention.

Generally speaking, the more "immunogenic" tumors would be more suitable for the MHC Class II approach involving, e.g., the cross-linking of T cells in the tumor through an anti-CD28/anti-tumor bispecific antibody, because these tumors are more likely to be infiltrated by T cells, a prerequisite for this method to be effective. Examples of immunogenic solid tumors include renal carcinomas, melanomas, a minority of breast and colon cancers, as well as possibly pancreatic, gastric, liver, lung and glial tumor cancers. These tumors are referred to as "immunogenic" because there is evidence that they elicit immune responses in the host and they have been found to be amenable to cellular immunotherapy (Yamaue et al., 1990). In the case of melanomas and large bowel cancers, the most preferred antibodies for use in these instances would be B72.3 (anti-TAG-72) and PRSC5/PR4C2 (anti-Lewis a) or 9.2.27 (anti-high Mr melanoma antigen).

For the majority of solid tumors of all origins, an anti-CD14 approach that employs a macrophage/monocyte intermediate would be more suitable. This is because most tumors are rich in macrophages. Examples of macrophage-rich tumors include most breast, colon and lung carcinomas. Examples of preferred anti-tumor antibodies for use in these instances would be anti-HER-2, B72.3, SM-3, HMFG-2, and SWA 11 (Smith et al., 1989).

(c) Coagulant-Inducible Markers

Coagulants, such as thrombin, Factor IX/IXa, Factor X/Xa, plasmin and metalloproteinases, such as interstitial collagenases, stromelysins and gelatinases, also act to induce certain markers. In particular, E-selectin, P-selectin, PDGF and ICAM-1 are induced by thrombin (Sugama et. al., 1992;Shankar et. al., 1994).

Therefore, for this induction, an anti-coagulant/anti-tumor bispecific antibody will be utilized. The antibody will localize in the tumor via its tumor binding activity. The bispecific will then concentrate the coagulant, e.g., thrombin, in the tumor, resulting in induction of E-selectin and P-selectin on the tumor vascular endothelial cells (Sugama et. al., 1991;Shankar et. al., 1994).

Alternatively, targeting of truncated Tissue Factor to tumor cells or endothelium will induce thrombin deposition within the tumor. As the thrombin is deposited, E-selectin and P-selectin will be induced on the tumor vascular endothelial cells.

(d) Antibodies to Vascular Endothelial Cell Markers

A straightforward means of recognizing a disease-associated vasculature target, whether induced in the natural environment or by artificial means, is through the use of an antibody that has binding affinity for the particular cell surface receptor, molecule or antigen. These include antibodies directed against all cell surface components that are known to be present on, e.g., tumor vascular endothelial cells, those that are induced or over-expressed in response to tumor-derived factors, and those that are induced following manipulation by the hand of man.

Anti-vWF recognizes the antigen VIII R Ag and stains 100% of tumor types presented and stains 100% of the vessels in the tumor and presents a strong staining pattern in normal vessels. FB5 recognizes the antigen endosialin and stains 50% of tumor types presented and stains 10–30% of the vessels in the tumor and presents a staining pattern in normal vessels in the lymphoid organs. TP3 recognizes the antigen 80 kDa osteosarcoma related antigen protein and stains 50% of tumor types presented and stains 10–30% of the vessels in the tumor and presents a strong staining pattern in normal vessels on the small blood vessels. BC-1 recognizes the antigen fibronectin isoforms and stains 60% of tumor types presented and stains 10–30% of the vessels in the tumor and presents no staining pattern in normal vessels. TV-1 recognizes the antigen fibronectin and stains 100% of tumor types presented and stains 100% of the vessels in the tumor and presents a strong staining pattern in all normal vessels. LM 609 recognizes the $\alpha_v\beta_e$ vitronectin receptor and stains 85% of tumor types presented and stains 70–80% of the vessels in the tumor and presents a medium staining pattern in normal vessels. TEC-11 recognizes endoglin and stains 100% of tumor types presented and stains 100% of the vessels in the tumor and present a weak staining pattern in most normal vessels. TEC 110 recognizes antigens VEGF and stains 100% of tumor types presented and stains 100% of the vessels in the tumor and present a weak staining pattern in most normal vessels.

In a comparative study of anti-EC mAbs on human tumors it was found that TEC 110, TV-1, and TEC 11, were positive in gastrointestinal, parotid, breast, ovarian uterine, lung and Hodgkin's type tumors. Whereas FB-5 had a slight staining in gastrointestinal and lung tumors and was negative in the other tumors listed. TP-3 was positive in gastrointestinal tumors and less so in parotid tumor types, ovarian and Hodgkins type tumors. BC-1 was positive for gastrointestinal tumors as wells as the reproductive and respiratory tumors IM 609 was positive in gastrointestinal, ovarian, uterine lung and Hodgkin's tumors as wells as the reproductive, and respiratory tumors.

Two further antibodies that may be used in this invention are those described by Rettig et al. (1992) and Wang et al. (1993) that are directed against unrelated antigens of unknown function expressed in the vasculature of human tumors, but not in most normal tissues.

The antibody described by Kim et. al. (1993) may also be used in this invention, particularly as this antibody inhibited angiogenesis and suppressed tumor growth in vivo.

Antibodies that have not previously been shown to be specific for human tumors may also be used. For example, Venkateswaran et al. (1992) described the production of anti-FGF MAbs. Xu et. al. (1992) developed and characterized a panel of 16 isoform and domain-specific polyclonal and monoclonal antibodies against FGF receptor (flg) isoforms. Massoglia et al. (1987) also reported MAbs against the FGF receptor.

(e) Generation of Antibodies to Disease Vasculature

In addition to utilizing a known antibody, such as those described above and others known and published in the scientific literature, one may also generate a novel antibody using standard immunization procedures, as described in more detail hereinbelow. To generate an antibody against a known disease-associated vascular marker antigen, one would immunize an animal with an immunogenic composition comprising the antigen. This may be a membrane preparation that includes, or is enriched for, the antigen; a relatively purified form of the antigen, as isolated from cells or membranes; a highly purified form of the antigen, as obtained by a variety of purification steps using, e.g., a native antigen extract or a recombinant form of the antigen obtained from a recombinant host cell.

The present invention also provides yet further methods for generating an antibody against an antigen present on disease-associated vasculature endothelial cells, which methods are suitable for use even where the biochemical identity of the antigen remains unknown. These methods are exemplified through the generation of an antibody against tumor vasculature endothelial cells. A first means of achieving antibody generation in this manner uses a preparation of vascular endothelial cells obtained from the tumor site of an animal or human patient. One simply immunizes an experimental animal with a preparation of such cells and collects the antibodies so produced. The most useful form of this method is that where specific antibodies are subsequently selected, as may be achieved using conventional hybridoma technology and screening against tumor vascular endothelial cells.

A development of the above method is that which mimics the tumor vasculature phenomenon in vitro, and where cell purification is not necessary. In using this method, endothelial cells are subjected to tumor-derived products, such as might be obtained from tumor-conditioned media, in cell culture rather than in an animal. This method generally involves stimulating endothelial cells with tumor-conditioned medium and employing the stimulated endothelial cells as immunogens to prepare a collection of antibodies. Again, specific antibodies should be selected, e.g., using conventional monoclonal antibody technology, or other techniques such as combinatorial immunoglobulin phagemid libraries prepared from RNA isolated from the spleen of the immunized animal. One would select a specific antibody that preferentially recognizes tumor-stimulated vascular endothelium and reacts more strongly with tumor-associated endothelial cells than with normal adult human tissues.

(f) Anti-Endoglin Antibodies

Antibodies having relative specificity for tumor vascular endothelium have been prepared and isolated by one of the inventors. The MAbs termed tumor endothelial cell antibody 4 and tumor endothelial cell antibody 11 (TEC4 and TEC11) were obtained using the above method (U.S. Ser. Nos. 08/457,229 and 08/457,031, each incorporated herein by reference). The antigen recognized by TEC4 and TEC11 was ultimately determined to be the molecule endoglin. The epitopes on endoglin recognized by TEC4 and TEC11 are present on the cell surface of stimulated HUVE cells, and only minimally present (or immunologically accessible) on the surface of non-stimulated cells. MAbs have previously been raised against endoglin. However, analyzing the reactivity with HUVEC or TCM-activated HUVEC cell surface determinants by FACS or indirect immunofluorescence shows the epitopes recognized by TEC-4 and TEC-11 to be distinct from those of a previous antibody termed 44G4 (Gougos and Letarte, 1988).

(g) Use of Vascular Endothelial Cell Binding Ligands

Biological ligands that are known to bind or interact with endothelial cell surface molecules, such as growth factor receptors, may also be employed as a targeting component.

The growth factors or ligands contemplated to be useful as targets in this sense include VEGF/VPF, FGF, TGFβ, ligands that bind to a TIE, tumor-associated fibronectin isoforms, scatter factor, hepatocyte growth factor (HGF), platelet factor 4 (PF4), PDGF and TIMP.

Particularly preferred targets are VEGF/VPF, the FGF family of proteins and TGFβ. Abraham et al. (1986) cloned FGF, which is therefore available as a recombinant protein. As reported by Ferrara et al. (1991), four species of VEGF having 121, 165, 189, and 206 amino acids have been cloned.

(h) Targeting of Bound Ligands

Antibodies or specific targeting ligands may also be directed to any component that binds to the surface of vascular endothelial cells in a disease site, such as a tumor. Such components are exemplified by tumor-derived ligands and antigens, such as growth factors, that bind to specific cell surface receptors already present on the endothelial cells, or to receptors that have been induced, or overexpressed, on such cells in response to the tumor environment. Tumor vasculature-associated targets may also be termed tumor-derived endothelial cell binding factors.

A level of specificity required for successful disease targeting will be achieved partly because the local endothelial cells will be induced to express, or reveal, receptors that are not present, or are under-expressed or masked, on normal endothelial cells. With tumors, further specificity will result due to the fact that endothelial cells in the tumor will capture the tumor-derived factors, and bind them to the cell surface, reducing the amount of ligand available for other tissues. When combined with the further dilution of the factor or ligand by distribution in the blood and tissue fluid pool, endothelial cells in normal tissues will be expected to bind relatively little of such factors. Thus, operationally, cell-surface bound ligands or factors will be able to used as a tumor endothelial cell marker.

In addition to manufacture by the tumor cells themselves, tumor endothelial cell binding factors may also originate from other cell types, such as macrophages and mast cells, that have infiltrated tumors, or may be elaborated by platelets that become activated within the tumor.

Further growth factors or ligands contemplated to be useful as tumor vasculature-associated targeting agents include EGF, FGF, VEGF, TGFβ, HGF (NaKamura, 1991), angiotropin, TGF-α, TNF-α, PD-ECGF and TIE binding ligands (Bicknell and Harris, 1992). The currently preferred targeting agents are VEGF/VPF, the FGF family of proteins, transforming growth factor-β (TGF-β); TGF-α; tumor necrosis factor-α (TNF-α); angiotropin; platelet-derived endothelial cell growth factor (PD-ECGF); TIE binding ligands; pleiotropin. In addition, non-antibody targeting components, such as annexins and peptides comprising the tripeptide sequence R-G-D, which specifically target the tumor vasculature (Pasqualini et al., 1997), are also contemplated for use in certain aspects of the invention.

Another aspect of the present invention is the use of targeting antibodies, or binding regions therefrom, that are specific for epitopes present only on ligand-receptor complexes, which epitopes are absent from both the individual (free) ligand and the receptor in its unbound form. These antibodies recognize and bind to the unique conformation that results when a ligand, such as a growth factor, binds to its receptor, such as a growth factor receptor, to form a specifically bound complex. Such epitopes are not present on the uncomplexed forms of the ligands or receptors.

The inventors contemplate that the ligand-receptor complexes to which these antibodies bind are present in significantly higher number on tumor-associated endothelial cells than on non-tumor associated endothelial cells. Such antibodies will therefore be useful as targeting agents and will serve to further increase the specificity of the bispecific coagulants of the invention.

(i) Receptor Constructs

Soluble binding domains of endothelial cell surface receptors are also contemplated for use as targeting ligands in the present invention. This concept is generally based upon the well-known sandwich binding phenomena that has been exploited in a variety of in vitro and in vivo binding protocols. Basically, as the endothelial cells express specific receptors, the cells bind to and adsorb the corresponding ligands, the ligands are then available for binding to further receptor constructs should they be introduced into the system.

A range of useful endothelial cell receptors has been identified in the foregoing sections, with VEGF/VPF, FGF, TGFβ, TIE-1 and TIE-2 being particularly preferred targets. Each of these receptors could be manipulated to form a soluble binding domain for use as a targeting ligand.

iv. Disease-Associated Stromal Cell Targets (a) Extracellular Matrix/Stromal Targets The usefulness of the basement membrane markers in tumoral pathology was described by Birembaut et al. (1985). These studies showed that the distribution of basement membrane (BM) markers, type IV collagen, laminin (LM), heparan sulphate proteoglycan (HSP) and fibronectin (FN) were disrupted in tumoral pathology. Burtin et. al. (1983) also described alterations of the basement membrane and connective tissue antigens in human metastatic lymph nodes.

A preferred target for use with the invention is RIBS. Ugarova et al. (1993) reported that conformational changes occur in fibrinogen and are elicited by its interaction with the platelet membrane glycoprotein GPIIb-IIIa. The binding of fibrinogen to membrane glycoprotein GPIIb-IIIa on activated platelets leads to platelet aggregation. This interaction results in conformational changes in fibrinogen as evidenced by the expression of receptor-induced binding sites, RIBS, epitopes which are expressed by the bound but not the free ligand.

Two RIBS epitopes have been localized by Ugarova et al. (1993). One sequence resides at γ112–119 and is recognized by MAb 9F9;the second is the RGDF sequence at Aα 95–98 and is recognized by mAb 155B16. These epitopes are also exposed by adsorption of fibrinogen onto a plastic surface and digestion of the molecule by plasmin. Proteolytic exposure of the epitopes coincides with cleavage of the carboxyl-terminal aspects of the Aα-chains to form fragment $X_2$. The inaccessibility of the RGDF sequence at Aα 95–98 in fibrinogen suggests that this sequence does not participate in the initial binding of the molecule to GPIIb-IIIa.

Binding of fibrinogen to its receptor alters the conformation of the carboxyl-terminal aspects of the Aα-chains, exposing the sequences which reside in the coiled-coil connector segments between the D and E domains of the molecule, generating the RIBS epitopes. In practical terms, the RIBS sequences are proposed as epitopes for use in targeting with a coaguligand. The MAbs 9F9 and 155B16 may thus be advantageously used, as may the antibodies described by Zamarron et al. (1991).

(b) Additional Cellular Targets

The combinations for use in the present invention have the further advantage that they may be used to direct coagulants to disease-associated vasculature by targeting them to cell types found within the disease region.

Platelets participate in hemostasis and thrombosis by adhering to injured blood vessel walls and accumulating at the site of injury. Although platelet deposition at sites of blood vessel injury is responsible for the primary arrest of bleeding under physiologic conditions, it can lead to vascular occlusion with ensuing ischemic tissue damage and thrombus embolization under pathologic conditions.

Interactions of platelets with their environment and with each other represent complex processes that are initiated at the cell surface. The surface membrane, therefore, provides a reactive interface between the external medium, including components of the blood vessel wall and plasma, and the platelet interior.

p-155, a multimeric platelet protein that is expressed on activated platelets (Hayward et al., 1991), may be targeted using the invention. Platelets respond to a large number of stimuli by undergoing complex biochemical and morphological changes. These changes are involved in physiological processes including adhesion, aggregation, and coagulation. Platelet activation produces membrane alterations that can be recognized by monoclonal antibodies. The monoclonal antibody JS-1 (Hayward et al., 1991) is one such antibody contemplated for use as part of a coaguligand.

Ligand-induced binding sites (LIBS) are sites expressed on cell surface receptors only after ligand binding causes the receptor to change shape, mediate subsequent biological events. These may be seen as counterparts to RIBS and are also preferred targets for use with the present invention.

13 anti-LIBS antibodies have been developed by Frelinger et. al. (1990; 1991), any one of which may be used to deliver a coagulant to a disease or tumor site in accordance herewith. The murine monoclonal anti-platelet antibodies MA-TSPI-1 (directed against human thrombospondin) and MA-PMI-2, MA-PMI-1, and MA-LIBS-1 (directed against LIBS on human platelet glycoprotein IIb/IIIa) of Dewerchin et al. (1991) may also be used, as may RUU 2.41 and LIBS-1 of Heynen et al. (1994); OP-G2 of Tomiyama et al. (1992); and Ab-15.

Many other targets, such as antigens on smooth muscle cells, pericytes, fibroblasts, macrophages and infiltrating lymphocytes and leukocytes may also be used.

v. Toxins

For certain applications, it is envisioned that the second therapeutic agents will be pharmacological agents attached to antibodies or growth factors, particularly cytotoxic or otherwise anti-cellular agents having the ability to kill or suppress the growth or cell division of endothelial cells. In general, the secondary aspects of the invention contemplate the use of any pharmacological agent that can be conjugated to a targeting agent, preferably an antibody, and delivered in active form to the targeted endothelium or stroma. Exemplary anti-cellular agents include chemotherapeutic agents, radioisotopes as well as cytotoxins. In the case of chemotherapeutic agents, the inventors propose that agents such as a hormone such as a steroid; an anti-metabolite such as cytosine arabinoside, fluorouracil, methotrexate or aminopterin; an anthracycline; mitomycin C; a vinca alkaloid; demecolcine; etoposide; mithramycin; or an anti-tumor alkylating agent such as chlorambucil or melphalan, will be particularly preferred. Other embodiments may include agents such as a cytokine, growth factor, bacterial endotoxin or the lipid A moiety of bacterial endotoxin. In any event, it is proposed that agents such as these may, if desired, be successfully conjugated to a targeting agent, preferably an antibody, in a manner that will allow their targeting, internalization, release or presentation to blood components at the site of the targeted endothelial cells as required using known conjugation technology (see, e.g., Ghose et al., 1983 and Ghose et al., 1987).

In certain preferred embodiments, the immunotoxins will include generally a plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. The use of toxin-antibody constructs is well known in the art of immunotoxins, as is their attachment to antibodies. Of these, a particularly preferred toxin for attachment to antibodies will be a deglycosylated ricin A chain. Deglycosylated ricin A chain is preferred because of its extreme potency, longer half-life, and because it is economically feasible to manufacture it a clinical grade and scale.

(a) Preparation of Targeting Agent-Toxin Conjugates

While the preparation of immunotoxins is, in general, well known in the art (see, e.g., patents U.S. Pat. No. 4,340,535, and EP 44167, both incorporated herein by reference), the inventors are aware that certain advantages may be achieved through the application of certain preferred technology, both in the preparation of the immunotoxins and in their purification for subsequent clinical administration. For example, while IgG based immunotoxins will typically exhibit better binding capability and slower blood clearance than their Fab' counterparts, Fab' fragment-based immunotoxins will generally exhibit better tissue penetrating capability as compared to IgG based immunotoxins.

Additionally, while numerous types of disulfide-bond containing linkers are known which can successfully be employed to conjugate the toxin moiety with the targeting agent, certain linkers will generally be preferred over other linkers, based on differing pharmacological characteristics and capabilities. For example, linkers that contain a disulfide bond that is sterically "hindered" are to be preferred, due to their greater stability in vivo, thus preventing release of the toxin moiety prior to binding at the site of action. Furthermore, while certain advantages in accordance with the invention will be realized through the use of any of a number of toxin moieties, the inventors have found that the use of ricin A chain, and even more preferably deglycosylated A chain, will provide particular benefits.

A wide variety of cytotoxic agents are known that may be conjugated to anti-endothelial cell antibodies. Examples include numerous useful plant-, fungus- or even bacteria-derived toxins, which, by way of example, include various A chain toxins, particularly ricin A chain, ribosome inactivating proteins such as saporin or gelonin, α-sarcin, aspergillin, restrictocin, ribonucleases such as placental ribonuclease, angiogenic, diphtheria toxin, and pseudomonas exotoxin, to name just a few. The most preferred toxin moiety for use in connection with the invention is toxin A chain which has been treated to modify or remove carbohydrate residues, so called deglycosylated A chain. The inventors have had the best success through the use of deglycosylated ricin A chain (dgA) which is now available commercially from Inland Laboratories, Austin, Tex.

However, it may be desirable from a pharmacological standpoint to employ the smallest molecule possible that nevertheless provides an appropriate biological response. One may thus desire to employ smaller A chain peptides which will provide an adequate anti-cellular response. To this end, it has been discovered by others that ricin A chain may be "truncated" by the removal of 30 N-terminal amino acids by Nagarase (Sigma), and still retain an adequate toxin activity. It is proposed that where desired, this truncated A chain may be employed in conjugates in accordance with the invention.

Alternatively, one may find that the application of recombinant DNA technology to the toxin A chain moiety will provide additional significant benefits in accordance the invention. In that the cloning and expression of biologically active ricin A chain has now been enabled through the publications of others (O'Hare et al., 1987;Lamb et al., 1985;Halling et al., 1985), it is now possible to identify and prepare smaller or otherwise variant peptides which nevertheless exhibit an appropriate toxin activity. Moreover, the fact that ricin A chain has now been cloned allows the application of site-directed mutagenesis, through which one can readily prepare and screen for A chain derived peptides and obtain additional useful moieties for use in connection with the present invention.

The cross-linking of the toxin A chain region of the conjugate with the targeting agent region is an important aspect of the invention. In certain cases, it is required that a cross-linker which presents disulfide function be utilized for the conjugate to have biological activity. The reason for this is unclear, but is likely due to a need for certain toxin moieties to be readily releasable from the targeting agent once the agent has "delivered" the toxin to the targeted cells. Each type of cross-linker, as well as how the cross-linking is performed, will tend to vary the pharmacodynamics of the resultant conjugate. Ultimately, in cases where a releasable toxin is contemplated, one desires to have a conjugate that will remain intact under conditions found everywhere in the body except the intended site of action, at which point it is desirable that the conjugate have good "release" characteristics. Therefore, the particular cross-linking scheme, including in particular the particular cross-linking reagent used and the structures that are cross-linked, will be of some significance.

Depending on the specific toxin compound used as part of the fusion protein, it may be necessary to provide a peptide spacer operatively attaching the targeting agent and the toxin compound which is capable of folding into a disulfide-bonded loop structure. Proteolytic cleavage within the loop would then yield a heterodimeric polypeptide wherein the targeting agent and the toxin compound are linked by only a single disulfide bond. See, for example, Lord et al. (1992). An example of such a toxin is a Ricin A-chain toxin.

When certain other toxin compounds are utilized, a non-cleavable peptide spacer may be provided to operatively attach the targeting agent and the toxin compound of the fusion protein. Toxins which may be used in conjunction with non-cleavable peptide spacers are those which may, themselves, be converted by proteolytic cleavage, into a cytotoxic disulfide-bonded form (see for example, Ogata et al., 1990). An example of such a toxin compound is a Pseudonomas exotoxin compound.

Nucleic acids that may be utilized herein comprise nucleic acid sequences that encode a targeting agent of interest and nucleic acid sequences that encode a toxin agent of interest. Such target agent-encoding and toxin agent-encoding nucleic acid sequences are attached in a manner such that translation of the nucleic acid yields the targeting agent/toxin compounds of the invention.

(b) Attachment of Other Agents to Targeting Agents

It is contemplated that most therapeutic applications of the additional IT aspects of the present invention will involve the targeting of a toxin moiety to the tumor endothelium or stroma. This is due to the much greater ability of most toxins to deliver a cell killing effect as compared to other potential agents. However, there may be circumstances, such as when the target antigen does not internalize by a route consistent with efficient intoxication by targeting agent/toxin compounds, such as immunotoxins, where one will desire to target chemotherapeutic agents such as anti-tumor drugs, other cytokines, antimetabolites, alkylating agents, hormones, and the like. The advantages of these agents over their non-targeting agent conjugated counterparts is the added selectivity afforded by the targeting agent, such as an antibody. One might mention by way of example agents such as steroids, cytosine arabinoside, methotrexate, aminopterin, anthracyclines, mitomycin C, vinca alkaloids, demecolcine, etoposide, mithramycin, and the like. This list is, of course, merely exemplary in that the technology for attaching pharmaceutical agents to targeting agents, such as antibodies, for specific delivery to tissues is well established (see, e.g., Ghose and Blair, 1987).

A variety of chemotherapeutic and other pharmacological agents have now been successfully conjugated to antibodies and shown to function pharmacologically (see, e.g., Vaickus et al., 1991). Exemplary antineoplastic agents that have been investigated include doxorubicin, daunomycin, methotrexate, vinblastine, and various others (Dillman et al., 1988; Pietersz et al., 1988). Moreover, the attachment of other agents such as neocarzinostatin (Kimura et al., 1983), macromycin (Manabe et al., 1984), trenimon (Ghose, 1982) and α-amanitin (Davis and Preston, 1981) has been described.

vi. Coaguligands

The second, targeted agent for optional use with the invention may also comprise a targeted component that is capable of promoting coagulation. Such "targeted coagulation promoting agents" or "coaguligands" include any of the foregoing targeting agents that are operably associated with one or more coagulation factors. The targeting agent may be directly linked to a factor that directly or indirectly stimulates coagulation, or the targeting agent may linked to a second binding region that is capable of binding and releasing a coagulation factor that directly or indirectly stimulates coagulation.

(a) Coagulation Factors

Exemplary coagulation factors are the types of tTF, dimeric, multimeric and mutant molecules of the present invention, as described in detail herein.

A variety of other coagulation factors may be used in connection with the present invention, as exemplified by the agents set forth below. Where a coagulation factor is covalently linked to a first binding or targeting agent, a site distinct from its functional coagulating site is used to join the molecules. Appropriate joining regions distinct from the active sites, or functional regions, of the coagulation factors are also described in each of the following sections.

Clotting Factors

Thrombin, Factor V/Va and derivatives, Factor VIII/VIIIa and derivatives, Factor IX/IXa and derivatives, Factor X/Xa and derivatives, Factor XI/XIa and derivatives, Factor XII/XIIa and derivatives, Factor XIII/XIIIa and derivatives, Factor X activator and Factor V activator may also be used in the present invention.

Venom Coagulants

Russell's viper venom was shown to contain a coagulant protein by Williams and Esnouf in 1962. Kisiel (1979) isolated a venom glycoprotein that activates Factor V; and Di Scipio et al. (1977) showed that a protease from the venom activates human Factor X. The Factor X activator is the component contemplated for use in this invention.

Monoclonal antibodies specific for the Factor X activator present in Russell's viper venom have also been produced (e.g., MP1 of Pukrittayakamee et al., 1983), and could be used to deliver the agent to a specific target site within the body.

Prostaglandins and Synthetic Enzymes

Thromboxane $A_2$ is formed from endoperoxides by the sequential actions of the enzymes cyclooxygenase and thromboxane synthetase in platelet microsomes. Thromboxane $A_2$ is readily generated by platelets and is a potent vasoconstrictor, by virtue of its capacity to produce platelet aggregation (Whittle et al., 1981).

Both thromboxane $A_2$ and active analogues thereof are contemplated for use in the present invention. A synthetic protocol for generating thromboxane $A_2$ is described by Bhagwat et al. (1985). The thromboxane $A_2$ analogues described by Ohuchida et. al. (1981) (especially compound 2) are particularly contemplated for use herewith.

It is possible that thromboxane synthase, and other enzymes that synthesize platelet-activating prostaglandins, may also be used as "coagulants" in the present context. Shen and Tai (1986) describe monoclonal antibodies to, and immunoaffinity purification of, thromboxane synthase; and Wang et. al. (1991) report the cDNA for human thromboxane synthase.

Inhibitors of Fibrinolysis

α2-antiplasmin, or α2-plasmin inhibitor, is a proteinase inhibitor naturally present in human plasma that functions to efficiently inhibit the lysis of fibrin clots induced by plasminogen activator (Moroi and Aoki, 1976). α2-antiplasmin is a particularly potent inhibitor, and is contemplated for use in the present invention.

α2-antiplasmin may be purified as first described by Moroi and Aoki (1976). Other purification schemes are also available, such as using affinity chromatography on plasminogen-Sepharose, ion-exchange chromatography on DEAE-Sephadex and chromatography on Concanavalin-A-Sepharose; or using affinity chromatography on a Sepharose column bearing an elastase-digested plasminogen formulation containing the three N-terminal triple-loop structures in the plasmin A-chain (LBSI), followed by gel filtration (Wiman and Collen, 1977;Wiman, 1980, respectively).

As the cDNA sequence for α2-antiplasmin is available (Tone et al., 1977), a preferred method for α2-antiplasmin production will be via recombinant expression.

Monoclonal antibodies against α2-antiplasmin are also available that may be used in the bispecific binding ligand embodiments of the invention. For example, Hattey et al. (1987) described two MAbs against α2-antiplasmin, MPW2AP and MPW3AP. As each of these MAbs were reported to react equally well with native α2-antiplasmin, they could both be used to deliver exogenous α2-antiplasmin to a target site or to garner endogenous α2-antiplasmin and concentrate it within the targeted region. Other antibodies, such as JTPI-2, described by Mimuro and colleagues, could also be used.

(b) Agents That Bind Coagulation Factors

Another group of targeted coagulating ligands for use with the TFs of this invention are those in which the targeting region is not directly linked to a coagulation factor, but is linked to a second binding region that binds to a coagulating factor.

Where a second binding region is used to bind and deliver a coagulation factor, the binding region is chosen so that it recognizes a site on the coagulation factor that does not significantly impair its ability to induce coagulation. The regions of the coagulation factors suitable for binding in this manner will generally be the same as those regions that are suitable for covalent linking to the targeting region, as described in the previous sections.

However, in that bispecific ligands of this class may be expected to release the coagulation factor following delivery to the tumor site or region, there is more flexibility allowed in the regions of the coagulation factor suitable for binding to a second binding agent or antibody.

Suitable second binding regions for use in this manner, will generally be antigen combining sites of antibodies that have binding specificity for the coagulation factor, including functional portions of antibodies, such as scFv, Fv, Fab', Fab and F(ab')$_2$ fragments.

Bispecific binding ligands that contain antibodies, or fragments thereof, directed against Tissue Factor, Thrombin, Prekallikein, Factor V/Va, Factor VIII/VIIIa, Factor IX/IXa, Factor XIXa, Factor XI/XIa, Factor XII/XIIa, Factor XIII/XIIIa, Russell's viper venom, thromboxane $A_2$ or α2-antiplasmin are exemplary embodiments of this aspect of the invention.

(c) TF Prodrugs

Exemplary tTF prodrugs have the following structures: $tTF_{1-219} (X)_{n1} (Y)_{n2}$ Z Ligand, where $tTF_{1-219}$ represents TF minus the cytosolic and transmembrane domains; X represents a hydrophobic transmembrane domain n1 amino acids (AA) in length (n=1–20 AA); Y represents a hydrophilic protease recognition sequence of n2 AA in length (sufficient AA to ensure appropriate protease recognition); Z represents a disulfide thioester or other linking group such as $(Cys)_{1-2}$; Ligand represents an antibody or other targeting moiety recognizing tumor-cells, tumor EC, connective tissue (stroma) or basal lamina markers.

The tTF prodrug is contemplated for injection intravenously allowing it to localize to diseased tissue (e.g., tumor). Once localized in the diseased tissue, endogenous proteases (e.g., metalloproteinases, thrombin, Factor Xa, Factor VIIa, Factor IXa, plasmin) will cleave the hydrophilic protease recognition sequence from the prodrug which will allow the hydrophobic transmembrane sequence to insert into a local cell membrane. Once the tail has inserted into the membrane, the tTF will regain its coagulation-inducing properties resulting in clot formation in the vasculature of the diseased tissue.

(d) Bispecific Antibodies

In general, the preparation of bispecific antibodies is also well known in the art, as exemplified by Glennie et al. (1987). Bispecific antibodies have been employed clinically, for example, to treat cancer patients (Bauer et al., 1991). One method for the preparation of bispecific antibodies involves the separate preparation of antibodies having specificity for the targeted tumor cell antigen, on the one hand, and the coagulating agent (or other desired target, such as an activating antigen) on the other.

Bispecific antibodies have also been developed particularly for use as immunotherapeutic agents. As mentioned earlier in conjunction with antigen-induction, certain of these antibodies were developed to cross-link lymphocytes and tumor antigens (Nelson, 1991;Segal et al., 1992). Examples include chimeric molecules that bind T cells, e.g., at CD3, and tumor antigens, and trigger lymphocyte-activation by physically cross-linking the TCR/CD3 complex in close proximity to the target cell (Staerz et al., 1985;Perez et al., 1985; 1986a;1986b; Ting et al., 1988).

Indeed, tumor cells of carcinomas, lymphomas, leukemias and melanomas have been reported to be susceptible to bispecific antibody-mediated killing by T cells (Nelson, 1991;Segal et al., 1992;deLeij et al., 1991). These type of bispecific antibodies have also been used in several Phase I clinical trials against diverse tumor targets. The bispecific cross-linking antibodies may be administered as described in references such as deLeij et al. (1991); Clark et al. (1991); Rivoltini et al. (1992); Bolhuis et al. (1992); and Nitta et al. (1990).

While numerous methods are known in the art for the preparation of bispecific antibodies, the Glennie et al. (1987) method involves the preparation of peptic F(ab'γ)$_2$ fragments from the two chosen antibodies, followed by reduction of each to provide separate Fab'γsh fragments. The SH groups on one of the two partners to be coupled are then alkylated with a cross-linking reagent such as o-phenylenedimaleimide to provide free maleimide groups on one partner. This partner may then be conjugated to the other by means of a thioether linkage, to give the desired F(ab'γ)$_2$ heteroconjugate.

Due to ease of preparation, high yield and reproducibility, the Glennie et al. (1987) method is often preferred for the preparation of bispecific antibodies, however, there are numerous other approaches that can be employed and that are envisioned by the inventors. For example, other techniques are known wherein cross-linking with SPDP or protein A is carried out, or a trispecific construct is prepared (Titus et al., 1987; Tutt et al., 1991).

Another method for producing bispecific antibodies is by the fusion of two hybridomas to form a quadroma (Flavell et al., 1991, 1992; Pimm et al., 1992; French et al., 1991; Embleton et al., 1991). As used herein, the term "quadroma" is used to describe the productive fusion of two B cell hybridomas. Using now standard techniques, two antibody producing hybridomas are fused to give daughter cells, and those cells that have maintained the expression of both sets of clonotype immunoglobulin genes are then selected.

A preferred method of generating a quadroma involves the selection of an enzyme deficient mutant of at least one of the parental hybridomas. This first mutant hybridoma cell line is then fused to cells of a second hybridoma that had been lethally exposed, e.g., to iodoacetamide, precluding its continued survival. Cell fusion allows for the rescue of the first hybridoma by acquiring the gene for its enzyme deficiency from the lethally treated hybridoma, and the rescue of the second hybridoma through fusion to the first hybridoma. Preferred, but not required, is the fusion of immunoglobulins of the same isotype, but of a different subclass. A mixed subclass antibody permits the use if an alternative assay for the isolation of a preferred quadroma.

In more detail, one method of quadroma development and screening involves obtaining a hybridoma line that secretes the first chosen MAb and making this deficient for the essential metabolic enzyme, hypoxanthine-guanine phosphoribosyltransferase (HGPRT). To obtain deficient mutants of the hybridoma, cells are grown in the presence of increasing concentrations of 8-azaguanine ($1\times10^{-7}$M to $1\times10^{-5}$M). The mutants are subdloned by limiting dilution and tested for their hypoxanthine/aminopterin/thymidine (HAT) sensitivity. The culture medium may consist of, for example, DMEM supplemented with 10% FCS, 2 mM L-Glutamine and 1 mM penicillin-streptomycin.

A complementary hybridoma cell line that produces the second desired MAb is used to generate the quadromas by standard cell fusion techniques (Galfre et al., 1981), or by using the protocol described by Clark et al. (1988). Briefly, $4.5\times10^7$ HAT-sensitive first cells are mixed with $2.8\times10^7$ HAT-resistant second cells that have been pre-treated with a lethal dose of the irreversible biochemical inhibitor iodoacetamide (5 mM in phosphate buffered saline) for 30 minutes on ice before fusion. Cell fusion is induced using polyethylene glycol (PEG) and the cells are plated out in 96 well microculture plates. Quadromas are selected using HAT-containing medium. Bispecific antibody-containing cultures are identified using, for example, a solid phase isotype-specific ELISA and isotype-specific immunofluorescence staining.

In one identification embodiment to identify the bispecific antibody, the wells of microtiter plates (Falcon, Becton Dickinson Labware) are coated with a reagent that specifically interacts with one of the parent hybridoma antibodies and that lacks cross-reactivity with both antibodies. The plates are washed, blocked, and the supernatants (SNs) to be tested are added to each well. Plates are incubated at room temperature for 2 hours, the supernatants discarded, the plates washed, and diluted alkaline phosphatase-antiantibody conjugate added for 2 hours at room temperature. The plates are washed and a phosphatase substrate, e.g., P-Nitrophenyl phosphate (Sigma, St. Louis) is added to each well. Plates are incubated, 3N NaOH is added to each well to stop the reaction, and the $OD_{410}$ values determined using an ELISA reader.

In another identification embodiment, microtiter plates pre-treated with poly-L-lysine are used to bind one of the target cells to each well, the cells are then fixed, e.g. using 1% glutaraldehyde, and the bispecific antibodies are tested for their ability to bind to the intact cell. In addition, FACS, immunofluorescence staining, idiotype specific antibodies, antigen binding competition assays, and other methods common in the art of antibody characterization may be used in conjunction with the present invention to identify preferred quadromas.

Following the isolation of the quadroma, the bispecific antibodies are purified away from other cell products. This may be accomplished by a variety of protein isolation procedures, known to those skilled in the art of immunoglobulin purification. Means for preparing and characterizing antibodies are well known in the art (See, e.g., Antibodies: A Laboratory Manual, 1988).

For example, supernatants from selected quadromas are passed over protein A or protein G sepharose columns to bind IgG (depending on the isotype). The bound antibodies are then eluted with, e.g. a pH 5.0 citrate buffer. The elute fractions containing the BsAbs, are dialyzed against an isotonic buffer. Alternatively, the eluate is also passed over an anti-immunoglobulin-sepharose column. The BsAb is then eluted with 3.5 M magnesium chloride. BsAbs purified in this way are then tested for binding activity by, e.g., an isotype-specific ELISA and immunofluorescence staining assay of the target cells, as described above.

Purified BsAbs and parental antibodies may also be characterized and isolated by SDS-PAGE electrophoresis, followed by staining with silver or Coomassie. This is possible when one of the parental antibodies has a higher molecular weight than the other, wherein the band of the BsAbs migrates midway between that of the two parental antibodies. Reduction of the samples verifies the presence of heavy chains with two different apparent molecular weights.

Furthermore, recombinant technology is now available for the preparation of antibodies in general, allowing the preparation of recombinant antibody genes encoding an antibody having the desired dual specificity (Van Duk et al., 1989). Thus, after selecting the monoclonal antibodies having the most preferred binding characteristics, the respective genes for these antibodies can be isolated, e.g., by immunological screening of a phage expression library (Oi and Morrison, 1986;Winter and Milstein, 1991). Then, through rearrangement of Fab coding domains, the appropriate chimeric construct can be readily obtained.

vii. Combined Treatment

The Tissue Factor compositions in combination with either immunotoxins or coaguligands are contemplated for use in the clinical treatment of various human cancers and even other disorders, such as benign prostatic hyperplasia and rheumatoid arthritis, in which the intermediate or longer term arrest of blood flow would be advantageous.

The combination of the Tissue Factor compositions disclosed in the present application with immunotoxins and coaguligands are considered to be particularly useful tools in anti-tumor therapy. From the data presented herein, including the animal studies, and the knowledge in the art regarding treatment of Lymphoma (Glennie et al., 1988), T-Cell targeting (Nolan and Kennedy, 1990) and drug targeting (Paulus, 1985) appropriate doses and treatment regimens may be straightforwardly developed.

It is currently proposed that effective doses of the immunotoxins and coaguligands for use with the Tissue Factor constructs described above in the treatment of cancer will be between about 0.1 mg/kg and about 2 mg/kg, and preferably, of between about 0.8 mg/kg and about 1.2 mg/kg, when administered via the IV route at a frequency of about 1 time per week. Some variation in dosage will necessarily occur depending on the condition of the subject being treated. The person responsible for administration will, in any event, determine the appropriate dose for the individual subject. Such optimization and adjustment is routinely carried out in the art and by no means reflects an undue amount of experimentation.

Naturally, before wide-spread use, further animal studies and clinical trials will be conducted. The various elements of conducting a clinical trial, including patient treatment and monitoring, will be known to those of skill in the art in light of the present disclosure. The following information is being presented as a general guideline for use in establishing such trials.

It is contemplated that patients chosen for combined studies would have failed to respond to at least one course of conventional therapy and had to have objectively measurable disease as determined by physical examination, laboratory techniques, or radiographic procedures. Where murine monoclonal antibody portions are employed in the immunotoxins or coaguligands, the patients should have no history of allergy to mouse immunoglobulin. Any chemotherapy should be stopped at least 2 weeks before entry into the study.

In regard to administration of the Tissue Factor constructs with either immunotoxins or coaguligands, it is considered that certain advantages will be found in the use of an indwelling central venous catheter with a triple lumen port. The therapeutic mixtures should be filtered, for example, using a 0.22μ filter, and diluted appropriately, such as with saline, to a final volume of 100 ml. Before use, the test sample should also be filtered in a similar manner, and its concentration assessed before and after filtration by determining the $A_{280}$. The expected recovery should be within the range of 87 to 99%, and adjustments for protein loss can then be accounted for.

These Tissue Factor and IT or coaguligand combinations may be administered over a period of approximately 4–24 hours, with each patient receiving 2–4 infusions at 2–7 day intervals. Administration can also be performed by a steady rate of infusion over a 7 day period. The infusion given at any dose level should be dependent upon any toxicity observed. Hence, if Grade II toxicity was reached after any single infusion, or at a particular period of time for a steady rate infusion, further doses should be withheld or the steady rate infusion stopped unless toxicity improved. Increasing doses of Tissue Factor with either immunotoxins or coaguligands should be administered to groups of patients until approximately 60% of patients showed unacceptable Grade III or IV toxicity in any category. Doses that are ⅔ of this value could be defined as the safe dose.

Physical examination, tumor measurements, and laboratory tests should, of course, be performed before treatment and at intervals up to 1 month later. Laboratory tests should include complete blood counts, serum creatinine, creatine kinase, electrolytes, urea, nitrogen, SGOT, bilirubin, albumin, and total serum protein. Serum samples taken up to 60 days after treatment should be evaluated by radioimmunoassay for the presence of the intact Tissue Factor, immunotoxin and/or coaguligand or components thereof and antibodies against any portions thereof. Immunological analyses of sera, using any standard assay such as, for example, an ELISA or RIA, will allow the pharmacokinetics and clearance of the therapeutic agent to be evaluated.

To evaluate the anti-tumor responses, it is contemplated that the patients should be examined at 48 hours to 1 week and again at 30 days after the last infusion. When palpable disease was present, two perpendicular diameters of all masses should be measured daily during treatment, within 1 week after completion of therapy, and at 30 days. To measure nonpalpable disease, serial CT scans could be performed at 1-cm intervals throughout the chest, abdomen, and pelvis at 48 hours to 1 week and again at 30 days. Tissue samples should also be evaluated histologically, and/or by flow cytometry, using biopsies from the disease sites or even blood or fluid samples if appropriate.

Clinical responses may be defined by acceptable measure. For example, a complete response may be defined by the disappearance of all measurable tumor 1 month after treatment. Whereas a partial response may be defined by a 50% or greater reduction of the sum of the products of perpendicular diameters of all evaluable tumor nodules 1 month after treatment, with no tumor sites showing enlargement. Similarly, a mixed response may be defined by a reduction of the product of perpendicular diameters of all measurable lesions by 50% or greater 1 month after treatment, with progression in one or more sites.

F. Prolonged Half-Life TF

It is demonstrated herein that the anti-tumor activity of tTF is enhanced by conjugating tTF to carrier molecules, such as immunoglobulins, that delay clearance of tTF from the body. For example, linking tTF to immunoglobulin enhances the anti-tumor activity by prolonging the in vivo half-life of tTF such that tTF persists for longer and has more time to induce thrombotic events in tumor vessels. The prolongation in half-life either results from the increase in size of tTF above the threshold for glomerular filtration; or from active readsorption of the conjugate within the kidney, a property of the Fc piece of immunoglobulin (Spiegelberg and Weigle, 1965). It is also possible that the immunoglobulin component changes the conformation of tTF to render it more active or stable. Other carrier molecules besides immunoglobulin are contemplated to produce similar effects and are thus encompassed within the present invention.

F1. Modifications

Given that a first interpretation of the prolonged half-life observed upon the linkage of tTF to immunoglobulin is simply that the resultant increase in size leads to prolonged plasma half-life, the inventors contemplate that other modifications that increase the size of TF constructs can be advantageously used in connection with the present invention, so long as the lengthening modification does not substantially restore membrane-binding functionality to the modified TF construct. Absent such a possibility, which can be readily tested, virtually any generally inert biologically acceptable molecule may be conjugated with a TF construct in order to prepare a modified TF with increased in vivo half-life.

Modification may also be made to the structure of TF itself to render it either more stable, or perhaps to reduce the rate of catabolism in the body. One mechanism for such modifications is the use of d-amino acids in place of l-amino acids in the TF molecule. Those of ordinary skill in the art will understand that the introduction of such modifications needs to be followed by rigorous testing of the resultant molecule to ensure that it still retains the desired biological properties. Further stabilizing modifications include the use of the addition of stabilizing moieties to either the N-terminal or the C-terminal, or both, which is generally used to prolong the half-life of biological molecules. By way of example only, one may wish to modify the termini of the TF constructs by acylation or amination. The variety of such modifications may also be employed together, and portions of the TF molecule may also be replaced by peptidomimetic chemical structures that result in the maintenance of biological function and yet improve the stability of the molecule.

F2. Conjugates i. Proteins

Techniques useful in connection with conjugation proteins of interest to carrier proteins are widely used in the scientific community. It will be generally understood that in the preparation of such TF conjugates for use in the present invention, the protein chosen as a carrier molecule should have certain defined properties. For example, it must of course be biologically compatible and not result in any significant untoward effects upon administration to a patient. Furthermore, it is generally required that the carrier protein be relatively inert, and non-immunogenic, both of which properties will result in the maintenance of TF function and will allow the resultant construct to avoid excretion through the kidney. Exemplary proteins are albumins and globulins.

ii. Non Proteins

In common with the protein conjugates described above, the TF molecules of the present invention may also be conjugated to non-protein elements in order to improve their half-life in vivo. Again, the choice of non-protein molecules for use in such conjugates will be readily apparent to those of ordinary skill in the art. For example, one may use any one or more of a variety of natural or synthetic polymers, including polysaccharides and PEG.

In the context of preparing conjugates, whether proteinaceous or non-proteinaceous, one should take care that the introduced conjugate does not substantially reassociate the modified TF molecule with the plasma membrane such that it increases its coagulation ability and results in a molecule that exerts harmful side effects following administration. As a general rule, it is believed that hydrophobic additions or conjugates should largely be avoided in connection with these embodiments.

iii. Immunoconjugates

Where antibodies are used to conjugate to the tTF compositions of the present invention, the choice of antibody will generally be dependent on the intended use of the TF-antibody conjugate. For example, where the TF immunoconjugates are contemplated for use in addition to the TF molecules alone, the type of tumor should be considered, e.g., whether it is preferable to target the tumor cells, or more preferably, the tumor vasculature or tumor stroma. Where the TF immunoconjugates are themselves the primary therapeutic agents, the immunoconjugates will not in any sense be a "targeted immunoconjugate". In these aspects, the conjugation of the TF molecule to an antibody or portion thereof is simply performed in order to generate a construct that has improved half-life and/or bioavailability in comparison to the original TF molecule. In any event, certain advantages may be achieved through the application of particular types of antibodies. For example, while IgG based antibodies may be expected to exhibit better binding capability and slower blood clearance than their Fab' counterparts, Fab' fragment-based compositions will generally exhibit better tissue penetrating capability.

(a) Monoclonal Antibodies

Means for preparing and characterizing antibodies are well known in the art (See, e.g., Antibodies: A Laboratory Manual, Cold Spring Harbor Laboratory, 1988).

The methods for generating monoclonal antibodies (MAbs) generally begin along the same lines as those for preparing polyclonal antibodies. Briefly, a polyclonal antibody is prepared by immunizing an animal with an immunogenic composition in accordance with the present invention, either with or without prior immunotolerizing, depending on the antigen composition and protocol being employed (e.g., tolerizing to a normal cell population and then immunizing with a tumor cell population), and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired titer level is obtained, the immunized animal can be bled and the serum isolated and stored, and/or the animal can be used to generate MAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified tumor cell or vascular endothelial cell protein, polypeptide, peptide, or intact cell composition. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986, pp. 60–61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986;Campbell, pp. 75–83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F, 4B210 or one of the above listed mouse cell lines; and U-266, GM1500-GRG2, LICR-LON-HMy2 and UC729-6, are all useful in connection with human cell fusions.

Methods for generating hybrids of antibody-producing spleen or lymph node cells and myeloma cells usually comprise mixing somatic cells with myeloma cells in a 4:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71–74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

The inventors also contemplate the use of a molecular cloning approach to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells e.g., normal-versus-tumor cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Where MAbs are employed in the present invention, they may be of human, murine, monkey, rat, hamster, chicken or even rabbit origin. The invention contemplates the use of human antibodies, "humanized" or chimeric antibodies from mouse, rat, or other species, bearing human constant and/or variable region domains, and other recombinant antibodies and fragments thereof. Of course, due to the ease of preparation and ready availability of reagents, murine monoclonal antibodies will typically be preferred.

(b) Functional Antibody Binding Regions Fab

Fab fragments can be obtained by proteolysis of the whole immunoglobulin by the non-specific thiol protease, papain. Papain must first be activated by reducing the sulphydryl group in the active site with cysteine, 2-mercaptoethanol or dithiothreitol. Heavy metals in the stock enzyme should be removed by chelation with EDTA (2 mM) to ensure maximum enzyme activity. Enzyme and substrate are normally mixed together in the ratio of 1:100 by weight. After incubation, the reaction can be stopped by irreversible alkylation of the thiol group with iodoacetamide or simply by dialysis. The completeness of the digestion should be monitored by SDS-PAGE and the various fractions separated by protein A-Sepharose or ion exchange chromatography.

F(ab')$_2$

The usual procedure for preparation of F(ab')$_2$ fragments from IgG of rabbit and human origin is limited proteolysis by the enzyme pepsin (Protocol 7.3.2). The conditions, 100× antibody excess w/w in acetate buffer at pH 4.5, 37° C., suggest that antibody is cleaved at the C-terminal side of the inter-heavy-chain disulfide bond. Rates of digestion of mouse IgG may vary with subclass and it may be difficult to obtain high yields of active F(ab')$_2$ fragments without some undigested or completely degraded IgG. In particular, IgG$_{2b}$ is highly susceptible to complete degradation. The other subclasses require different incubation conditions to produce optimal results.

Digestion of rat IgG by pepsin requires conditions including dialysis in 0.1 M acetate buffer, pH 4.5, and then incubation for four hours with 1% w/w pepsin; IgG$_1$ and IgG$_{2a}$ digestion is improved if first dialyzed against 0.1 M formate buffer, pH 2.8, at 4° C., for 16 hours followed by acetate buffer. IgG$_{2b}$ gives more consistent results with incubation in staphylococcal V8 protease (3% w/w) in 0.1 M sodium phosphate buffer, pH 7.8, for four hours at 37° C.

iv. Second Generation TF Immunoconjugates

The inventors contemplate that the Fc portion of the immunoglobulin in the tTF-immunoglobulin construct employed in the advantageous studies disclosed herein may actually be the relevant portion of the antibody molecule, resulting in increased in vivo half-life. It is reasonable to presume that the conjugation to the Fc region results in active readsorption of a TF-Fc conjugate within the kidney, restoring the conjugate to the systemic circulation. As such, one may conjugate any of the coagulation-deficient TF constructs or variants of the invention to an Fc region in order to increase the in vivo half-life of the resultant conjugate.

Various methods are available for producing Fc regions in sufficient purity to enable their conjugation to the TF constructs. By way of example only, the chemical cleavage of antibodies to provide the defined domains or portions is well known and easily practiced, and recombinant technology can also be employed to prepare either substantial quantities of Fc regions or, indeed, to prepare the entire TF-Fc conjugate following generation of a recombinant vector that expresses the desired fusion protein.

Further manipulations of the general immunoglobulin structure may also be conducted with a view to providing second generation TF constructs with increased half-life. By way of example only, one may consider replacing the C$_H$3 domain of an IgG molecule with a truncated Tissue Factor or variant thereof. In general, the most effective mechanism for producing such a hybrid molecule will be to use molecular cloning techniques and recombinant expression. All such techniques are generally known to those of ordinary skill in the art, and are further described in detail herein.

F3. Linkage Means

The compositions above may be linked to the Tissue Factor compositions in any operative manner that allows each region to perform its intended function without significant impairment of the Tissue Factor functions. Thus, the linking components will be capable prolonging the half life of the construct, and the Tissue Factor is capable of promoting blood coagulation or clotting.

i. Biochemical Cross-Linkers

The joining of any of the above components, to a Tissue Factor composition will generally employ the same technology as developed for the preparation of immunotoxins. It can be considered as a general guideline that any biochemical cross-linker that is appropriate for use in an immunotoxin will also be of use in the present context, and additional linkers may also be considered.

Cross-linking reagents are used to form molecular bridges that tie together functional groups of two different molecules, e.g., a stabilizing and coagulating agent. To link two different proteins in a step-wise manner, heterobifunctional cross-linkers can be used that eliminate unwanted homopolymer formation.

TABLE IV

HETERO-BIFUNCTIONAL CROSS-LINKERS

| linker | Reactive Toward | Advantages and Applications | Spacer Arm Length\after cross-linking |
|---|---|---|---|
| SMPT | Primary amines Sulfhydryls | . Greater stability | 11.2 A |
| SPDP | Primary amines Sulfhydryls | . Thiolation . Cleavable cross-linking | 6.8 A |
| LC-SPDP | Primary amines Sulfhydryls | . Extended spacer arm | 15.6 A |
| Sulfo-LC-SPDP | Primary amines Sulfydryls | . Extended spacer arm . Water-soluble | 15.6 A |
| SMCC | Primary amines | . Stable maleimide reactive group | 11.6 A |

TABLE IV-continued

HETERO-BIFUNCTIONAL CROSS-LINKERS

| linker | Reactive Toward | Advantages and Applications | Spacer Arm Length\after cross-linking |
|---|---|---|---|
| | Sulfhydryls | . Enzyme-antibody conjugation<br>. Hapten-carrier protein conjugation | |
| Sulfo-SMCC | Primary amines<br>Sulfhydryls | . Stable maleimide reactive group<br>. Water-soluble<br>. Enzyme-antibody conjugation | 11.6 A |
| MBS | Primary amines<br>Sulfhydryls | . Enzyme-antibody conjugation<br>. Hapten-carrier protein conjugation | 9.9 A |
| Sulfo-MBS | Primary amines<br>Sulfhydryls | . Water-soluble | 9.9 A |
| SIAB | Primary amines<br>Sulfhydryls | . Enzyme-antibody conjugation | 10.6 A |
| Sulfo-SIAB | Primary amines<br>Sulfhydryls | . Water-soluble | 10.6 A |
| SMPB | Primary amines<br>Sulfhydryls | . Extended spacer arm<br>. Enzyme-antibody conjugation | 14.5 A |
| Sulfo-SMPB | Primary amines<br>Sulfhydryls | . Extended spacer arm<br>. Water-soluble | 14.5 A |
| EDC/Sulfo-NHS | Primary amines<br>Carboxyl groups | . Hapten-Carrier conjugation | 0 |
| ABH | Carbohydrates<br>Nonselective | . Reacts with sugar groups | 11.9 A |

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the coagulant).

It can therefore be seen that the preferred Tissue Factor composition will generally have, or be derivatized to have, a functional group available for cross-linking purposes. This requirement is not considered to be limiting in that a wide variety of groups can be used in this manner. For example, primary or secondary amine groups, hydrazide or hydrazine groups, carboxyl alcohol, phosphate, or alkylating groups may be used for binding or cross-linking. For a general overview of linking technology, one may wish to refer to Ghose and Blair (1987).

The spacer arm between the two reactive groups of a cross-linkers may have various length and chemical compositions. A longer spacer arm allows a better flexibility of the conjugate components while some particular components in the bridge (e.g., benzene group) may lend extra stability to the reactive group or an increased resistance of the chemical link to the action of various aspects (e.g., disulfide bond resistant to reducing agents). The use of peptide spacers, such as L-Leu-L-Ala-L-Leu-L-Ala, is also contemplated.

It is preferred that a cross-linker having reasonable stability in blood will be employed. Numerous types of disulfide-bond containing linkers are known that can be successfully employed to conjugate targeting and coagulating agents. Linkers that contain a disulfide bond that is sterically hindered may prove to give greater stability in vivo, preventing release of the Tissue Factor prior to binding at the site of action. These linkers are thus one preferred group of linking agents.

One of the most preferred cross-linking reagents for use in immunotoxins is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the tumor site. It is contemplated that the SMPT agent may also be used in connection with the bispecific coagulating ligands of this invention.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers can also be employed in accordance herewith. Other useful cross-linkers, not considered to contain or generate a protected disulfide, include SATA, SPDP and 2-iminothiolane (Wawrzynczak and Thorpe, 1987). The use of such cross-linkers is well understood in the art.

Once conjugated, the tTF will generally be purified to separate the conjugate from unconjugated targeting agents or coagulants and from other contaminants. A large a number of purification techniques are available for use in providing conjugates of a sufficient degree of purity to render them clinically useful. Purification methods based upon size separation, such as gel filtration, gel permeation or high performance liquid chromatography, will generally be of most use. Other chromatographic techniques, such as Blue-Sepharose separation, may also be used.

ii. Recombinant Fusion Proteins

The tTF compositions of the invention may also be fusion proteins prepared by molecular biological techniques. The use of recombinant DNA techniques to achieve such ends is now standard practice to those of skill in the art. These methods include, for example, in vitro recombinant DNA techniques, synthetic techniques and in vivo recombination/genetic recombination. DNA and RNA synthesis may, additionally, be performed using an automated synthesizers (see, for example, the techniques described in Sambrook et al., 1989; and Ausubel et al., 1989).

The preparation of such a fusion protein generally entails the preparation of a first and second DNA coding region and the functional ligation or joining of said regions, in frame, to prepare a single coding region that encodes the desired fusion protein. In the present context, the tTF or TF mutant DNA sequence will generally be joined in frame with a DNA sequence encoding an inert protein carrier, immunoglobulin, Fc region, or such like. It is not generally believed to be particularly relevant whether the TF portion of the fusion protein or the inert portion is prepared as the N-terminal region or as the C-terminal region. In connection with the second generation TF immunoglobulin molecules, the TF coding sequences may further be inserted within the immunoglobulin coding regions, such that the TF sequences functionally interrupt the immunoglobulin sequences and the encoded protein may be considered a "tribrid".

Once the coding region desired has been produced, an expression vector is created. Expression vectors contain one or more promoters upstream of the inserted DNA regions that act to promote transcription of the DNA and to thus promote expression of the encoded recombinant protein. This is the meaning of "recombinant expression" and has been discussed elsewhere in the specification.

F4. Assays

As with other aspects of the present invention, once a candidate TF construct has been generated with the intention of providing a construct with increased in vivo half-life, the construct should generally be tested to ensure that the desired properties have been imparted to the resultant compound. The various assays for use in determining such changes in function are routine and easily practiced by those of ordinary skill in the art.

In TF conjugates designed simply in order to increase their size, confirmation of increased size is completely routine. For example, one will simply separate the candidate composition using any methodology that is designed to separate biological components on the basis of size and one will analyze the separated products in order to determine that a TF construct of increased size has been generated. By way of example only, one may mention separation gels and separation columns, such as gel filtration columns. The use of gel filtration columns in the separation of mixtures of conjugated and non-conjugated components may also be useful in other aspects of the present invention, such as in the generation of relatively high levels of conjugates, immunotoxins or coaguligands.

As the objective of the present class of conjugates is to provide a coagulation-deficient TF molecule having an increased in vivo half-life, the candidate TF modified variants or conjugates should generally be tested in order to confirm that this property is present. Again, such assays are routine in the art. A first simple assay would be to determine the half-life of the candidate modified or conjugated TF in an in vitro assay. Such assays generally comprise mixing the candidate molecule in sera and determining whether or not the molecule persists in a relatively intact form for a longer period of time, as compared to the initial sample of coagulation-deficient Tissue Factor. One would again sample aliquots from the admixture and determine their size, and preferably, their biological function.

In vivo assays of biological half-life or "clearance" can also be easily conducted. In these systems, it is generally preferred to label the test candidate TF constructs with a detectable marker and to follow the presence of the marker after administration to the animal, preferably via the route intended in the ultimate therapeutic treatment strategy. As part of this process, one would take samples of body fluids, particularly serum and/or urine samples, and one would analyze the samples for the presence of the marker associated with the TF construct, which will indicate the longevity of the construct in the natural environment in the body.

Any one or more or a combination of the TF molecules with increased half-life may thus be used in conjunction with the therapeutic methods disclosed herein. The doses proposed for administration will generally be between about not 0.2 mg and about 200 mg per patient, as with the original TF constructs described above. However, in that these TF molecules have been modified, it is possible that the effective doses may be even lower, such as on the order of about not 0.1 mg. It is more likely that the therapeutic treatment regimens will be altered when using the increased half-life TFs in the number of times that the pharmaceuticals are administered, rather than in alteration of the given doses. For example, where an original TF construct is proposed for use on days 1, 3 and 7 within the treatment period, the counterpart improved TF with longer half-life may rather be administered only on day 1 and day 7. In any event, all such optimizations in terms of doses and times for administration will be easily determined by those of ordinary skill in the art.

G. TF and Factor VIIa Combinations

The inventors have further demonstrated that coagulation-inducing activity of tTF bound to A20 cells was markedly enhanced in the presence of Factor VIIa. In common with earlier studies, these in vitro results also translated to the in vivo environment. Studies are presented herein to demonstrate that the anti-tumor activity of various coagulation-deficient TF constructs is enhanced upon co-administration with Factor VIIa. Even using an experimental animal model of the HT29 tumor, which is notoriously difficult to coagulate, the co-administration of coagulation-deficient TF constructs and exogenous Factor VIIa resulted in considerable necrosis of the tumor tissue.

This data can be explained as tTF binds Factor VII but does not efficiently mediate its activation to Factor VIIa by Xa and adjacent Factor VIIa molecules. Providing a source of preformed (exogenous) Factor VIIa overcomes this block, enabling more efficient coagulation. The success of the combined coagulation-deficient TF and Factor VIIa treatment is generally based upon the surprising localization of the TF construct within the vasculature of the tumor. Absent such surprising localization and specific functional effects, the co-administration of Factor VIIa would not be meaningful in the context of tumor treatment, and may even be harmful as it may promote unwanted thrombosis in various healthy tissues. The combined use of tTF and Factor VIIa in a non-targeted manner has previously been proposed in connection with the treatment of hemophiliacs and patients with other bleeding disorders, in which there is a fundamental impairment of the coagulation cascade. In the present invention, the coagulation cascade is generally fully operative, and the therapeutic intervention concentrates this activity within a defined region of the body.

It is therefore a further object of the present invention to increase the anti-tumor effects of any one of the TF constructs of the invention by combining the use of TF with the additional administration of Factor VIIa. As tTF binds to tumor vascular endothelium, it is possible to inject tTF into tumor-bearing animals, wait a period of time for excess tTF to be cleared, and then inject Factor VIIa to magnify the thrombotic action of the tTF within tumor vessels. In this manner, the tTF or other coagulation-deficient TF construct can be seen to form a reservoir within the tumor, allowing the subsequent administration of Factor VIIa to increase and perpetuate the anti-tumor effect.

A further observation of the present invention is that the thrombotic activity of the Factor VII activation mutants of tTF (G164A) and tTF (W158R) was largely restored by Factor VIIa. These mutations lie within a region of tTF that is important for the conversion of Factor VII to Factor VIIa. As with tTF itself, the studies herein show that adding preformed Factor VIIa overcomes this block in coagulation complex formation. The present invention exploits these and the aforementioned observations with a view to providing in vivo therapy of cancer.

Indeed, the studies presented herein confirm that the co-administration of a Factor VII activation mutant variant of TF with preformed Factor VIIa results in considerable necrotic damage to the tumors, even in small tumor models which are not the most amenable to treatment with the present invention. This aspect of the invention is particularly surprising as it was not previously believed that such mutants would have any therapeutic utility in any embodiments other than, perhaps, in the competitive inhibition of TF as may be used to inhibit or reduce coagulation. Apart from such hypotheses, the generation of such mutants has been motivated by scientific interest and they could perhaps be used as controls in certain in vitro studies. Only the studies of the present inventors render such mutants clinically useful, either in the context of targeted delivery (WO 96/01653), or in the even more surprising combined uses of the present invention.

In particular embodiments, this application of the present invention therefore first involves injecting tTF (G164A), tTF (W158R) or an equivalent thereof into tumor bearing animals. The tTF mutant is then allowed to localize to tumor vessels and the residue is cleared. This is then followed by the injection of Factor VIIa, which allows the localized tTF mutants to express thrombotic activity. This strategy offers the advantage that it is very safe. The tTF mutants are practically non-toxic, as is Factor VIIa itself. Thus, administering the tTF mutant followed by Factor VIIa will be harmless to the host, yet efficiently induce thrombosis of tumor vessels.

G1. Factor VIIa

Factor VII can be prepared as described by Fair (1983), and as shown in U.S. Pat. Nos. 5,374,617, 5,504,064 and 5,504,067, each of which is incorporated herein by reference. The coding portion of the human Factor VII cDNA sequence was reported by Hagen et al., (1986). The amino acid sequence from 1 to 60 corresponds to the pre-pro/leader sequence that is removed by the cell prior to secretion. The mature Factor VII polypeptide chain consists of amino acids 61 to 466. Factor VII is converted to its active form, Factor VIIa, by cleavage of a single peptide bond between arginine-212 and isoleucine-213.

Factor VII can be converted in vitro to Factor VIIa by incubation of the purified protein with Factor Xa immobilized on Affi-Gel™ 15 beads (Bio-Rad). Conversion can be monitored by SDS-polyacrylamide gel electrophoresis of reduced samples. Free Factor Xa in the Factor VIIa preparation can be detected with the chromogenic substrate methoxycarbonyl-D-cyclohexylglycyl-glycyl-arginine-p-nitroanilide acetate (Spectrozyme™ Factor Xa, American Diagnostica, Greenwich, Conn.) at 0.2 mM final concentration in the presence of 50 mM EDTA.

Recombinant Factor VIIa can also be purchased from Novo Biolabs (Danbury, Conn.).

G2. Treatment

The use of Factor VIIa in connection with the present invention is not confined to its ability to significantly improve the utility of the Factor VII activation mutants disclosed herein. It is equally contemplated that Factor VIIa will be used in conjunction with the coagulation-deficient Tissue Factor molecules of equivalent activity to the truncated tTF first employed. In such treatment embodiments, the dose of the TF construct will generally be between about not 0.2 mg and about 200 mg per patient. The appropriate doses of Factor VIIa can best be determined in light of this information.

For example, it may be desired to create a 1:1 ratio of the TF construct and Factor VIIa in a precomplex and to administer the precomplexed composition to the animal. Should this be desired, one would generally admix an amount of TF and an amount of Factor VIIa sufficient to allow the formation of an equimolar complex. To achieve this, it may be preferable to use a 2–3 molar excess of Factor VIIa in order to ensure that each of the TF molecules are adequately complexed. One would then simply separate the uncomplexed TF and Factor VIIa from the complexed mixture using any suitable technique, such as gel filtration. After formation of the TF:VIIa complex, one may simply administer the complex to a patient in need of treatment in a dose of between about not 0.2 mg and about 200 mg per patient.

As stated above, it may generally be preferred to administer the coagulation-deficient TF construct to a patient in advance, allowing the TF sufficient time to localize specifically within the tumor. Following such preadministration, one would then design an appropriate dose of Factor VIIa sufficient to coordinate and complex with the TF localized within the tumor vasculature. Again, one may design the dose of Factor VIIa in order to allow a 1:1 molar ratio of TF and Factor VIIa to form in the tumor environment. Given the differences in molecular weight of these two molecules, it will be seen that it would be advisable to add approximately twice the amount in milligrams of Factor VIIa in comparison to the milligrams of TF.

However, the foregoing analysis is merely exemplary, and any doses of Factor VIIa that generally result in an improvement in coagulation would evidently be of clinical significance. In this regard, it is notable that the studies presented herein in fact use a 16:1 excess of TF in comparison to Factor VIIa, which is generally about a 32-fold molar excess of the TF construct. Nevertheless, impressive coagulation and necrosis was specifically observed in the tumor. Therefore, it will be evident that the effective doses of Factor VIIa are quite broad. By way of example only, one may consider administering to a patient a dose of Factor VIIa between about 0.01 mg and about 500 mg per patient.

Each of the foregoing analyses may be equally applied to the use of Tissue Factor constructs that have been mutated to impair their ability to activate Factor VII. Given that the foregoing calculations are based upon a ratio of binding, it is not believed to be necessary to use particularly increased levels of Factor VIIa in combination with the activation mutants described. However, given that the administration of Factor VIIa is not believed to be particularly harmful in itself, the potential for using increased doses of Factor VIIa is certainly evident.

Although the detailed guidance provided above is believed to be sufficient to enable one of ordinary skill in the art how to practice these aspects of the invention, one may also refer to other quantitative analyses to assist in the optimization of the TF and Factor VIIa doses for administration. By way of example only, one may refer to U.S. Pat. Nos. 5,374,617; 5,504,064; and 5,504,067, which describe a range of therapeutically active doses and plasma levels of Factor VIIa.

Morrissey and Comp have reported that, in the context of bleeding disorders, the coagulation-deficient Tissue Factor may be administered in a dosage effective to produce in the plasma an effective level of between 100 ng/ml and 50 µg/ml, or a preferred level of between 1 µg/ml and 10 µg/ml or 60 to 600 µg/kg body weight, when administered systemically; or an effective level of between 10 µg/ml and 50 µg/ml, or a preferred level of between 10 µg/ml and 50 µg/ml, when administered topically (U.S. Pat. No. 5,504,064).

The Factor VIIa is administered in a dosage effective to produce in the plasma an effective level of between 20 ng/ml and 10 µg/ml, (1.2 to 600 µg/kg), or a preferred level of between 40 ng/ml and 700 µg/ml (2.4 to 240 µg/kg), or a level of between 1 µg Factor VIIa/ml and 10 µg Factor VIIa/ml when administered topically.

In general, one would administer coagulation-deficient Tissue Factor and Factor VII activator to produce levels of up to 10 µg coagulation-deficient Tissue Factor/ml plasma and between 40 ng and 700 µg Factor VIIa/ml plasma. While these studies were performed in the context of bleeding disorders, they have also relevance in the context of the present invention, in that levels must be effective but appropriately monitored to avoid systemic toxicity due to elevated levels of coagulation-deficient Tissue Factor and activated Factor VIIa. Therefore, the Factor VII activator is administered in a dosage effective to produce in the plasma an effective level of Factor VIIa, as defined above.

G3. Factor VII Activators

As described in U.S. Pat. No. 5,504,064, incorporated herein by reference, activators of endogenous Factor VII may also be administered in place of Factor VIIa itself. As described in the foregoing patent, Factor VIIa can also be formed in vivo, shortly before, at the time of, or preferably slightly after the administration of the coagulation-deficient Tissue Factors. In such embodiments, endogenous Factor VII is converted into Factor VIIa by infusion of an activator of Factor VIIa, such as Factor Xa (FXa) in combination with phospholipid (PCPS).

Activators of Factor VII in vivo include Factor Xa/PCPS, Factor IXa/PCPS, thrombin, Factor XIIa, and the Factor VII activator from the venom of *Oxyuranus scutellatus* in combination with PCPS. These have been shown to activate Factor VII to Factor VIIa in vitro. Activation of Factor VII to Factor VIIa for Xa/PCPS in vivo has also been measured directly. In general, the Factor VII activator is administered in a dosage between 1 and 10 µg/ml of carrier (U.S. Pat. No. 5,504,064).

The phospholipid can be provided in a number of forms such as phosphatidyl choline/phosphatidyl serine vesicles (PCPS). The PCPS vesicle preparations and the method of administration of Xa/PCPS is described in Giles et al., (1988), the teachings of which are specifically incorporated herein. Other phospholipid preparations can be substituted for PCPS, so long as they accelerate the activation of Factor VII by Factor Xa. Effectiveness, and therefore determination of optimal composition and dose, can be monitored as described below.

A highly effective dose of Xa/PCPS, which elevates Factor VIIa levels in vivo in the chimpanzee, has been reported to be 26 pmoles FXa+40 pmoles PCPS per kg body weight. That dose yielded an eighteen fold increase in endogenous levels of Factor VIIa (to 146 ng/ml). A marginally detectable effect was observed using a smaller dose in dogs, where the infusion of 12 pmoles Factor Xa+19 pmoles PCPS per kg body weight yielded a three fold increase in endogenous Factor VIIa levels. Accordingly, doses of Factor Xa that are at least 12 pmoles Factor Xa per kg body weight, and preferably 26 pmoles Factor Xa per kg body weight, should be useful. Doses of PCPS that are at least 19 pmoles PCPS per kg body weight, and preferably 40 pmoles PCPS per kg body weight, are similarly useful (U.S. Pat. No. 5,504,064).

The effectiveness of any infusible Factor VII activator can be monitored, following intravenous administration, by drawing citrated blood samples at varying times (at 2, 5, 10, 20, 30, 60, 90 and 120 min.) following a bolus infusion of the activator, and preparing platelet-poor plasma from the blood samples. The amount of endogenous Factor VIIa can then be measured in the citrated plasma samples by performing a coagulation-deficient Tissue Factor-based Factor VIIa clotting assay. Desired levels of endogenous Factor VIIa would be the same as the target levels of plasma Factor VIIa indicated for co-infusion of purified Factor VII and coagulation-deficient Tissue Factor. Therefore, other activators of Factor VII could be tested in vivo for generation of Factor VIIa, without undue experimentation, and the dose adjusted to generate the desirable levels of Factor VIIa, using the coagulation-deficient Tissue Factor-based Factor VIIa assay of plasma samples. The proper dose of the Factor VII activator (yielding the desired level of endogenous Factor VIIa) can then be used in combination with the recommended amounts of coagulation-deficient Tissue Factor.

Doses can be timed to provide prolong elevation in Factor VIIa levels. Preferably doses would be administered until the desired anti-tumor effect is achieved, and then repeated as needed to control bleeding. The half-life of Factor VIIa in vivo has been reported to be approximately two hours, although this could vary with different therapeutic modalities and individual patients. Therefore, the half-life of Factor VIIa in the plasma in a given treatment modality should be determined with the coagulation-deficient Tissue Factor-based clotting assay.

H. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Synthesis of Truncated Tissue Factor tTF is herein designated as the extracellular domain of the mature Tissue Factor protein (amino acid 1–219 of the mature protein; SEQ ID NO:1). SEQ ID NO:1 is encoded by, e.g., SEQ ID NO:10.

A. $H_6$[tTF]

$H_6$ Ala Met Ala[tTF]. The tTF complimentary DNA (cDNA) was prepared as follows: RNA from J-82 cells (human bladder carcinoma) was used for the cloning of tTF.

Total RNA was isolated using the GlassMax™ RNA microisolation reagent (Gibco BRL). The RNA was reverse transcribed to cDNA using the GeneAmp RNA PCR kit (Perkin Elmer). tTF cDNA was amplified using the same kit with the following two primers:

5' primer: 5' GTC ATG CCA TGG CC<u>T CAG GCA CTA CAA</u>
(SEQ ID NO: 15)
3' primer: 5' TGA CAA GCT TA<u>T TCT CTG AAT TCC CCT TTC T</u>
(SEQ ID NO: 16)

The underlined sequences codes for the N-terminus of tTF. The rest of the sequence in the 5' primer is the restriction site for NcoI allowing the cloning of tTF into the expression vector. The sequence in the 3' primer is the HindIII site for cloning tTF into the expression vector. PCR amplification was performed as suggested by the manufacturer. Briefly, 75 µM dNTP;0.6 µM primer, 1.5 mM MgCl$_2$ were used and 30 cycles of 30" at 95° C., 30" at 55° C. and 30" at 72° C. were performed.

The tTF was expressed as a fusion protein in a non-native state in *E. coli* inclusion bodies using the expression vector H$_6$pQE-60 (Qiagen). The *E. coli* expression vector H$_6$ pQE-60 was used for expressing tTF (Lee et al., 1994). The PCR amplified tTF cDNA was inserted between the NcoI and HindIII site. H$_6$ pQE-60 has a built-in (His)$_6$ encoding sequence such that the expressed protein has the sequence of (His)$_6$ at the N terminus, which can be purified on a Ni-NTA column. In addition, the fusion protein has a thrombin cleavage site and residues 1–219 of TF.

To purify tTF, tTF containing H6 pQE-60 DNA was transformed to *E. coli* TG-1 cells. The cells were grown to OD$_{600}$=0.5 and IPTG was added to 30 µM to induce the tTF production. The cells were harvested after shaking for 18 h at 30° C. The cell pellet was denatured in 6 M Gu-HCl and the lysate was loaded onto a Ni-NTA column (Qiagen). The bound tTF was washed with 6 M urea and tTF was refolded with a gradient of 6 M–1 M urea at room temperature for 16 h. The column was washed with wash buffer (0.05 Na H$_2$PO$_4$, 0.3 M NaCl, 10% glycerol) and tTF was eluted with 0.2 M Imidozole in wash buffer. The eluted tTF was concentrated and loaded onto a G-75 column. tTF monomers were collected.

B. tTF

Gly[tTF]. The GlytTF complimentary DNA (cDNA) was prepared the same way as described in the previous section except the 5' primer was replaced by the following primer in the PCR.

5' primer: 5' GTC ATG CCA TGG CCC TGG TGC CTC GTG
CT<u>T CTG GCA CTACAA ATA CT</u>    (SEQ ID NO:17)

The underlined sequence codes for the N-terminus of tTF. The remaining sequence encodes a restriction site for NcoI and a cleavage site for thrombin.

The H$_6$ pQE60 expression vector and the procedure for protein purification is identical to that described above except that the final protein product was treated with thrombin to remove the H$_6$ peptide. This was done by adding 1 part of thrombin (Sigma) to 500 parts of tTF (w/w), and the cleavage was carried out at room temperature for 18 h. Thrombin was removed from tTF by passage of the mixture through a Benzamidine Sepharose 6B thrombin affinity column (Pharmacia). The resultant tTF, designated tTF$_{219}$, consisted of residues 1–219 of TF plus an additional glycine at the N-terminus. It migrated as a single band of molecular weight 26 kDa when analyzed by SDS-PAGE, and the N-terminal sequence was confirmed by Edman degradation. It has the sequence of SEQ ID NO: 1.

C. Cysteine-Modified tTFs (His)$_6$-N'-cys'tTF$_{219}$-tTF, hereafter abbreviated to H$_6$-N'-cys-tTF$_{219}$, was prepared by mutating tTF$_{219}$ by PCR with a 5' primer encoding a Cys in front of the N'-terminus of mature tTF. H$_6$-tTF$_{219}$-cys-C' was prepared likewise using a 3' primer encoding a Cys after amino acid 219 of tTF. Expression and purification were as for tTF$_{219}$ except that Ellman's reagent (5'5'-dithio-bis-2-nitrobenzoic acid) was applied after refolding to convert the N'- or C'-terminal Cys into a stable activated disulfide group. The products have the sequences shown in SEQ ID NO:2 and SEQ ID NO:3. Thrombin cleavage removed the (His)$_6$ tag and converted the proteins into N'-cys-tTF$_{219}$ and tTF$_{219}$-cys-C' having the sequences shown in SEQ ID NO:4 and SEQ ID NO:5. The products were >95% pure as judged by SDS-polyacrylamide gel electrophoresis.

H$_6$-tTF$_{220}$-cys-C' and H$_6$-tTF$_{221}$-cys-C' were prepared by mutating tTF$_{219}$ by PCR with 3' primers encoding Ile-Cys and Ile-Phe-Cys after amino acid 219 of tTF. Expression, refolding and purification were as for H$_6$-tTF$_{219}$-cys-C'. The proteins have the sequences shown in SEQ ID NO:6 and SEQ ID NO:7.

EXAMPLE II

Synthesis of Dimeric Tissue Factor

The inventors' reasoned that Tissue Factor dimers may be more potent than monomers at initiating coagulation. It is possible that native Tissue Factor on the surface of J82 bladder carcinoma cells may exist as a dimer (Fair et al., 1987). The binding of one Factor VII or Factor VIIa molecule to one Tissue Factor molecule may also facilitate the binding of another Factor VII or Factor VIIa to another Tissue Factor (Fair et al., 1987;Bach et al., 1986). Furthermore, Tissue Factor shows structural homology to members of the cytokine receptor family (Edgington et al., 1991) some of which dimerize to form active receptors (Davies and Wlodawer, 1995). The inventors therefore synthesized TF dimers, as follows. While the synthesis of dimers hereinbelow is described in terms of chemical conjugation, recombinant and other means for producing the dimers of the present invention are also contemplated by the inventors.

A. [tTF] Linker [tTF]

The Gly [tTF] Linker [tTF] with the structure Gly[tTF] (Gly)$_4$ Ser (Gly)$_4$ Ser (Gly)$_4$ Ser [tTF] was made. Two pieces of DNA were PCR amplified separately and were ligated and inserted into the vector as follows:

PCR 1: Preparation of tTF and the 5' half of the linker DNA. The primer sequences in the PCR are as follows:

5' primer: 5' GTC ATG CCA TGG CCC TGG TGC CTC GTG GTT CTT GCG GCA
CTA CAA ATA CT (SEQ ID NO: 18)
3' primer: 5' CGC GGA TCC ACC GCC ACC AGA TCC ACC GCC TCC TTC TCT
GAA TTC CCC TTT CT (SEQ ID NO: 19)

Gly[tTF] DNA was used as the DNA template. Further PCR conditions were as described in the tTF section.

PCR 2: Preparation of the 3' half of the linker DNA and tTF DNA. The primer sequences in the PCR were as follows:

---

5' primer: 5' CGC GGA TCC GGC GGT GGA GGC TCT TCA GGC ACT ACA AAT ACT GT (SEQ ID NO: 20)
3' primer: 5' TGA CAA GCT TAT TCT CTG AAT TCC CCT TTC T (SEQ ID NO: 21)

--- tTF DNA was used as the template in the PCR. The product from PCR 1 was digested with NcoI and BamH. The product from PCR 2 was digested with HindIII and BamH1. The digested PCR1 and PCR2 DNA were ligated with NcoI and HindIII-digested $H_6$ pQE 60 DNA.

For the vector constructs and protein purification, the procedures were the same as described in the Gly [tTF] section.

B. Cys [tTF] Linker [tTF]

The Cys [tTF] Linker [tTF] with the structure Ser Gly Cys [tTF 2–219] (Gly)$_4$ Ser (Gly)$_4$ Ser(Gly)$_4$ Ser [tTF] was also constructed. DNA was made by PCR using the following primers were used:

---

5' primer: 5' GTC ATG CCA TGG CCC TGG TGC CTC GTG GTT CTT GCG GCA CTA CAA ATA CT (SEQ ID NO: 22)
3' primer: 5' TGA CAA GCT TAT TCT CTG AAT TCC CCT TTC T (SEQ ID NO: 23)

---

[tTF] linker [tTF] DNA was used as the template. The remaining PCR conditions were the same as described in the tTF section. The vector constructs and protein purification were all as described in the purification of $H_6$C[tTF].

C. [tTF] Linker [tTF]cys

The [tTF] Linker [tTF]cys dimer with the protein structure [tTF] (Gly)$_4$ Ser (Gly)$_4$ Ser (Gly)$_4$ Ser [tTF] Cys was also made. The DNA was made by PCR using the following primers:

---

5' primer: 5' GTC ATG CCA TGG CCC TGG TGC CTC GTG GTT GCA CTA CAA ATA CT (SEQ ID NO: 24)
3' primer: 5' TGA CAA GCT TAG CAT TCT CTG AAT TCC CCT TTC T (SEQ ID NO: 25).

---

[tTF] linker [tTF] DNA was used as the template. The remaining PCR conditions were the same as described in the tTF section. The vector constructs and protein purification were again performed as described in the purification of [tTF]cys section.

D. Chemically Conjugated Dimers

[tTF] Cys monomer, which had been treated with Ellman's reagent to convert the free Cys to an activated disulfide group, was reduced with half a molar equivalent of dithiothreitol. This generated free Cys residues in half of the molecules. The monomers are conjugated chemically to form [tTF] Cys—Cys [tTF] dimers. This is done by adding an equal molar amount of DTT to the protected [tTF] Cys at room temperature for 1 hr to deprotect and expose the cysteine at the C-terminus of [tTF] Cys. An equal molar amount of protected [tTF] Cys is added to the DTT/[tTF] Cys mixture and the incubation is continued for 18 h at room temperature. The dimers are purified on a G-75 gel filtration column. Dimers of $H_6$-tTF$_{220}$-cys-C', $H_6$-tTF$_{221}$-cys-C' and $H_6$-N'-cys-tTF$_{219}$ were prepared likewise. The Cys [tTF] monomer is conjugated chemically to form dimers using the same method.

EXAMPLE III

Synthesis of Tissue Factor Mutants

Three tTF mutants are described that lack the capacity to convert tTF-bound Factor VII to Factor VIIa. There is 300-fold less Factor VIIa in the plasma compared with Factor VII (Morrissey et al., 1993). Therefore, circulating mutant tTF should be less able to initiate coagulation and hence exhibit very low toxicity. However, once the mutant tTF has localized to the tumor site, as is surprisingly demonstrated herein, Factor VIIa may be injected to exchange with the tTF-bound Factor VII. The mutated proteins have the sequences shown in SEQ ID NO:8 and SEQ ID NO:9 and are active in the presence of Factor VIIa.

A. [tTF]G164A

The "[tTF]G164A" has the mutant protein structure with the amino acid 164 (Gly) of tTF$_{219}$ being replaced by Ala. The Chameleon double-stranded site directed mutagenesis kit (Stratagene) was used for generating the mutant. The DNA template is Gly[tTF] DNA and the sequence of the mutagenizing primer is:

5' CAA GTT CAG CCA AGA AAAC    (SEQ ID NO:26)

The G164A mutant is represented by SEQ ID NO:9. The vector constructs and protein purification procedures described above were used in the purification of Gly[tTF].

B. [tTF]W158R

The tryptophan at amino acid 158 of tTF$_{219}$ was mutated to an arginine by PCR™ with a primer encoding this change. Expression, refolding and purification was as for tTF$_{219}$. The mutated protein has the sequences shown in SEQ ID NO:8.

C. [tTF]W158R S162A

The [tTF]W158R S162A is a double mutant in which amino acid 158 (Trp) of tTF$_{219}$ is replaced by Arg and amino acid 162 (Ser) is replaced by Ala. The same mutagenizing method is used as described for [tTF] G164A and [tTF] W158R. The mutagenizing primer is:

5' ACA CTT TAT TAT CGG AAA TCT TCA GCT TCA GGA
AAG (SEQ ID NO:27)

The foregoing vector constructs and protein purification procedures are the same as used for purifying Gly[tTF].

EXAMPLE IV

Preparation of tTF-Bispecific Antibody Adducts and Synthesis of Tissue Factor Conjugates

A. Preparation of tTF-Bispecific Antibody Adducts

Bispecific antibodies were constructed that had one Fab' arm of the 10H10 antibody that is specific for a non-inhibitory epitope on tTF linked to one Fab' arm of antibodies (OX7, Mac51, CAMPATH-2) of irrelevant specificity. When mixed with tTF, the bispecific antibody binds the tTF via the 10H10 arm, forming a non-covalent adduct. The bispecific antibodies were synthesized according to the method of Brennan et al. (1985;incorporated herein by reference) with minor modifications.

In brief, F(ab')$_2$ fragments were obtained from the IgG antibodies by digestion with pepsin (type A; EC 3.4.23.1) and were purified to homogeneity by chromatography on Sephadex G100. F(ab')$_2$ fragments were reduced for 16 h at 20° C. with 5 mM 2-mercaptoethanol in 0.1 M sodium phosphate buffer, pH 6.8, containing 1 mM EDTA (PBSE buffer) and 9 mM NaAsO$_2$. Ellman's reagent (ER) was added to give a final concentration of 25 mM and, after 3 h at 20° C., the Ellman's derivatized Fab' fragments (Fab'-ER) were separated from unreacted ER on columns of Sephadex G25 in PBSE.

To form the bispecific antibody, Fab'-ER derived from one antibody was concentrated to approximately 2.5 mg/ml in an Amicon ultrafiltration cell and was reduced with 10 mM 2-mercaptoethanol for 1 h at 20° C. The resulting Fab'-SH was filtered through a column of Sephadex G25 in PBSE and was mixed with a 1:1-fold molar excess of Fab'-ER prepared from the second antibody. The mixtures were concentrated by ultrafiltration to approximately 3 mg/ml and were stirred for 16 h at 20° C. The products of the reaction were fractionated on columns of Sephadex G100 in PBS. The fractions containing the bispecific antibody (110 kDa) were concentrated to 1 mg/ml, and stored at 4° C. in 0.02% sodium azide.

To form the tTF-bispecific antibody adducts, the bispecific antibody was mixed with a molar equivalent of tTF or derivatives thereof for 1 hour at 4° C. The adduct eluted with a molecular weight of approximately 130 kDa on gel filtration columns, corresponding to one molecule of bispecific antibody linked to one molecule of tTF.

1. Preparation of IgG-H$_6$-N'-cys-tTF$_{219}$ and IgG-H$_6$-tTF$_{219}$-cys-C'

To 26 mg IgG at a concentration of 10 mg/ml in N$_2$-flushed phosphate-saline buffer was added 250 μg SMPT (Pharmacia) in 0.1 ml dry DMF. After stirring for 30 minutes at room temperature, the solution was applied to a column (1.6 cm diameter×30 cm) of Sephadex G25(F) equilibrated in the same buffer. The derivatized IgG was collected in a volume of 10 to 12 ml and concentrated to about 3.5 ml by ultrafiltration (Amicon, YM2 membrane). The H$_6$-N'-cys-tTF$_{219}$ or H$_6$-tTF$_{219}$-cys-C' (15 mg) was reduced by incubation at room temperature in the presence of 0.2 mM DTT until all Ellman's agent was released (i.e. OD at 412 nm reached a maximum). It was then applied to the Sephadex G25(F) column (1.6 cm diameter×30 cm) equilibrated with N$_2$-flushed buffer.

The Cys-tTF (~15 ml) was added directly to the derivatized IgG solution. The mixture was concentrated to about 5 ml by ultrafiltration and incubated at room temperature for 18 hours before resolution by gel filtration chromatography on Sephacryl S200. The peak containing material having a molecular weight of 175,000–200,000 was collected. This component consisted of one molecule of IgG linked to one or two molecules of tTF. The conjugates have the structure:

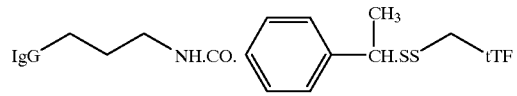

2. Preparation of Fab'-H6-N'-cys-tTF219

Fab' fragments were produced by reduction of F(ab')$_2$ fragments of IgG with 10 mM mercaptoethylamine. The resulting Fab' fragments were separated from reducing agent by gel filtration on Sephadex G25. The freshly-reduced Fab' fragment and the Ellman's modified H$_6$-N'-cys-tTF$_{219}$ were mixed in equimolar amounts at a concentration of 20 μM. The progress of the coupling reaction was followed by the increase in absorbance at 412 nm due to the 3-carboxylato-4-nitrothiophenolate anion released as a result of conjugation. The conjugate has the structure:

Fab'-SS-tTF

B. Synthesis of Tissue Factor Conjugates

1. Chemical Derivatization and Antibody Conjugation

Antibody tTF conjugates were synthesized by the linkage of chemically derivatized antibody to chemically derivatized tTF via a disulfide bond.

Antibody was reacted with a 5-fold molar excess of succinimidyl oxycarbonyl-α-methyl α-(2-pyridyldithio) toluene (SMPT) for 1 hour at room temperature to yield a derivatized antibody with an average of 2 pyridyldisulphide groups per antibody molecule. Derivatized antibody was purified by gel permeation chromatography.

A 2.5-fold molar excess of tTF over antibody was reacted with a 45-fold molar excess of 2-iminothiolane (2IT) for 1 hour at room temperature to yield tTF with an average of 1.5 sulfhydryl groups per tTF molecule. Derivatized tTF was also purified by gel permeation chromatography and immediately mixed with the derivatized antibody.

The mixture was left to react for 72 hours at room temperature and then applied to a Sephacryl S-300 column to separate the antibody-tTF conjugate from free tTF and released pyridine-2-thione. The conjugate was separated from free antibody by affinity chromatography on a anti-tTF column. The predominant molecular species of the final conjugate product was the singly substituted antibody-tTF conjugate (Mr approx. 176,000) with lesser amounts of multiply substituted conjugates (Mr≧approx. 202,000) as assessed by SDS-PAGE.

2. Conjugation of Cysteine-Modified tTF to Derivatized Antibody

Antibody-C[TF] and [tTF]C conjugates were synthesized by direct coupling of cysteine-modified tTF to chemically derivatized antibody via a disulfide bond.

Antibody was reacted with a 12-fold molar excess of 2IT for 1 hour at room temperature to yield derivatized antibody with an average of 1.5 sulfhydryl groups per antibody molecule. Derivatized antibody was purified by gel permeation chromatography and immediately mixed with a 2-fold molar excess of cysteine-modified tTF. The mixture was left to react for 24 hours at room temperature and then the conjugate was purified by gel permeation and affinity chromatography as described above.

The predominant molecular species of the final conjugate was the singly substituted conjugate (Mr approx. 176,000) with lesser amounts of multiple substituted conjugates (Mr≧approx. 202,000) as assessed by SDS-PAGE.

3. Conjugation of Cysteine-Modified tTF to Fab' Fragments

Antibody Fab'-C[tTF] and [tTF]C conjugates are prepared. Such conjugates may be more potent in vivo because they should remain on the cell surface for longer than bivalent conjugates due to their limited internalization capacity. Fab' fragments are mixed with a 2-fold molar excess of cysteine-modified tTF for 24 hours and then the conjugate purified by gel permeation and affinity chromatography as described above.

EXAMPLE V

Tumor Infraction by Tissue Factor

A. Methods

1. In Vitro Coagulation Assay

This assay was used to verify that tTF, various derivatives and mutants thereof, and immunoglobulin-tTF conjugates acquire coagulation inducing activity once localized at a cell surface. A20 lymphoma cells (I-$A^d$ positive) ($2\times10^6$ cells/ml, 50 μl) were incubated for 1 h at room temperature with a bispecific antibody (50 μg/ml, 25 μl) consisting of a Fab' arm of the B21-2 antibody directed against I-$A^d$ linked to a Fab' arm of the 10H10 antibody directed against a non-inhibitory epitope on tTF. The cells were washed at room temperature and varying concentrations of tTF, derivatives or mutants thereof, or immunoglobulin-tTF conjugates were added for 1 hour at room temperature. The bispecific antibody captures the tTF or tTF linked to immunoglobulin, bringing it into close approximation to the cell surface, where coagulation can proceed.

The cells were washed again at room temperature, resuspended in 75 μl of PBS and warmned to 37° C. Calcium (12.5 mM) and citrated mouse or human plasma (30 μl) were added. The time for the first fibrin strands to form was recorded. Clotting time was plotted against tTF concentration and curves compared with standard curves prepared using standard $tTF_{219}$ preparations.

In some studies, varying concentrations of recombinant human Factor VIIa were added together with $tTF_{219}$ and mutants thereof, to determine whether coagulation rate was enhanced by the presence of Factor VIIa.

2. Factor Xa Production Assays

This assay is useful in addition to or as an alternative to the in vitro coagulation assay to demonstrate that tTF and immunoglobulin-tTF conjugates acquire coagulation inducing activity once localized at a cell surface. The assay measures factor X to Xa conversion rate by means of a chromophore-generating substrate (S-2765) for factor Xa.

A20 cells ($2\times10^7$ cells) were suspended in 10 ml medium containing 0.2% w/v sodium azide. To 2.5 ml cell suspension were added 6.8 μg of B21-2/10H10 "capture" bispecific antibody for 50 minutes at room temperature. The cells were washed and resuspended in 2.5 ml medium containing 0.2% w/v sodium azide. The tTF and immunoglobulin-tTF conjugates dissolved in the same medium were distributed in 100 μl volumes at a range of concentrations into wells of 96-well microtiter plates. To the wells was then added 100 μl of the cell/bispecific antibody suspension. The plates were incubated for 50 minutes at room temperature.

The plates were centrifuged, the supernatants were discarded and the cell pellets were resuspended in 250 μl of Wash Buffer (150 mM NaCl;50 mM Tris-HCl, pH 8; 0.2% w/v bovine serum albumin). The cells were washed again and cells resuspended in 100 μl of a 12.5-fold dilution of Proplex T (Baxter, Inc.) containing Factors II, VII, IX and X in Dilution Buffer (Wash Buffer supplemented with 12.5 mM calcium chloride). Plates were incubated at 37° C. for 30 minutes. To each well was added Stop Solution (12.5 mM sodium ethylenediaminetetracetic acid (EDTA)) in wash buffer. Plates were centrifuged. 100 μl of supernatant from each well were added to 11 μl of S-2765 (N-α-benzyloxycarbonyl-D-Arg-L-Gly-L-Arg-p-nitroanilide dihydrochloride, Chromogenix AB, Sweden). The optical density of each solution was measured at 409 nm. Results were compared to standard curves generated from standard $tTF_{219}$.

3. In Vivo Tumor Thrombosis

This model was used to demonstrate that tTF and immunoglobulin-tTF conjugates induced thrombosis of tumor blood vessels and caused tumor infarction in vivo.

Tumor test systems were of four types: i) 3LL mouse lung carcinoma growing subcutaneously in C57BL/6 mice; ii) C1300 mouse neuroblastoma growing subcutaneously in BALB/c nu/nu mice; iii) HT29 human colorectal carcinoma growing subcutaneously in BALB/c nu/nu mice; and iv) C1300 Muγ mouse neuroblastoma growing subcutaneously in BALB/c nu/nu mice. The C1300 Muγ tumor is an interferon-γ secreting transfectant derived from the C1300 tumor (Watanabe et al., 1989).

Further, the C1300 (Muγ) tumor model of (Burrows, et al., 1992;incorporated herein by reference) was employed and modified as follows: (i) antibody B21-2 was used to target I-$A^d$; (ii) C1300(Muγ) tumor cells, a subline of C1300(Muγ) 12 tumor cells, that grew continuously in BALB/c nu/nu mice were used; and (iii) tetracycline was omitted from the mice's drinking water to prevent gut bacteria from inducing I-$A^d$ on the gastrointestinal epithelium. Unlike immunotoxins, coaguligands and Tissue Factor constructs do not damage I-$A^d$-expressing intestinal epithelium.

4. Tumor Establishment

To establish tumors, $10^6$ to $1.5\times10^7$ tumor cells were injected subcutaneously into the right anterior flank of the mice. When tumors had grown to various sizes, mice were randomly assigned to different study groups. Mice then received an intravenous injection of 0.5 mg/kg of tTF alone or linked to IgG, Fab', or bispecific antibody. Other mice received equivalent quantities IgG, Fab' or bispecific antibody alone. The injections were performed slowly into one of the tail veins over approximately 45 seconds, usually followed by 200 μl of saline.

In some studies, the effect of administering cancer chemotherapeutic drugs on the thrombotic action of tTF on tumor blood vessels was investigated. Mice bearing subcutaneous HT29 human colorectal tumors of 1.0 cm diameter were given intraperitoneal injections of doxorubicin (1 mg/kg/day), camptothecin (1 mg/kg/day), etoposide (20 mg/kg/day) or interferon gamma ($2\times10^5$ units/kg/day) for two days before the tTF injection and again on the day of the tTF injection.

Twenty-four hours after being injected with tTF or immunoglobulin-tTF conjugates, the mice were anesthetized with metophane and were exsanguinated by perfusion with heparinized saline. Tumors and normal tissues were excised and immediately fixed in 3% (v/v) formalin. Paraffin sections were cut and stained with hematoxylin and eosin. Blood vessels having open lumens containing erythrocytes and blood vessels containing thrombi were counted. Paraffin sections were cut and stained with hematoxylin and eosin or with Martius Scarlet Blue (MSB) trichrome for the detection of fibrin.

5. Anti-Tumor Effects

Accepted animal models were used to determine whether administration of tTF or immunoglobulin-tTF conjugates suppressed the growth of solid tumors in mice. The tumor test systems were: i) L540 human Hodgkin's disease tumors growing in SCID mice; ii) C1300 Muγ (interferon-secreting) neuroblastoma growing in nu/nu mice; iii) H460 human non-small cell lung carcinoma growing in nu/nu mice. To establish solid tumors, $1.5 \times 10^7$ tumor cells were injected subcutaneously into the right anterior flank of SCID or BALB/c nu/nu mice (Charles River Labs., Wilmingham, Mass.). When the tumors had grown to various diameters, mice were assigned to different experimental groups, each containing 4 to 9 mice.

Mice then received an intravenous injection of 0.5 mg/kg of tTF alone or linked to bispecific antibody. Other mice received equivalent quantities of bispecific antibody alone. The injections were performed over ~45 seconds into one of the tail veins, followed by 200 μl of saline. The infusions were repeated six days later. Perpendicular tumor diameters were measured at regular intervals and tumor volumes were calculated.

B. Results

1. In vitro Coagulation by tTF and Variants

Figure 4A:
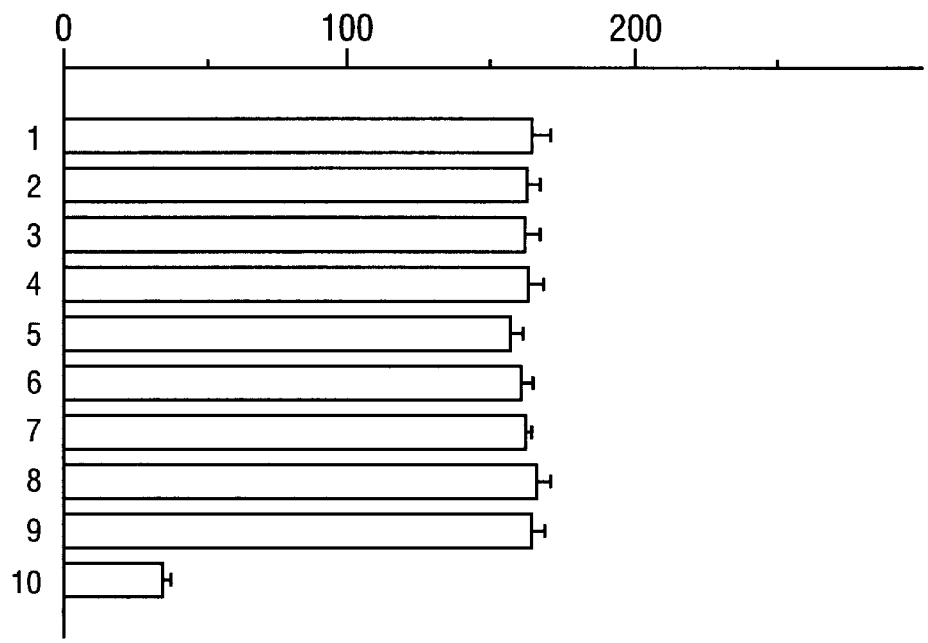
FIG. 4A and FIG. 4B.
Figure 5:
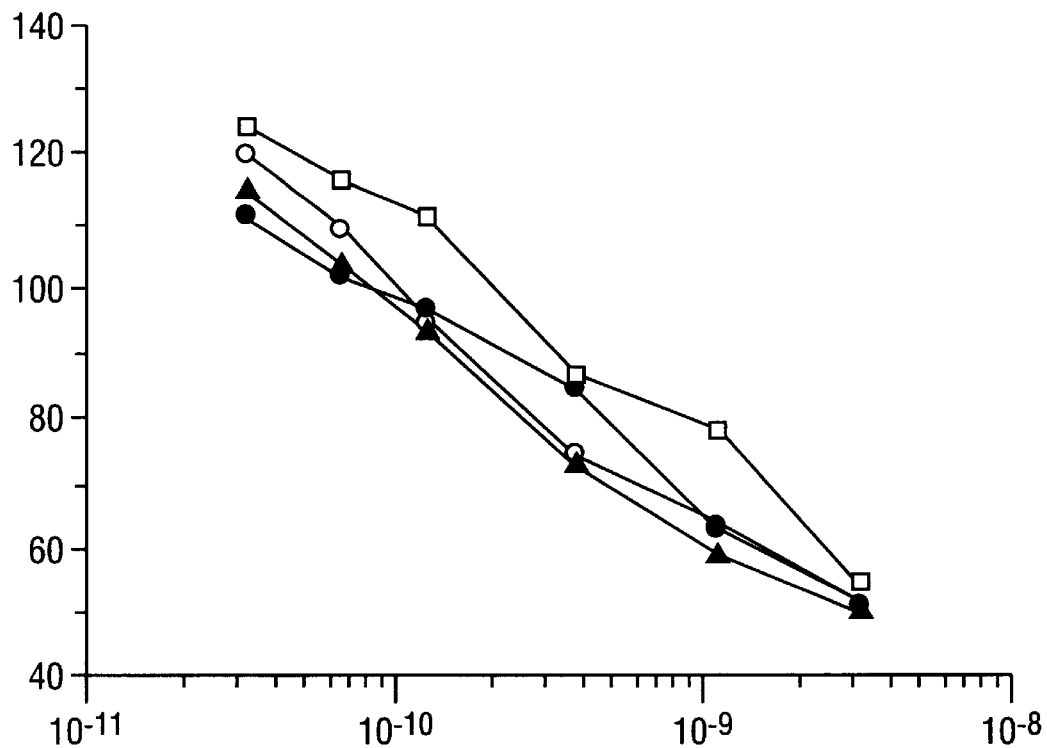
FIG. 5: Coagulation of mouse plasma by cell-associated tTF$_{219}$, H$_6$-N'-cys-tTF$_{219}$ and H$_6$-tTF$_{219}$-cys-C'. A20 lymphoma cells (I-A$^d$ positive) were treated at room temperature with the "capture" bispecific antibody, B21-2/10H10, recognizing both I-A$^d$ and tTF. Cells were washed and two different preparations of tTF$_{219}$ [standard tTF$_{219}$ (○) and tTF$_{219}$ (▲),], H$_6$-N'-cys-tTF$_{219}$ (□) or H$_6$-tTF$_{219}$-cys-C' (●) were added at a range of tTF concentrations (concentration, M; horizontal axis). Cells were washed and warmed to 37° C. Calcium and citrated mouse plasma were added and the time for the first strands of fibrin to form was recorded (clotting time, seconds; vertical axis).

To target tTF to I-A$^d$ on tumor vascular endothelium, the inventors prepared a bispecific antibody with the Fab' arm of the B21-2 antibody, specific for I-A$^d$, linked to the Fab' arm of the 10H10 antibody, specific for a non-inhibitory epitope on the C-module of tTF. This bispecific antibody, B21-2/10H10, mediated the binding of tTF in an antigen-specific manner to I-A$^d$ on A20 mouse B-lymphoma cells in vitro. When mouse plasma was added to A20 cells to which tTF had been bound by B21-2/10H10, it coagulated rapidly. Fibrin strands were visible 36 seconds after the addition of plasma to antibody-treated cells, as compared with 164 seconds when plasma was added to untreated cells (FIG. 4A). Only when tTF was bound to the cells was this enhanced coagulation observed: no effect on coagulation time was seen with cells incubated with tTF alone, with homodimeric F(ab')$_2$, with Fab' fragments, or with tTF plus bispecific antibodies that had only one of the two specificities needed for binding tTF to A20 cells.

tTF$_{219}$ prepared as in Example I had identical ability to a "standard" tTF$_{219}$ preparation obtained from Dr. Thomas Edgington (The Scripps Research Institute, La Jolla, Calif.) to induce coagulation of mouse or human plasma after its binding via B21-2/10H10 bispecific antibody to A20 lymphoma cells (FIG. 5). Mouse plasma coagulated in 50 seconds when both the preparation of tTF$_{219}$ of Example I and the "standard" tTF were applied to the cells at $3 \times 10^{-9}$ M. Thus, the tTF$_{219}$ prepared as described herein appears to be correctly refolded and fully active.

Figure 4B:
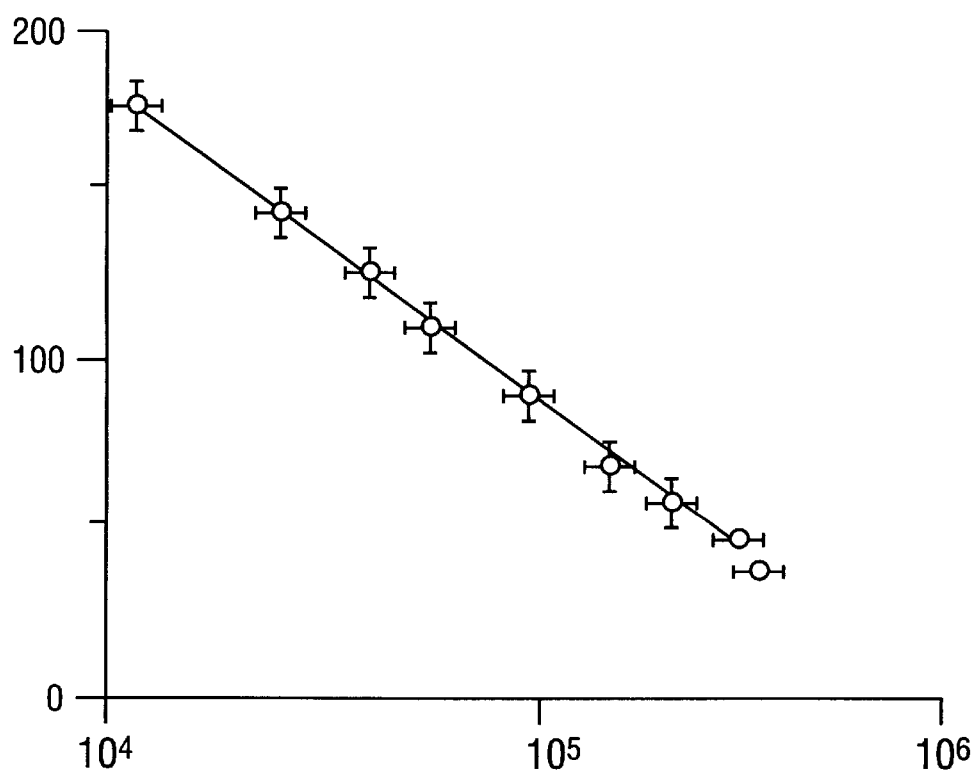

There was a linear relationship between the logarithm of the number of tTF molecules bound to the cells and the rate of plasma coagulation by the cells (FIG. 4B). In the presence of cells alone, plasma coagulated in 190 seconds, whereas at 300,000 molecules of tTF per cell coagulation time was 40 seconds. Even with only 20,000 molecules per cell, coagulation was faster (140 seconds) than with untreated cells. These in vitro studies showed that the thrombogenic potency of tTF is enhanced by cell surface proximity mediated through antibody-directed binding to Class II antigens on the cell surface.

H$_6$-N'-cys-tTF$_{219}$ and H$_6$-tTF$_{219}$-cys-C' were as active as tTF at inducing coagulation of plasma once bound via the bispecific antibody to A20 cells. Plasma coagulated in 50 seconds when H$_6$-N'-cys-tTF$_{219}$ and H$_6$-tTF$_{219}$-cys-C' were applied at $3 \times 10^{-9}$ M, the same concentration as for tTF (FIG. 5). Thus, mutation of tTF to introduce a (His)$_6$ sequence and a Cys residue at the N' or C' terminus does not reduce its coagulation-inducing activity.

Figure 6:
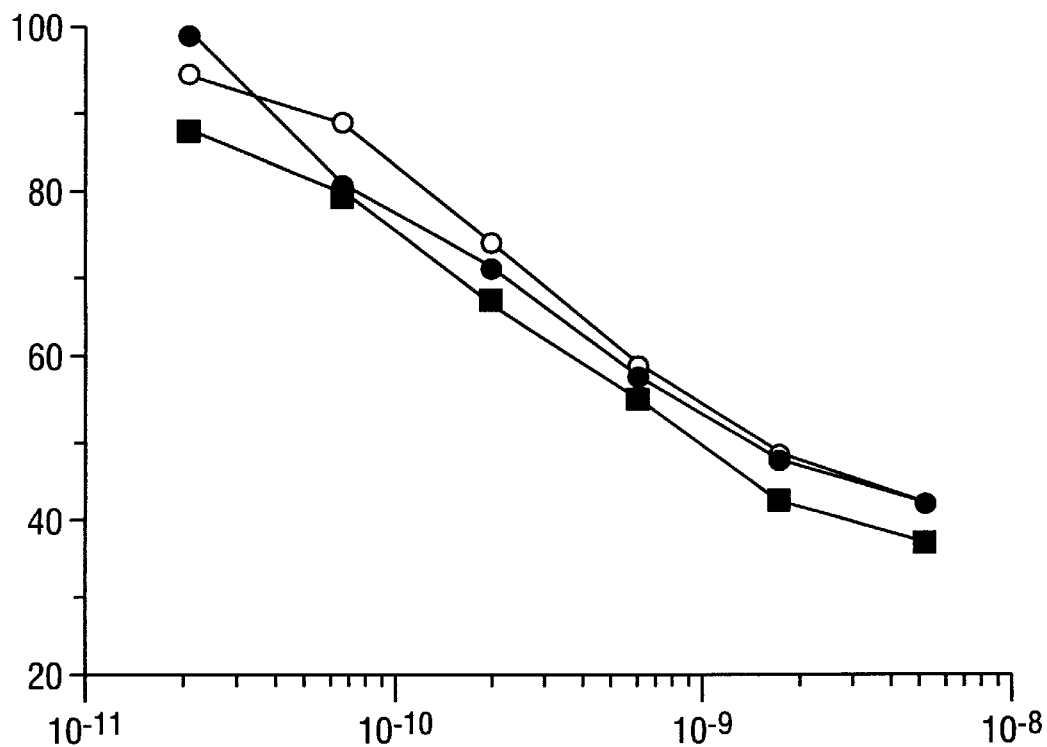
FIG. 6: Coagulation of mouse plasma by cell-associated H$_6$-tTF$_{220}$-cys-C' and tTF$_{220}$-cys-C'. A20 lymphoma cells (I-A$^d$ positive) were treated at room temperature with the "capture" bispecific antibody, B21-2/10H10, recognizing both I-A$^d$ and tTF. Cells were washed and standard tTF$_{219}$ (■), H$_6$-tTF$_{220}$-cys-C' (○) and tTF$_{220}$-cys-C' (●) were added at a range of concentrations (concentration, M; horizontal axis). Cells were washed and warmed to 37° C. Calcium and citrated mouse plasma were added and the time for the first strands of fibrin to form was recorded (clotting time, seconds; vertical axis).
Figure 7:
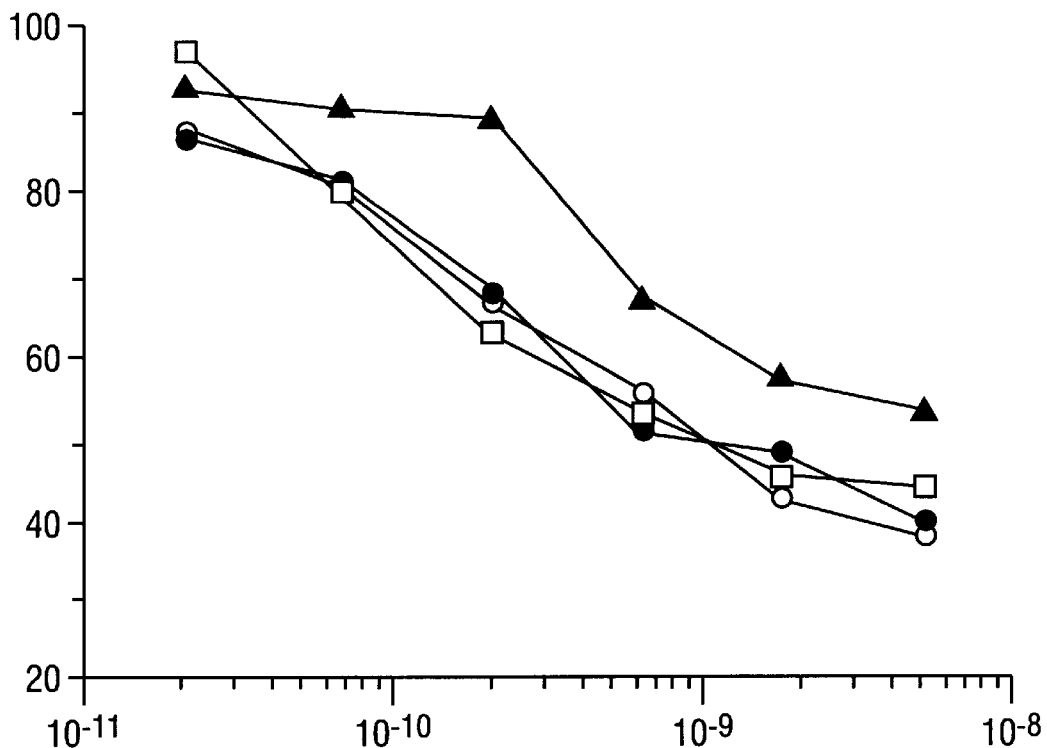
FIG. 7: Coagulation of mouse plasma by cell associated H$_6$-tTF$_{221}$-cys-C', tTF$_{221}$-cys-C' and H$_6$-tTF$_{221}$-cys-C' dimer. A20 lymphoma cells (I-A$^d$ positive) were treated at room temperature with the "capture" bispecific antibody, B21-2/10H10, recognizing both I-A$^d$ and tTF. Cells were washed and standard tTF$_{219}$ (○), H$_6$- tTF$_{221}$-cys-C' (○), tTF$_{221}$-cys-C' (□), or H$_6$-tTF$_{221}$-cys-C' dimer (▲) were added at a range of concentrations (concentration, M; horizontal axis). Cells were washed and warmed to 37° C. Calcium and citrated mouse plasma were added and the time for the first strands of fibrin to form was recorded (clotting time, seconds; vertical axis).

H$_6$-tTF$_{220}$-cys-C', tTF$_{220}$-cys-C', H$_6$-tTF$_{221}$-cys-C' and tTF$_{221}$-cys-C' were as active as tTF$_{219}$ at inducing coagulation of plasma once localized on the surface of A20 cells via the bispecific antibody, B21-2/10H10. With all samples at $5 \times 10^{-10}$ M, plasma coagulated in 50 seconds (FIG. 6 and FIG. 7).

2. In Vitro Coagulation by tTF Dimers

Figure 8:
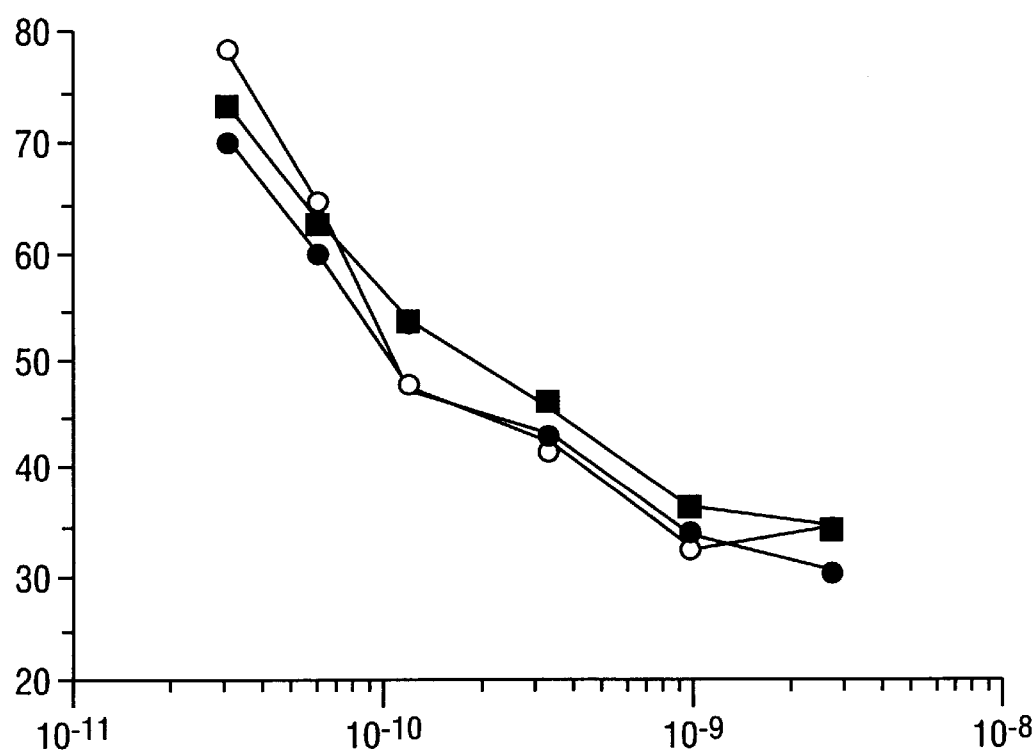
FIG. 8: Coagulation of mouse plasma by cell-associated H$_6$-N'-cys-tTF$_{219}$ and H$_6$-N'-cys-tTF$_{219}$ dimer. A20 lymphoma cells (I-A$^d$ positive) were treated at room temperature with the "capture" bispecific antibody, B21-2/10H10, recognizing both I-A$^d$ and tTF. Cells were washed and standard tTF$_{219}$ (○), H$_6$-N'-cys-tTF$_{219}$ (■) and H$_6$-N'-cys-tTF$_{219}$ dimer (●) were added at a range of concentrations (concentration, M; horizontal axis). Cells were washed and warmed to 37° C. Calcium and citrated mouse plasma were added and the time for the first strands of fibrin to form was recorded (clotting time, seconds; vertical axis).

H$_6$-N'cys-tTF$_{219}$ dimer was as active as tTF$_{219}$ itself at inducing coagulation of plasma once localized on the surface of A20 cells via the bispecific antibody, B21-2/10H10. At a concentration of $1-2 \times 10^{-10}$ M, both samples induced coagulation in 50 seconds (FIG. 8). In contrast, H$_6$-tTF$_{221}$-cys-C' dimer was 4-fold less active than H$_6$-tTF$_{221}$-cys-C' monomer or tTF$_{219}$ itself. At a concentration of $4 \times 10^{-9}$M, H$_6$-tTF$_{221}$-cys-C' dimer induced coagulation of plasma in 50 seconds, whereas the corresponding monomer needed to be applied at $1 \times 10^{-9}$ M for the same effect on coagulation.

3. In vivo Tumor Thrombosis

Figure 9:
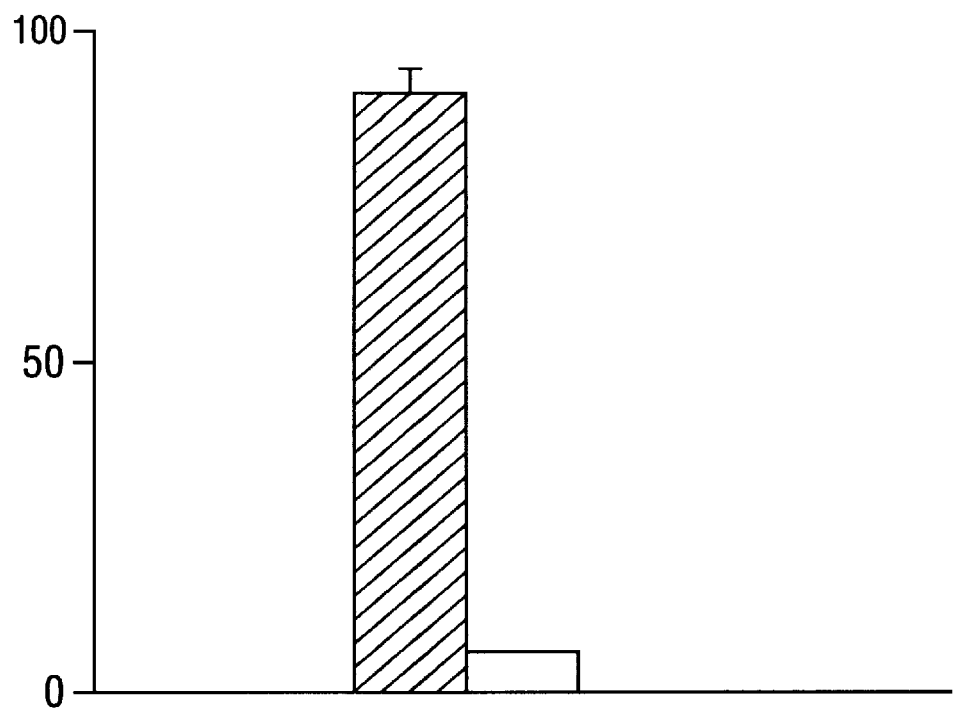
FIG. 9: Thrombosis of vessels in large C1300 Muγ tumors by tTF$_{219}$. Nu/Nu mice bearing large (>1000 mm$^3$) subcutaneous C1300 Muγ tumors were injected intravenously with 16–20 μg tTF$_{219}$. Twenty-four hours later, mice were anesthetized, exsanguinated and tumors and organs were removed. Paraffin sections of the tissues were evaluated for the presence of thrombosed vessels. The numbers of thrombosed vessels and open vessels in sections of tumors were counted. The percent of tumor vessels thrombosed is shown on the vertical axis. The hatched bar represents tTF$_{219}$ injected mice, the open bar represents PBS injected mice.

A histological study was performed to determine whether intravenous administration of the B21-2/10H10-tTF coaguligand induced selective thrombosis of tumor vasculature in mice bearing subcutaneous C1300(Muγ) neuroblastomas of 0.8 to 1.0 cm diameter (FIG. 9). Within 30 minutes, all vessels throughout the tumor were thrombosed, containing occlusive platelet aggregates, packed erythrocytes, and fibrin. At this time, tumor cells were indistinguishable histologically from tumor cells of untreated mice.

After 4 hours, however, there were signs of tumor cell injury. The majority of tumor cells had separated from one another and had pyknotic nuclei, and the tumor interstitium commonly contained erythrocytes. By 24 hours, the tumor showed advanced necrosis, and by 72 hours, the entire central region of the tumor had condensed into amorphous debris. These studies indicated that the predominant occlusive effect of the B21-2/10H10-tTF coaguligand on tumor vessels is mediated through binding to Class II antigens on tumor vascular endothelium.

Surprisingly it was observed that there was a non-specific thrombotic action of tTF discernible in tumor vessels at later times: In tumors from mice which had been injected 24 hours previously with tTF alone or tTF mixed with the control bispecific antibody, OX7/10H10, the tumors assumed a blackened, bruised appearance starting within 30 minutes and becoming progressively more marked up to 24 hours. A histological study revealed that 24 hours after injection of tTF$_{219}$ practically all vessels in all regions of the tumor were thrombosed (FIG. 9). Vessels contained platelet aggregates, packed red cells and fibrin. The majority of tumor cells had separated from one another and had developed pyknotic nuclei and many regions of the tumors were necrotic. These were most pronounced in the tumor core. Erythrocytes were commonly observed in the tumor interstitium.

It is possible that the resident thrombogenic activity of tumor vasculature (Zacharski, et al., 1993) renders these vessels more susceptible to thrombosis even by untargeted tTF. Alternatively, enhanced procoagulant changes might have been induced by the tumor-derived IFNγ.

Figure 10:
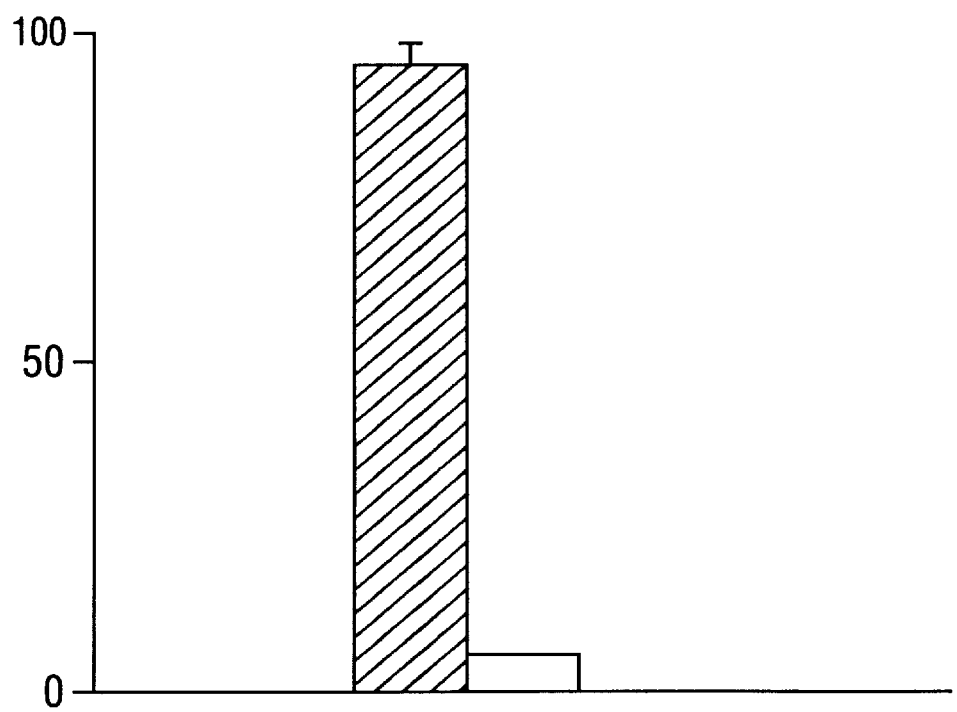
FIG. 10: Thrombosis of vessels in large C1300 tumors by tTF$_{219}$. Nu/nu mice bearing large (>1000 mm$^3$) subcutaneous C1300 tumors were injected intravenously with 16–20 μg tTF$_{219}$. Twenty-four hours later, mice were anesthetized, exsanguinated and tumors and organs were removed. Paraffin sections of the tissues were evaluated for the presence of thrombosed vessels. The numbers of thrombosed vessels and open vessels in sections of tumors were counted. The percent of tumor vessels thrombosed is shown on the vertical axis. The hatched bar represents tTF$_{219}$ injected mice, the open bar represents PBS injected mice.

Similar results were obtained when tTF$_{219}$ was administered to mice bearing large C1300 tumors (>1000 mm$^3$). Again, virtually all vessels were thrombosed 24 hours after injection (FIG. 10). Thus, the effects observed on C1300 Muγ tumors were not related to the interferon γ secretion by the tumor cells.

Figure 11:
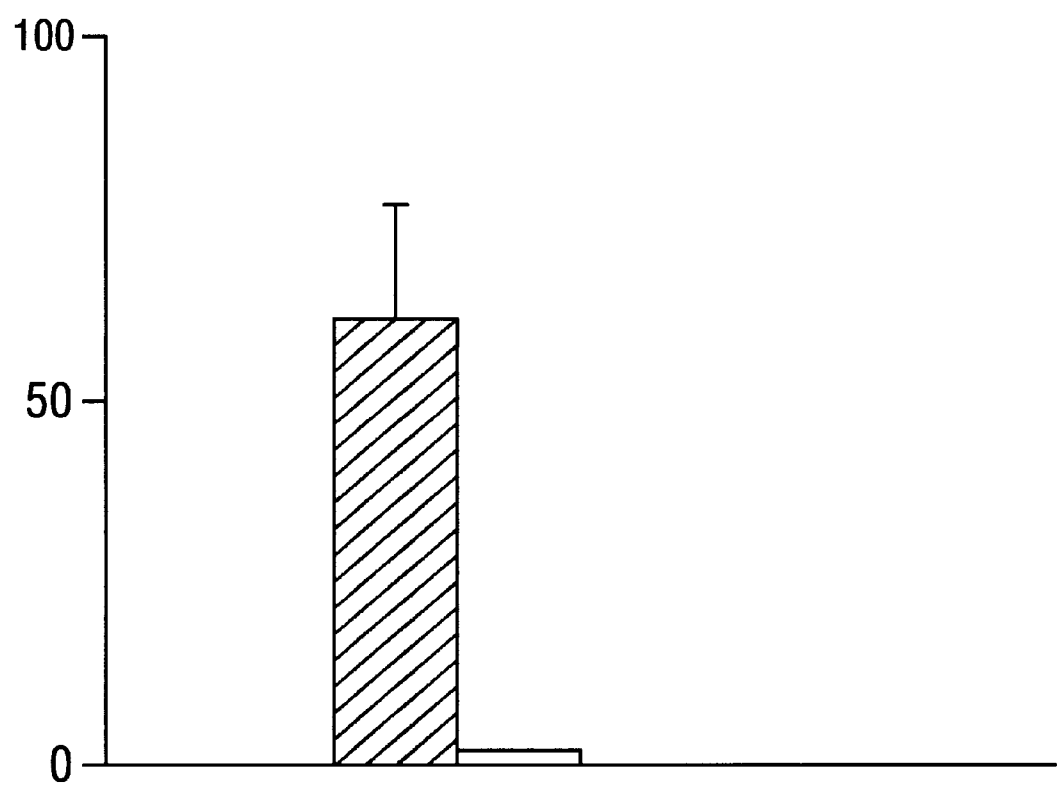
FIG. 11: Thrombosis of vessels in large 3LL tumors by tTF$_{219}$. C57BL/6 mice bearing large (>800 mm$^3$) subcutaneous 3LL tumors were injected intravenously with 16–20 μg tTF$_{219}$. Twenty-four hours later, mice were anesthetized, exsanguinated and tumors and organs were removed. Paraffin sections of the tissues were evaluated for the presence of thrombosed vessels. The numbers of thrombosed vessels and open vessels in sections of tumors were counted. The percent of tumor vessels thrombosed is shown on the vertical axis. The hatched bar represents tTF$_{219}$ injected mice, the open bar represents PBS injected mice.

Further studies were performed in C57BL/6 mice bearing large (>800 mm$^3$) 3LL tumors. Again, thrombosis of tumor vessels was observed, though somewhat less pronounced than with the C1300 and C1300 Muγ tumor. On average 62% of 3LL tumor vessels were thrombosed (FIG. 11).

Vessels in small (<500 mm$^3$) C1300 and C1300 Muγ were largely unaffected by tTF$_{219}$ administration. Thus, as the tumors grow, their susceptibility to thrombosis by tTF$_{219}$ increases. This is possibly because cytokines released by tumor cells or by host cells that infiltrate the tumor activate the tumor vascular endothelium, inducing procoagulant changes in the vessels.

Coaguligand treatment was well tolerated, mice lost no weight and retained normal appearance and activity levels. At the treatment dose of 0.6 mg/kg B21-2/10H10 plus 0.5 mg/kg tTF, toxicity was observed in only two of forty mice (thrombosis of tail vein). It is important to note that neither thrombi, nor histological or morphological abnormalities were visible in paraffin sections of liver, kidney, lung, intestine, heart, brain, adrenals, pancreas, or spleen from the tumor-bearing mice 30 minutes or 24 hours after administration of coaguligand or free tTF. Furthermore, no signs of toxicity (behavioral changes, physical signs, weight changes) were observed in treated animals.

4. Anti-Tumor Effects

Figure 12A:
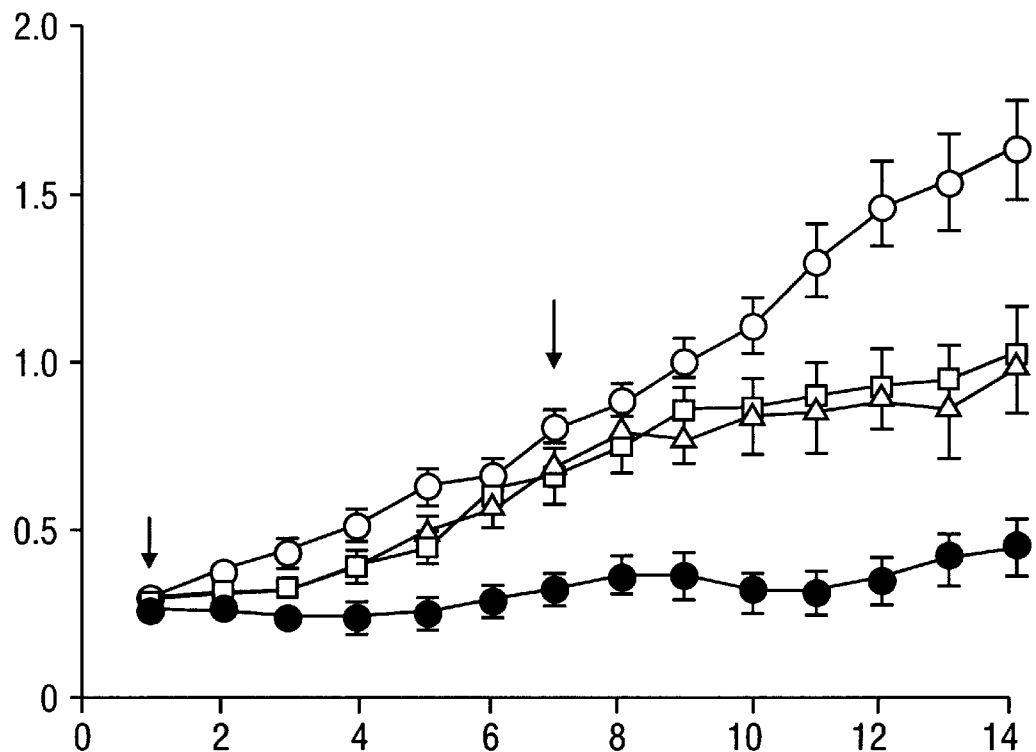
FIG. 12A and FIG. 12B: Inhibition of growth of C1300 Muγ tumors in mice by tTF$_{219}$.

The inventors next investigated whether intravenous administration of the B21-2/10H10-tTF coaguligand could inhibit the growth of large (0.8 to 1.0 cm diameter) tumors in mice. The pooled results from three separate studies indicate that mice receiving B21-2/10H10-tTF coaguligand had complete tumor regressions lasting four months or more. These anti-tumor effects were significantly greater than for all other treatment groups (FIG. 12A).

Figure 12B:
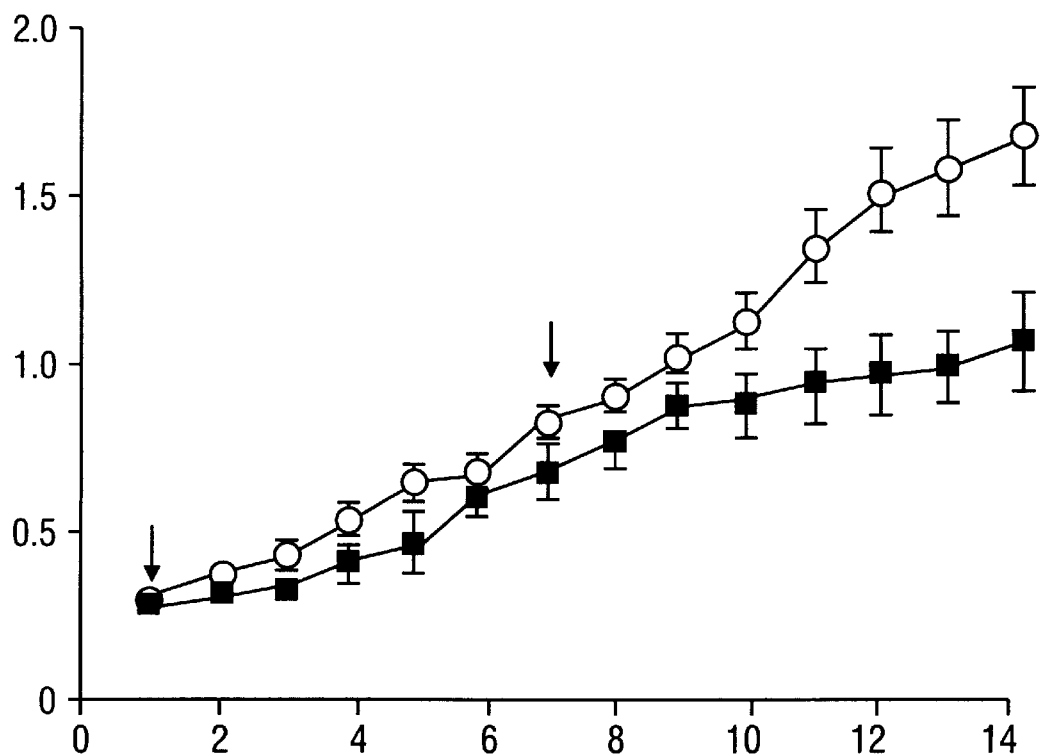

Surprisingly, the inventors found that the anti-tumor effect of the B21-2/10H10-tTF coaguligand was attributable, in part, to a non-targeted effect of tTF. Tumors in mice receiving tTF alone or mixed with control bispecific antibodies (CAMPATH II/10H10 or B21-2/OX7) grew significantly more slowly than tumors in mice receiving antibodies or saline alone (FIG. 12A; FIG. 12B).

Mice bearing small (300 mm$^3$) C1300 Muγ tumors were injected intravenously with 16–20 μg tTF$_{219}$. The treatment was repeated one week later. The first treatment with tTF$_{219}$ had a slight inhibitory effect on tumor growth, consistent with the lack of marked thrombosis observed with small tumors above (FIG. 12B). The second treatment had a substantially greater, statistically significant (P<0.01), effect on tumor growth, probably because the tumors had increased in size. One week after the second treatment with tTF$_{219}$, tumors were 60% of the size of tumors in mice receiving diluent alone. The greater effectiveness of the second injection probably derives from the greater thrombotic action of tTF$_{219}$ on vessels in large tumors, observed above.

Figure 13:
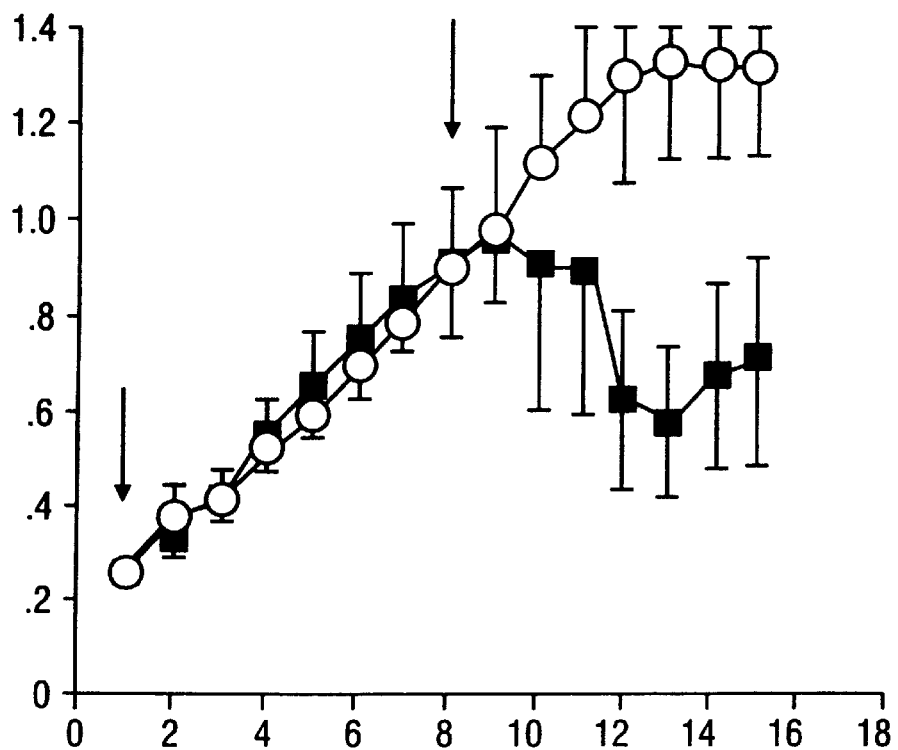
FIG. 13: Inhibition of growth of H460 tumors in mice by tTF$_{219}$. Nu/nu mice bearing small (350 mm$^3$) subcutaneous H460 tumors were injected intravenously with 16–20 μg tTF$_{219}$ (■) or PBS (○). The treatment was repeated one week later. The time of injections are designated by arrows. Tumors were measured daily and tumor volumes (+one standard deviation) were calculated. The number of mice per treatment group was 8–10. Mean tumor volume (cm$^3$) is shown on the vertical axis, days after first treatment is shown on the horizontal axis.

Similar anti-tumor effects were observed in mice bearing H460 human lung carcinomas (FIG. 13). The first treatment with tTF$_{219}$ was given when the tumors were small (250 mm$^3$) and had little effect on growth rate. The second treatment with tTF$_{219}$ was given when the tumors were larger (900 mm$^3$) and caused the tumors to regress to 550 mm$^3$ before regrowing.

Figure 14:
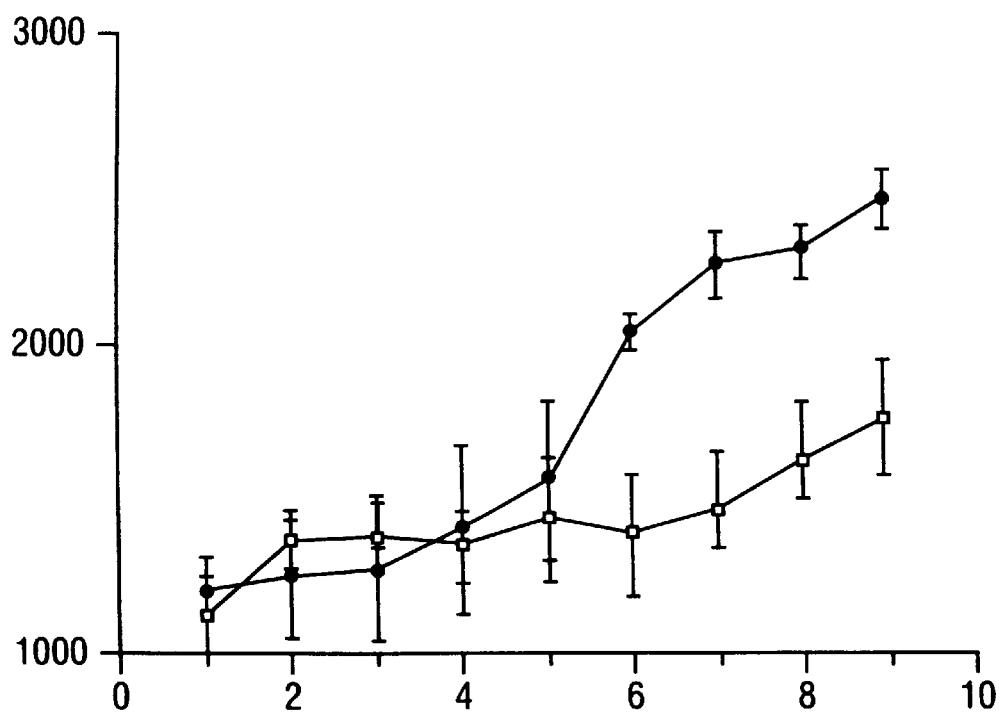
FIG. 14: Inhibition of growth of HT29 tumors in mice by $tTF_{219}$. Nu/nu mice bearing large (1200 mm$^3$) subcutaneous HT29 tumors were injected intravenously with 16 μg or 64 μg $tTF_{219}$ (□) or PBS (●). Tumors were measured daily (days after injection; horizontal axis), and tumor volumes (+one standard deviation) were calculated (tumor volume, mm$^3$; vertical axis). The number of mice per treatment group was 3–4.

Anti-tumor effects were also observed in mice bearing HT29 human colorectal carcinomas (FIG. 14). Nu/nu mice bearing large (1200 mm$^3$) tumors on their flanks were injected intravenously with tTF$_{219}$ or PBS (control), and growth of the tumors was monitored each day for 10 days. The tumors in the tTF$_{219}$ treated mice discontinued growth for about 7 days after treatment, whereas the tumors in mice treated with PBS continued to grow unchecked.

In animals that did not show complete tumor regression after B21-2/10H10-tTF coaguligand treatment, the tumors grew back from a surviving microscopic rim of cells at the periphery of the tumor. Immunohistochemical examination of these tumors revealed that the vascular endothelium at the invading edge of the tumors lacked detectable Class II antigens, consistent with a lack of thrombosis of these vessels by the coaguligand permitting local tumor cell survival. Thus, coadministration of a drug acting on the tumor cells themselves would likely improve efficacy, as has been observed with another antivascular therapy (Burrows and Thorpe, 1992;Burrows and Thorpe 1993;Burrows and Thorpe 1994;U.S. Ser. Nos. 07/846,349; 08/205,330; 08/295,868;and 08/350,212).

The inventors previously demonstrated that a powerfully cytotoxic ricin A-chain immunotoxin directed against the tumor cells themselves was virtually devoid of anti-tumor activity when administered to mice with large C1300(Muγ) tumors (Burrows and Thorpe, 1993; U.S. Ser. Nos. 07/846, 349; 08/205,330; 08/295,868;and 08/350,212). The lack of activity was due to the inability of the immunotoxin to gain access to tumor cells in large tumor masses, thus attesting to the comparative effectiveness of coaguligand therapy.

The studies using coaguligands confirm the therapeutic potential of selective initiation of the blood coagulation cascade in tumor vasculature (U.S. Ser. Nos. 08/273,567; 08/482,369; 08/485,482; 08/487,427; 08/479,733; 08/472, 631; 08/479,727;and 08/481,904). The induction of tumor infarction by targeting a thrombogen to tumor endothelial cell markers is therefore an effective anti-cancer strategy and may even result in the eradication of primary solid tumors and vascularized metastases.

The successful use of tTF alone or tTF immunoconjugates with an antibody of irrelevant specificity was initially a surprising outcome of the targeting studies. Although mice receiving tTF alone did not have complete tumor regressions, it is clear that the surprising anti-tumor activity of tTF renders this and functionally related TF derivatives useful in the treatment of solid tumors. The benefits of such compositions as detailed herein are far reaching and include the lack of side effects from the use of such TFs. Further, it is well within the skill of those in the art to produce the type of tTF compositions presented in the instant invention. Such compositions can then be employed in the treatment of solid tumors alone or in combination with other anti-cancer agents.

EXAMPLE VI

Coagulation of Mouse Plasma by Immunogloubulin-TF Conjugates

Figure 15:
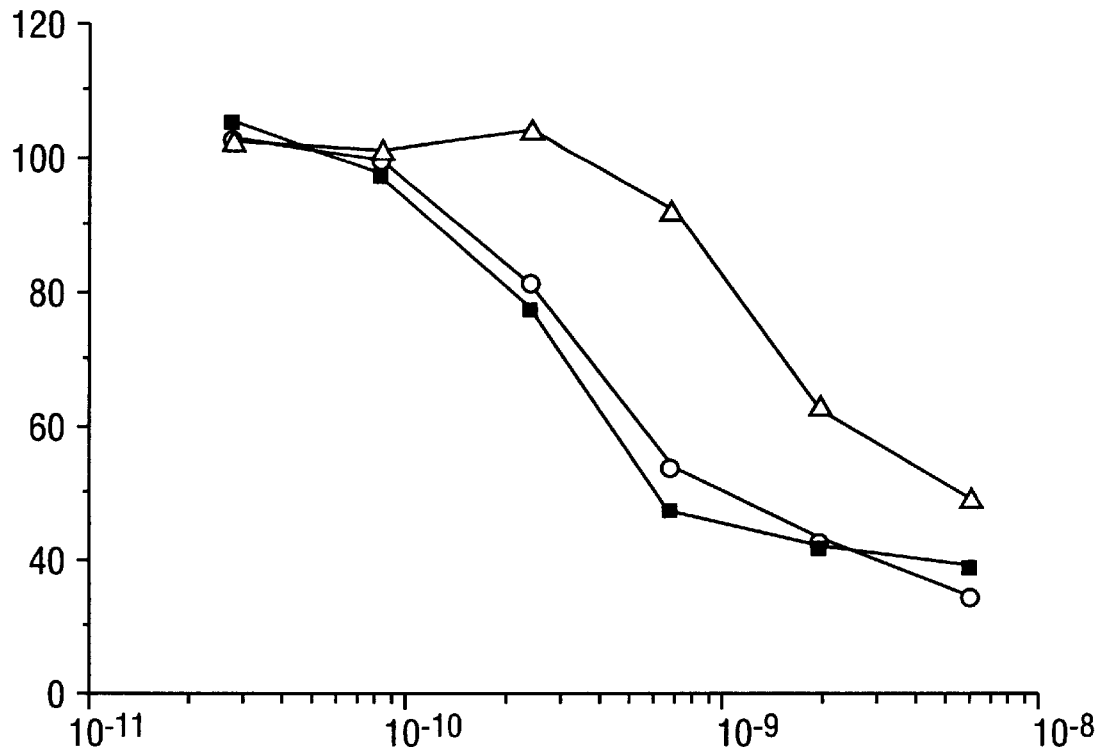
FIG. 15: Coagulation of mouse plasma by cell-associated IgG-H$_6$-N'-cys-tTF$_{219}$. A20 lymphoma cells (I-A$^d$ positive) were treated with the "capture" bispecific antibody, B21-2/10H10, recognizing both I-A$^d$ and tTF$_{219}$. IgG-H$_6$-N'-cys-tTF$_{219}$ (△), H$_6$-N'-cys-tTF$_{219}$ (■) or tTF$_{219}$ (○) were added at a range of concentrations at room temperature (concentration, M; horizontal axis). Cells were washed and warmed to 37° C. Calcium and citrated mouse plasma were added and the time for the first strands of fibrin to form was recorded (clotting time, seconds; vertical axis).
Figure 16:
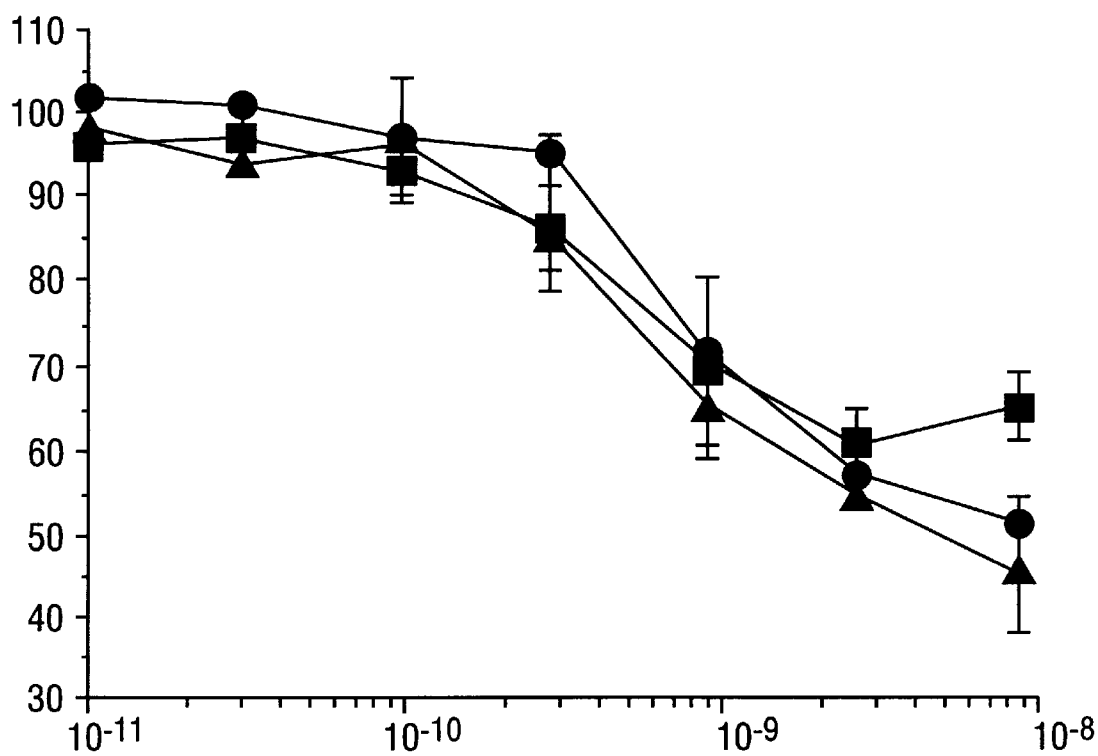
FIG. 16: Coagulation of mouse plasma by cell-associated IgG-H$_6$-N'-cys-tTF$_{219}$ and IgG-H$_6$-tTF$_{219}$-cys-C'. Immunoglobulin-tTF conjugates were prepared by linking B21-2 IgG (against I-A$^d$) to H$_6$-N'-cys-tTF$_{219}$ (▲) or H$_6$-tTF$_{219}$-cys-C' (■). The conjugates were added at a range of concentrations to A20 lymphoma cells (I-A$^d$ positive) at room temperature, and compared to tTF$_{219}$ (●) (concentration, M; horizontal axis). Cells were washed and warmed to 37° C. Calcium and citrated mouse plasma were added. The time (seconds) for the first strands of fibrin to form was recorded. The vertical axis shows clotting time as a percent of the control.
Figure 17:
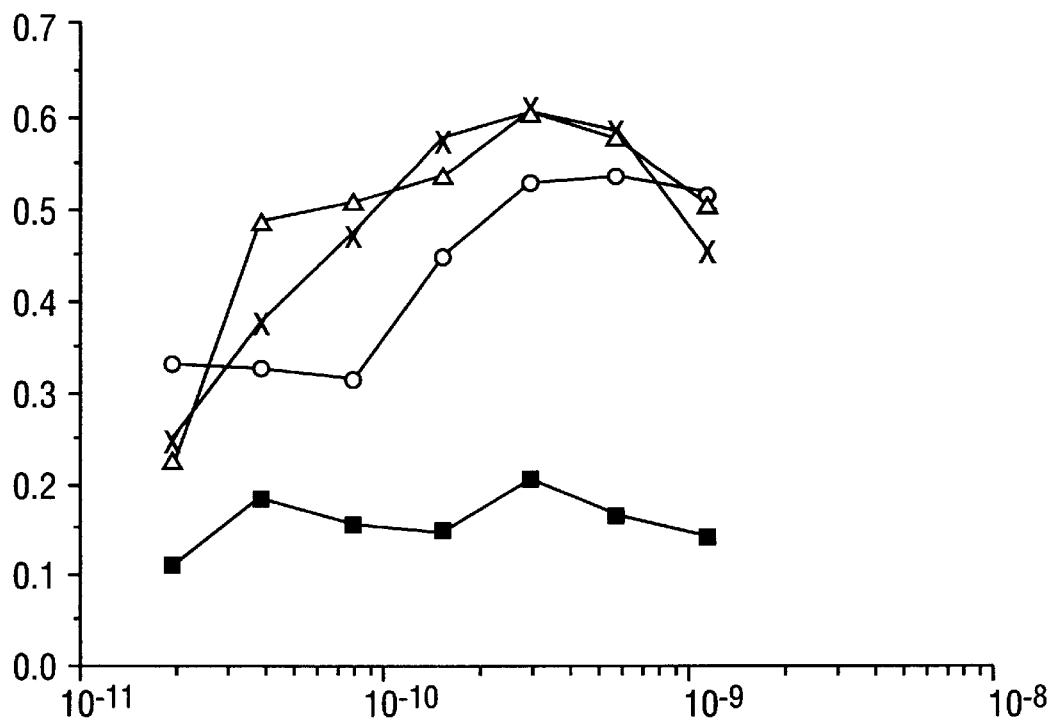
FIG. 17: Conversion of Factor X to Factor Xa by cell-associated IgG-H$_6$-N'-cys-tTF$_{219}$ and Fab'-H$_6$-N'-cys-tTF$_{219}$, measured by a chromogen assay. A20 cells (I-A$^d$ positive) were treated with the "capture" bispecific antibody, B21-2/10H10, recognizing both I-A$^d$ and tTF, was added with IgG-H$_6$-N'-cys-tTF$_{219}$ (○) or Fab'-H$_6$-N'-cys-tTF$_{219}$ (△), which were added at a range of concentrations at room temperature. B21-2/10H10 plus H$_6$-N'-cys-tTF$_{219}$ (×) and Mac51/10H10 plus H$_6$-N'-cys-tTF$_{219}$ (control, ■) were also added (concentration, M; horizontal axis). Cells were washed and warmed to 37° C. Calcium and "Proplex T" were added (Proplex T contains Factors II, VII, IX and X). The production of Xa was measured by adding the chromophore-releasing substrate, S-2765, and measuring the optical density at 409 nm (OD$_{409}$ nm; vertical axis).
Figure 18:
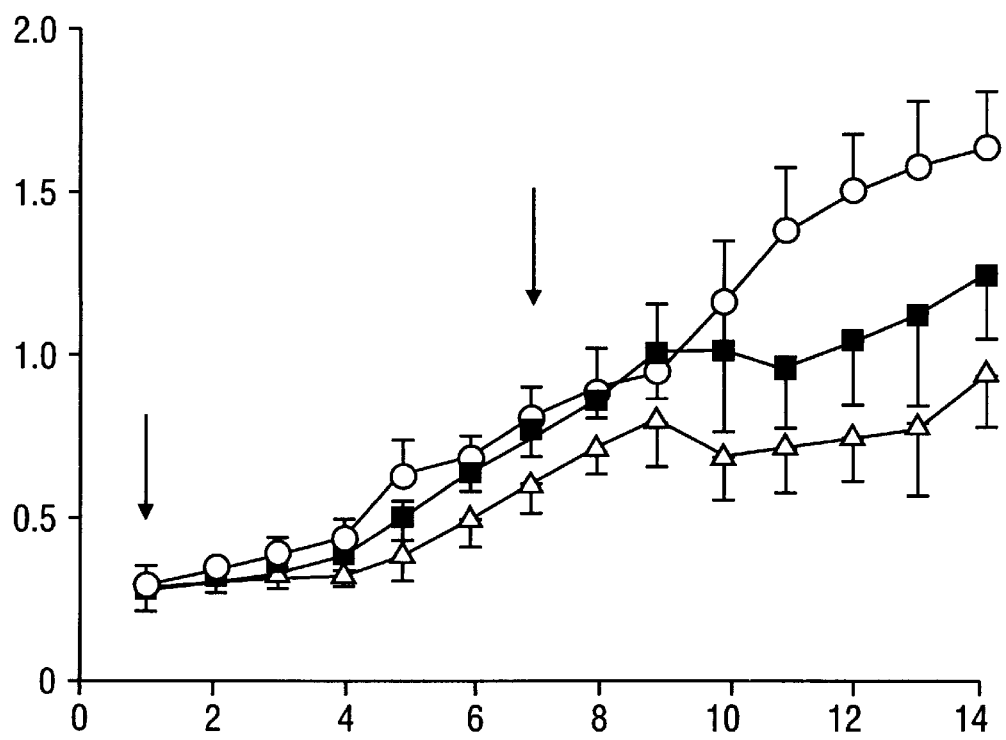
FIG. 18: Inhibition of growth of C1300 Muγ tumors in mice by immunoglobulin-tTF conjugate. Nu/nu mice bearing small (300 mm$^3$) subcutaneous C1300 Muγ tumors were injected intravenously with 16–20 μg tTF$_{219}$ complexed with OX7 Fab'/10H10 Fab bispecific "carrier" antibody (△). Other mice received tTF$_{219}$ alone (■), or diluent (PBS, ○). The treatment was repeated one week later. The day treatments were given are designated by arrows. Tumors were measured daily and tumor volumes (+one standard deviation) were calculated. The number of mice per treatment group was 7–10. Mean tumor volume (cm$^3$) is shown on the vertical axis, days after first treatment is shown on the horizontal axis.
Figure 19:
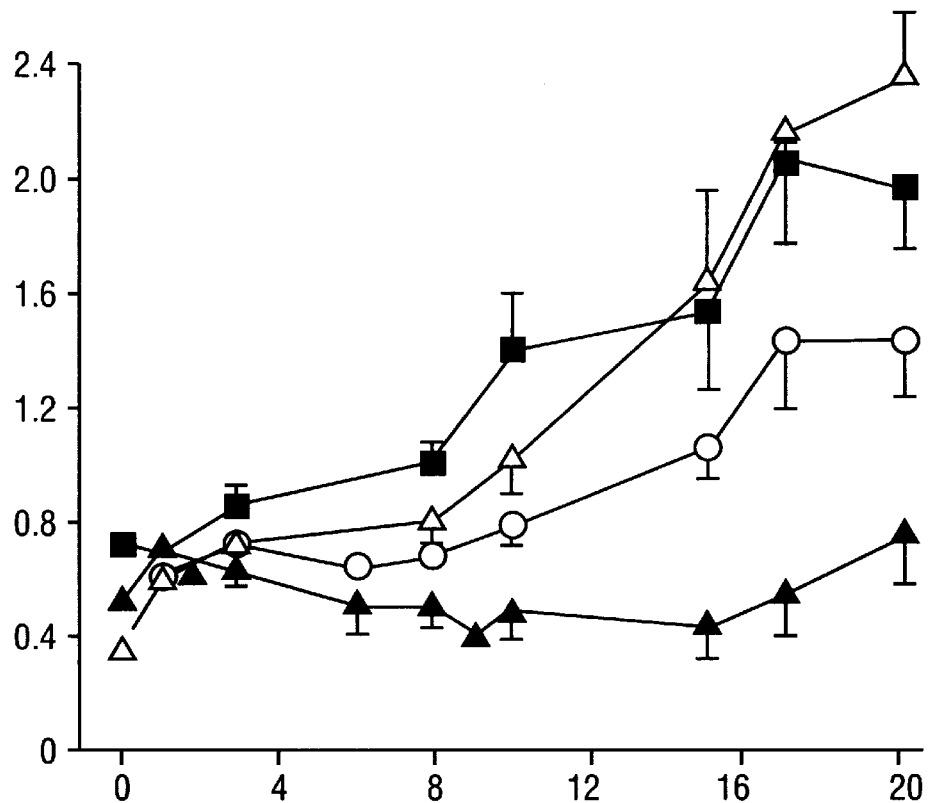
FIG. 19: Enhancement of anti-tumor activity of immunoglobulin-tTF by etoposide. SCID mice bearing subcutaneous L540 human Hodgkin's tumors were given a single intravenous injection of a complex of tTF$_{219}$ and the "carrier" bispecific antibody Mac51Fab'/10H10 Fab' (■). Other mice received 480 μg of etoposide intraperitoneally 2 days before, 1 day before and on the day of treatment with immunoglobulin-tTF conjugate (▲). Other mice received etoposide alone (○) or diluent (PBS, △). Tumors were measured daily and tumor volumes (+one standard deviation) were calculated. Mean tumor volume (cm$^3$) is shown on the vertical axis, days after treatment is shown on the horizontal axis.
Figure 20:
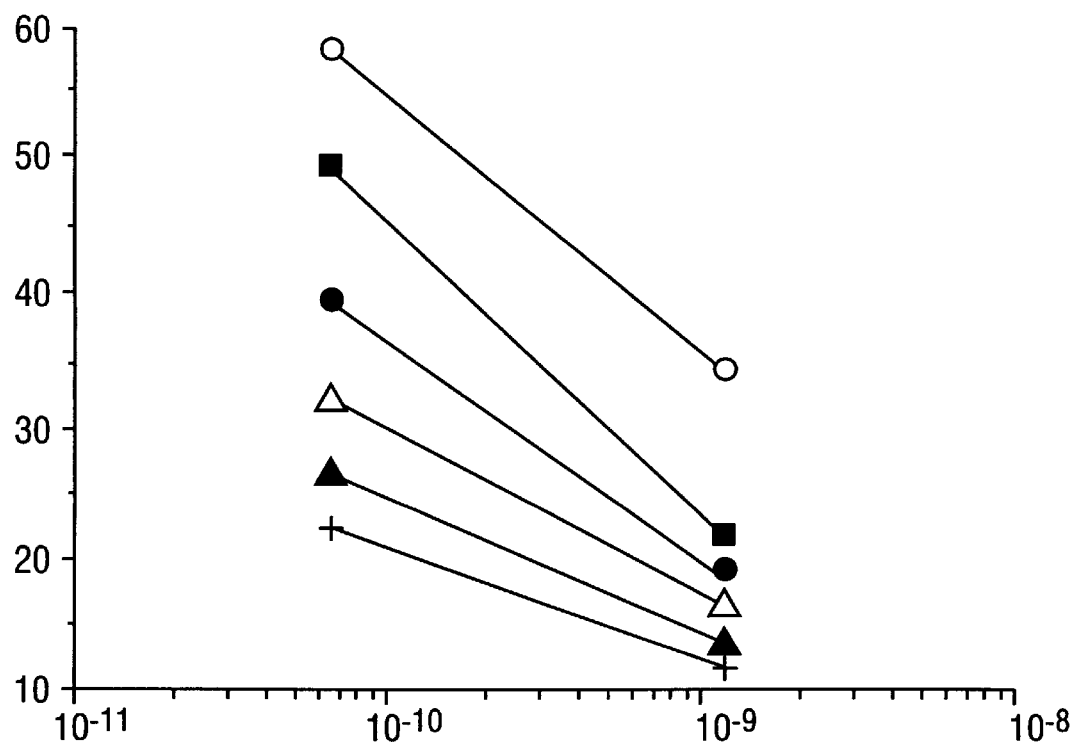
FIG. 20: Enhancement of plasma coagulation by Factor VIIa. A20 lymphoma cells (I-A$^d$ positive) were treated at room temperature with the "capture" bispecific antibody, B21-2/10H10, recognizing both I-A$^d$ and tTF. Cells were washed and tTF$_{219}$ alone (○) or tTF$_{219}$ with Factor VIIa were added at a range of concentrations of Factor VIIa, as follows: 0.1 nM (■); 0.3 nM (●); 0.9 nM (△); 2.7 nM (▲); and 13.5 nM (+) (concentration, M; horizontal axis). Cells were washed and warmed to 37° C. Calcium and citrated mouse plasma were added and the time for the first strands of fibrin to form was recorded (clotting time, seconds; vertical axis).

IgG-H$_6$-N'-cys-tTF$_{219}$ was active at inducing coagulation of mouse plasma when localized on the surface of A20 cells by means of the bispecific antibody, B21-2/10H10. It induced coagulation in 50 seconds when applied at a tTF concentration of 5×10$^{-9}$ M as compared with 1×10$^{-9}$ M for non-conjugated tTF$_{219}$ and H$_6$-N'-cys-tTF$_{219}$ (FIG. 15). The coagulation inducing activity of IgG-H$_6$-N'-cys-tTF$_{219}$ is therefore reduced 5-fold relative to unconjugated H$_6$-N'-cys-tTF$_{219}$ or tTF$_{219}$ itself.

The slight reduction upon IgG conjugation could be because the IgG moiety of IgG-H$_6$-N'-cys-tTF$_{219}$ impedes access of the B21-2/10H10 bispecific antibody to the tTF moiety (i.e., an artifactual reduction related to the assay method). It is probably not because the IgG moiety of IgG-H6-N'-cys-tTF219 interferes with formation of the coagulation initiation complexes because, in prior work, the inventors have found that the tTF moiety in an analogous construct, B21-2 IgG-$H_6$-N'-cys-$tTF_{219}$, is as active as tTF bound via B21-2/10H10 to I-$A^d$ antigens on A20 cells (FIG. 16). Similarly, B21-2 IgG-$H_6$-$tTF_{219}$-cys-C' was as active at inducing coagulation as was the N'-linked conjugation (FIG. 16).

IgG-$H_6$-N'-cys-$tTF_{219}$ and Fab'-$H_6$-N'-cys-$tTF_{219}$ were tested for their ability to convert Factor X to Xa in the presence of Factors II, VII and IX, once localized on the surface of A20 lymphoma cells by means of the bispecific antibody, B21-2/10H10. The Fab'-tTF construct was as active as $H_6$-N'-cys-$tTF_{219}$ itself at inducing Xa formation. The IgG-tTF construct was slightly (2-fold) less active than $H_6$-N'-cys-$tTF_{219}$ itself (FIG. 17).

EXAMPLE VII

Inhibition of Growth of C1300 Muγ Tumors by Immunpglobulin-TF Conjugate

Mice bearing small (300 $mm^3$) subcutaneous C1300 Muγ tumors were treated with $tTF_{219}$ or with a complex of $tTF_{219}$ and a bispecific antibody, OX7 Fab'/10H10 Fab', not directed to a component of the tumor environment. The treatment was repeated 6 days later (FIG. 18). The bispecific antibody was simply designed to increase the mass of the $tTF_{219}$ from 25 kDa to 135 kDa, and thus prolong its circulatory half life, and was not intended to impart a targeting function to tTF.

Tumors in mice treated with the immunoglobulin-tTF conjugate grew more slowly than those in mice receiving $tTF_{219}$ alone. Fourteen days after the first injection, tumors were 55% of the size of those in controls receiving diluent alone. In mice receiving $tTF_{219}$ alone, tumors were 75% of the size in controls receiving diluent alone (FIG. 18).

EXAMPLE VIII

Enhancement of Anti-Tumor Activity of Immunoglobulin-tTF Conjugate by Etoposide Mice bearing L540 human Hodgkin's disease tumors were treated with a complex of $tTF_{219}$ and a bispecific antibody together with the conventional anti-cancer drug, etoposide. Etoposide greatly enhanced the action of the immunoglobulin-tTF conjugate. In this tumor model alone, mice receiving the antibody-tTF complex alone showed little reduction in tumor growth relative to tumors in mice receiving diluent alone (FIG. 19).

In contrast, tumors in mice receiving both etoposide and the immunoglobulin-tTF conjugate regressed in size and did not recommence growth for seventeen days. At the end of the study (day 20), tumors in mice receiving etoposide plus immunoglobulin-tTF were an average of 900 $mm^3$ in volume as compared with 2300 $mm^3$ in mice treated with diluent and 2000 $mm^3$ in mice treated with immunoglobulin-tTF alone. In mice receiving etoposide alone, tumors averaged 1400 $mm^3$ on day 14 (FIG. 19). These results indicate that etoposide may predispose tumor vessels to thrombosis by tTF or immunoglobulin-tTF conjugates. Irrespective of the mechanism, the results clearly show advantageous combination of TF, or a TF-conjugate, with a classical chemotherapeutic agent.

EXAMPLE IX

Enhancement of Plasma Coagulation by VIIa

The ability of cell-associated $tTF_{219}$ to induce coagulation of mouse or human plasma was strongly enhanced in the presence of free Factor VIIa (FIG. 20). In the absence of Factor VIIa, A20 cells treated with B21-2/10H10 bispecific antibody and $10^{-10}$ M $tTF_{219}$ coagulated plasma in 60 seconds, whereas in the presence of 13.5 nM Factor VIIa, it coagulated plasma in 20 seconds (FIG. 20). This represents approximately a 100-fold enhancement in the coagulation-inducing potency of tTF in the presence of Factor VIIa. Even in the presence of 0.1 nM Factor VIIa, a 2–5 fold increase in coagulation-inducing potency of tTF was observed.

This finding leads to the aspects of the invention that concern the coadministration of Factor VIIa along with tTF or derivatives thereof, or with immunoglobulin-tTF conjugates, in order to enhance tumor vessel thrombosis in vivo.

EXAMPLE X

Reduced Coagulation of Mouse Plasma by TF Factor VII Activation Mutants

Mutations in W158 and G164 of $tTF_{219}$ have been reported to reduce markedly the ability of TF to induce coagulation of recalcified plasma (Ruf et al., 1992;Martin et al, 1995). Residues 157–167 of TF appear to be important in accelerating activation of Factor VII to Factor VIIa, but not the binding of Factor VII to TF. The inventors mutated W158 to R and G164 to A and determined whether the mutants acquired the ability to coagulate plasma once localized by means of a bispecific antibody, B21/2-10H10, on the surface of A20 cells. It was found that the mutants were 30–50-fold less effective than was $tTF_{219}$ at inducing coagulation of plasma (FIG. 21).

EXAMPLE XI

Restoration of Coagulating Ability of Factor VII Activation Muntants by Factor VIIa Mutant $tTF_{219}$ (G164A) is a very weakly coagulating mutant of $tTF_{219}$ (Ruf, et al, 1992). The mutation is present in a region of TF (amino acids 157–167) thought to be important for the conversion of Factor VII to Factor VIIa. Thus, addition of Factor VIIa to cells coated with bispecific antibody and $tTF_{219}$ (G164A) would be reasoned to induce the coagulation of plasma. In support of this, A20 cells coated with B21-2/10H10 followed by $tTF_{219}$ (G164A) had increased ability to induce coagulation of plasma in the presence of Factor VIIa (FIG. 22). Addition of Factor VIIa at 1 nM or greater produced only marginally slower coagulation times than observed with $tTF_{219}$ and Factor VIIa at the same concentrations.

Mutant $tTF_{219}$ (W158R) gave similar results to $tTF_{219}$ (G164A). Again, addition of Factor VIIa at 1 nM or greater to A20 cells coated with B21-2/10H10 followed by $tTF_{219}$ gave only marginally slower coagulation times than did $tTF_{219}$ and Factor VIIa at the same concentrations.

These results support those aspects of the invention that provide that $tTF_{219}$ (G164A) or $tTF_{219}$ (W158R), when coadministered with Factor VIIa to tumor-bearing animals, will induce the thrombosis of tumor vessels. This approach is envisioned to be advantageous because tTF (G164A), tTF (W158R) or Factor VIIa given separately are practically non-toxic to mice, and the same is reasonably expected in humans. Coadministration of the mutant tTF and Factor VIIa is expected not to cause toxicity, yet to cause efficient thrombosis of tumor vessels. Giving mutant tTF together with Factor VIIa is thus contemplated to result in an improved therapeutic index relative to $tTF_{219}$ plus Factor VIIa.

EXAMPLE XII

Enhanced Anti-Tumor Activity of Activation Mutants and Factor VIIa

For these studies, the inventors chose the HT29 (human colorectal carcinoma) xenograft tumor model. HT29 cells ($10^7$ cells/mouse) were subcutaneously injected into BALB/c nu/nu mice. Tumor dimensions were monitored and animals were treated when the tumor size was between 0.5 and 1.0 $cm^3$. Animals were given an intravenous injection of one of the following: $tTF_{219}$ (16 μg), $tTF_{219}$ (16 μg)+Factor VIIa (1 μg), $tTF_{219}$(G164A) (64 μg), $tTF_{219}$(G164A) (64 μg)+Factor VIIa (1 μg), Factor VIIa alone (1 μg), or saline.

Animals were sacrificed 24 hours after treatment, perfused with saline and heparin and exsanguinated. Tumors and organs were collected, formalin fixed and histological sections were prepared. The average area of necrosis in sections of the tumors was quantified and calculated as a percentage of the total area of tumor on the section.

Figure 23:
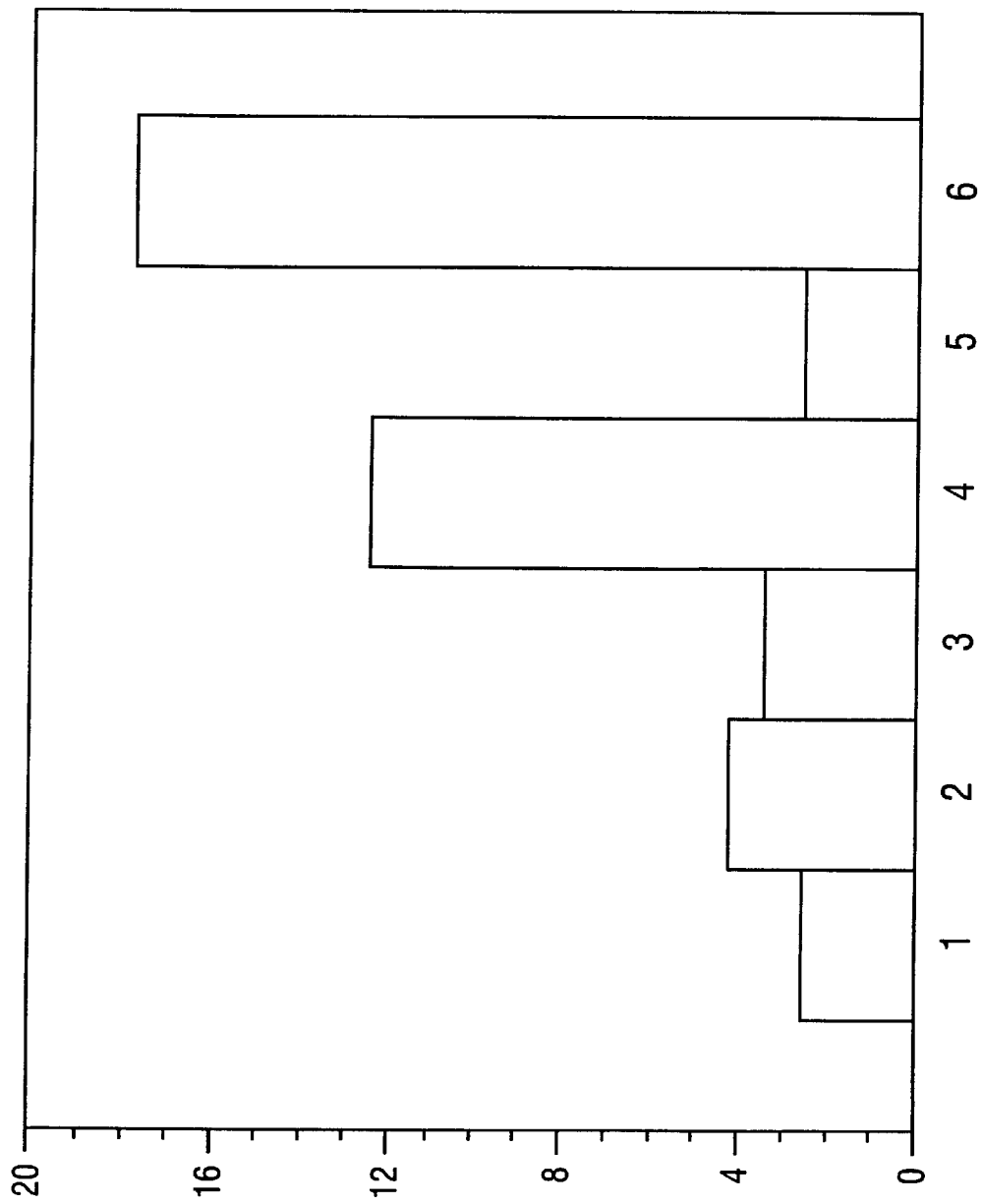
FIG. 23: Antitumor activity of tTF219:VIIa and tTF219 (G164A):VIIa complexes in mice bearing HT29 human colorectal carcinomas. From left to right, the bars represent: saline (1); tTF (2); Factor VIIa (3); tTF plus Factor VIIa (4); G164A (5); and G164A plus Factor VIIa (6). The vertical axis shows the average percent of necrosis in tumors examined.

In these small HT29 tumors, analysis of tumor sections from animals treated with saline, Factor VIIa, $tTF_{219}$ or $tTF_{219}$(G164A) showed some necrosis (FIG. 23). The tTF-induced tumor necrosis was the most developed, although this was not as striking, on this occasion, as results from earlier studies using different tumor models and/or large tumors. An analysis of tumor sections from animals treated with $tTF_{219}$+Factor VIIa or $tTF_{219}$(G164A)+Factor VIIa revealed considerable necrosis (12.5% and 17.7% respectively; FIG. 23) and a strong correlation between newly thrombosed blood vessels and areas of necrosis. The combined use of Factor VIIa with TF, even a TF construct with particularly deficient in vitro coagulating activity, is therefore a particularly advantageous aspect of the present invention. As the HT29 tumor model is difficult to thrombose in general and these tumors were small in size, these results are likely to translate to even further striking results in other systems and in humans.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Antibodies: *A Laboratory Manual,* Cold Spring Harbor Laboratory, 1988.
Abraham et al., *Science,* 233:545–548, 1986.
Abrams and Oldham, *Monoclonal Antibody Therapy of Human Cancer,* Foon and Morgan (Eds.), Martinus Nijhoff Publishing, Boston, pp. 103–120, 1985.
Ausubel et al., *Current Protocols in Molecular Biology,* Greene Publishing Associates and Wiley Interscience, N.Y., 1989.
Bach et al., *Biochemistry,* 25, 4007–4020, 1986.
Bauer, et al., *Vox Sang,* 61:156–157, 1991.
Baxter, et al., *Micro. Res.,* 41(1):5–23, 1991.
Bevilacqua, et al., *Proc. Natl. Acad. Sci. USA,* 84:9238–9242, 1987.
Bhagwat et al., *Nature,* 316:511–513, 1985.
Bicknell and Harris, *Seminars in Cancer Biology,* 3:399–407, 1992.
Birembaut et al., *J. Pathology,* 145:283–296, 1985.
Bjomdahl et al., *Eur. J. Immunol.,* 19:881–887, 1989.
Bolhuis et al., *J. Immunol.,* 149:1840–1846, 1992.
Borden et al., *Cancer,* 65:800–814, 1990.
Brennan et al., *Science,* 229:81–83, 1985.
Brinkmann et al., *Proc. Natl. Acad. Sci.,* 88(19):8616–8620, 1991.
Broze, *Seminars in Hematol.,* 29:159–169, 1992.
Burchell et al., *J. Immunol.,* 131(1):508–513, 1983.
Burrows et al., *Cancer Res.,* 52:5965–5962, 1992.
Burrows et al., *Cancer Res.,* 51:4768–4775, 1991.
Burrows and Thorpe, *Proc. Natl. Acad. Sci., USA,* 90:8996–9000, 1993.
Burtin et al., *Cancer,* 31:719–726, 1983.
Byers and Baldwin *Immunol.,* 65:329–335, 1988.
Campbell, In: *Monoclonal Antibody Technology, Laboratory Techniques in Biochemistry and Molecular Biology,* Vol. 13, Burden and Von Knippenberg (Eds.), Elseview, Amsterdam, pp. 75–83, 1984.
Chen et al., *J. Immunol.,* 145:8–12, 1990.
Cherwinski et al., *J. Exp. Med.,* 166:1229–1244, 1989.
Clark et al., *Biochem. Biophys. ACTA,* 867:244–251, 1986.
Clark et al., *Int. J. Cancer,* 2:15–17, 1988.
Clark et al., *Cancer Res.,* 51:944–948, 199 1.
Colcher et al., *Cancer Res.,* 47:1185 and 4218, 1987.
Collins et al., *Proc. Natl. Acad. Sci. USA,* 81:4917–4921, 1984.
Cotran et al., *J. Exp. Med.,* 164:661–666, 1986.
Daar el al., *Transplantation,* 38(3):293–298, 1984.
Davie et al., *Biochem.,* 30: 10363–10310, 1991.
Davies and Wlodawer, *FASEB J,* 9:50–56, 1995.
Davis and Preston, *Analytical Biochemistry,* 116(2):402–407, 1981.
DeFranco, *Nature,* 352:754–755, 1991.
deLeij et al., *Bispecific Antibodies and Targeted Cellular Cytotoxicity,* Romet-Lemonne et al., p. 249, 1991.
Denekamp et al., *Brit. J. Cancer,* 461:711–720, 1982.
Dewerchin et al., *Blood,* 78(4):1005–1018, 1991.
Di Scipio el al., *Biochemistry,* 16:5253–5260, 1977.
Dillman et al., *Antibody Immunocon. Radiopharm.,* 1:65–77, 1988.
Drake et al., *J. Cell Biol.,* 109:389–95, 1989.
Dustin et al., *J. Immunol.,* 137:245–254, 1986.
Dvorak et al., *J. Exp. Med.,* 174:1275–1278, 1991.
Edgington et al., *Thrombosis and Haemostatis,* 66(1):67–79, 1991.
Embleton et al., *Br. J. Cancer,* 63(5):670–674, 1991.
Epenetos el al., *Cancer Res.,* 46:3183–3191, 1986.
Fair, *Blood,* 62:784–791, 1983.
Fair et al., *J. Biol. Chem.,* 262, 11692–11698, 1987.

Ferrara, *J. Cell. Biochem.*, 47:211–218, 1991.
Flavell et al., *Br. J. Cancer,* 64(2):274–280, 1991.
Flavell et al., *Br. J. Cancer,* 65:545–551, 1992.
Folkman, *Adv. Cancer Res.,* 43:175–230, 1985a
Folkman, In: *Important Advances in Oncology, Part I,* DeVita et al., (Eds.), J B Lippincott, Philadelphia, pp. 42–62, 1985b.
Fox et al., *J. Biol. Resp.,* 9:499–511, 1990.
Frelinger III, et al., *J. Biol. Chem.,* 265(11):6346–6352, 1990.
Frelinger III, et al., *J. Biol. Chem.,* 266(26):17106–17111, 1991.
French et al., *Cancer Res.,* 51:2358–2361, 1991.
Galfre et al., *Methods Enzymol.,* 73:1–46, 1981.
Gefter et al., *Somatic Cell Genet.,* 3:231–236, 1977.
Geppert et al., *Immunological Reviews,* 117:5–66, 1990.
Ghose and Blair, *CRC Critical Reviews in Therapeutic Drug Carrier Systems,* 3:262–359, 1987.
Ghose, *CRC Critical Review in Therapeutic Drug Carrier Systems,* 3:262–359, 1982.
Ghose et al., *Meth. Enzymology,* 93:280–333, 1983.
Ghose et al., *CRC Critical Reviews in Therapeutic Drug Carrier Systems,* 3:262–359, 1987.
Giles et al., *Brit. J. Haematol.,* 69:491–497, 1988.
Glennie et al., *J. Immunol.,* 139:2367–2375, 1987.
Glennic et al., 1988
Goding, In: *Monoclonal Antibodies: Principles and Practice,* 2d Ed., Academic Press, Orlando, Fla., pp. 60–61, 65–66, 71–74, 1986.
Gougos and Letarte, *J. Immunol.,* 141:1925–1933, 1988.
Groenewegen et al., *Nature,* 316:361–363, 1985.
Hagen, et al., *Proc. Natl. Acad. Sci. U.S.A.,* 83:2412–2416, 1986.
Hailing et al., *Nucl. Acids Res.,* 13:8019–8033, 1985.
Hammerling, *Transplant Rev.,* 30:64–82, 1976.
Hattey et al., *Thrombosis Research,* 45(5):485–495, 1987.
Hayward et al., *Biological Chemistry,* 266(11):7114–7120, 1991.
Hess et al., *Transplantation,* 6:1232–1240, 1991.
Heynen et al., *J. Clin. Invest.,* 94:1098–1112, 1994.
Jain, *Cancer Meta. Rev.,* 9(3):253–266, 1990.
June et al., *Mol. Cell Biol.,* 12:4472–4481, 1987.
June et al., *Immunology Today,* 11(6):211–216, 1990.
Juweid et al., *Cancer Res.,* 52:5144–5153, 1992.
Kandel et al., *Cell,* 66:1095–1104, 1991.
Kim et al., *Nature,* 362:841–844, 1993.
Kimura et al., *Immunogenetics,* 11:373–381, 1983.
Kisiel, *J. Biol. Chem.,* 254(23):12230–12234, 1979.
Klagsburn and Folkman, *Angiogenesis Handbook of Experimental Pharmacology,* Vol. 95, Sporn and Roberts, Springer-Verlag, Berlin, pp. 549–586, 1990.
Kohler and Milstein, *Nature,* 256:495–497, 1975.
Kohler and Milstein, *Eur. J. Immunol.,* 6:511–519, 1976.
Krishnaswamy et al., *J. Biol. Chem.,* 267:26110–26120, 1992.
Kyte and Doolittle, *J. Mol. Biol.,* 157(1):105–132, 1982.
Lamb et al., *Eur. J. Biochem.,* 148:265–270, 1985.
Lee et al., *Methods in Enzymology,* 237:146–164, 1994.
Leith et al., *British J. Cancer,* 66(2):345–348, 1992.
Lord et al., In: *Genetically Engineered Toxins,* Frank (Ed.), M. Dekker Publ., p. 183, 1992.
Lowder et al., *Blood,* 69:199–210, 1987.
Lowe et al., *Immunol. Lett.,* 12:263–269, 1986.
Maedae et al., *J. Invest. Derm.,* 97:183–189, 1991.
Manabe et al., *J. Lab. Clin. Med.,* 104(3):445–454, 1984.
Martin, *FASEB J,* 9:852–859, 1995.
Massoglia et al., *J. Cell. Phys.,* 132:531–537, 1987.
Mazzocchi et al., *Cancer Immunol. Immuother.,* 32:13–21, 1990.
Mignatti et al., *J. Cell. Biol.,* 113:1193–1201, 1991.
Miotti et al., *Cancer Res.,* 65:826, 1985.
Moroi and Aoki, *J. Biol. Chem.,* 251(19):5956–5965, 1976.
Morrissey et al., *Cell,* 50:129–135, 1987.
Morrissey et al., *Thrombosis Research,* 52:247–261, 1988.
Morrissey et al., *Blood,* 81:734–744, 1993.
Mueller et al., *Proc. Natl. Acad. Sci. USA* 89:11832–11836, 1992.
Murray, Clauss, Thurston, Stern, *Int. J. Radiat. Biol.,* 60:273–277, 1991.
Nakamura, *Prog. Growth Factor Res.,* 3:67–86, 1991.
Nawroth, Handley, Matsueda, de Waal., Gerlach, Blohm, Stern, *J. Exp. Med.,* 168:637–648, 1988.
Nawroth and Stern, *J. Exp. Med.,* 163:740–745, 1986.
Nelson, *Cancer Cells,* 3 (5) p163–72, 1991.
Nemerson, *Blood,* 71(1):1–8, 1988.
Nitta et al., *Lancet,* 335:368–371, 1990.
Nolan and Kennedy, 1990
O'Brien et al., *J. Clin. Invest.,* 82:206–211, 1988.
O'Connell et al., *J. Immunol.,* 144(2):521–525, 1990.
O'Hare et al., *FEBS Lett,* 210:731, 1987.
Ogata, *J. Biol. Chem.,* 256:20678–20685, 1990.
Ogawa, Shreeniwas, Brett, Clauss, Furie, Stern, *Brit. J. Haematol.,* 75:517–524, 1990.
Ohuchida et al., *J. Am. Chem. Soc.,* 103(15):4597–4599, 1981.
Oi and Morrison, *Mt. Sinai J. Med.,* 53(3):175–180, 1986.
Osborn et al., *Cell,* 59:1203–1211, 1989.
Osterud et al., *Thrombosis Res.,* 42:323–329, 1986.
Paborsky et al., *J. Biol. Chem.,* 266(32):21911–21916, 1991.
Palleroni et al., *Int. J. Cancer,* 49:296–302, 1991.
Pasqualini et al., *Nat. Biotechnol.* 15:542–546, 1997.
Paulus, 1985
Perez et al., *Nature,* 316:354–356, 1985.
Perez et al., *J. Immunol.,* 137:2069–2072, 1986a.
Perez et al., *J. Exp. Med.,* 163:166–178, 1986b.
Pieterez et al., *Antibody Immunoconj. Radiopharm.,* 1:79–103, 35, 1988.
Pimm et al., *J. Cancer Res. Clin. Oncol.,* 118:367–370, 1992.
Pober et al., *J. Exp. Med.,* 157:1339–1353, 1991.
Pukrittayakamee et al., *Mol. Biol. Med.,* 1:123–135, 1983.
Qian et al., *Cancer Res.,* 140:3250, 1991.
Rehemtulla et al., *Thrombosis and Haemostatis.* 65(5):521–527, 1991.
Reisfeld et al., *Melanoma Antigens and Antibodies,* p. 317, 1982.
*Remington's Pharmaceutical Sciences,* 16th Ed., Mack Publishing Company, 1980.
Rettig et al., *Proc. Natl. Acad. Sci. USA.,* 89:10832–10836, 1992.
Rivoltini et al., *3rd Int. Conf. Bispecific Antibodies and Targeted Cellular Cytotoxicity,* 1992.
Ruco et al., *Am. J. Pathol.,* 137(5):1163–1171, 1990.
Ruf and Edgington, *Proc. Natl. Acad. Sci. USA.,* 88:8430–8434, 1991a.
Ruf and Edgington, *Thrombosis and Haemostasis,* 66(5):529–533, 40, 1991b.
Ruf, et al., *J. Biol. Chem.,* 266, pg. 2158, 1991.
Ruf and Edgington, *FASEB J.,* 8:385–390, 1994.
Ruf et al., *J. Biol. Chem.,* 267:22206–22210, 1992a.
Ruf et al., *J. Biol. Chem.,* 267:6375–6381, 1992b.
Ruf et al., *J. Biol. Chem.,* 267(31):22206–22210, 1992c.
Sakai and Kisiel, *Thrombosis Res.,* 60:213–222, 1990.
Sambrook et al., *Molecular Cloning, A Laboratory Manual.,* Cold Spring Harbor Laboratory, N.Y., 1989.

Sands, *Immunoconjugates and Radiopharmaceuticals*, 1:213–226, 1988.
Schutt et al., *Immunol. Lett.*, 19:321–328, 1988.
Shen and Tai, *J. Biol. Chem.*, 261(25):11585–11591, 1986.
Segal et al., *Int. J. Cancer Suppl.*, 7 p36–8, 1992
Shankar et al., *J. Biol. Chem.*, 269(19): 13936–13941, 1994.
Shepard et al., *J. Clin. Immunol.*, 11 :117–127, 1991.
Shockley et al., *Ann. N.Y. Acad. Sci.*, 617:367–382, 1991.
Smith et al., *Br. J. Cancer,* 59 (2) p 174–8, 1989.
Spiegelberg and Weigle, *J. Exp. Med.*, 121:323–338, 1965.
Staerz et al., *Nature,* 314(6012):628–631, 1985.
Stevenson et al., *Chem. Immunol,* 48:126–166, 1990.
Stone, et al., *Biochem J.,* 310:605, 1995.
Street et al., *Cell. Immunol.,* 120:75–81, 1989.
Sugama et al., *Jpn. J. Pharmacol.*, 55:2, pp. 287–290, 1991.
Sugama et al., *J. Cell. Biol.,* 119(4):935–944, 1992.
ten Cate et al., *J. Clin. Invest.,* 92:1207–1212, 1993.
Thieme et al., *Diabetes,* 44(1):98–103, 1995.
Thor et al., *Cancer Res.,* 46:3118, 1986.
Ting et al., *J. Immunol.,* 141:741–748, 1988.
Titus et al., *J. Immunol.,* 138:4018–4022, 1987.
Tomiyama et al., *Blood.,* 79(9):2303–2312, 1992.
Tone 1977
Tuttet al., *Eur. J. Immunol.,* 21:1351–1358, 1991.
U.S. Pat. No. 4,196,265
U.S. Pat. No. 4,554,101
U.S. Pat. No. 4,975,369
U.S. Pat. No. 5,017,556
U.S. Pat. No. 5,110,730
U.S. Pat. No. 5,139,941
U.S. Pat. No. 5,183,756
U.S. Pat. No. 5,223,427
U.S. Pat. No. 5,242,813
U.S. Pat. No. 5,288,641
U.S. Pat. No. 5,346,991
U.S. Pat. No. 5,374,617
U.S. Pat. No. 5,437,864
U.S. Pat. No. 5,504,064
U.S. Pat. No. 5,504,067
U.S. Pat. No. 5,589,173
U.S. Pat. No. 5,589,363
Ugarova et al., *J. Biol. Chem.,* 268(28):21080–21087, 1993.
Vaickus et al., *Cancer Invest.,* 9:195–209, 1991.
Van Duk et al., *Int. J. Cancer,* 43:344–349, 1989.
Venkateswaran et al., *Hybridoma,* 11(6):729–739, 1992.
Vitetta et al., *Cancer Res.,* 15:4052–4058, 1991.
Wang et al., *Biochem. and Biophys. Res. Comm.,* 177(1):286–291, 1991.
Wang et al., *Int. J. Cancer,* 54:363–370, 1993.
Warret al., *Blood,* 75:1481–1489, 1990.
Watanbe et al., *Proc. Natl. Acad. Sci. USA,* 86:9456–9460, 1989.
Wawrzynczak and Thorpe In: *Immunoconjugates: Antibody Conjugates in Radioimaging and Therapy of Cancer,* Vogel (ed.), New York, Oxford University Press, pp. 28–55, 1987.
Weiss et al., *Blood,* 73:968–975, 1989.
Whittle et al., *Nature,* 292:472–474, 1981.
Wildgoose et al., *Blood,* 80:25–28, 1992.
Williams and Esnouf, *Biochem. J,* 84:52–62, 1962.
Wiman and Collen, *Eur. J. Biochem.,* 78:19–26, 1977.
Wiman, *Biochem. J.,* 191:229–232, 1980.
Winter and Milstein, Nature, 349:293–299, 1991.
WO 94/05328, PCT Application
WO 94/07515, PCT Application
WO 94/28017, PCT Application
WO 96/01653, PCT Application
Wuet al., *Int. J. Pharm.,* 12:235–239, 1990.
Xu et al., *J. Biol. Chem.,* 267(25):17792–17803, 1992.
Yamaue et al., *Biotherapy,* 2:247–259, 1990.
Zamarron et al., *J. Biol. Chem.,* 266(24):16193–16199, 1991.

What is claimed is:

1. A method for treating an animal having a vascularized tumor, comprising administering to said animal at least a first coagulation-deficient Tissue Factor compound and at least a first anti-cancer agent in a combined amount effective to promote coagulation in the tumor vasculature and to induce tumor necrosis.

2. The method of claim 1, wherein said coagulation-deficient Tissue Factor compound is administered to said animal systemically.

3. The method of claim 2, wherein said coagulation-deficient Tissue Factor compound is administered to said animal via intravenous injection.

4. The method of claim 1, wherein said anti-cancer agent is administered to said animal via intravenous injection.

5. The method of claim 1, wherein said coagulation-deficient Tissue Factor compound and said anti-cancer agent are administered to said animal simultaneously.

6. The method of claim 5, wherein a single composition comprising said coagulation-deficient Tissue Factor compound and said anti-cancer agent is administered to said animal.

7. The method of claim 1, wherein said coagulation-deficient Tissue Factor compound is administered to said animal at a biologically effective time prior to administration of said anti-cancer agent.

8. The method of claim 1, wherein said anti-cancer agent is administered to said animal at a biologically effective time prior to administration of said coagulation-deficient Tissue Factor compound.

9. The method of claim 1, wherein said anti-cancer agent is a chemotherapeutic agent.

10. The method of claim 9, wherein said anti-cancer agent is a chemotherapeutic agent listed in Table II.

11. The method of claim 10, wherein said anti-cancer agent is etoposide.

12. The method of claim 1, wherein said anti-cancer agent is an antibody construct comprising an antibody or antigen binding region that specifically binds to a component of a tumor cell, tumor vasculature or tumor stroma, the antibody operatively attached to a cytotoxic agent or to a coagulation factor.

13. The method of claim 12, wherein said antibody construct comprises an antibody or antigen binding region that specifically binds to a component of tumor vasculature.

14. The method of claim 12, wherein said antibody construct comprises an antibody or antigen binding region that specifically binds to a component of tumor stroma.

15. The method of claim 12, wherein said antibody construct comprises an antibody or antigen binding region operatively attached to a cytotoxic agent.

16. The method of claim 12, wherein said antibody construct comprises an antibody or antigen binding region operatively attached to a coagulant.

17. The method of claim 16, wherein said antibody construct comprises an antibody or antigen binding region operatively attached to Tissue Factor or a Tissue Factor derivative.

18. The method of claim 1, wherein said coagulation-deficient Tissue Factor compound is between about 100-fold and about 1,000,000-fold less active in coagulation than full length, native Tissue Factor.

19. The method of claim 18, wherein said coagulation-deficient Tissue Factor compound is at least about 1,000-fold less active in coagulation than full length, native Tissue Factor.

20. The method of claim 19, wherein said coagulation-deficient Tissue Factor compound is at least about 10,000-fold less active in coagulation than full length, native Tissue Factor.

21. The method of claim 20, wherein said coagulation-deficient Tissue Factor compound is at least about 100,000-fold less active in coagulation than full length, native Tissue Factor.

22. The method of claim 1, wherein said coagulation-deficient Tissue Factor compound is a human Tissue Factor compound.

23. The method of claim 1, wherein said coagulation-deficient Tissue Factor compound is prepared by recombinant expression.

24. The method of claim 1, wherein said coagulation-deficient Tissue Factor compound is a truncated Tissue Factor.

25. The method of claim 24, wherein said coagulation-deficient Tissue Factor compound consists essentially of the amino acid sequence of SEQ ID NO:1.

26. The method of claim 1, wherein said coagulation-deficient Tissue Factor compound is a dimeric Tissue Factor.

27. The method of claim 1, wherein said coagulation-deficient Tissue Factor compound is a mutant Tissue Factor deficient in the ability to activate Factor VII.

28. The method of claim 27, further comprising administering to said animal an amount of Factor VIIa sufficient to increase tumor vasculature coagulation and tumor necrosis.

29. The method of claim 1, further comprising administering to said animal a therapeutically effective amount of at least one of Factor VIIa or an activator of Factor VII.

30. The method of claim 1, wherein said coagulation-deficient Tissue Factor compound has been modified to increase its biological half life.

31. The method of claim 1, wherein at least a second coagulation-deficient Tissue Factor compound is administered to said animal, said second coagulation-deficient Tissue Factor compound being of a distinct type from said first coagulation-deficient Tissue Factor compound.

32. The method of claim 31, wherein said first and second coagulation-deficient Tissue Factor compounds are distinct types of coagulation-deficient Tissue Factor compounds selected from the group consisting of truncated, mutant, homodimeric, heterodimeric, polymeric, multimeric and increased biological half life coagulation-deficient Tissue Factor compounds.

33. The method of claim 1, wherein said animal has a vascularized tumor of at least about medium size.

34. The method of claim 33, wherein said animal has a large vascularized tumor.

35. The method of claim 1, wherein said animal is a human subject.

36. The method of claim 1, wherein at least a second anti-cancer agent is administered to said animal.

37. The method of claim 36, wherein said second anti-cancer agent is of a type distinct from said first anti-cancer agent.

38. The method of claim 1, wherein said anti-cancer agent is a radiotherapeutic agent.

39. The method of claim 1, wherein said anti-cancer agent is an agent that induces apoptosis.

40. The method of claim 1, wherein said anti-cancer agent is a cytokine.

41. A method for treating an animal having a vascularized tumor, comprising administering to said animal at least a first coagulation-impaired Tissue Factor compound and at least a first anti-cancer agent in a combined amount effective to promote coagulation in the tumor vasculature and to induce tumor necrosis.

42. A method for treating an animal having a vascularized tumor, comprising administering to said animal at least a first coagulation-impaired Tissue Factor compound and at least a first anti-cancer agent in a combined amount effective to achieve coagulation and tissue necrosis that are substantially confined to the vascularized tumor and do not substantially extend to normal, healthy tissues.

43. A method for treating an animal having a vascularized tumor, comprising administering to said animal at least a first Tissue Factor compound and at least a first anti-cancer agent in a combined amount effective to promote coagulation in the tumor vasculature and to induce tumor necrosis; wherein said at least a first Tissue Factor compound is rendered coagulation-deficient by being deficient in binding to a phospholipid surface or deficient in inserting into a phospholipid membrane or lipid bilayer.

44. A method for treating an animal having a vascularized tumor, comprising administering to said animal at least a first Tissue Factor compound and at least a first anti-cancer agent in a combined amount effective to promote coagulation in the tumor vasculature and to induce tumor necrosis; wherein said at least a first Tissue Factor compound is rendered coagulation-deficient by including a mutation that confers a deficiency in the ability to activate Factor VII.

45. A method for treating an animal having a vascularized tumor, comprising administering to said animal at least a first coagulation-deficient Tissue Factor compound and at least a first anti-cancer agent in a combined amount effective to promote coagulation in the tumor vasculature and to induce tumor necrosis; wherein said coagulation-deficient Tissue Factor compound substantially retains its ability to bind to Factor VII or Factor VIIa and is rendered coagulation-deficient by being deficient in binding to a phospholipid surface, deficient in inserting into a phospholipid membrane or deficient in activating Factor VII.

46. A method for treating an animal having a vascularized tumor, comprising administering to said animal at least a first coagulation-deficient Tissue Factor compound and at least a first anti-cancer agent in a combined amount effective to promote coagulation in the tumor vasculature and to induce tumor necrosis; wherein said coagulation-deficient Tissue Factor compound is rendered coagulation-deficient by being deficient in binding to a phospholipid surface, deficient in inserting into a phospholipid membrane or deficient in activating Factor VII and yet retains the catalytic activity of activating Factor X in the presence of Factor VIIa.

* * * * *

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
      (A) LENGTH: 220 amino acids
      (B) TYPE: amino acid
      (C) STRANDEDNESS:
      (D) TOPOLOGY: linear (xi) SEQUENCE DESCRIPTION: SEQ ID NO:1:

```
Gly Ser Gly Thr Thr Asn Thr Val Ala Ala Tyr Asn Leu Thr Trp Lys
1               5                   10                  15

Ser Thr Asn Phe Lys Thr Ile Leu Glu Trp Glu Pro Lys Pro Val Asn
                20                  25                  30

Gln Val Tyr Thr Val Gln Ile Ser Thr Lys Ser Gly Asp Trp Lys Ser
            35                  40                  45

Lys Cys Phe Tyr Thr Thr Asp Thr Glu Cys Asp Leu Thr Asp Glu Ile
        50                  55                  60

Val Lys Asp Val Lys Gln Thr Tyr Leu Ala Arg Val Phe Ser Tyr Pro
65                  70                  75                  80
```

```
Ala Gly Asn Val Glu Ser Thr Gly Ser Ala Gly Glu Pro Leu Tyr Glu
                85                  90                  95

Asn Ser Pro Glu Phe Thr Pro Tyr Leu Glu Thr Asn Leu Gly Gln Pro
            100                 105                 110

Thr Ile Gln Ser Phe Glu Gln Val Gly Thr Lys Val Asn Val Thr Val
        115                 120                 125

Glu Asp Glu Arg Thr Leu Val Arg Arg Asn Asn Thr Phe Leu Ser Leu
    130                 135                 140

Arg Asp Val Phe Gly Lys Asp Leu Ile Tyr Thr Leu Tyr Tyr Trp Lys
145                 150                 155                 160

Ser Ser Ser Ser Gly Lys Lys Thr Ala Lys Thr Asn Thr Asn Glu Phe
                165                 170                 175

Leu Ile Asp Val Asp Lys Gly Glu Asn Tyr Cys Phe Ser Val Gln Ala
            180                 185                 190

Val Ile Pro Ser Arg Thr Val Asn Arg Lys Ser Thr Asp Ser Pro Val
        195                 200                 205

Glu Cys Met Gly Gln Glu Lys Gly Glu Phe Arg Glu
    210                 215                 220
```

(2) INFORMATION FOR SEQ ID NO:2:

(i) SEQUENCE CHARACTERISTICS:
        (A) LENGTH: 234 amino acids
        (B) TYPE: amino acid
        (C) STRANDEDNESS:
        (D) TOPOLOGY: linear (xi) SEQUENCE DESCRIPTION: SEQ ID NO:2:

```
His His His His His His Ala Met Ala Leu Val Pro Arg Gly Ser Cys
1               5                   10                  15

Gly Thr Thr Asn Thr Val Ala Ala Tyr Asn Leu Thr Trp Lys Ser Thr
                20                  25                  30

Asn Phe Lys Thr Ile Leu Glu Trp Glu Pro Lys Pro Val Asn Gln Val
            35                  40                  45

Tyr Thr Val Gln Ile Ser Thr Lys Ser Gly Asp Trp Lys Ser Lys Cys
        50                  55                  60

Phe Tyr Thr Thr Asp Thr Glu Cys Asp Leu Thr Asp Glu Ile Val Lys
65                  70                  75                  80

Asp Val Lys Gln Thr Tyr Leu Ala Arg Val Phe Ser Tyr Pro Ala Gly
                85                  90                  95

Asn Val Glu Ser Thr Gly Ser Ala Gly Glu Pro Leu Tyr Glu Asn Ser
            100                 105                 110

Pro Glu Phe Thr Pro Tyr Leu Glu Thr Asn Leu Gly Gln Pro Thr Ile
        115                 120                 125

Gln Ser Phe Glu Gln Val Gly Thr Lys Val Asn Val Thr Val Glu Asp
    130                 135                 140

Glu Arg Thr Leu Val Arg Arg Asn Asn Thr Phe Leu Ser Leu Arg Asp
145                 150                 155                 160

Val Phe Gly Lys Asp Leu Ile Tyr Thr Leu Tyr Tyr Trp Lys Ser Ser
                165                 170                 175

Ser Ser Gly Lys Lys Thr Ala Lys Thr Asn Thr Asn Glu Phe Leu Ile
            180                 185                 190

Asp Val Asp Lys Gly Glu Asn Tyr Cys Phe Ser Val Gln Ala Val Ile
        195                 200                 205

Pro Ser Arg Thr Val Asn Arg Lys Ser Thr Asp Ser Pro Val Glu Cys
    210                 215                 220
```

```
Met Gly Gln Glu Lys Gly Glu Phe Arg Glu
225                 230
```

(2) INFORMATION FOR SEQ ID NO:3:

(i) SEQUENCE CHARACTERISTICS:
        (A) LENGTH: 234 amino acids
        (B) TYPE: amino acid
        (C) STRANDEDNESS:
        (D) TOPOLOGY: linear (xi) SEQUENCE DESCRIPTION: SEQ ID NO:3:

```
His His His His His His Ala Met Ala Leu Val Pro Arg Gly Ser Gly
1               5                   10                  15

Thr Thr Asn Thr Val Ala Ala Tyr Asn Leu Thr Trp Lys Ser Thr Asn
                20                  25                  30

Phe Lys Thr Ile Leu Glu Trp Glu Pro Lys Pro Val Asn Gln Val Tyr
            35                  40                  45

Thr Val Gln Ile Ser Thr Lys Ser Gly Asp Trp Lys Ser Lys Cys Phe
        50                  55                  60

Tyr Thr Thr Asp Thr Glu Cys Asp Leu Thr Asp Glu Ile Val Lys Asp
65                  70                  75                  80

Val Lys Gln Thr Tyr Leu Ala Arg Val Phe Ser Tyr Pro Ala Gly Asn
                85                  90                  95

Val Glu Ser Thr Gly Ser Ala Gly Glu Pro Leu Tyr Glu Asn Ser Pro
            100                 105                 110

Glu Phe Thr Pro Tyr Leu Glu Thr Asn Leu Gly Gln Pro Thr Ile Gln
        115                 120                 125

Ser Phe Glu Gln Val Gly Thr Lys Val Asn Val Thr Val Glu Asp Glu
    130                 135                 140

Arg Thr Leu Val Arg Arg Asn Asn Thr Phe Leu Ser Leu Arg Asp Val
145                 150                 155                 160

Phe Gly Lys Asp Leu Ile Tyr Thr Leu Tyr Tyr Trp Lys Ser Ser Ser
                165                 170                 175

Ser Gly Lys Lys Thr Ala Lys Thr Asn Thr Asn Glu Phe Leu Ile Asp
            180                 185                 190

Val Asp Lys Gly Glu Asn Tyr Cys Phe Ser Val Gln Ala Val Ile Pro
        195                 200                 205

Ser Arg Thr Val Asn Arg Lys Ser Thr Asp Ser Pro Val Glu Cys Met
    210                 215                 220

Gly Gln Glu Lys Gly Glu Phe Arg Glu Cys
225                 230
```

(2) INFORMATION FOR SEQ ID NO:4:

(i) SEQUENCE CHARACTERISTICS:
        (A) LENGTH: 220 amino acids
        (B) TYPE: amino acid
        (C) STRANDEDNESS:
        (D) TOPOLOGY: linear (xi) SEQUENCE DESCRIPTION: SEQ ID NO:4:

```
Ser Cys Gly Thr Thr Asn Thr Val Ala Ala Tyr Asn Leu Thr Trp Lys
1               5                   10                  15

Ser Thr Asn Phe Lys Thr Ile Leu Glu Trp Glu Pro Lys Pro Val Asn
                20                  25                  30

Gln Val Tyr Thr Val Gln Ile Ser Thr Lys Ser Gly Asp Trp Lys Ser
            35                  40                  45
```

```
Lys Cys Phe Tyr Thr Thr Asp Thr Glu Cys Asp Leu Thr Asp Glu Ile
 50                  55                  60

Val Lys Asp Val Lys Gln Thr Tyr Leu Ala Arg Val Phe Ser Tyr Pro
 65                  70                  75                  80

Ala Gly Asn Val Glu Ser Thr Gly Ser Ala Gly Glu Pro Leu Tyr Glu
                 85                  90                  95

Asn Ser Pro Glu Phe Thr Pro Tyr Leu Glu Thr Asn Leu Gly Gln Pro
                100                 105                 110

Thr Ile Gln Ser Phe Glu Gln Val Gly Thr Lys Val Asn Val Thr Val
            115                 120                 125

Glu Asp Glu Arg Thr Leu Val Arg Arg Asn Asn Thr Phe Leu Ser Leu
130                 135                 140

Arg Asp Val Phe Gly Lys Asp Leu Ile Tyr Thr Leu Tyr Tyr Trp Lys
145                 150                 155                 160

Ser Ser Ser Ser Gly Lys Lys Thr Ala Lys Thr Asn Thr Asn Glu Phe
                165                 170                 175

Leu Ile Asp Val Asp Lys Gly Glu Asn Tyr Cys Phe Ser Val Gln Ala
            180                 185                 190

Val Ile Pro Ser Arg Thr Val Asn Arg Lys Ser Thr Asp Ser Pro Val
            195                 200                 205

Glu Cys Met Gly Gln Glu Lys Gly Glu Phe Arg Glu
210                 215                 220

(2) INFORMATION FOR SEQ ID NO:5:

(i) SEQUENCE CHARACTERISTICS:
        (A) LENGTH: 220 amino acids
        (B) TYPE: amino acid
        (C) STRANDEDNESS:
        (D) TOPOLOGY: linear (xi) SEQUENCE DESCRIPTION: SEQ ID NO:5:

Ser Gly Thr Thr Asn Thr Val Ala Ala Tyr Asn Leu Thr Trp Lys Ser
 1               5                  10                  15

Thr Asn Phe Lys Thr Ile Leu Glu Trp Glu Pro Lys Pro Val Asn Gln
                 20                  25                  30

Val Tyr Thr Val Gln Ile Ser Thr Lys Ser Gly Asp Trp Lys Ser Lys
             35                  40                  45

Cys Phe Tyr Thr Thr Asp Thr Glu Cys Asp Leu Thr Asp Glu Ile Val
 50                  55                  60

Lys Asp Val Lys Gln Thr Tyr Leu Ala Arg Val Phe Ser Tyr Pro Ala
 65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Leu Gly Gln Pro Thr
                100                 105                 110

Ile Gln Ser Phe Glu Gln Val Gly Thr Lys Val Asn Val Thr Val Glu
            115                 120                 125

Asp Glu Arg Thr Leu Val Arg Arg Asn Asn Thr Phe Leu Ser Leu Arg
130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
```

-continued

```
              180                 185                 190
Ile Pro Ser Arg Thr Val Asn Arg Lys Ser Thr Asp Ser Pro Val Glu
            195                 200                 205
Cys Met Gly Gln Glu Lys Gly Glu Phe Arg Glu Cys
210                 215                 220
```

(2) INFORMATION FOR SEQ ID NO:6:

(i) SEQUENCE CHARACTERISTICS:
        (A) LENGTH: 235 amino acids
        (B) TYPE: amino acid
        (C) STRANDEDNESS:
        (D) TOPOLOGY: linear (xi) SEQUENCE DESCRIPTION: SEQ ID NO:6:

```
His His His His His His Ala Met Ala Leu Val Pro Arg Gly Ser Gly
1               5                   10                  15
Thr Thr Asn Thr Val Ala Ala Tyr Asn Leu Thr Trp Lys Ser Thr Asn
            20                  25                  30
Phe Lys Thr Ile Leu Glu Trp Glu Pro Lys Pro Val Asn Gln Val Tyr
            35                  40                  45
Thr Val Gln Ile Ser Thr Lys Ser Gly Asp Trp Lys Ser Lys Cys Phe
        50                  55                  60
Tyr Thr Thr Asp Thr Glu Cys Asp Leu Thr Asp Glu Ile Val Lys Asp
65                  70                  75                  80
Val Lys Gln Thr Tyr Leu Ala Arg Val Phe Ser Tyr Pro Ala Gly Asn
                85                  90                  95
Val Glu Ser Thr Gly Ser Ala Gly Glu Pro Leu Tyr Glu Asn Ser Pro
            100                 105                 110
Glu Phe Thr Pro Tyr Leu Glu Thr Asn Leu Gly Gln Pro Thr Ile Gln
            115                 120                 125
Ser Phe Glu Gln Val Gly Thr Lys Val Asn Val Thr Val Glu Asp Glu
        130                 135                 140
Arg Thr Leu Val Arg Arg Asn Asn Thr Phe Leu Ser Leu Arg Asp Val
145                 150                 155                 160
Phe Gly Lys Asp Leu Ile Tyr Thr Leu Tyr Tyr Trp Lys Ser Ser Ser
                165                 170                 175
Ser Gly Lys Lys Thr Ala Lys Thr Asn Thr Asn Glu Phe Leu Ile Asp
            180                 185                 190
Val Asp Lys Gly Glu Asn Tyr Cys Phe Ser Val Gln Ala Val Ile Pro
            195                 200                 205
Ser Arg Thr Val Asn Arg Lys Ser Thr Asp Ser Pro Val Glu Cys Met
        210                 215                 220
Gly Gln Glu Lys Gly Glu Phe Arg Glu Ile Cys
225                 230                 235
```

(2) INFORMATION FOR SEQ ID NO:7:

(i) SEQUENCE CHARACTERISTICS:
        (A) LENGTH: 236 amino acids
        (B) TYPE: amino acid
        (C) STRANDEDNESS:
        (D) TOPOLOGY: linear (xi) SEQUENCE DESCRIPTION: SEQ ID NO:7:

```
His His His His His His Ala Met Ala Leu Val Pro Arg Gly Ser Gly
1               5                   10                  15
Thr Thr Asn Thr Val Ala Ala Tyr Asn Leu Thr Trp Lys Ser Thr Asn
```

-continued

```
                    20                  25                  30
Phe Lys Thr Ile Leu Glu Trp Glu Pro Lys Pro Val Asn Gln Val Tyr
                35                  40                  45
Thr Val Gln Ile Ser Thr Lys Ser Gly Asp Trp Lys Ser Lys Cys Phe
 50                  55                  60
Tyr Thr Thr Asp Thr Glu Cys Asp Leu Thr Asp Glu Ile Val Lys Asp
 65                  70                  75                  80
Val Lys Gln Thr Tyr Leu Ala Arg Val Phe Ser Tyr Pro Ala Gly Asn
                 85                  90                  95
Val Glu Ser Thr Gly Ser Ala Gly Glu Pro Leu Tyr Glu Asn Ser Pro
                100                 105                 110
Glu Phe Thr Pro Tyr Leu Glu Thr Asn Leu Gly Gln Pro Thr Ile Gln
                115                 120                 125
Ser Phe Glu Gln Val Gly Thr Lys Val Asn Val Thr Val Glu Asp Glu
130                 135                 140
Arg Thr Leu Val Arg Arg Asn Asn Thr Phe Leu Ser Leu Arg Asp Val
145                 150                 155                 160
Phe Gly Lys Asp Leu Ile Tyr Thr Leu Tyr Tyr Trp Lys Ser Ser Ser
                165                 170                 175
Ser Gly Lys Lys Thr Ala Lys Thr Asn Thr Asn Glu Phe Leu Ile Asp
                180                 185                 190
Val Asp Lys Gly Glu Asn Tyr Cys Phe Ser Val Gln Ala Val Ile Pro
                195                 200                 205
Ser Arg Thr Val Asn Arg Lys Ser Thr Asp Ser Pro Val Glu Cys Met
                210                 215                 220
Gly Gln Glu Lys Gly Glu Phe Arg Glu Ile Phe Cys
225                 230                 235

(2) INFORMATION FOR SEQ ID NO:8:

(i) SEQUENCE CHARACTERISTICS:
        (A) LENGTH: 219 amino acids
        (B) TYPE: amino acid
        (C) STRANDEDNESS:
        (D) TOPOLOGY: linear (xi) SEQUENCE DESCRIPTION: SEQ ID NO:8:

Ser Gly Thr Thr Asn Thr Val Ala Ala Tyr Asn Leu Thr Trp Lys Ser
 1               5                  10                  15
Thr Asn Phe Lys Thr Ile Leu Glu Trp Glu Pro Lys Pro Val Asn Gln
                20                  25                  30
Val Tyr Thr Val Gln Ile Ser Thr Lys Ser Gly Asp Trp Lys Ser Lys
                35                  40                  45
Cys Phe Tyr Thr Thr Asp Thr Glu Cys Asp Leu Thr Asp Glu Ile Val
 50                  55                  60
Lys Asp Val Lys Gln Thr Tyr Leu Ala Arg Val Phe Ser Tyr Pro Ala
65                  70                  75                  80
Gly Asn Val Glu Ser Thr Gly Ser Ala Gly Glu Pro Leu Tyr Glu Asn
                 85                  90                  95
Ser Pro Glu Phe Thr Pro Tyr Leu Glu Thr Asn Leu Gly Gln Pro Thr
                100                 105                 110
Ile Gln Ser Phe Glu Gln Val Gly Thr Lys Val Asn Val Thr Val Glu
                115                 120                 125
Asp Glu Arg Thr Leu Val Arg Arg Asn Asn Thr Phe Leu Ser Leu Arg
                130                 135                 140
```

```
Asp Val Phe Gly Lys Asp Leu Ile Tyr Thr Leu Tyr Arg Lys Ser
145                 150                 155                 160

Ser Ser Ser Gly Lys Lys Thr Ala Lys Thr Asn Thr Asn Glu Phe Leu
            165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
            195                 200                 205

Cys Met Gly Gln Glu Lys Gly Glu Phe Arg Glu
            210                 215
```

(2) INFORMATION FOR SEQ ID NO:9:

(i) SEQUENCE CHARACTERISTICS:
        (A) LENGTH: 219 amino acids
        (B) TYPE: amino acid
        (C) STRANDEDNESS:
        (D) TOPOLOGY: linear (xi) SEQUENCE DESCRIPTION: SEQ ID NO:9:

```
Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
            35                  40                  45

Cys Phe Tyr Thr Thr Asp Thr Glu Cys Asp Leu Thr Asp Glu Ile Val
            50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
            115                 120                 125

Asp Glu Arg Thr Leu Val Arg Arg Asn Asn Thr Phe Leu Ser Leu Arg
            130                 135                 140

Asp Val Phe Gly Lys Asp Leu Ile Tyr Thr Leu Tyr Trp Lys Ser
145                 150                 155                 160

Ser Ser Ser Ala Lys Lys Thr Ala Lys Thr Asn Thr Asn Glu Phe Leu
            165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
            195                 200                 205

Cys Met Gly Gln Glu Lys Gly Glu Phe Arg Glu
            210                 215
```

(2) INFORMATION FOR SEQ ID NO:10:

(i) SEQUENCE CHARACTERISTICS:
        (A) LENGTH: 657 base pairs
        (B) TYPE: nucleic acid
        (C) STRANDEDNESS: single
        (D) TOPOLOGY: linear (xi) SEQUENCE DESCRIPTION: SEQ ID NO:10:

-continued

| | |
|---|---|
|TCAGGCACTA CAAATACTGT GGCAGCATAT AATTTAACTT GGAAATCAAC TAATTTCAAG | 60|
|ACAATTTTGG AGTGGGAACC CAAACCCGTC AATCAAGTCT ACACTGTTCA AATAAGCACT | 120|
|AAGTCAGGAG ATTGGAAAAG CAAATGCTTT TACACAACAG ACACAGAGTG TGACCTCACC | 180|
|GACGAGATTG TGAAGGATGT GAAGCAGACG TACTTGGCAC GGGTCTTCTC CTACCCGGCA | 240|
|GGGAATGTGG AGAGCACCGG TTCTGCTGGG GAGCCTCTGT ATGAGAACTC CCCAGAGTTC | 300|
|ACACCTTACC TGGAGACAAA CCTCGGACAG CCAACAATTC AGAGTTTTGA ACAGGTGGGA | 360|
|ACAAAAGTGA ATGTGACCGT AGAAGATGAA CGGACTTTAG TCAGAAGGAA CAACACTTTC | 420|
|CTAAGCCTCC GGGATGTTTT TGGCAAGGAC TTAATTTATA CACTTTATTA TTGGAAATCT | 480|
|TCAAGTTCAG GAAAGAAAAC AGCCAAAACA AACACTAATG AGTTTTTGAT TGATGTGGAT | 540|
|AAAGGAGAAA ACTACTGTTT CAGTGTTCAA GCAGTGATTC CCTCCCGAAC AGTTAACCGG | 600|
|AAGAGTACAG ACAGCCCGGT AGAGTGTATG GGCCAGGAGA AAGGGGAATT CAGAGAA | 657|

(2) INFORMATION FOR SEQ ID NO:11:

(i) SEQUENCE CHARACTERISTICS:
  (A) LENGTH: 13865 base pairs
  (B) TYPE: nucleic acid
  (C) STRANDEDNESS: single
  (D) TOPOLOGY: linear (xi) SEQUENCE DESCRIPTION: SEQ ID NO:11:

| | |
|---|---|
|GAATTCTCCC AGAGGCAAAC TGCCAGATGT GAGGCTGCTC TTCCTCAGTC ACTATCTCTG | 60|
|GTCGTACCGG GCGATGCCTG AGCCAACTGA CCCTCAGACC TGTGAGCCGA GCCGGTCACA | 120|
|CCGTGGCTGA CACCGGCATT CCCACCGCCT TTCTCCTGTG CGACCCGCTA AGGGCCCCGC | 180|
|GAGGTGGGCA GGCCAAGTAT TCTTGACCTT CGTGGGGTAG AAGAAGCCAC CGTGGCTGGG | 240|
|AGAGGGCCCT GCTCACAGCC ACACGTTTAC TTCGCTGCAG GTCCCGAGCT TCTGCCCCAG | 300|
|GTGGGCAAAG CATCCGGGAA ATGCCCTCCG CTGCCCGAGG GGAGCCCAGA GCCCGTGCTT | 360|
|TCTATTAAAT GTTGTAAATG CCGCCTCTCC CACTTTATCA CCAAATGGAA GGGAAGAATT | 420|
|CTTCCAAGGC GCCCTCCCTT TCCTGCCATA GACCTGCAAC CCACCTAAGC TGCACGTCGG | 480|
|AGTCGCGGGC CTGGGTGAAT CCGGGGGCCT TGGGGGACCC GGGCAACTAG ACCCGCCTGC | 540|
|GTCCTCCAGG GCAGCTCCGC GCTCGGTGGC GCGGTTGAAT CACTGGGGTG AGTCATCCCT | 600|
|TGCAGGGTCC CGGAGTTTCC TACCGGGAGG AGGCGGGGCA GGGGTGTGGA CTCGCCGGGG | 660|
|GCCGCCCACC GCGACGGCAA GTGACCCGGG CCGGGGGCGG GGAGTCGGGA GGAGCGGCGG | 720|
|GGGCGGGCGC CGGGGGCGGG CAGAGGCGCG GGAGAGCGCG CCGCCGGCCC TTTATAGCGC | 780|
|GCGGGGCACC GGCTCCCCAA GACTGCGAGC TCCCCGCACC CCCTCGCACT CCCTCTGGCC | 840|
|GGCCCAGGGC GCCTTCAGCC CAACCTCCCC AGCCCCACGG GCGCCACGGA ACCCGCTCGA | 900|
|TCTCGCCGCC AACTGGTAGA CATGGAGACC CCTGCCTGGC CCCGGGTCCC GCGCCCCGAG | 960|
|ACCGCCGTCG CTCGGACGCT CCTGCTCGGC TGGGTCTTCG CCCAGGTGGC CGGCGCTTCA | 1020|
|GGTGAGTGGC ACCAGCCCCT GGAAGCCGG GGCGCGCCAC ACGCAGGAGG GAGGCGACAG | 1080|
|TCCTGGCTGG CAGCGGGCTC GCCCTGGTTC CCCGGGGCGC CCATGTTGTC CCCGCGCCT | 1140|
|ACGGGACTCG GCTGCGCTCA CCCAGCCCGG CTTGAATGAA CCGAGTCCGT CGGGCGCCGG | 1200|
|CGGGAGTTGC AGGGAGGGAG TTGGCGCCCC AGACCCCGCT GCCCCTTCCG CTGGAGAGTT | 1260|
|TTGCTCGGGG TGTCCGAGTA ATTGGACTGT TGTTGCATAA GCGGACTTTT AGCTCCCGCT | 1320|
|TTAACTCTGG GGAAAGGGCT TCCCAGTGAG TTGCGACCTT CAATATGATA GGACTTGTGC | 1380|

```
CTGCGTCTGC ACGTGTTGGC GTGCAGAGGT TTGGATATTA TCTTTCATTA TATGTGCATC    1440

TTCCCTTAAT AAAGAGCGTC CCTGGTCTTT TCCTGGCCAT CTTTGTTCTA GGTTTGGGTA    1500

GAGGCAATCC AAAAGGGCTG GATTGCTGCT TAGATTGGAG CAGGTACAAC GTTGTGCATG    1560

CCCCGTATTT CTACGAGGTG TTCGGGACGG CGTAGAGACT GGGACCTGCT GCGTACTGGC    1620

AAAGCAGACC TTCATAAGAA ATAATCCTGA TCCAATACAG CCGACGGTGT GACAGGCCAC    1680

ACGTCCCCGT GGGTCTCTGT GGAAGTTTCA GTGTAGCGAC ATTTCAGATA AAAGTGGAAA    1740

AAGTGAAGTT TGGCTTTTTT CATTTGTATG CAGTCCTAAC TCTTGTCACA CGTGTGGGAT    1800

TTATCTTTTT CCATAACTTA CTGAAAACCC TTCCTGGCGG GCTGAACCTG ACTCTTCCTG    1860

AGCTGAGTCC TGGACTGGCA CACTGATGGC TCTGGGCTCT TCCCGGTCAA GTTATAACAA    1920

GGCTTTGCCC ATGAATAATT TCAAACGAAA ATGTCAAGAT CCTTGCCGGT GTCCTGGGAT    1980

TACAAGGTGA ATCTTGTCAT GAAGAAATTC TAGGTCTAGA AAAAATTTGA AGATTCTTTT    2040

TCTCTTGATA ATTCACTAAT GAAGCTTTTG TGGTTGAAAA ATAAAAAGTG AGGTTTATGG    2100

TGATGTCAGG TGGGAAGGTG TTTTATACAT CAATACATTC GAGTGCTCTG AAGTGCATGT    2160

AATAATAGCT GTTTCTCTGT TGTTTAAAGG CACTACAAAT ACTGTGGCAG CATATAATTT    2220

AACTTGGAAA TCAACTAATT TCAAGACAAT TTTGGAGTGG GAACCCAAAC CCGTCAATCA    2280

AGTCTACACT GTTCAAATAA GGTAAGCTGG GTACAGAAAA AGAAAATTAA GGTCTTTGAT    2340

GTTTCTACTG TCCTATGCTG AACAAGAATG TCTTTAAAGC TGATTACTGG ATGAAATTAT    2400

TTAACAGATG ACGAAGAAGA AGGGATTCTT GGCAATTCGC TGGCCGGTGT CATACTCTAT    2460

TAGGCCTGCA ACATTTCCAG ACCTTAAACT GATAGAACAT TTTAATTGTT TTAATTGTTT    2520

TTGGAAATGA TGGGAGAGTT CCTAAGTGGA GTATAAACTG TGGAGAGATG AACCATCTTG    2580

AGTAGGCACT GAAGTGTGCT TTGGGTCATG ATAGATTAAT TAATCTCATC TAAACATTGA    2640

TGTCTTTTTC CGTTGCTGTC TAGACTGTGA ACAATGTCTA ACACCTTAGG GAAGAGGTGG    2700

GGAGGAATCC CAATGTATAC ATTGCCCTTA AGCAGTGTTT GATTCATTCA TCTTTGGACT    2760

CCATGAATCG AAATCTGGTA GAATACATGA TCTTAGTGGA GGAGGCCAAA TGCGTGACTC    2820

ACTGAGCCTG GCAGAGCAGA AATACTCTGC TGTCTGCACC CTCTGGGTCT GGTGTGGCTC    2880

TGCTTCTTGG TGCTTCAACT CTGACTGGCA GCTGTCCCCA GGAGGCGATA ATTCAGCATG    2940

TTCAATCTAA AGGTTATGAC TTCCTTGATG GTTTTCACCA TATTCTTGGC AAGTTTTTGG    3000

TTTTTGAAAT GTTCTAGGAG GCTTGGTAGA GATCTTATGA AATAGAGAAT AGCTGCTGTG    3060

GAAATTATTT TAATGCTAAT TACATAAAAG TACAAAAGTA GCACTAGCTA AAACAAAAGG    3120

TATTTTGCTG TTCTGTTTTG TTTTAGCTTG TGCCAGGCCT TTTACAGCAT TAGGAATGCA    3180

ACTTCTAGAT AACGATGCAT CTTTTAAGTG AATGTTCTTG TTTTTCAAAA TGAACTTCAT    3240

GACAGTAGTT GCCAAACCAG CAAGGAGAAC TTGCATGCAT ACGTGCATGC ATGTGTGGAT    3300

ATGTATGGGG GTGGGGGAG AGAAAGATGA AGGAATTTCA TAACATGAAA TAATGATTAC    3360

AGTTCTGGTC AAACTTGTCA ATTCAGATTT CACCAATTGA GAATTAGTAA GTAATTTCTC    3420

TGATACAGGC CTGAAGTTTA CCTTAGTAAA CACTTTACTT CCATATGGTA AAAATTAGAT    3480

TTTGGGAGGA ATGCTTACCT CCTAAATATA TTCAATCTAA TATTTGAGGA CACATGGGAA    3540

TATATTTATG ATTCATCTGC TTTTTAAACA TAAGCCTTTG TTAACTGTAA GTTCTTGAAC    3600

TTTATAAGGC TGCTGTTATT TAAATGAGCA CAGCTCCTGA TCTGCAAACA GCAGAGCGCA    3660

GGGCTACAGC TTGGGGGATG CCAGCCGACT CAGGGTGGTC CTGTGGACTG AACAATCTCT    3720

TGCTGCTGTA CTGGAGGGCC TGGGAGCTTT TCCATCAGCC TCGGCCTGAG GTGTGCACTC    3780
```

```
TTCTCCTGCC CACCCCAGGA ATAAATGAGA TTCCTGGTTA AAAAGGACCA GAGCAGTCAT    3840

TTTACAGTTG AGGAAACTGT TGCTCTGAGA AGTGAGGGAT TTATTCATGA CTACACTGAT    3900

GGTGAGTGCC CATGTCAGGT CTGGAACCAA AGTCTACCCA GTATCCACAC ACCACCATCC    3960

CTCAGGTGGC TCTGCCACAG TCTGATGGGA GGCTCCAAAG CGGGAGGAAG AAGGAAAGTC    4020

TTGCCCACTG CATCTCCTCA GTTGGCCTTC CTCTCTGCCT GTTTTCCCTC CCTACAGTTA    4080

GCATCTTAAG CAGCTGCCTC TCTTCCCTCC CGACTGCTCT CACTACTGCA GCCTGGCTCC    4140

AGCCGCAGGA CACTACTGCT GTGCAGAAGC CCCTACTTGG AACTCCAACT GCATTTTTCA    4200

CCTTTGCTAA CAGTTTTCAG TGGTGGTTGG GAAATGTTAT TGGCTTAAGC CTTAGCACAA    4260

ACCGTCACCG GTGATATTCA TTCCATGGAA ATGTTCTGAA TTCTAAAGCT GAATTTACAA    4320

AGCTTCTGGA AAACAACCTG CAACCAAATT AGTGACTGAA TTTTTTAGTT AACTCAAAAT    4380

TCCAAATCAG AGGGTTTTGC AATGCCTGGA GGAACCTTGG AGGCTTTTAA AGTGTTAATG    4440

CTATTAATGG CATTCAGAGG GATTTTCTAC AGAATTGTCC CTTCATTACC TGTTTATACA    4500

GTTTTACTAC TTACCAGGGT ACTGTATAAA TCCTTGTGCT AAATTTTGCT ATAGAGTATG    4560

TGGTCCCTGC TGTGAGCTGG GAGGAACCAA ATACTGTATC TCTATGTTAC ATAGAAAGCC    4620

CTAGGAGACT TTCTCCTGTT ATCTGAACAA CTATTTGCTG TACTGATAAA AAGGAAACAG    4680

CATAGTCTCA TTCACTTTTT GAAATGGAAA TGATAAAATA AAACACATTT TGGTCATTCG    4740

GGAACAAAAT ACCCTCTCTA CTTTTATCAC ATAAAATTAA ATAAATAGAA ACCAAAATAT    4800

TTCAGTATCA ATCTTAGTTT GTGCACTTTA GGATAAAGAA TGTGTTACC CAAATCCTTT     4860

TGGCCTGGTT ACTTAGTTCA GATTTTGAAA GAAAATATAT TTGTGGCTTT TATGTGTGAA    4920

TTTAGACAAT GGAATCCATG TGGTGCCTCG TTTTCCCTGA GATTATGTAT TAATTCAACC    4980

TGTAAATGCA AACCATCTAA TAGTCAGCGA GACCCTATAG CCCTGCTGCT TAATGGGGGC    5040

ACACAAGGGC ATGCAGCCCT CGTACCAGGC AGACTGTGTT CATATTAACA GCATCGTGGA    5100

GAAACTCATG CTGGGGGACA GGGGAGGGAG ATGTAAATGC TCAGCAGGGA GATCTGGAGA    5160

TTCCTGGAGC AGGTGGAGTT GGGACCTGGC CTTGAACGAT GGGTCTGGCT CTGGCAGTCA    5220

GTAATGCCAA AGGGAAGAGC AGCATAACTG TCACTTTCCA TGGGACAGAA GTGTGTGAAT    5280

CAAGTTGCAG TGACGCTTCA CCTATTTATT ATTTTGGTCA TTTAGAAGAA TTTCATTGTC    5340

AGTAGAAGTC CTTTAAATCA TTTCCCCTTC AGTGACGTCT CACAAAAAAA AGATCTGTCT    5400

TTAGCTTTTT AGTCTCAGAC TTTATTAGAC AGATACTACC TGTACTCTTA TTCTGTAATC    5460

TTTGTTGGGA TGGATTCACA TCTTGCAAAG GAAGGGAGGC ATGTAGTATA ATGGGGCAAA    5520

CAGACCCAGC TCTGCCACTC GTTAGATATG TGACCTTCTG CAAGTTGCTT AGTGCCTGTG    5580

AGCTTCAGTG TCCTCATGGA TAAGAAAGAT CCAACACCTT CTTGGAAGGA TTATATCAAA    5640

TGAAGTAACA TGAGTAAAGG GTCCAGCAGA ATACCTGGCA TATAGTGGAG TCAATGAATG    5700

ATTAATAATA TTATTAATAG TGGTCATGAG AGATATATGT ATAACATGTT ATTATGTAGA    5760

CTCACTATAT AGACTCTATT CTACATAGAA TATAGAACAT TATATAACAA ACAACTATAA    5820

TAAGTAGACT ATAGTAAACA ACCTCACTTT GTCTCAGTTG CCTCATCTTG ATGGAAAACT    5880

GCTCTTTCTC TCCTGTTACC CTGACAGAGA GCGTCTACAT TCTAAAAGAA AGATATTTAA    5940

CAAAATGGTT GAGTACAGAT CCAAGAGTCA AATAGCTGTC TGGTTCAAAG TCCAGCTGTG    6000

TGATTTTGAG CTAGTCACCC AATCTCACTT TGTCTCAGTA GCCTTATTTG TAAAAACAAG    6060

GCAAATTACA GAGCCATCCC CTGGGTTGCT ATGAGGACTC AAACATGCAT CCCAAGTGCT    6120
```

```
CGGTGTTGCT AGGTATGATG GCTCACACCT GTACATTCAG CACTTTGGGA GGCCGAAGCA    6180

GAAGGATCAG CCTGGGCAAC ATAGCAGGAC CCCATCTCTA CAAAACAATG TTTAAAAAAA    6240

AGCAAAGTGC TCAGCACAGT GACTGCATCA TTAGGATTGA TTGTAGGGCT CCTGATGTTA    6300

GCACAGAACA CCACAGCCAG GAAGCAGTCT ATCTTGTTGG GTGCAAATTG TAACATTCCA    6360

TTTATGTTTC TTCCTTCTTT TCTTTCTTTA GCACTAAGTC AGGAGATTGG AAAAGCAAAT    6420

GCTTTTACAC AACAGACACA GAGTGTGACC TCACCGACGA GATTGTGAAG GATGTGAAGC    6480

AGACGTACTT GGCACGGGTC TTCTCCTACC CGGCAGGGAA TGTGGAGAGC ACCGGTTCTG    6540

CTGGGGAGCC TCTGTATGAG AACTCCCCAG AGTTCACACC TTACCTGGAG AGTAAGTGGC    6600

TTGGGCTGTA ATACCGTTCA TTCTTGTTAG AAACGTCTGA ACATTCTCGT GATCTTGTGC    6660

CTTTAGGGGC TACAAAATTA AAAATATTTA TTCTTTTTTT CTCAGAAACT GGTATGTATC    6720

ACAGCCCTCT TCACACATTC CAGATGTGGT AGGAGGTTCA CAGAATGTGA ACTTTTGGAG    6780

CTGATGACAG TGTCATCAAG TAACTTTCTC CCCCAGTCTG TCCCCAGACC CTGTTACTGT    6840

CCTCAGTAAG CGGCTGAATG TGTGTTGGGA GAGGGCGGGC CAGGGAAGCG GGTAGGGATA    6900

GGAAATCCAC CAAGGCCGGG GTTTTAGCTT TTCCCTATAT ATATATCATG TATCCTGATT    6960

TTTCTGTCCC GTTATCACAC TAAAAATCCC AGTTGAGGAT TTTTCCCAAA CGGTCATAAA    7020

TCAATGAGGA AAGTCCATGG TTTCCCTCTG AGCCCATAAT TAGCCTAATT ATGCTGACCT    7080

TTTCTAATCA GTTGGCCATG ATTTGAGTTC CGTGATGTGC CAGCACCTGC CCAGCCATCT    7140

GCCTGTCACC CTCGTTCTGG TTTTGGAAAG GTGGAATACT TTCCTCCTCA GCCTTTGCCC    7200

CTGTAAGCTG GCCCTAGGAG CCAGTAAAAG AATGAAGAGA ATTCCTGTCA AGTAGGAGAT    7260

TTATTCTTTT GCCGCAACTG TGGCTCTGAG CTAGGCAATT TAGATAAATG CATGTAGCAC    7320

ATTGAGTAGA GTGAAATTAG CTTCTCTTGT AAGGCCAGCT GGTTAGAATG AAGGTGTTGT    7380

GTGAGTGTTA GGCCCAGCGA GAGAGAACAG TTTCTCAAGG TAGGAATGGT GAAAAGAAGG    7440

GGTGGACGGA CAACCAACCA ACCATCCTCC TCTGGTATCT ACTTTGAGGG TTGAAATAGG    7500

GGGCCTGACC CCAGGTGAAT GTGGCTGCCT TCCCAGAGCC CCCATTTGCA AGACCCTCCA    7560

GACCCCCAGG TGCTTCTGCT TGTGTCTTTT GTGGCACCAG GCAAGAATGT AGCAGCGTCA    7620

GCAGCCCCTC TGGTGACTGT GGCATGGTTG ACATTCATTT CCCCCCTAAT TAATGGCATC    7680

CTCATGATTC TCTTTTATAT TAATAGTTCT TGAGTTTTTT TGTAAGCTAC TTCAAATCCT    7740

TTGTTGGTGC AAGATAGAAG ATATTTTATG TGTTTGTTTT GCATGTGCAC ACACATATTT    7800

GGCCTGTGAA TTGATGTTTG TTTTCCTGTC ATTTAACCAA AGCACATGAG ATAATTGAGC    7860

CATTGCAGAG ACCCCGTGGT TAAATCCGGC TTCTCGAGGT ACCAAGGACA TTTCCTGGGC    7920

TTTCTCACAG CCCTACATAT TTTTGAACCT AAAATATCGT AGTTTATGCT ACCACCCTGT    7980

TCAGTATAGT AGCCACTAGC CACATGTGGC TGTTGACCAC TTGAAATATG GCTAATGCTC    8040

TAAGTATAAA GTACACACTG GAATTTAAGA AGTGTAGAAT ATCTCAAAAC TTTTTTATAT    8100

TGATTACACA TTAAAATGAT TATATTCCAG ATATATGCAG TTGACTCAAG CAATGCATGG    8160

CTGAGAGGCA CCGACTCCCT GTGCAGTTGA AAATCCGAGT ATAACTTGAC TCCCCAAAAA    8220

CTTAACTACT AATAGCCTAC CTATCGGTTG ACTGTTGACT GCAGCCTTAC CAATAAGATA    8280

AACAGTCAAT TAACACACAT TTTTCATGTT GCGTGTATTA TATACTGTAT TCTTACAATA    8340

AAGTAAGCTA GAGGAAAGAA AATGTTATTA AGAAAATTAT AAGGAAAAGA GGCTGGGCAT    8400

GGTGGCTCGT GCCTGTAATC TCAGAACTTT GGGATGCTAA GGCGGGTGGA TCACTTGAGG    8460

TCAGGAGTTC AAGACCAGCC TGGCCAACAT GGTGAAACCC CATCTCTACT AAAAATACAA    8520
```

```
AAATTAGCCA GGCGTGGTTG TGGGTGCCTG TAATCCCAGC TACTTGGGAG GCTGAGGCAG    8580

GAGAATCACT TCGACCCAGG TGGAGGAGGT TGCAGTGAAC TGAGATTGCG CCACTGCACT    8640

CCGGCCTGGG TGACAGAGCG AGACTCTGTC TAAAAAAGAA AGGGAAAGAA AGAAAAAAAA    8700

GAAAAGAAAA GAAAGAAAG AAGGAAGGAA GAGAAAGAAT TATAAGGAAG AGAAAATATA     8760

TTTACTATTG ATAAAGTGGA AGTGGATCAT CATAAAGGTG TTCATCCTCG TCATCTTCAT    8820

GTTGAGTAGG CTGAGGAGGA GGAGGAGGAG GAAGAGCAGG GGCCACGGCA GGAGAAAAGA    8880

TGGAGGAAGT AGGAGGCGGC ACACTTGGTG TAACTTTTAT TTAAAAAAAT TTGCATACAA    8940

GTGGATCCAC AGAGTTCAAA CCCATGTTGT TCAGGGGTCA ACTGTCTTTG GTTAAATAAA    9000

ATATATTATT AAAATTAATT TCACCTGTTC CTTTTTACTT TTTCTAATGT GACTACTAGA    9060

AAACTTAAAA TGACATCTGA GGCTCCATTG TCTTCCCCTT GGGCCAGCAC TACCACAGAA    9120

TGTCTTAGGA TTCAGCTCCA GGCCGCCACG CCTGCTTCTT TCAGGGAGCT GGTTCTATGC    9180

ACATGTTTTA TATGAGAGAT AATTAAGTTG TCAATTGTGA TAACAAAACA GGATTTGACT    9240

TTGTACAGAA TTCTTTGGTT CCAACCAAGC TCATTTCCTT TGTTTCAGCA AACCTCGGAC    9300

AGCCAACAAT TCAGAGTTTT GAACAGGTGG GAACAAAAGT GAATGTGACC GTAGAAGATG    9360

AACGGACTTT AGTCAGAAGG AACAACACTT TCCTAAGCCT CCGGGATGTT TTTGGCAAGG    9420

ACTTAATTTA TACACTTTAT TATTGGAAAT CTTCAAGTTC AGGAAAGGTG AGCATTTTTT    9480

AATTTGTTTT TATGACCTGT TTTAAATTGT GAATACTTGG TTTTACAACC CATTTCTTCC    9540

CCAATTCAAA AATAGCAGAA CAGAGTTGTT GAGAAGGTGA TGGAGTAGAA GGGGGAGCGC    9600

GCACTGTGGG GAGGGTGGA CAACAGGCCT GGTCCTACCT GTGACTCTGC ACTACCCTGT     9660

GACTCTGGCA GGGCCCCCTC GGAGACCCAG GTTCCTCAGC CAACCGGCTG GATCAGGTCA    9720

TCTCTAAAGG TCCCGCCACG CTCACATTTC TCCCTCTATT GAGGATCCCA GGCACAAAAT    9780

TTGTTTTTGG TTCAATGCAT AATACTCCCT TCCTTTTTCT TTTACTGCAG ATATCTTCTA    9840

AAGGGGCTCA ATAGGGTTCA ATATGCCTAA ATTGGATCTT CTCAGTCTTG GAAAAGGCAT    9900

TTTTAGCAGT GATCAAGGGA AACTGATTAG CGAAGTCACT TCTAATCCTT CACGTGTCAG    9960

CTGTGTTCTT GTAGGCTTTG CTTAGAACCT AGGTTTTTAC TTCCACAGTG ACTTAATAAA    10020

GGGGAAAGAA TTGACTCAGA GCCCAGATGA ATTAAGAACT CTATCTTTTT ACAGAAAACA    10080

GCCAAAACAA ACACTAATGA GTTTTTGATT GATGTGGATA AAGGAGAAAA CTACTGTTTC    10140

AGTGTTCAAG CAGTGATTCC CTCCCGAACA GTTAACCGGA AGAGTACAGA CAGCCCGGTA    10200

GAGTGTATGG GCCAGGAGAA AGGGGAATTC AGAGGTGAGT GGCTCTGCCA GCCATTTGCC    10260

TGGGGGTATG GGTGCTGTGG GTGACTTCTG GAGGAGTAGC TCCACCCTCA GGGCTGGGAT    10320

ATACTTCCTT GGTTAAATAT TCAGGAAAAC AAACTGCCTG GAGGTTTTTT GTTGTTATTT    10380

GTTTGTTTTG GTTTTGATTT TGCTTTGGTA CAAAAAAGAT TTTGGACATT TAGAAATGTT    10440

TCTGTGTTGA TTGTGCCCTT GTATTAGCAG GTGTTTTCTT GAGCACCTGT CATGTGCTAA    10500

GCCCTCTGCT GAGCACTGGA TACACAAACT GTGTTTAGGA TTTAGCAACA AGTCACAGAT    10560

TTCCCTGGGC ATTTTTTCAT GCTTAAATTC TAATTCTGGG GGTGGCTTCT GGACCAGCTG    10620

CAACAGGACA CAGTAGACAT TCGTGAGTAC CCACTGTGGG CTGTTGCCAC AGAGGCTGTA    10680

GAGTCTAACC CATCAAGGGA AGGGATTGAG TATATCAAAT ATACCCACAT GCATGCATGT    10740

GTGTATATGG CGGACACGTG TGTGTACATG CATGTGCATA TGTTGGGAGC TCAGGCCCAT    10800

TGTGCGAGGA ACAGTCCCTA ACCGGAAGTG CTGTGGGCCT TCAGACTCTT GCAGGAAGCT    10860
```

```
GCAAGCCTGT GTGTCTCGAT CCATGCCTTA CAGGGAAAGT ATTCTGAGTA CTTTCAGTGA    10920

AGAAAAGAGT CAGGGGATAT AAACGATGGC TTACGCTGGG TGTGGTGGCT CACGCCTGTA    10980

GTCCCTGCAC TTTGGGAGGC CCAGACAGGC AAATCACTTG AGGTCAGGAG TTTGGGACCA    11040

GCCTGGCCAA CATGGTAAAA GCCCATCTCT ACTCAAAATA CAAAAAGTAG CTGGGTGTGG    11100

TTGCACGTGT CTGTAGTCCC AGCTACTCAG GAGGTTGAGG CAGGAGAATT GCTTGAACCT    11160

GGGAGGCGGA GGCTGAAGTG AGCTGAGATT GGACCACTGT ACTCCAGCCT GGGTGACAGA    11220

GCGAGATTCC ATCTCAAAAA AAAAAAAAAG AAACAACGAA AAAAGAAATG ATGGCTTAGC    11280

TCCATGTGAA GATGATATTT GAACATTTTA AAACACTTTA AATAAACTGT TCTCTCCTGT    11340

TTATTGCCAC TGACAGGAGA GGTTTCTCTT TACCTCTGGT CCTGCACCCC TCTGAGCCAT    11400

CCTACCCACA GCCTTCAGTC ATTGTCCTAA AGCCTAGCTC TAATTCCACT GCCTCTCCTT    11460

TTGTGCACAC ACACTTCTCT GCTTCCCTGG CCGTTCTCTA TCTTGGAGAG GCATTTCAAA    11520

CGCCACTTCC ACCAGAAGGC CTTGCTACTG CACCAACTAG TTACTATCTC TTCTTCACCC    11580

AAATCCTGGT AGCACTTTGG ATCTCCCACT TGCACTTAGG GTTCACCTTC CGTTATAATC    11640

ATTGCCATCA ATCTCAGCAT CGTTTTAGGC ACTTCTTTCC AGCCATTGTT CTTACCTCCA    11700

ACTACATATC TTTTCTGGAC TGTGCATTAT TCAGTTTATT AAATGCCCAT TAAATGTGTT    11760

TAGCCATTGT CAATTACTCT GAAACGTTCA GGTTTTGACA AATTCTTTCC TAATGTAAGT    11820

GTGGTGGAAA GAGTGAAAGA AAGTCAAATT GCACAAAAAT AGGATGGTGT AATTTGGGGT    11880

TATGCCGTCA ATTTTGTCCA CTGATAAATG GGATTTGAGC TCTCCAAGTT GACTAGATGC    11940

CCTTTATTTT TCAGAAATAT TCTACATCAT TGGAGCTGTG GTATTTGTGG TCATCATCCT    12000

TGTCATCATC CTGGCTATAT CTCTACACAA GTGTAGAAAG GCAGGAGTGG GGCAGAGCTG    12060

GAAGGAGAAC TCCCCACTGA ATGTTTCATA AAGGAAGCAC TGTTGGAGCT ACTGCAAATG    12120

CTATATTGCA CTGTGACCGA GAACTTTTAA GAGGATAGAA TACATGGAAA CGCAAATGAG    12180

TATTTCGGAG CATGAAGACC CTGGAGTTCA AAAAACTCTT GATATGACCT GTTATTACCA    12240

TTAGCATTCT GGTTTTGACA TCAGCATTAG TCACTTTGAA ATGTAACGAA TGGTACTACA    12300

ACCAATTCCA AGTTTTAATT TTTAACACCA TGGCACCTTT TGCACATAAC ATGCTTTAGA    12360

TTATATATTC CGCACTCAAG GAGTAACCAG GTCGTCCAAG CAAAAACAAA TGGGAAAATG    12420

TCTTAAAAAA TCCTGGGTGG ACTTTTGAAA AGCTTTTTTT TTTTTTTTT TTTTTGAGAC    12480

GGAGTCTTGC TCTGTTGCCC AGGCTGGAGT GCAGTAGCAC GATCTCGGCT CACTGCACCC    12540

TCCGTCTCTC GGGTTCAAGC AATTGTCTGC CTCAGCCTCC CGAGTAGCTG GGATTACAGG    12600

TGCGCACTAC CACGCCAAGC TAATTTTTGT ATTTTTTAGT AGAGATGGGG TTTCACCATC    12660

TTGGCCAGGC TGGTCTTGAA TTCCTGACCT CAGGTGATCC ACCCACCTTG GCCTCCCAAA    12720

GTGCTAGTAT TATGGGCGTG AACCACCATG CCCAGCCGAA AAGCTTTTGA GGGGCTGACT    12780

TCAATCCATG TAGGAAAGTA AAATGGAAGG AAATTGGGTG CATTTCTAGG ACTTTTCTAA    12840

CATATGTCTA TAATATAGTG TTTAGGTTCT TTTTTTTTTC AGGAATACAT TTGGAAATTC    12900

AAAACAATTG GCAAACTTTG TATTAATGTG TTAAGTGCAG GAGACATTGG TATTCTGGGC    12960

ACCTTCCTAA TATGCTTTAC AATCTGCACT TTAACTGACT TAAGTGGCAT TAAACATTTG    13020

AGAGCTAACT ATATTTTTAT AAGACTACTA TACAAACTAC AGAGTTTATG ATTTAAGGTA    13080

CTTAAAGCTT CTATGGTTGA CATTGTATAT ATAATTTTTT AAAAAGGTTT TCTATATGGG    13140

GATTTTCTAT TTATGTAGGT AATATTGTTC TATTTGTATA TATTGAGATA ATTTATTTAA    13200

TATACTTTAA ATAAAGGTGA CTGGGAATTG TTACTGTTGT ACTTATTCTA TCTTCCATTT    13260
```

```
ATTATTTATG TACAATTTGG TGTTTGTATT AGCTCTACTA CAGTAAATGA CTGTAAAATT    13320

GTCAGTGGCT TACAACAACG TATCTTTTTC GCTTATAATA CATTTTGGTG ACTGTAGGCT    13380

GACTGCACTT CTTCTCAATG TTTTCTCATT CTAGGATGCA AACCAATGGA GAAGCCCCTA    13440

ATTAGATCAG GGCAGAGGGA AAAACAAAAA ACTGGTAGAA ACCGGCAACC ACAGCTTCAA    13500

GCTTTAAGCC CATCTCCTAC ACTTCTGCTC TGTACGTGCC CATTGTCACT TCTGTTCACA    13560

TGCTACTGTC CCAAGCAAGT GACCAAGCCT GACAATACTT TGTCTACTGG AGTCACTGCA    13620

AGGCACATGA CGGGGCAGGG ATGTCGTCTT ACAGGGAAGA GAAAAGATAA TGCTCTCTAC    13680

TGCAGACTTG GAGAGATTTC TTCCCATTGG CAGTAGTTTG ACTAATTGGA GATGAGAAAA    13740

AAAGAAACAT TCTTGGGATG ATTGTATTGA AACAAAATTA GGTAAAAGGA CAATATAGGA    13800

TAGGGAGAGA TATAAGTGGA ATGAGATCTC TAGAGTCCAT TAAAAGCAAG CTAGATTGAG    13860

AGCTC                                                                13865
```

(2) INFORMATION FOR SEQ ID NO:12:

(i) SEQUENCE CHARACTERISTICS:
        (A) LENGTH: 263 amino acids
        (B) TYPE: amino acid
        (C) STRANDEDNESS:
        (D) TOPOLOGY: linear (xi) SEQUENCE DESCRIPTION: SEQ ID NO:12:

```
Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu Ile Phe Tyr Ile Ile
    210                 215                 220

Gly Ala Val Val Phe Val Val Ile Ile Leu Val Ile Ile Leu Ala Ile
225                 230                 235                 240
```

```
Ser Leu His Lys Cys Arg Lys Ala Gly Val Gly Gln Ser Trp Lys Glu
            245                 250                 255

Asn Ser Pro Leu Asn Val Ser
            260

(2) INFORMATION FOR SEQ ID NO:13:

(i) SEQUENCE CHARACTERISTICS:
        (A) LENGTH: 1440 base pairs
        (B) TYPE: nucleic acid
        (C) STRANDEDNESS: single
        (D) TOPOLOGY: linear (xi) SEQUENCE DESCRIPTION: SEQ ID NO:13:

TCAACAGGCA GGGGCAGCAC TGCAGAGATT TCATCATGGT CTCCCAGGCC CTCAGGCTCC      60

TCTGCCTTCT GCTTGGGCTT CAGGGCTGCC TGGCTGCAGG CGGGGTCGCT AAGGCCTCAG     120

GAGGAGAAAC ACGGGACATG CCGTGGAAGC CGGGGCCTCA CAGAGTCTTC GTAACCCAGG     180

AGGAAGCCCA CGGCGTCCTG CACCGGCGCC GGCGCGCCAA CGCGTTCCTG GAGGAGCTGC     240

GGCCGGGCTC CCTGGAGAGG GAGTGCAAGG AGGAGCAGTG CTCCTTCGAG GAGGCCCGGG     300

AGATCTTCAA GGACGCGGAG AGGACGAAGC TGTTCTGGAT TTCTTACAGT GATGGGGACC     360

AGTGTGCCTC AAGTCCATGC CAGAATGGGG GCTCCTGCAA GGACCAGCTC CAGTCCTATA     420

TCTGCTTCTG CCTCCCTGCC TTCGAGGGCC GGAACTGTGA GACGCACAAG GATGACCAGC     480

TGATCTGTGT GAACGAGAAC GGCGGCTGTG AGCAGTACTG CAGTGACCAC ACGGGCACCA     540

AGCGCTCCTG TCGGTGCCAC GAGGGGTACT CTCTGCTGGC AGACGGGGTG TCCTGCACAC     600

CCACAGTTGA ATATCCATGT GGAAAAATAC CTATTCTAGA AAAAAGAAAT GCCAGCAAAC     660

CCCAAGGCCG AATTGTGGGG GGCAAGGTGT GCCCCAAAGG GGAGTGTCCA TGGCAGGTCC     720

TGTTGTTGGT GAATGGAGCT CAGTTGTGTG GGGGACCCT GATCAACACC ATCTGGGTGG     780

TCTCCGCGGC CCACTGTTTC GACAAAATCA AGAACTGGAG GAACCTGATC GCGGTGCTGG     840

GCGAGCACGA CCTCAGCGAG CACGACGGGG ATGAGCAGAG CCGGCGGGTG GCGCAGGTCA     900

TCATCCCCAG CACGTACGTC CCGGGCACCA CCAACCACGA CATCGCGCTG CTCCGCCTGC     960

ACCAGCCCGT GGTCCTCACT GACCATGTGG TGCCCCTCTG CCTGCCCGAA CGGACGTTCT    1020

CTGAGAGGAC GCTGGCCTTC GTGCGCTTCT CATTGGTCAG CGGCTGGGGC CAGCTGCTGG    1080

ACCGTGGCGC CACGGCCCTG GAGCTCATGG TGCTCAACGT GCCCCGGCTG ATGACCCAGG    1140

ACTGCCTGCA GCAGTCACGG AAGGTGGGAG ACTCCCCAAA TATCACGGAG TACATGTTCT    1200

GTGCCGGCTA CTCGGATGGC AGCAAGGACT CCTGCAAGGG GGACAGTGGA GGCCCACATG    1260

CCACCCACTA CCGGGGCACG TGGTACCTGA CGGGCATCGT CAGCTGGGGC CAGGGCTGCG    1320

CAACCGTGGG CCACTTTGGG GTGTACACCA GGGTCTCCCA GTACATCGAG TGGCTGCAAA    1380

AGCTCATGCG CTCAGAGCCA CGCCCAGGAG TCCTCCTGCG AGCCCCATTT CCCTAGCCCA    1440

(2) INFORMATION FOR SEQ ID NO:14:

(i) SEQUENCE CHARACTERISTICS:
        (A) LENGTH: 466 amino acids
        (B) TYPE: amino acid
        (C) STRANDEDNESS:
        (D) TOPOLOGY: linear (xi) SEQUENCE DESCRIPTION: SEQ ID NO:14:

Met Val Ser Gln Ala Leu Arg Leu Leu Cys Leu Leu Leu Gly Leu Gln
1               5                   10                  15
```

-continued

```
Gly Cys Leu Ala Ala Gly Val Ala Lys Ala Ser Gly Gly Glu Thr
             20                  25                  30

Arg Asp Met Pro Trp Lys Pro Gly Pro His Arg Val Phe Val Thr Gln
             35                  40                  45

Glu Glu Ala His Gly Val Leu His Arg Arg Arg Ala Asn Ala Phe
 50                  55                  60

Leu Glu Glu Leu Arg Pro Gly Ser Leu Glu Arg Glu Cys Lys Glu Glu
 65                  70                  75                  80

Gln Cys Ser Phe Glu Glu Ala Arg Glu Ile Phe Lys Asp Ala Glu Arg
                 85                  90                  95

Thr Lys Leu Phe Trp Ile Ser Tyr Ser Asp Gly Asp Gln Cys Ala Ser
            100                 105                 110

Ser Pro Cys Gln Asn Gly Gly Ser Cys Lys Asp Gln Leu Gln Ser Tyr
            115                 120                 125

Ile Cys Phe Cys Leu Pro Ala Phe Glu Gly Arg Asn Cys Glu Thr His
            130                 135                 140

Lys Asp Asp Gln Leu Ile Cys Val Asn Glu Asn Gly Gly Cys Glu Gln
145                 150                 155                 160

Tyr Cys Ser Asp His Thr Gly Thr Lys Arg Ser Cys Arg Cys His Glu
                165                 170                 175

Gly Tyr Ser Leu Leu Ala Asp Gly Val Ser Cys Thr Pro Thr Val Glu
            180                 185                 190

Tyr Pro Cys Gly Lys Ile Pro Ile Leu Glu Lys Arg Asn Ala Ser Lys
            195                 200                 205

Pro Gln Gly Arg Ile Val Gly Gly Lys Val Cys Pro Lys Gly Glu Cys
            210                 215                 220

Pro Trp Gln Val Leu Leu Leu Val Asn Gly Ala Gln Leu Cys Gly Gly
225                 230                 235                 240

Thr Leu Ile Asn Thr Ile Trp Val Val Ser Ala Ala His Cys Phe Asp
                245                 250                 255

Lys Ile Lys Asn Trp Arg Asn Leu Ile Ala Val Leu Gly Glu His Asp
            260                 265                 270

Leu Ser Glu His Asp Gly Asp Glu Gln Ser Arg Arg Val Ala Gln Val
            275                 280                 285

Ile Ile Pro Ser Thr Tyr Val Pro Gly Thr Thr Asn His Asp Ile Ala
290                 295                 300

Leu Leu Arg Leu His Gln Pro Val Val Leu Thr Asp His Val Val Pro
305                 310                 315                 320

Leu Cys Leu Pro Glu Arg Thr Phe Ser Glu Arg Thr Leu Ala Phe Val
                325                 330                 335

Arg Phe Ser Leu Val Ser Gly Trp Gly Gln Leu Leu Asp Arg Gly Ala
            340                 345                 350

Thr Ala Leu Glu Leu Met Val Leu Asn Val Pro Arg Leu Met Thr Gln
            355                 360                 365

Asp Cys Leu Gln Gln Ser Arg Lys Val Gly Asp Ser Pro Asn Ile Thr
            370                 375                 380

Glu Tyr Met Phe Cys Ala Gly Tyr Ser Asp Gly Ser Lys Asp Ser Cys
385                 390                 395                 400

Lys Gly Asp Ser Gly Gly Pro His Ala Thr His Tyr Arg Gly Thr Trp
                405                 410                 415

Tyr Leu Thr Gly Ile Val Ser Trp Gly Gln Gly Cys Ala Thr Val Gly
            420                 425                 430

His Phe Gly Val Tyr Thr Arg Val Ser Gln Tyr Ile Glu Trp Leu Gln
```

```
                    435                 440                 445
Lys Leu Met Arg Ser Glu Pro Arg Pro Gly Val Leu Leu Arg Ala Pro
        450                 455                 460
Phe Pro
465
```

(2) INFORMATION FOR SEQ ID NO:15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:15:

GTCATGCCAT GGCCTCAGGC ACTACAA                                                  27

(2) INFORMATION FOR SEQ ID NO:16:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:16:

TGACAAGCTT ATTCTCTGAA TTCCCCTTTC T                                       31

(2) INFORMATION FOR SEQ ID NO:17:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:17:

GTCATGCCAT GGCCCTGGTG CCTCGTGCTT CTGGCACTAC AAATACT            47

(2) INFORMATION FOR SEQ ID NO:18:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:18:

GTCATGCCAT GGCCCTGGTG CCTCGTGGTT CTTGCGGCAC TACAAATACT        50

(2) INFORMATION FOR SEQ ID NO:19:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (xi) SEQUENCE DESCRIPTION: SEQ ID NO:19:

CGCGGATCCA CCGCCACCAG ATCCACCGCC TCCTTCTCTG AATTCCCCTT TCT     53

(2) INFORMATION FOR SEQ ID NO:20:

(i) SEQUENCE CHARACTERISTICS:
        (A) LENGTH: 44 base pairs
        (B) TYPE: nucleic acid

```
        (C) STRANDEDNESS: single
        (D) TOPOLOGY: linear (xi) SEQUENCE DESCRIPTION: SEQ ID NO:20:

CGCGGATCCG GCGGTGGAGG CTCTTCAGGC ACTACAAATA CTGT                              44

(2) INFORMATION FOR SEQ ID NO:21:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:21:

TGACAAGCTT ATTCTCTGAA TTCCCCTTTC T                                            31

(2) INFORMATION FOR SEQ ID NO:22:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:22:

GTCATGCCAT GGCCCTGGTG CCTCGTGGTT CTTGCGGCAC TACAAATACT                        50

(2) INFORMATION FOR SEQ ID NO:23:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:23:

TGACAAGCTT ATTCTCTGAA TTCCCCTTTC T                                            31

(2) INFORMATION FOR SEQ ID NO:24:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:24:

GTCATGCCAT GGCCCTGGTG CCTCGTGGTT GCACTACAAA TACT                              44

(2) INFORMATION FOR SEQ ID NO:25:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:25:

TGACAAGCTT AGCATTCTCT GAATTCCCCT TTCT                                         34

(2) INFORMATION FOR SEQ ID NO:26:

(i) SEQUENCE CHARACTERISTICS:
        (A) LENGTH: 19 base pairs
        (B) TYPE: nucleic acid
        (C) STRANDEDNESS: single
```

-continued (D) TOPOLOGY: linear (xi) SEQUENCE DESCRIPTION: SEQ ID NO:26:

CAAGTTCAGC CAAGAAAAC                                            19

(2) INFORMATION FOR SEQ ID NO:27:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:27:

ACACTTTATT ATCGGAAATC TTCAGCTTCA GGAAAG                         36